United States Patent
Landa et al.

(10) Patent No.: US 11,179,315 B2
(45) Date of Patent: Nov. 23, 2021

(54) COMPOSITIONS, KITS AND METHODS FOR COLORING FIBERS

(71) Applicant: Henkel AG & Co. KGaA, Duesseldorf (DE)

(72) Inventors: Benzion Landa, Nes Ziona (IL); Sagi Abramovich, Ra'anana (IL); Meir Soria, Jerusalem (IL); Yishai Karton, Nes Ziona (IL); Lior Shahar, Kiryat Ono (IL)

(73) Assignee: HENKEL AG & CO. KGAA, Duesseldorf (DE)

( * ) Notice: Subject to any disclaimer, the term of this patent is extended or adjusted under 35 U.S.C. 154(b) by 17 days.

(21) Appl. No.: 16/500,353

(22) PCT Filed: Apr. 2, 2018

(86) PCT No.: PCT/US2018/025758
§ 371 (c)(1),
(2) Date: Oct. 2, 2019

(87) PCT Pub. No.: WO2018/187246
PCT Pub. Date: Oct. 11, 2018

(65) Prior Publication Data
US 2021/0113453 A1     Apr. 22, 2021

Related U.S. Application Data

(60) Provisional application No. 62/619,995, filed on Jan. 22, 2018, provisional application No. 62/536,378, filed on Jul. 24, 2017.

(30) Foreign Application Priority Data

Apr. 2, 2017 (GB) ..................... 1705315
Sep. 13, 2017 (GB) ..................... 1714730
Dec. 5, 2017 (GB) ..................... 1720264

(51) Int. Cl.
*A61Q 5/10* (2006.01)
*A61K 8/898* (2006.01)
(Continued)

(52) U.S. Cl.
CPC .......... *A61K 8/898* (2013.01); *A45D 19/0066* (2021.01); *A61K 8/062* (2013.01);
(Continued)

(58) Field of Classification Search
CPC . A61Q 5/10; A61Q 5/065; A61K 8/19; A61K 2800/884; A61K 8/25;
(Continued)

(56) References Cited

U.S. PATENT DOCUMENTS 6,106,577 A    8/2000  Audousset et al.
2010/0083446 A1*  4/2010  Brun .................. A61Q 5/004
                                                    8/405
(Continued)

FOREIGN PATENT DOCUMENTS

EP    0528602 A1    2/1993
WO    9718795 A1    5/1997
(Continued)

OTHER PUBLICATIONS

EPO, International Search Report issued in International Application No. PCT/US2018/025758, dated Jun. 14, 2018.
(Continued)

*Primary Examiner* — Eisa B Elhilo
(74) *Attorney, Agent, or Firm* — Lorenz & Kopf, LLP

(57) ABSTRACT

There is disclosed a method of producing a coating on an external surface of individual mammalian hair fibers, the method comprising (a) applying on the external surface of the individual fibers, an oil-in-water emulsion including an amino-silicone film forming pre-polymer, so as to form an at least partially cured amino-silicone film; and (b) applying an
(Continued)

aqueous dispersion on said amino-silicone film, to produce an overlying, optionally pigmented, polymeric film that coats said at least partially cured amino-silicone film; wherein the aqueous dispersion contains: (i) a polymeric material having neutralized acid moieties; and optionally (ii) a plurality of pigment particles, at least partially enveloped by the polymeric material, and dispersed within said aqueous dispersion. Suitable coating or coloring compositions and kits including the same are also disclosed, as well as methods for preparing the compositions or removing films formed therewith.

25 Claims, 6 Drawing Sheets

(51) Int. Cl.
| | | |
|---|---|---|
| *A45D 19/00* | (2006.01) | |
| *A61K 8/06* | (2006.01) | |
| *A61K 8/19* | (2006.01) | |
| *A61K 8/41* | (2006.01) | |
| *A61K 8/49* | (2006.01) | |
| *A61K 8/81* | (2006.01) | |
| *A61Q 5/06* | (2006.01) | |

(52) U.S. Cl.
CPC ............... *A61K 8/19* (2013.01); *A61K 8/41* (2013.01); *A61K 8/49* (2013.01); *A61K 8/8147* (2013.01); *A61K 8/8158* (2013.01); *A61Q 5/065* (2013.01); *A61Q 5/10* (2013.01); *A61K 2800/624* (2013.01); *A61K 2800/884* (2013.01); *A61K 2800/95* (2013.01)

(58) Field of Classification Search
CPC ...... A61K 2800/432; A61K 8/04; A61K 8/41; A61K 8/8147; A61K 2800/624; A61K 2800/95; A61K 8/49; A61K 8158
USPC .............................................. 8/405; 132/208
See application file for complete search history.

(56) References Cited

U.S. PATENT DOCUMENTS

| | | |
|---|---|---|
| 2011/0236334 A1 | 9/2011 | Jordan et al. |
| 2011/0305653 A1 | 12/2011 | Jordan |
| 2014/0308229 A1 | 10/2014 | Bouzeloc et al. |
| 2015/0174051 A1 | 6/2015 | Teboul |
| 2015/0297495 A1 | 10/2015 | Patel et al. |
| 2016/0235655 A1 | 8/2016 | Herrlein et al. |

FOREIGN PATENT DOCUMENTS

| | | |
|---|---|---|
| WO | 2009061360 A1 | 5/2009 |
| WO | 2018130912 A1 | 7/2018 |

OTHER PUBLICATIONS

Dow website: https://www.dow.com/en-us/product-search/nucrelacidcopolymer accessed Jul. 3, 2019 (1995-2019).
Genesee Polymers Corporation website: https://www.gpcsilicones.com/products/silicone-fluids/amine-functional accessed Jul. 3, 2019.
International Organization for Standardization: 9277:2010 Determination of the specific surface area of solids by gas adsorption—BET method; https://www.iso.org/standard/44941.html; Sep. 2010.
EPO, International Search Report issued in International Application No. PCT/US2019/014633, dated Apr. 24, 2019.

* cited by examiner

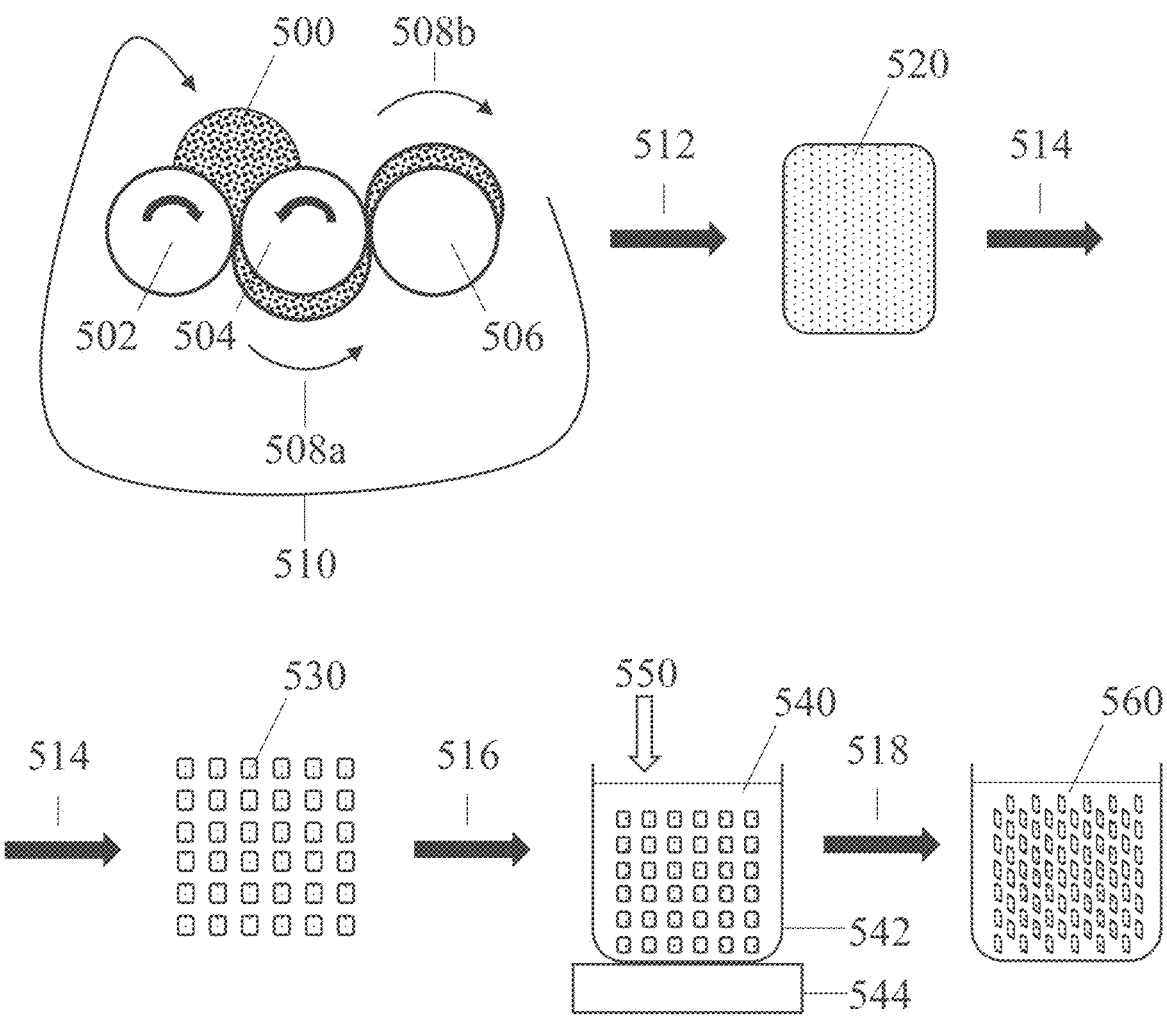
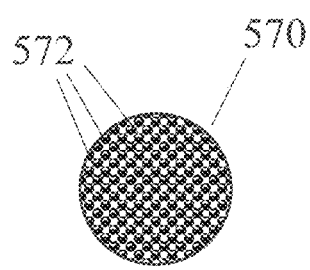
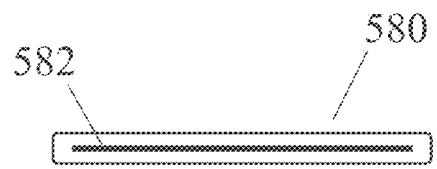
Fig. 5A
Fig. 5B
Fig. 5C

COMPOSITIONS, KITS AND METHODS FOR COLORING FIBERS

CROSS-REFERENCE TO RELATED APPLICATIONS

This is a National Stage of International Application No. PCT/US2018/025758, filed Apr. 2, 2018, which claims the benefit of U.S. Provisional Application No. 62/619,995, filed Jan. 22, 2018, U.S. Provisional Application No. 62/536,378, filed Jul. 24, 2017, Great Britain Patent Application No. 1720264.9, filed on Dec. 5, 2017, Great Britain Patent Application No. 1714730.7, filed Sep. 13, 2019, and Great Britain Patent Application No. 1705315.8, filed on Apr. 2, 2017.

FIELD

The present disclosure relates to compositions, kits, and methods for coating or coloring fibers such as keratinous fibers, typically hair.

BACKGROUND

Natural hair color is the pigmentation of hair follicles due to two types of melanin: eumelanin and pheomelanin. Generally, if more eumelanin is present, the color of the hair is darker; if less eumelanin is present, the hair shade is lighter. Levels of melanin can vary over time causing hair color to change.

Melanin production decreases in the hair roots of humans with ageing, causing lightening of the hair, and finally ceases. Once melanin production ceases, new hairs grow out gray or white when light reflects through them.

Hair coloring is the practice of changing the color of hair. The main reasons for this practice are cosmetic (e.g., to cover gray hair, to change to a color regarded as more fashionable or desirable, or to restore the original hair color after it has been colored, for instance by hairdressing processes or sun bleaching). Hair coloring is achieved by use of coloring compositions comprising chemical, organic, herbal or natural coloring agents. The coloring agents generally fall into two categories, a) soluble dyes that may penetrate the hair (but can also remain external) and may be reacted to induce the desired coloring effect, and b) water-insoluble pigments, which in view of their dimensions are typically restricted to external coloring of hair fibers.

Based on how long the effect lasts, coloring may be permanent, demi-permanent, semi-permanent or temporary.

Permanent hair coloring typically involves penetration of direct dye or oxidation dye precursor deep into the hair shaft, generally preceded by the removal of any existing melanin, requiring bleaching, and sealing of the coloring agent into the hair cortex. Permanent coloring further requires an oxidizing agent or coupler in order for the color to fully develop. The color does not wash out with shampoo for at least 30 shampoo washes. However, such permanent coloration may severely damage the hair.

Demi-permanent hair coloring compositions are also known as deposit-only hair colors. These are chemically milder than permanent hair coloring compositions, penetrate only partially into the hair shaft, and typically do not remove the hair's natural pigment. Demi-permanent hair color washes out after about 10-30 shampoo washes.

Semi-permanent hair coloring compositions are chemically milder than either permanent or demi-permanent coloring compositions, involving only a small extent of penetration into the hair shaft. Semi-permanent coloring compositions remain on the hair for only 4-10 shampoo washes.

Permanent, demi-permanent or semi-permanent coloring processes are known to damage keratin fibers. Moreover, certain processes raise health concerns, some compositions being possibly carcinogenic.

Temporary hair coloring compositions do not penetrate into the hair shaft, but remain on the outer surface of the hair shaft. Such coloring compositions may easily be washed out by a single shampoo, resisting at most 2-3 shampoos under favorable circumstances.

There remains a need for coloring compositions for coloring keratin fibers, such as hair, which exhibit reduced penetration and impact on the integrity of the fibers being colored as compared to known coloring compositions, while providing long-lasting coloration of the fibers.

There further remains a need for coloring compositions for dark-colored keratin fibers, wherein such coloring compositions provide a lighter color than that of the native keratin fiber, wherein such coloring compositions are used without the need for bleaching of the keratin fiber.

SUMMARY

Aspects of the present disclosure relate to methods for coating and/or coloring keratinous fibers, such as human hair.

In one aspect, there is provided a method of treating an outer surface of a mammalian hair fiber, the method comprising:
(a) forming, on the outer surface of the mammalian hair fiber, an amino-silicone layer; and
(b) applying, on said amino-silicone layer, an aqueous dispersion containing:
  a plurality of polymeric particles, formed of a hydrophilic polymeric material having neutralized acid moieties, wherein, in each of at least a portion of said polymeric particles, said hydrophilic polymeric material envelops at least one pigment core particle,
  said plurality of polymeric particles being dispersed within said aqueous dispersion;
so as to produce an overlying, pigmented polymeric layer adhering to an external surface of said amino-silicone layer.

In one aspect, there is provided a method of coating mammalian hair, the method comprising:
(a) applying, on an external surface of individual hairs of the mammalian hair, an oil-in-water emulsion comprising:
  (A) an aqueous phase containing water; and
  (B) an oil phase containing at least one reactive condensation-curable film-forming amino-silicone pre-polymer that, subsequent to condensation curing, forms an amino-silicone coat;
  wherein said oil phase fulfills at least one of the following:
    (i) said at least one reactive condensation-curable film-forming amino-silicone pre-polymer includes at least one reactive condensation-curable film-forming amino-silicone monomer having a molecular weight of at most 1000 g/mole;
    (ii) said oil phase further contains a non-amino cross-linking agent adapted or selected to cure said pre-polymer, said non-amino cross-linking agent having a molecular weight in the range of at most 1000 g/mole;
(b) after partial condensation curing of said pre-polymer has occurred so as to form an at least partially cured film on the external surface of the individual hairs, washing the hair with a rinsing liquid to remove any excess of said oil-in-water emulsion; and (c) applying an aqueous dispersion to produce an overlying, polymeric layer adhering to the at least partially cured film on the external surface of individual hairs, said aqueous dispersion containing a plurality of polymeric particles, formed of a hydrophilic polymeric material having neutralized acid moieties, said plurality of polymeric particles being dispersed within said aqueous dispersion.

In another aspect, there is provided a method of coloring mammalian hair, the method comprising:

(a) applying, on an external surface of individual hairs of the mammalian hair, an oil-in-water emulsion comprising:
  (A) an aqueous phase containing water; and
  (B) an oil phase containing at least one reactive condensation-curable film-forming amino-silicone pre-polymer that, subsequent to condensation curing, forms an amino-silicone coat;
  wherein said oil phase fulfills at least one of the following:
    (i) said at least one reactive condensation-curable film-forming amino-silicone pre-polymer includes at least one reactive condensation-curable film-forming amino-silicone monomer having a molecular weight of at most 1000 g/mole;
    (ii) said oil phase further contains a non-amino cross-linking agent adapted or selected to cure said pre-polymer, said non-amino cross-linking agent having a molecular weight in the range of at most 1000 g/mole;
    (iii) said oil phase further optionally contains a plurality of sub-micronic pigment particles dispersed in said oil phase, in presence of a pigment dispersant;

(b) after partial condensation curing of said pre-polymer has occurred so as to form an at least partially cured film on the external surface of the individual hairs, washing the hair with a rinsing liquid to remove any excess of said oil-in-water emulsion; and (c) applying an aqueous dispersion to produce an overlying, pigmented polymeric layer adhering to the at least partially cured film on the external surface of individual hairs, said aqueous dispersion containing:
  a plurality of polymeric particles, formed of a hydrophilic polymeric material having neutralized acid moieties, wherein, in each of at least a portion of said polymeric particles, said hydrophilic polymeric material optionally envelops at least one pigment core particle, said plurality of polymeric particles being dispersed within said aqueous dispersion.

In some embodiments, pigment particles are contained in at least one of said oil phase of said oil-in-water emulsion and said aqueous dispersion.

The formulations (e.g., oil-in-water emulsions) comprising, among others, the condensation-curable amino-silicone reactant capable of forming the at least partially cured amino-silicone film on the fibers, according to the present teachings, are said to form a first coat. The aqueous dispersions comprising, among others, the polymeric material having neutralized acid moieties able to produce a polymeric film capable of covering the first coats, as herein taught, are said to form a second coat. These terms of "first coat" and "second coat" are provided for simplicity and should not be deemed limiting, as such or similar formulations and dispersions may serve to form a third and fourth coat, respectively, and so on.

Oil-in-Water Emulsion

Polymer-forming amino-silicone reactants (also termed pre-polymers) generally refer to materials (e.g., uncured/curable monomers of a single unit, oligomers of a few repeating units and/or polymers) that can be cross-linked to form larger macro molecules through cross-linkable groups, also termed reactive groups, by techniques known as curing processes. Typically, the polymer-forming amino-silicone reactants are deemed reactive (being still able to participate in polymerization or curing) when they lack a glass transition (Tg) temperature. A variety of curing processes exist depending on the chemical composition of the reactants to be cross-linked, their reactive groups and their curing auxiliary factors (cross-linkers, curing accelerators or catalysts, and the like).

The polymer-forming amino-silicone reactants of the present disclosure includes amino-silicone monomers, oligomers or polymers that are condensation-curable, namely bearing functional groups or moieties capable of reacting with one another so as to form, by condensation, a siloxane bond, while liberating in the process a molecule of alcohol, oxime or water. In some cases, the condensation-curable amino-silicone reactants, as afore-described, include materials also known as condensation-curable amino silanes. Condensation-curable amino functional silicones are further characterized by the presence of amino groups attached via carbon atoms, as terminal or side chains, to the backbone of the silicone pre-polymers. These amino groups are further capable of attaching to or interacting with other molecules through nucleophilic reactions or interactions (for example, carboxylic, anhydride or epoxy functional molecules). Therefore, while some of the monomers, oligomers or polymers disclosed herein are termed "condensation-curable amino functional silicones" or "reactive condensation-curable amino-silicone pre-polymers" and like variants, this terminology is not intended to be limiting the curing process exclusively through condensation of the reactive, condensation-curable groups, the amino groups being capable of curing also through "non-condensation" processes, such as resulting in the formation of nitrogen-carbon bonding. The products of such curing processes are networks of cross-linked oligomers or polymers termed elastomers or elastomeric networks (rubber like), in reference to their viscoelastic properties. While elastomers generally refer to cured polymers having a glass transition temperature below typical ambient values, thin coats of "elastomeric" polymers having a Tg above such ambient values, and behaving for all practical purposes as formal elastomers, can be tolerated. Thus, as the cured amino-silicone coats resulting from the present methods are thin, both elastomers (e.g., having a Tg<30° C.) and elastomeric networks (e.g., having a Tg>30° C.) are suitable. As such cured networks (preferably three-dimensional to enhance cohesivity) may form a continuous film, the polymer-forming pre-polymers reactants participating in such formation, alone or in combination with additional film-forming agents, can also be termed film-forming reactants or pre-polymers.

Organosilicon pre-polymers include repeats of siloxane units (—O—Si—) the silicone atom of the siloxane repeats being further substituted as herein detailed. Amino-silanes are one example of low MW amino-silicones having one, two or at most three atoms of silicon substituted by alkoxy or hydroxyl groups. As a rule, amino-silanes serve as cross-linking agents and are used in the present disclosure in combination with amino-silicone pre-polymers or with amino-silicone oils having at least 4 atoms of silicon, at least 10 atoms of silicon, or at least 15 atoms of silicon. It has been observed that an amino-silicone composition consisting exclusively or almost exclusively of amino-silanes having up to 3 atoms of silicones yield a brittle coat unpleasant to the touch and easily breaking away from the hair surface, even when forming relatively thin films.

In a preferred embodiment, the reactive amino-silicone pre-polymer contains at least three silanol groups and/or hydrolysable reactive groups able to form silanol moieties upon hydrolysis. Additionally, the composition being applied on the hair fibers comprise condensation-curable amino-silicone pre-polymers having at least 4 atoms of silicon.

The polymer-forming amino-silicone reactants can be characterized by the number of condensation-curable reactive groups harbored by each molecule. A reactant having a single silanol or hydrolysable group per molecule would act as terminating reactant with respect to network formation, hence it is preferably avoided. In some embodiments, the concentration of such reactants having a single condensation-cure reactive group per molecule is at most 7 wt. %, at most 5 wt. %, at most 2 wt. %, or at most 1 wt. % by weight of the oil phase. In some embodiments, the oil phase is devoid of said terminating reactant.

Conversely, polymer-forming amino-silicone first reactants having two condensation-cure reactive groups per molecule can participate in network formation. Preferably, such a network should not rely exclusively on linear chain extension to enable the formation of a cohesive 3D-matrix in-between such chains. A reactive polymer-forming condensation-curable amino-silicone reactant having at least three condensation-curable reactive groups (e.g., 3 silanol and/or hydrolysable groups) advantageously favors the formation of a 3-dimensional network. Similarly, "tri-functional" reactants accelerating or otherwise enhancing the formation of a 3D-network is preferred over less functionalized counterparts. Examples of such "tri-functional" reactants include some cross-linking agents and reactive fillers. In some embodiments, the polymer-forming amino-silicone first reactant includes at least one reactant and/or 3D-network former having at least three condensation-cure reactive groups per molecule.

In some embodiments, the condensation-curable polymer-forming amino-silicone reactants includes a mixture of at least two types of reactants selected from condensation-curable amino-silicone monomers, amino-silicone oligomers and amino-silicone polymers. For instance, the pre-polymer mix can comprise condensation-curable amino-silicone monomers (e.g., for their rapidity to cure), condensation-curable amino-silicone oligomers (e.g., for their ability to control the density of the cross-linking) and condensation-curable amino-silicone polymers (e.g., for their contribution to the coat flexibility).

Such amino functional silicone reactants (alternatively referred to as amino-silicones or amine-silicones), may be considered as positively charged or positively chargeable under suitable chemical environment (e.g., relatively low pH above the isoelectric point of hair). Such materials can in part be characterized by their Amine Number, indicative of the amount of amino groups per molecule (or per a given weight of an amino-silicone material, whether or not film-forming). In some embodiments, at least one of, and optionally all of the reactive condensation-curable film-forming amino-silicone pre-polymers disposed in the reactive oil phase, has an Amine Number or weight average Amine Number in a range of 3-1000, 3-500 or 3-200. In some embodiments, the entire reactive oil phase displays an Amine Number in a range of 3-1000, 3-500 or 3-200.

The term "reactive group" and the like is understood to mean any group capable of forming a covalent bond with another polymeric backbone or with a cross linker at least by way of condensation curing. Examples of reactive groups on a reactive condensation-curable amino-silicone are:
  $C_1$-$C_6$ or $C_1$-$C_4$ alkoxy group, such as methoxy, ethoxy, propoxy, isopropoxy, or methoxyethoxy groups; or
  Hydroxyl group, such as silanol functional; or
  Acyloxy groups, or aryloxy groups; or
  Oxime groups, such as methylethylketoxime.
The amino functional group can be:
  primary amine (I) groups, such as aminoalkyl groups,
  secondary amine (II) groups, such as aminoethylaminopropyl group, which can be located in the amino-silicone polymer chain at terminal position or as side chain (pendant);
  or tertiary (III) amino group, such as in N,N-dialkylaminopropyl group, which are typically located in branched amino-silicone polymer chain.

The amino-silicone can have one or more amine reactive groups, and be accordingly referred to as a monamino, diamino, triamino, tetramino and so on, amino-silicone.

Additionally, the functional amines can be used as catalysts to promote condensation curing of alkoxy groups as found, for example, in amine/alkoxy functional silicones.

In some embodiments, the condensation-curable film-forming amino-silicone reactant consists of, consists essentially of, or includes mixtures of amino-silicone monomers. The amino-silicone monomers of the present disclosure have an average molecular weight in the range of 100 to 600, and are able to condensation-cure more rapidly than their oligomer or polymer counterparts, in view of their smaller size/higher accessibility to reactive groups. Such monomers can form three-dimensional (3D) network with high cross-linking density. In some embodiments, the condensation-curable amino-silicone monomer has an Amine Number of at least 200, at least 220, at least 240, at least 275, at least 325, or at least 400. In some embodiments, the condensation-curable amino-silicone monomer has an Amine Number of at most 1500, at most 1250, at most 1150, at most 1050, or at most 1000. In some embodiments, the condensation-curable amino-silicone monomer has an Amine Number within a range of 200 to 1500, 220 to 1250, 200 to 1250, 200 to 1150, 200 to 1100, 220 to 1250, or 220 to 1150. In some embodiments, when the polymer forming amino-silicone reactants are predominantly monomers, the reactive oil phase can further include silicone oils and/or amino-silicone oils.

In some embodiments, the condensation-curable film-forming amino-silicone reactant consists of, consists essentially of, or includes mixtures of amino-silicone oligomers. The amino-silicone oligomers of the present disclosure have an average molecular weight in the range of 200 to 2,000, and are able to condensation-cure more rapidly than polymer counterparts, while providing a more flexible coat than sole monomers. Such oligomers can form 3D networks with cross-linking lower than monomers and higher than polymers. In some embodiments, when the film-forming amino-silicone reactants are predominantly oligomers, the reactive oil phase can further include silicone oils, amino-silicone oils, non-amino cross-linking agents (e.g. condensation-curable film-forming non-amino-silicone monomers) and/or reactive fillers.

In some embodiments, the condensation-curable amino-silicone oligomer has an Amine Number of at least 20, at least 40, at least 60, at least 75, at least 85, at least 100, at least 125, at least 150, at least 200, or at least 250. In some embodiments, the condensation-curable amino-silicone oligomer has an Amine Number of at most 600, at most 500, at most 450, or at most 400. In some embodiments, the condensation-curable amino-silicone oligomer has an Amine Number within a range of 20 to 600, 40 to 600, 60 to 500, 60 to 400, or 75 to 500.

In some embodiments, the condensation-curable film-forming amino-silicone reactant includes polymers. The film-forming amino-silicone polymers of the present disclosure have an average molecular weight in the range of 2,000 to 100,000, and are able to provide a flexible 3D network with low cross-linking density, as suitable for supple substrates such as hair. In some embodiments, when the film-forming amino-silicone reactants are predominantly polymers, the reactive oil phase can further include non-amino cross-linking agents and/or reactive fillers. In some embodiments, the condensation-curable amino-silicone polymer has an Amine Number of at least 2, at least 5, at least 10, at least 15, at least 25, at least 40, at least 75, at least 100, or at least 125. In some embodiments, the condensation-curable amino-silicone polymer has an Amine Number of at most 200, at most 180, at most 160, or at most 140. In some embodiments, the condensation-curable amino-silicone polymer has an Amine Number within a range of 2 to 200, 5 to 200, 10 to 200, 25 to 200, 5 to 150, or 10 to 135.

In some embodiments, the condensation-curable amino-silicone monomers are present in a mixture of film-forming reactants in an amount greater than the amount of condensation-curable amino-silicone oligomers. In some embodiments, the condensation-curable amino-silicone monomers are present in an amount greater than the amount of condensation-curable amino-silicone polymers. In some embodiments, the condensation-curable amino-silicone monomers are present in an amount greater than the total amount of condensation-curable amino-silicone oligomers and polymers.

In some embodiments, the condensation-curable amino-silicone reactant (monomer, oligomer, or polymer) is insoluble or substantially insoluble in water, in which case the reactant can also be said to be hydrophobic. While water soluble amino-silicone reactants may enable coloration of the fiber by a subsequent coat including pigments, the end result is generally fainter as compared to water insoluble amino-silicone reactants, which are therefore generally preferred. Typically, the condensation-curable amino-silicone reactants form a phase separate from water, being substantially non-miscible therewith. Such a distinct phase may also be referred to as an "oil phase", a reactive oil phase or the like.

As used herein in the specification, unless clear from context or otherwise stated, the term "pigments" is meant to refer to pigment particles which can be of the same or different type or color.

Water-soluble reactants, typically monomers such as silanes, are to be preferably avoided as the sole or predominant polymer-forming reactant. At low concentrations of relevance to the cost effectiveness of a composition, water-soluble monomers may migrate out of the reactive oil phase to the aqueous phase and would only form thin monolayers, unable to build-up a coat of sufficient thickness to modify hair properties in a manner meaningful for the attachment of a subsequent coat. Moreover, water-soluble amino-silicone pre-polymers, even if forming a very thin coat, may readily wash away in a subsequent rinsing step, if employed before the application of the subsequent coat.

Such situation of insufficient coating of the hair fibers is expected if the polymer-forming amino-silicone reactants predominantly include (75 wt. % or more) water-soluble pre-polymers. Lesser amounts of water-soluble reactants and minor ones can nevertheless be tolerated, as long as the mixture of all pre-polymers with any additional component of the reactive phase (e.g., silicone oils, amino-silicone oils, non-amino cross-linking agents, reactive fillers, etc.) forms a water-insoluble oil blend.

In some embodiments, wherein a condensation-curable amino-silicone reactant is relatively soluble in water (e.g., to an extent it may form a clear solution to the naked eye at a concentration of 1% or more by weight of the material in water at 23° C.) or becomes relatively water-soluble during preparation of a composition (e.g., as a result of hydrolysis), within less than 30 minutes from mixing with water, it may be rendered relatively less soluble and even substantially insoluble in water. For instance, a hydrophilic siloxane can be rendered relatively insoluble by reacting it with a different second material (e.g., a hydrophobic silane) capable of modifying its tendency to solubilize in water, the reaction product of the two resulting in a third material being less soluble ("desolubilized") or substantially insoluble ("insolubilized"). This process, which for simplicity may be termed "desolubilization" or "insolubilization" of a desired reactant, can be carried out prior to the emulsification of the amino-silicone pre-polymer reactant rendered less soluble with the additional constituents of a condensation-curable amino-silicone formulation according to the present teachings.

In some embodiments, the solubility of the condensation-curable polymer-forming amino-silicone reactant (including of the "desolubilized" or "insolubilized" ones) is of 1 wt. % or less, 0.5 wt. % or less, or 0.1 wt. % or less, with respect to the weight of the aqueous composition wherein it is disposed. A pre-polymer reactant is said to be water-soluble if the micelles formed therefrom are undetectable to the naked eye at or above a threshold concentration of 1 wt. %, the water carrier (typically at 23° C.) remaining clear. Conversely, the polymer-forming amino-silicone reactant is insoluble if not water-soluble (e.g., forming a visually detectable dispersion or emulsion at a concentration below the threshold).

As used herein in the specification and in the claims section that follows, the term "solubility" with respect to a component or mixture of components ("component") and a solvent or solvent mixture ("solvent"), is meant to refer to the solubility of the component in the solvent at the native pH, i.e., at the natural pH attained by adding solely the component to the solvent, in the absence of other components and in the absence of any pH modifiers. When the solvent is water, the definition assumes the water has an initial pH of 7.

Suitable amino-silicone reactants are at ambient temperature (or at any moderate temperature of relevance to the application of the composition) in a liquid state, solids being incompatible for the present purpose. The moderate temperatures of curing (i.e., of up to 40° C. etc.) further indicate that the pre-polymers suitable for the present disclosure need not be hot melt polymers.

The amino-silicone reactants suitable for the present disclosure lack a glass transition temperature (Tg). Once applied on the hair fibers and following sufficient curing, a network forms and for the at least partially cured amino-silicone film to behave as a flexible elastomer, lacking brittleness, the pre-polymers preferably cure to form a 3D network having a glass transition temperature (Tg) below about 25° C., namely having a Tg between −100° C. and +20° C., the Tg often not exceeding +10° C., or 0° C., being possibly below −5° C., below −15° C., or below −25° C.;

and optionally in the range between −80° C. and −20° C. or between −70° C. and −30° C. However, brittleness can also be avoided by using very thin coats (e.g., of one micron or less thickness). In such a case, films of cured polymers having a Tg above about 25° C. can also be used. Cured films having a relatively high Tg have a higher cross-linking density than cured films having a comparatively lower Tg. Cured films having a higher Tg/cross-linking density are expected to be more resistant to abrasion, swelling or chemical attacks (e.g., resistant to alcohols).

The condensation-curable amino-silicone monomers, oligomers or polymers which may constitute a reactant or the first reactant of the amino-silicone film forming formulation can be classified by the number of reactive groups that may form silanol moieties in each molecule: for instance having two silanol forming groups per molecule (2Sil), at least two silanol forming groups per molecule (2$^+$Sil), three silanol forming groups per molecule (3Sil), or at least three silanol forming groups per molecule (3$^+$Sil). As a variety of chemical moieties may constitute condensation-curable reactive groups as herein defined, it should be noted that the reactive group(s) of one first reactant need not be identical to the reactive group(s) of another first reactant or of any other molecule or particle bearing such same or distinct condensation-curable reactive groups.

According to some embodiments, the reactive condensation-curable amino-silicone reactant (or amino-silicone pre-polymer) of the amino-silicone film forming formulation (including the first reactant) satisfies at least one, at least two or at least three of the following structural properties:

a) the amino-silicone film forming reactant includes reactive groups selected from the group of alkoxy-silane reactive groups, silanol reactive groups and combinations thereof;

b) the amino-silicone film forming reactant has no glass transition temperature;

c) the amino-silicone film forming reactant is not solid at 23° C.;

d) the amino-silicone film forming reactant has a viscosity in the range of 1-2,000 milliPascal-second (mPa·s, also referred to as cps), 2-2,000 mPa·s, 10-2,000 mPa·s, 2-1,000 mPa·s, 2-500 mPa·s, 5-100 mPa·s, 10-20,000 mPa·s, 10-15,000 mPa·s, 20-15,000 mPa·s, 30-15,000 mPa·s, 40-10,000 mPa·s or 50-10,000 mPa·s as measured at 23° C. in a suitable rheometer;

e) the amino-silicone film forming reactant is capable of wetting the hair;

f) the amino-silicone film forming reactant is a film-forming pre-polymer;

g) the amino-silicone film forming reactant includes a primary amine;

h) the amino-silicone film forming reactant has an Amine Number in the range of 3-1000, 3-500 or 3-200;

i) the amino-silicone film forming reactant includes terminal amino-moieties;

j) the amino-silicone film forming reactant includes pendant amino-moieties;

k) the amino-silicone film forming reactant is miscible in a reactive oil phase comprising, in addition to the pre-polymer reactant, at least one of a different pre-polymer reactant, a non-reactive silicone oil, a non-reactive amino-silicone oil, a cross-linker and a pigment dispersant;

l) the amino-silicone film forming reactant has a refractive index within 10% of a refractive index of a reactive oil phase comprising at least one of a different pre-polymer reactant, a non-reactive silicone oil, a non-reactive amino-silicone oil, a cross-linker, a hydrophobic fumed silica and a pigment dispersant;

m) the amino-silicone film forming reactant is hydrophobic;

n) the amino-silicone film forming reactant has a solubility in water (e.g., circa pH 7) at 23° C. of less than 1% by weight, less than 0.5% by weight, or less than 0.25% by weight;

o) the amino-silicone film forming reactant is a linear or a branched polymer;

p) the amino-silicone film forming reactant is a linear or a branched oligomer;

q) the amino-silicone film forming reactant is a monomer; and r) the amino-silicone film forming reactant has a ratio of Amine Number (AN) to viscosity (Visc.) in mPa·s, which when multiplied by 1000, is of at least 40, at least 100, at least 200, or at least 500, which can be mathematically expressed as $1000*(AN/Visc.) \geq 40$, and so on.

While silicone materials, solid at 23° C., have been disclosed as suitable to improve hair lubricity, when applied as particles, it is readily apparent that such solids are non-reactive and unable to participate in the prospective formation of a continuous layer, as enabled by the coalescence of droplets of silicone materials fluid at same temperature. Solid silicone particles are believed to act as friction reducers in a manner similar to mechanical bearings.

The term "non-reactive group" refers to any group of a condensation-curable monomer, oligomer or polymer amino-silicone film-forming agent as herein described that is not capable of forming a covalent bond with another group of said materials. Examples of non-reactive groups include saturated $C_1$-$C_6$ or $C_1$-$C_4$ alkyl groups, such as a methyl group, or any other group unable to undergo hydrolysis or any other chemical transformation enabling the formation of a covalent bond with another amino-silicone reactant.

In some embodiments, the oil phase of the oil-in-water emulsion forming the formulation of the first coat, exclusive of all inorganic content, has no glass transition temperature.

In some embodiments, the at least one reactive condensation-curable film-forming amino-silicone reactant is a liquid at 23° C.

In some embodiments, the amino-silicone reactant has no glass transition temperature and has a solubility in water (pH 7) at 23° C. of less than 1 wt. %, less than 0.5 wt. %, or less than 0.25 wt. % by weight of aqueous composition.

In some embodiments, the amino-silicone reactant has no glass transition temperature and has a viscosity in the range of 1-2000 mPa·s, 2-1000 mPa·s, 2-500 mPa·s, 2-300 mPa·s, 2-200 mPa·s, 5-1000 mPa·s, 5-500 mPa·s, 5-300 mPa·s, 7-500 mPa·s, 7-300 mPa·s, or 7-200 mPa·s as measured at 23° C.

In some embodiments, the amino-silicone reactant has no glass transition temperature and has reactive groups selected from the group of alkoxy-silane reactive groups, silanol reactive groups and combinations thereof.

In some embodiments, the amino-silicone reactant has an Amine Number in the range of 3-1000, 3-500 or 3-200 and has a viscosity in the range of 1-2000 mPa·s, 2-1000 mPa·s, 2-500 mPa·s, 2-300 mPa·s, 2-200 mPa·s, 5-1000 mPa·s, 5-500 mPa·s, 5-300 mPa·s, 7-500 mPa·s, 7-300 mPa·s, or 7-200 mPa·s as measured at 23° C.

In some embodiments, the amino-silicone reactant has an Amine Number in the range of 3-1000, 3-500 or 3-200 and has a solubility in water (pH 7) at 23° C. of less than 1 wt. %, less than 0.5 wt. %, or less than 0.25 wt. % by weight of aqueous composition.

In some embodiments, the amino-silicone reactant has an Amine Number in the range of 3-1000, 3-500 or 3-200 and is miscible in a reactive oil phase comprising, in addition to the amino-silicone reactant, at least one of a different amino-silicone reactant, a non-reactive silicone oil, a non-reactive amino-silicone oil, a cross-linker and an optional pigment dispersant.

In some embodiments, the amino-silicone reactant has no glass transition temperature; has reactive groups selected from the group of alkoxy-silane reactive groups, silanol reactive groups and combinations thereof, and has a viscosity in the range of 1-2000 mPa·s, 2-1000 mPa·s, 2-500 mPa·s, 2-300 mPa·s, 2-200 mPa·s, 5-1000 mPa·s, 5-500 mPa·s, 5-300 mPa·s, 7-500 mPa·s, 7-300 mPa·s, or 7-200 mPa·s as measured at 23° C. in a suitable rheometer.

In some embodiments, the amino-silicone reactant has an Amine Number in the range of 3-1000, 3-500 or 3-200; has a solubility in water (pH 7) at 23° C. of less than 1 wt. %, less than 0.5 wt. %, or less than 0.25 wt. % by weight of aqueous composition; and is miscible in a reactive oil phase comprising, in addition to the amino-silicone reactant, at least one of a different amino-silicone reactant, a non-reactive silicone oil, a non-reactive amino-silicone oil, a cross-linker and an optional pigment dispersant.

In some embodiments, the amino-silicone reactant has no glass transition temperature; has reactive groups selected from the group of alkoxy-silane reactive groups, silanol reactive groups and combinations thereof, has a viscosity in the range of 1-2000 mPa·s, 2-1000 mPa·s, 2-500 mPa·s, 2-300 mPa·s, 2-200 mPa·s, 5-1000 mPa·s, 5-500 mPa·s, 5-300 mPa·s, 7-500 mPa·s, 7-300 mPa·s, or 7-200 mPa·s as measured at 23° C.; and has an Amine Number in the range of 3-1000, 3-500 or 3-200.

In some embodiments, the amino-silicone reactant has no glass transition temperature; has reactive groups selected from the group of alkoxy-silane reactive groups, silanol reactive groups and combinations thereof, has a viscosity in the range of 1-2000 mPa·s, 2-1000 mPa·s, 2-500 mPa·s, 2-300 mPa·s, 2-200 mPa·s, 5-1000 mPa·s, 5-500 mPa·s, 5-300 mPa·s, 7-500 mPa·s, 7-300 mPa·s, or 7-200 mPa·s as measured at 25° C.; has an Amine Number in the range of 3-1000, 3-500 or 3-200; and has a solubility in water (pH 7) at 23° C. of less than 1 wt. %, less than 0.5 wt. %, or less than 0.25 wt. % by weight of aqueous composition.

In some embodiments, a reactive oil phase comprising at least one of an amino-silicone reactant, a non-reactive silicone oil, a non-reactive amino-silicone oil, a cross-linker, a reactive filler and an optional pigment dispersant, has a viscosity in the range of 1-2000 mPa·s, 2-1000 milliPascal-second (mPa·s), 2-500 mPa·s, 2-300 mPa·s, 2-200 mPa·s, 5-1000 mPa·s, 5-500 mPa·s, 5-300 mPa·s, 7-500 mPa·s, 7-300 mPa·s, or 7-200 mPa·s, as measured at 23° C. in a suitable rheometer.

In some embodiments, a reactive oil phase comprising at least one of an amino-silicone reactant, a non-reactive silicone oil, a non-reactive amino-silicone oil, a liquid hydrophobic cross-linker and an optional pigment dispersant, has no glass transition temperature.

In some embodiments, a reactive oil phase comprising at least one of an amino-silicone reactant, a non-reactive silicone oil, a non-reactive amino-silicone oil, a liquid hydrophobic cross-linker and an optional pigment dispersant, has a solubility in water (pH7) at 23° C. of less than 5% by weight, less than 2% by weight, less than 1% by weight, less than 0.5% by weight, less than 0.25% by weight of the total aqueous composition.

When assessing the solubility of an oil phase is desired, but the phase is in an emulsified or any other mixed form, the oil can be separated by any suitable method known to the skilled person (e.g., by centrifugation). The oil phase so extracted can then be assessed for any desired property (e.g., solubility, glass transition temperature, chemical analysis), by any appropriate standard method.

According to some embodiments, the oil-in-water emulsion formulation has a pH of at least 4.0, at least 5.5, at least 7.0, at least 8.5, at least 10.0; and optionally of at most 11.0. In some embodiments, the oil-in-water emulsion has a pH within a range of 4.0 to 11.5, 5.5 to 11.5, 7.0 to 11.0, or 8.5 to 11.0. A pH above the isoelectric point of the hair fibers to be coated enables a negative charging of the fibers and/or a positive charging of amino functions of the amino-silicone pre-polymers. Taking for example human hairs, the isoelectric point was reported to be between about pH 2.5 (e.g., for damaged hair) and approximately pH 3.5-3.7 (e.g., for virgin hair). As shall be detailed in the following, a gradient of charge between the surface of hair fibers and the pre-polymers of the composition is expected to permit electrostatic attachment between the two, as a first step in the formation of a coat. In particular embodiments, the oil-in-water emulsion has a basic pH of at least 7.5, at least, 8.0, at least 9.0 or at least 9.5, and of at most 11.0.

According to some embodiments, the oil-in-water emulsion is applied on the hair for sufficient time for such a gradient to drive enough droplets to wet and form a continuous coat on the fibers. In one embodiment, the application time is between 5 seconds and 10 minutes, or between 10 seconds and 2 minutes, or of 1 minute or less. According to some embodiments, the duration of time enabling the partial curing of the condensation-curable amino-silicone reactants, following their application on the fibers, is between 5 seconds and 30 minutes, or between 1 minute and 15 minutes. While partial curing may initiate at the time of application of the oil-in-water emulsion, it can also proceed once excess of the emulsion is removed (e.g., before rinsing the hair fibers).

In some embodiments, the reactive oil phase of the oil-in-water emulsion further includes, in addition to the polymer-forming amino-silicone reactant, a silicone oil, an amino-silicone oil, a non-amino cross-linking agent, and/or a reactive reinforcement filler. The emulsion may further include a thickening agent in the aqueous phase.

As opposed to the first reactant of the amino-silicone polymer forming formulation, which necessarily includes condensation-curable groups, the silicone oils are lacking reactive moieties that may enable the formation of siloxane bonds. The (non-amino) silicone oils can be linear, branched or cyclic organosiloxanes, such as decamethylcyclopentasiloxane (D5), octamethylcyclotetrasiloxane (D4), or hexamethyl-disiloxane (M2). The amino-silicone oils are silicone oils additionally containing amine moieties, which may enable the formation of nitrogen-carbon bonds. Amino-silicone oils include, as non-limiting examples, GP-965 and GP-967, commercially available from Genesee Polymers. In some embodiments, the non-amino silicone oils and the amino-silicone oils are miscible with the film-forming amino-silicone reactants. In some embodiments, the optional non-amino silicone oil and/or amino-silicone oil is a cosmetically acceptable oil. Cosmetically acceptable ingredients, and similarly cosmetically acceptable compositions or formulations, refer to the suitability of such materials for use in contact with keratinous fibers, in particular human hair, without undue toxicity, instability, allergic response, and the like.

Silicone oils can serve as carriers, water repellents, lubricants and like functions. Depending on their molecular weight, silicone oils can be volatile or not. Silicone oils can also be functionalized, for instance, they can include amine moieties, forming amino-silicone oils. In some embodiments, amino-silicone oils are used to modify the charge density of the reactive oil phase (by modifying the amount of amine groups in the oil phase able to interact as herein described). Furthermore, it has been reported that amine-moieties (as present in amino-silicone oils) can catalyze condensation curing of the pre-polymers. Hence, in some embodiments the silicone oil optionally used in the present compositions is an amino-silicone oil.

It has been found that mixing the different types of condensation-curable amino-silicone pre-polymer reactants or mixing at least a particular type of reactant with additional non-reactive silicones allows tailoring the characteristics of a cured film that may result therefrom, by harvesting the advantages of each type, while reducing their respective drawbacks. For instance, while the following observations may depend on the exact chemical compounds of each sub-type, it is generally observed that monomers, if used alone, can result in the formation of too brittle coats, while polymers alone may be too slow to fully cure or result in coats lacking sufficient cohesivity. Hence, in order to reduce brittleness, it may be desired to reduce the extent of cross-linking amongst the pre-polymers. Such effect can be achieved, for instance, by adding larger pre-polymers, usually condensation-curable amino-silicone polymers. Alternatively or additionally, amino-silicone oils and/or non-amino silicone oils may be added. Such molecules can diminish the cross-linking density, alleviating brittleness.

Too much of such large pre-polymers and silicone oils may reduce cross-linking density and may also compromise various mechanical properties of the film or coating. In addition, too much non-amino silicone oils may reduce the positive charge density of the amino groups, detracting from the electrostatic attraction mechanism, and/or weakening or destroying the self-terminating mechanism of the film.

In some embodiments, the total concentration of amino-silicone oil within the oil phase, by weight, is at most 40%, at most 35%, at most 30%, at most 20%, at most 15%, at most 10%, or at most 5%, or within a range of 1% to 40%, 5% to 40%, 10% to 40%, 20% to 40%, 1% to 30%, 5% to 30%, 10% to 30%, 15% to 30%, 20% to 35%, or 20% to 30%.

In some embodiments, the total concentration of non-amino-silicone oil within the oil phase, by weight, is at most 15%, at most 12%, at most 10%, at most 7%, or at most 5%, subject to a surface zeta potential of the oil-in-water emulsion being greater than zero, or at least +1 mV, at least +2 mV, at least +3 mV, at least +5 mV, at least +7 mV, or at least +10 mV.

In some embodiments, the total concentration of non-amino-silicone oil within the oil phase, by weight, is within a range of 1% to 15%, 3% to 15%, 5% to 15%, 8% to 15%, 1% to 12%, 3% to 12%, 5% to 12%, 3% to 10%, 3% to 8%, or 2% to 5%.

In some embodiments, the cross-linking agent is an amino-silicone monomer. Alternatively, the cross-linking agent can be a non-amino cross-linking agent (e.g., ethyl silicate). In such case, a combined concentration of the amino-silicone reactant and the non-amino cross-linking agent, within the oil phase, is within a range of 35-95%, 40-95%, 40-85%, 40-75%, 45-95%, 45-85%, 50-95%, 50-85%, 55-95%, 55-85%, 55-75%, 60-95%, 60-90%, 60-85%, or 60-80%, by weight, of said oil phase. In some embodiments, a concentration of the non-amino cross-linking agent within the combined concentration is limited by a condition that the oil-in-water emulsion has a surface zeta potential greater than zero (>0), or at least +1 mV, at least +2 mV, at least +3 mV, at least +5 mV, at least +7 mV, or at least +10 mV.

Cross-linking agents suitable for the polymerization of such condensation-curable amino-silicone reactants may comprise similar reactive groups, and be for instance condensation-curable amino-silicone monomers (e.g., amino-silanes). Cross-linking agents may display only amino functional groups, or additional reactive groups, such as aliphatic carbon moieties, vinyl, allyl, mercapto, epoxy, acrylate or methacrylate functional groups. In some embodiments, the non-amino cross-linking agent includes, mainly includes, or consists of an ethyl silicate, a poly(dimethoxysiloxane), and a poly(diethoxysiloxane).

In some embodiments, the total concentration of the non-amino cross-linking agent within the oil phase is at most 35%, at most 30%, at most 20%, at most 15%, at most 10%, or at most 5%, subject to a surface zeta potential of the oil-in-water emulsion being greater than zero, or at least +1 mV, at least +2 mV, at least +3 mV, at least +5 mV, at least +7 mV, or at least +10 mV.

Cross-linking may be catalyzed using additional organic amines species or amino functional silicone for better compatibility with the reactive amino functional silicone pre-polymer.

In some embodiments, within the oil phase, a total concentration of the amino-silicone oil, the non-amino-silicone oil and the at least one reactive condensation-curable film-forming amino-silicone pre-polymer, having up to 2 silanol and/or hydrolysable groups, is within a range of 3% to 65%, 3% to 60%, 3% to 55%, 3% to 50%, 3% to 45%, 3% to 40%, 7% to 40%, 10% to 40%, 10% to 50%, 15% to 50%, 15% to 45%, 15% to 40%, 20% to 45%, 25% to 45%, 25% to 50%, 30% to 45%, 30% to 60%, 35% to 50%, or 35% to 60%, by weight. In some embodiments, the total concentration of the afore-said different constituents of the oil phase is subject to the oil phase having a viscosity of no more than 2,000 mPa·s, no more than 500 mPa·s, or no more than 100 mPa·s, as measured at 23° C.

When the one or more condensation-curable amino-silicone reactants are present in an oil phase further comprising at least one of the afore-mentioned non-reactive silicones, it is preferred that the oil phase has a positive zeta potential.

In some embodiments, the formulation further comprises a condensation-cure auxiliary, such as a condensation-cure accelerator or catalyst adapted to cure the pre-polymer(s).

Curing accelerators suitable for the cross-linking of these condensation-curable oligomers or polymers include carbodiimides (R—N=C=N—R') catalysts, such as diisopryl-carbodiimide and preferably multifunctional polycarbodiimides, such as commercially available under the trade name of Carbodilite from Nisshinbo Chemical Inc., Japan. Additionally, amino-silicone oils can act as condensation-curing accelerators thanks to the presence of amine moieties, in addition to any other function they can fulfil in the composition.

Curing accelerators (other than amino-silicone oils) can typically be present in the curable composition, in relatively low amount not exceeding 5% by total weight of the composition, or in less than 2 wt. %, less than 1 wt. % or less than 0.5 wt. %.

In some embodiments, the oil-in-water emulsion formulation or sub-formulations is substantially devoid of an organic solvent or of a water-miscible co-solvent able to solubilize at least one of a polymer-forming amino-silicone reactant, a non-reactive silicone oil, a non-reactive amino-silicone oil, and a cross-linker.

As used herein in the specification and in the claims section that follows, the term "organic solvent" within or with respect to an oil phase, refers to an organic liquid that is disposed within an oil phase containing at least one solute, and which organic liquid does not positively participate in the intra-polymer bonding nor in the bonding to the surface of the mammalian hair.

As used herein in the specification and in the claims section that follows, the term "co-solvent" within or with respect to an aqueous phase, refers to an organic liquid that is at least partially miscible within an aqueous phase, the organic liquid further exemplified in that it increases the solubility, within the aqueous phase, of at least one component that is disposed in the oil phase.

Organic solvents may include, by way of non-limiting examples, volatile $C_1$-$C_6$ alkanols, such as ethanol; volatile $C_5$-$C_7$ alkanes such as hexane; esters of liquid $C_1$-$C_{20}$ acids and of volatile $C_1$-$C_8$ alcohols such as methyl acetate; volatile ketones that are liquid at RT, such as acetone; volatile hydrocarbon-based oils, such as $C_8$-$C_{16}$ alkanes, for instance isododecane; volatile ethers or glycol ethers such as dimethoxymethane or diethylene glycol monomethyl ether; and mixtures thereof.

Water-miscible co-solvents may include, by way of non-limiting examples, volatile $C_1$-$C_6$ alkanols, such as ethanol; esters of liquid $C_1$-$C_{20}$ acids and of volatile $C_1$-$C_8$ alcohols such as methyl acetate; and volatile ketones that are liquid at RT, such as acetone; and mixtures thereof.

It is believed that such solvents, in addition to detracting from the efficacy of an oil phase and/or preventing the formation of an emulsion, may also, if present in the same phase as the condensation-curable amino-silicone pre-polymer, reduce or delay condensation curing.

In some embodiments, the oil-in-water emulsion formulation (or sub-formulations being jointly emulsified to form the same) according to the present teachings contains 10% of an organic solvent or water-miscible co-solvent or less by weight of the formulation or sub-formulation, or less than 5 wt. %, or less than 4 wt. %, or less than 3 wt. %, or less than 2 wt. %, or less than 1 wt. % of any such solvent or mixture thereof.

In some embodiments, the total concentration of organic solvents within the oil phase of the emulsion, on a weight basis, is at most 10%, at most 5%, at most 2%, or at most 1%. In some embodiments, the oil phase is devoid of any organic solvent.

In some embodiments, the total concentration of water-miscible co-solvents within the aqueous phase of the emulsion, on a weight basis, is at most 10%, at most 5%, at most 2%, or at most 1%. In some embodiments, the aqueous phase is devoid of any said co-solvent.

In some embodiments, in particular, but not exclusively, when the condensation-curable amino-silicone reactant comprises at least one condensation-curable amino-silicone polymer, the oil-in-water emulsion further comprises a solid, hydrophobic reactive inorganic filler. Said filler, disposed or dispersed within the oil phase, is selected or adapted to facilitate curing of the condensation-curable film-forming amino-silicone pre-polymer(s).

Advantageously, the reactive reinforcement filler is a hydrophobic 3D network former contributing to the increase in cohesivity of the amino-silicone film. Suitable reactive fillers can be selected from an amorphous hydrophobic fumed silica, the surface of which being at least partially covered by siloxane groups or other groups having a hydrophobic nature, such groups typically reacting with silanol functional units on the silica. Hence, in such cases, the hydrophobic fumed silica can be referred to as a silanol blocked silica, the surface treatment of the fumed silica blocking the silanol functionalities being achieved by one or more of HDMS, poly siloxane, cyclic poly siloxane, silazane, amino silane and silicone oils. The blocking treatment needs not to be complete, some residual silanol groups being permissible and even desirable for ensuring or facilitating at least partial curing. A hydrophobic fumed silica, if present in the emulsion of the first coat according to the present teachings, is typically disposed in the oil phase of the oil-in-water emulsion. It is believed that fumed silica, if disposed in the non-reactive phase of the composition during application, would not only deprive the reactive oil phase of the composition from its contribution to the formation of the amino-silicone film, but may further interact with the droplets of amino-silicone pre-polymers reducing their attachment to the hair fibers. Hydrophilic fumed silica, typically used as thickeners of aqueous compositions, would therefore be detrimental to compositions according to the present teachings. For instance, aggregates of fumed silica, as generally used for thickening purposes, may additionally affect the gloss and the feel of the hair. In contrast, reactive hydrophobic fumed silica well dispersed in oil are size reduced to have dimensions compatible with the desired reactive surface area intended to promote the 3D network formation and the thickness of the coatings, thus avoiding any negative impact on hair appearance and touch.

Additional reinforcement fillers can also be selected from the group of precipitated silica, magnesia, alumina (e.g., $Al_2O_3.3H_2O$), black, amorphous, carbon (carbon black, channel black, or lamp black). The reinforcement filler can be selected to suit a particular coloration. For instance, if a reinforcement filler is desired in a relatively high quantity, then black fillers are to be avoided if in a size range that may affect a relatively light shade. Conversely, if a dark shade is desired, then black reinforcement fillers can be advantageous.

In some embodiments, the reactive filler includes, mainly includes, or consists of, a hydrophobic fumed silica.

In some embodiments, the average particle size (Dv50) of the solid, hydrophobic reactive inorganic filler is within a range of 5 to 500 nm, 5 to 250 nm, 10 to 200 nm, 20 to 500 nm, 20 to 250 nm, 20 to 200 nm, 40 to 300 nm, 60 to 300 nm, 60 to 250 nm, or 60 to 200 nm.

In some embodiments, the concentration of the solid, hydrophobic reactive inorganic filler disposed or dispersed within the oil phase is within a range of 0.2% to 12%, 0.2 to 10%, 0.2 to 8%, 0.4 to 10%, 0.4 to 8%, 0.6 to 10%, 0.6 to 8%, 0.8 to 8%, or 0.8 to 6%, by weight.

In some embodiments, the concentration of the solid, hydrophobic reactive inorganic filler within the oil-in-water emulsion is within a range of 0.005% to 0.5%, 0.005% to 0.3%, by weight.

In some embodiments, the refractive index of the solid, hydrophobic reactive inorganic fumed silica filler is within a range of 10%, 7%, ±5%, or 3%, of a refractive index of the oil phase, exclusive of any pigment particles, if present and disposed therein.

According to features in the described preferred embodiments, the hydrophobic 3D network former (the cross-linking agent or the hydrophobic fumed silica) has a refractive index ($R_{3D}$) forming a differential refractive index ($\Delta R$) with respect to a refractive index of the at least partially cured amino-silicone film ($R_S$), $\Delta R$ being defined by:

$$\Delta R = |R_{3D} - R_S|,$$

wherein ΔR is at most 0.15, at most 0.10, at most 0.07, at most 0.06, at most 0.05, at most 0.04, at most 0.03, at most 0.02, or at most 0.01. In some embodiments, $R_{3D}$ is within a range of 1.20 to 1.60, 1.30 to 1.50, or 1.35 to 1.45.

The difference in refractive index between the hydrophobic 3D network former and the cured amino-silicone film can also be expressed in a normalized percentage (ΔR % or ΔRN), ΔR % being defined by ΔR %=100×ΔR/$R_S$. In some embodiments, ΔR % is at most 10%, at most 7.5%, at most 5%, at most 4%, at most 3%, at most 2%, or at most 1%.

In some embodiments, the at least partially cured film is self-terminated on the external surface of the individual hairs.

While temperature can to some extent accelerate the reaction rate of condensation curing, accordingly shortening the time required for partial curing to occur or for curing to complete, this auxiliary factor is not critical for the present disclosure and satisfactory coatings can be obtained at a moderate temperature of up to 60° C., or up to 50° C., 45° C., or up to 40° C., or up to 38° C., or up to 36° C., or up to 35° C., or up to 34° C., or up to 32° C. or up to 30° C., or up to 25° C., and optionally, at least 15° C.

According to features in the described preferred embodiments, the partial condensation curing of the at least one condensation-curable amino-silicone reactant is performed (e.g., actively assisted) or occurring at a temperature of at most 45° C., at most 42° C., or at most 40° C., at most 38° C., at most 36° C., at most 35° C., at most 34° C., or at most 32° C., or at most 30° C., or at most 25° C.; optionally, at least 10° C., at least 15° C., at least 20° C., or at least 25° C., and optionally within the range of 10° C. to 45° C., 15° C. to 42° C. or 20° C. to 40° C.

In some embodiments, the total concentration of the condensation-curable amino-silicone reactant, the non-amino cross-linking agent, the solid, hydrophobic reactive inorganic filler, the amino-silicone oil and the non-amino-silicone oil within the oil phase, including any pigment particles and dispersant for the pigment particles, if present, is at least 90%, at least 93%, at least 95%, at least 97%, at least 98%, or at least 95%, by weight.

According to features in the described preferred embodiments, the total concentration of the water, the reactive condensation-curable film-forming amino-silicone reactant within the formulation is at least 60%, at least 70%, at least 80%, at least 85%, at least 90%, at least 95%, at least 97%, at least 98%, at least 99%, at least 99.5%, or at least 99.8%, by weight of the total formulation.

According to features in the described preferred embodiments, the amino-silicone oil-in-water emulsion formulation contains at least one formulation pigment dispersed therein. According to some embodiments, the pigment particles are dispersed in the condensation-curable film-forming amino-silicone reactants and/or in the water (e.g., for metallic pigments). Without wishing to be bound by any particular theory, it is believed that as pigments are being applied in a composition comprising reactive amino-silicones able to complete condensation-curing on the hair fiber, such reaction would "entrap" the pigments in the growing 3D-network of the amino-silicone film. As an amino-silicone film formed according to the present teachings displays at least cohesivity (cross-linking between the pre-polymers to form the film coating the hair), the entrapped pigments cannot wash away significantly, as in the case of mere physical deposition.

In some embodiments, the aqueous phase of the oil-in-water emulsion of the $1^{st}$ coat contains, by weight, at most 20%, at most 10%, at most 5%, or at most 2%, of the amount of the pigment within the oil phase. In some embodiments, the aqueous phase of the $1^{st}$ coat is devoid of said pigment.

According to some embodiments, the first reactant or its different constituents each selected from the reactive condensation-curable amino-silicone monomers, oligomers, and polymers, and each of the foregoing amino-silicone polymer-forming reactants (some being optional) having at least two condensation-cure reactive groups, are present in a same formulation each separately dispersed in the carrier in the form of emulsion droplets. Such separation of reactants into distinct droplets is believed to delay film-formation until the constituents are brought into close contact following droplet deposition on the fibers and their coalescence upon removal (e.g., evaporation) of their carrier. Emulsions are known two-phase systems, and in some embodiments, oil-in-water emulsions are preferred. Emulsification typically requires emulsifiers (when the constituents lack self-emulsifying properties), which can be ionic or non-ionic. When it includes at least one of a condensation-curable amino-silicone monomer and a condensation-curable amino-silicone oligomer (e.g., having an average MW between about 200 and about 2,000 g/mol), the polymer-forming amino-silicone reactant can, in some embodiments, provide for the self-emulsification of the emulsion, thereby obviating the need for any added dedicated emulsifier. Compositions comprising non self-emulsifying amino-silicone polymers (e.g., having an average MW of more than 2,000 g/mol) generally require the inclusion of an emulsifier so as to form the emulsion of condensation-curable amino-silicone reactants. Such dedicated emulsifiers can have a hydrophile-lipophile balance (HLB) value between 10 and 18, between 12 and 18, between 12 and 17, between 12 and 16, between 12 to 15, between 13 and 16 or between 13 and 15, on a Griffin scale. In some embodiments, the total concentration of the water and any emulsifier, within the aqueous phase, is at least 90%, at least 95%, at least 97% at least 99%, on a weight basis.

In some embodiments, the aqueous phase further contains a pH modifying agent. In some embodiments, the pH modifying agent is added to the aqueous phase so that the oil-in-water emulsion has a suitable pH as herein described.

According to some embodiments, the method further comprises combining at least first and second sub-formulations to produce the formulation including the amino-silicone condensation-curable polymer forming materials. The contents and number of these sub-formulations may depend on the types of materials jointly constituting the formulation upon combination of the sub-formulations. For instance, if the formulation comprises only one type of either monomer, oligomer or condensation-curable amino-silicone polymer, the first sub-formulation may include the unique first reactant, and when desired, a plurality of sub-micronic pigment particles of at least one formulation pigment and optionally a suitable pigment dispersant selected or adapted to disperse the at least one formulation pigment in said first sub-formulation; while the second sub-formulation may include water, and when desired, an emulsifier, a 3D network former, a (pigment) dispersant, a thickening agent, etc.

In other embodiments, in particular if the formulation comprises more than one type of amino-silicone polymer-forming first reactants and/or if the formulation further includes non-amino condensation-curable monomers and/or 3D network formers (that may each serve as cross-linkers for the condensation-curable amino-silicone monomers, oligomers or polymers), the formulation may advantageously be supplied as two or more sub-formulations. In such a case, each sub-formulation may include a distinct material, so as to avoid having different materials which may react one with another within a particular sub-formulation. Such separation of materials is expected to reduce or prevent polymer-forming reactions from taking place in vitro, before application of the formulation to the intended fibers. For instance, the first sub-formulation may include a condensation-curable amino-silicone polymer, and when desired, a plurality of sub-micronic pigment particles of at least one formulation pigment and optionally a suitable pigment dispersant selected or adapted to disperse the at least one formulation pigment in said first sub-formulation and in said formulation; and the second sub-formulation may include a condensation-curable monomer or oligomer (whether or not of amino-silicone type) and/or a 3D network former (the foregoing serving as cross-linking agent for the polymer). Depending on the contents of the second sub-formulation, the water would be in a further compartment, if the materials could react therewith. It cannot be ruled out that some cross-linking may occur between reactive materials of a same type, hence reactants having a rapid rate of hydrolysis/ cross-reactivity are preferably supplied under conditions preventing, delaying or reducing such self-reactivity, for instance in absence of water and/or under sub-atmospheric pressure.

In some embodiments, the amino-silicone condensation-curable first reactants are disposed in the first sub-formulation or in the second sub-formulation (following water addition from another compartment) as a positively charged emulsion in water. In other embodiments, in particular when the second sub-formulation includes non-amino condensation-curable monomers or oligomers, such materials can be disposed therein as a negatively-charged emulsion in water.

In some embodiments, the method further comprises combining with at least one of the afore-said sub-formulations, a third sub-formulation comprising a 3D network former, which in one embodiment can be a reactive hydrophobic fumed silica, having an amorphous structure.

The combination of the at least two sub-formulations can result in an emulsion, typically an oil-in-water emulsion. The hydrophobic fumed silica, also referred to as a reactive filler, if present, is typically disposed/dispersed within the reactive oil phase of the oil-in-water emulsion.

According to some such embodiments, the method further comprises mixing together the at least first and second sub-formulations at most 4 hours, at most 2 hours, at most 60 minutes, at most 45 minutes, at most 30 minutes, at most 20 minutes, or at most 10 minutes prior to applying. The mixing of the sub-formulations (if two or more) can be performed a few seconds before application to the hair, at least 10 seconds, at least 30 seconds, at least 60 seconds or at least 5 minutes prior to applying the formulation combined therefrom. In some embodiments, when two or more sub-formulations are mixed for the preparation of the complete formulation being applied to the hair fibers, the mixing can be performed within a range of 10 seconds to 60 minutes prior to application, or within 20 seconds and 30 minutes, or within 1 to 20 minutes.

According to some embodiments, the formulation or any of the first and second sub-formulation further comprises a non-ionic or an anionic emulsifier.

According to some embodiments, the formulation is charged and has a positive surface zeta potential of above 0 mV. As such, the zeta potential is of at least +1 mV, at least +2 mV, at least +3 mV, at least +5 mV, at least +7 mV, at least +10 mV, at least +15 mV, at least +20 mV, at least +30 mV, at least +40 mV, or at least +60 mV; and of no more than +100 mV, or no more than +80 mV. In some embodiments, the formulation has a positive surface zeta potential within the range of 1-50 mV, 1-30 mV, 1-20 mV, 1-15 mV, 2-100 mV, 2-30 mV, 3-100 mV, 3-50 mV, 3-30 mV, 3-20 mV, 5-100 mV, 5-50 mV, 5-30 mV, 5-20 mV, 7-100 mV, 10-80 mV, 15-80 mV, 20-80 mV, or 20-60 mV.

According to some embodiments, the first sub-formulation containing the condensation-curable amino-silicone monomer, oligomer and/or polymer is charged and has a positive surface zeta potential of above 0 mV. As such, the zeta potential is of at least +1 mV, at least +2 mV, at least +3 mV, at least +5 mV, at least +7 mV, at least +10 mV, at least +15 mV, at least +20 mV, at least +30 mV, at least +40 mV, or at least +60 mV; and at most +100 mV, or at most +80 mV. In some embodiments, the sub-formulation has a positive surface zeta potential within the range of 1-50 mV, 1-30 mV, 1-20 mV, 1-15 mV, 2-100 mV, 2-30 mV, 3-100 mV, 3-50 mV, 3-30 mV, 3-20 mV, 5-100 mV, 5-50 mV, 5-30 mV, 5-20 mV, 7-100 mV, 10-80 mV, 15-80 mV, 20-80 mV, or 20-60 mV.

According to some embodiments, the second sub-formulation includes the non-amino-silicone cross-linking agent, such as a non-amino-silicone, condensation-curable monomer or oligomer, which material is charged and has a negative surface zeta potential whose negativity is at least −1 mV, at least −10 mV, at least −20 mV, at least −40 mV, or at least −60 mV; and whose negativity is at most −100 mV, or at most −80 mV. In some embodiments, the second sub-formulation has a negative surface zeta potential within the range of −100 mV to −1 mV, or −100 mV to −10 mV, or −80 mV to −20 mV, or −80 mV to −40 mV. Typically, such negative zeta potential is observed when the cross-linker lacks an amine moiety.

It should be noted that even if one of the sub-formulations forming the oil-in-water emulsion can be negatively charged, in combination with the other sub-formulations, the resulting formulation is typically positively charged.

In some embodiments, the surface zeta potential can be measured in an appropriate zeta sizer at a pH of at least 8.0 and at most 11.5, said measurement being optionally performed at a pH of 9.0. In other embodiments, the surface zeta potential is measured at a native pH of the oil-in-water emulsion (circa pH 10). Conveniently, the measurement of the zeta potential of a material or of a composition can be performed at low concentration of the material in an appropriate carrier or on a diluted form of the composition. For instance, a test sample may comprise 2 wt. % or less of solid material or composition ingredients, 1 wt. % or less, or 0.1 wt. % or less.

An alternative way of describing the threshold conditions favoring the present method relies on the initial surface zeta potential of the materials due to interact with one another. At the pH of the applied aqueous dispersion, the mammalian hair fiber pre-coated with the amino-silicone coat has a first surface zeta potential ($\zeta_1$), and the aqueous dispersion has a second zeta potential ($\zeta_2$). The gap between the two values, also termed the zeta differential ($\Delta\zeta$) at said pH is defined as $\Delta\zeta=\zeta_1-\zeta_2$, each of $\zeta_1$, $\zeta_2$ and $\Delta\zeta$ being provided in millivolts (mV).

In some embodiments $\Delta\zeta$ is at least 10, at least 15, at least 20, at least 25, at least 30, at least 40, or at least 50. In some embodiments, $\Delta\zeta$ is within a range of 10 to 80 mV, 10 to 70 mV, 10 to 60 mV, 15 to 80 mV, 15 to 70 mV, 15 to 60 mV, 20 to 80 mV, 20 to 70 mV, 20 to 60 mV, 25 to 80 mV, 25 to 70 mV, 25 to 60 mV, 30 to 80 mV, 30 to 70 mV, 30 to 60 mV, 35 to 80 mV, 35 to 70 mV, or 35 to 60 mV. The pH of the aqueous dispersion being within a range of 4 to 11, 4 to 10.5, 4 to 10, 6 to 11, 6 to 10.5, 6 to 10, 7 to 11, 7 to 10.5, or 7 to 10, the first surface zeta potential ($\zeta_1$) of the aminosilicone coat, is greater than zero ($\zeta_1 > 0$). The surface zeta potential of a material is typically measured in liquid phase. Zeta potential of a solid coat can be measured using a streaming current detector in a zeta potential analyzer adapted to force a flow of water through a tube wherein the sample is disposed. Results obtained by such method reflect to some degree the zeta potential of same particles in suspension. Vice versa the zeta potential of the amino-silicone oil-in-water emulsion is deemed predictive of the surface zeta potential of the amino-silicone coat resulting therefrom.

According to some embodiments, in particular when the amino-silicone polymer forming formulation further includes pigments, the formulation may further include a dispersant. In such embodiments, the dispersant can be present in the formulation or sub-formulation in an amount ranging from 25% to 400% by weight of the sub-micronic organic or inorganic pigment particles. In some embodiments, the dispersant and the pigment particles are present at a relative weight per weight ratio in the range of 0.5:1 to 2:1, 0.75:1 to 1.5:1, or 0.8:1 to 1.2:1.

According to some embodiments, the dispersant adapted to disperse the pigments is compatible with the condensation-curable formulation. By compatible, it is meant, for instance, that the pigment dispersant is miscible in the reactive oil phase of the formulation, that the pigment dispersant does not delay, reduce or prevent curing, and that the pigment dispersant is stable (e.g., non-reactive) during the size reduction of the pigment. For instance, a pigment dispersant would not be compatible if, among other things, preventing the curing of the condensation-curable amino-silicone pre-polymers, or reducing or retarding curing to an extent that the amino-silicone film would not sufficiently and/or rapidly attach to a substrate hair fiber, or would be deleterious to the pigments, and any like undesired effects. In some embodiments, compatibility may additionally mean that the materials deemed compatible share a common property, such as a common silicon-based chemistry or a similar physical parameter. For instance, materials having a similar refractive index (RI; within 10% from one another) are believed to yield clearer cured films, as compared to materials having relatively dissimilar RI that may appear more turbid. While exemplified with a pigment dispersant and internal compatibility, materials used for the formation of any particular coat or layer should advantageously be compatible with adjacent layers (e.g., not affecting their respective formation).

Preferably, the pigment dispersant can have a positive charge. Such dispersant can have a silicone backbone, such as silicone polyether and silicone amine dispersants. According to some embodiments, the silicone amine dispersants may be positively charged. In some embodiments, the pigment dispersants being amino-silicones have an Amine Number in the range of 3-1000, 3-500 or 3-200.

Pigment dispersants having functional moieties able to react with the reactants of the reactive oil phase may advantageously, in addition to pigment dispersion per se, further improve the amino-silicone 3D network forming therefrom. For instance, silicone epoxy pigment dispersants can favorably interact with the amine-moieties of the amino-silicone pre-polymer to further increase the cohesivity of the pigmented amino-silicone film.

In some embodiments, the method further includes removing an excess of the oil-in-water emulsion including the polymer-forming amino-silicone reactants from the individual fibers, before applying a second coat as herein described.

Aqueous Dispersions

In another aspect, the mammalian fiber, coated with the amino-silicone coating, is further treated by an aqueous dispersion containing polymeric particles, formed of a hydrophilic polymeric material having neutralized acid moieties, wherein, in each of at least a portion of said polymeric particles, said hydrophilic polymeric material may optionally further envelop at least one pigment core particle. Aqueous dispersions including pigment particles may provide inter alia hair coloration, while aqueous dispersions devoid of pigments may provide hair volume and like hair styling advantages, which may be readily appreciated by a person skilled in the art of hair care.

While termed polymeric particles for simplicity, in the process described herein the acid moieties of the polymeric material can be modified (e.g., neutralized), and may, following such a modification, reverse to a native chemical composition or adopt a different one (e.g., ionomers). The polymeric particles may therefore encompass beads (e.g., of hydrophobic polymeric material having neutralizable acid moieties) and micelles (e.g., of polymeric material wherein neutralizable acid moieties have been neutralized, leading to a hydrophilic material). The present disclosure further relates to oligomers or polymers, including copolymers, having an acidic polar group or functionality, either as comonomers or grafted monomers, or mixtures thereof.

Typical polymers of this group include alkene copolymers, for instance ethylene-acrylic acid (EAA) and ethylene-methacrylic acid (EMAA) copolymers, such as those available by way of non-limiting examples under the tradenames Primacor™ of Dow Chemical Company, Nucrel® of DuPont, Joncryl® and Luwax® of BASF and Escor™ of ExxonMobil Chemical. The acrylic acid (AA) or methacrylic acid (MA) co-monomers, or any other monomer bearing the acid moieties of such polymers can be termed the acid monomer or acid co-monomer. Other polymers or copolymers having an acidic moiety include ethylene ethyl acrylate (EEA), ethylene methyl methacrylate (EMMA), ethylene vinyl acrylate (EVA) and ethylene butyl acrylate (EBA). However, such acidic moieties can be found on copolymers other than alkene based. For instance, previously mentioned acrylic acid (AA) or methacrylic acid (MA) can appear in acrylamide copolymers.

Such oligomers or polymers bearing an acid moiety or functionality are often considered as negatively charged or negatively chargeable under suitable chemical environment (e.g., relatively high pH). Depending on the exact chemical structure of such materials, which can also be referred to as acidic pre-polymers in their pre-cured form, the acid moieties can be more or less exposed on the polymeric backbone. Polymeric materials having more accessible acid moieties tend to be more polar, and somewhat more adhesive to polar surfaces. Polymeric materials having less accessible—hindered—acid moieties tend to be less polar, and somewhat less adhesive to polar surfaces.

In some embodiments, the acid moiety of the polymeric material that can be neutralized is at least one of (i) an acrylic acid and (ii) a methacrylic acid. In some embodiments, the polymeric material having neutralized acid moieties is at least one of (i) an ethylene-acrylic acid (EAA) copolymer having neutralized acid moieties, (ii) an ethylene-methacrylic acid (EMAA) copolymer having neutralized acid moieties and (iii) an acrylate/acrylamide (AAA) copolymer having neutralized acid moieties.

Such materials can in part be characterized by the relative weight content of the monomer bearing the acid moiety in the co-polymer (e.g., the Acrylic Acid (wt. % AA) in EAA copolymers or the Methacrylic Acid (wt. % MA) in EMAA), assessed by standard methods, such as described in ASTM D 4094. Alternatively or additionally, these materials can be characterized by their Acid Number (also termed Acid Value or Neutralization Value, which assesses the amount of carboxylic acid groups in a chemical compound, and corresponds to the mass of potassium hydroxide (KOH) in milligrams that is required to neutralize one gram of the polymeric material). The acid number is generally provided by the manufacturers of such polymeric materials, or can be independently assessed by standard methods, such as described in ASTM D 974-04. In a typical procedure, a known amount of sample dissolved in organic solvent is titrated with a solution of potassium hydroxide (KOH) with known concentration and with a color indicator. Polymeric materials having a relatively higher acid number or % wt. content of acid monomer, and/or more accessible acid moieties are expected to have a better dispersibility in a polar medium such as water and possibly an higher cross-linkability, than similar polymeric materials having a relatively lower acid number, wt. % content of acid monomer, and/or less accessible acid moieties.

In some embodiments, the polymeric material, prior to neutralization of the neutralized acid moieties, has an acid number of at least 100 mg KOH/g, at least 115 mg KOH/g, at least 130 mg KOH/g, or at least 145 mg KOH/g.

In some embodiments, the polymeric material, prior to neutralization of the neutralized acid moieties, has an acid number of at most 230 mg KOH/g, at most 215 mg KOH/g, at most 200 mg KOH/g, or at most 185 mg KOH/g.

In some embodiments, the polymeric material, prior to neutralization of the neutralized acid moieties, has an acid number within a range of 100 to 230 mg KOH/g, 115 to 215 mg KOH/g, 130 to 200 mg KOH/g, 130 to 185 mg KOH/g, 145 to 185 mg KOH/g, or 145 to 170 mg KOH/g.

In some embodiments, the acid moieties of the hydrophobic polymeric material make up 8% to 30%, 10% to 30%, 12% to 30%, 12% to 28%, 12% to 26%, 15% to 30%, 15% to 28%, 15% to 26%, 17% to 22%, 17% to 23%, 18% to 30%, 18% to 28%, 18% to 26%, 20% to 30%, 20% to 28%, or 20% to 26%, by weight, of said hydrophobic polymeric material.

In some embodiments, the acid moieties of the hydrophilic polymeric material make up 8% to 30%, 10% to 30%, 12% to 30%, 12% to 28%, 12% to 26%, 15% to 30%, 15% to 28%, 15% to 26%, 17% to 22%, 17% to 23%, 18% to 30%, 18% to 28%, 18% to 26%, 20% to 30%, 20% to 28%, or 20% to 26%, by weight, of said hydrophilic polymeric material.

It is also believed that the acid number or % wt. content of acid monomer can be indicative of the quantity of pigment that may be loaded in the acidic polymer, a higher acid value suggesting a possibility for an increased pigment loading. A relatively higher pigment loading may in turn provide for a relatively more intense coloring effect or optical density following the application of the polymeric material having neutralized acid moieties embedding the pigment on an amino-silicone first coat. In some embodiments, the polymeric material having neutralized acid moieties can disperse the pigment in absence of an added dispersant. A dispersant, if added, should be compatible with the polymer and the pigment and should not affect the mechanical properties and the thermal behavior of the polymer film that may result therefrom.

It has been found that too low an acid number or % wt. content of acid monomer in the polymeric material may prevent proper dispersion and/or sufficient uptake of pigment particles. On the other hand, too high an acid number or % wt. content of acid monomer in the polymeric material may render the polymeric material sufficiently polar to dissolve within the aqueous carrier. In this case, the pigment particles (even if present in relatively higher concentration with respect to the polymer, as a result of the relatively high acid content) would no longer remain embedded in dispersed polymeric beads, so that their ability to coat and attach to a first coat on the fibers may be reduced. In other words, selecting a polymeric material having too high a content of neutralizable acid groups may be deleterious to the intended coloring effect.

Moreover, the acid number of the polymeric material may affect the mechanical properties of the polymeric film that may result therefrom. Coatings prepared using polymeric films having too low an acid number tend to display a weak attachment to the amino-silicone coat. It has been surprisingly discovered that too high an acid number may also be deleterious to the mechanical properties of the coating. These contradictory constraints, notwithstanding, it has been discovered that a narrow range of neutralizable acid content within which the polymeric material is (i) sufficiently dispersible and (ii) capable of embedding enough pigment so as to enable the build-up of a second coat adequate for the desired coloring effect, and without (iii) being overly soluble so as to detract from the optical density of the intended coloring. The selection of polymeric materials within this window shall be described in more detail herein-below.

According to features in the described preferred embodiments, the acid moieties and/or the neutralized acid moieties of the polymeric material are distributed in a random or irregular fashion.

According to features in the described preferred embodiments, the acid moieties and/or the neutralized acid moieties of the polymeric material are distributed in a regular fashion.

According to features in the described preferred embodiments, the polymeric material has an acid co-monomer percent weight content of at least 10%, at least 12%, at least 15%, at least 16%, at least 17%, or at least 18% per weight of the polymeric material, the acid co-monomer optionally being at least one of acrylic acid and methacrylic acid.

According to features in the described preferred embodiments, the acid co-monomer percent weight content is at most 30%, at most 28%, at most 26%, or at most 24% per weight of the polymeric material, the acid co-monomer optionally being at least one of acrylic acid and methacrylic acid.

According to features in the described preferred embodiments, the polymeric material has an acid co-monomer percent weight content within a range of 10% to 30%, 15% to 30%, 16% to 28%, 17% to 26%, 17% to 24%, 18% to 24%, or 18% to 22% per weight of the polymeric material, the acid co-monomer optionally being at least one of acrylic acid and methacrylic acid.

In some embodiments, the method first includes neutralizing the acid moieties of the polymeric material. The acidic moieties (e.g., COOH) of such polar polymers or copolymers are partially or fully neutralized with a neutralizing agent to form the corresponding salt or anionic moiety. In some embodiments, a partial neutralization of at least 75%, at least 80%, at least 85%, or at least 90% of the acid moieties is desirable. A copolymer is said to be neutralized if 75-100% of its acid moieties are neutralized.

Neutralized hydrophilic acidic polymers can be dispersible in aqueous dispersions, the dispersed particles of polymeric material being preferably sub-micronic or even in the nanometric size range (e.g., forming micelles). The basic medium enhances the solubility of the at least partly neutralized polymeric material of at least 5 wt. % of the polymeric material in the aqueous dispersion. In some embodiments, the solubility of the neutralizable polymeric material is of 1 wt. % or more or 2 wt. % or more, with respect to the weight of the aqueous dispersion containing the neutralizing agent. In some embodiments, the neutralizable acidic polymeric material is substantially insoluble in water (i.e., in absence of the neutralizing agent).

Those having ordinary skill in the art will appreciate that the selection of an appropriate neutralizing agent depends on the polymeric material, its acid number or content, the specific composition formulated, and its intended characteristics. The strength and/or amount of the neutralizing agent and any such choice are within the knowledge of those of ordinary skill in the art. For instance, for EAA, EMAA or AAA copolymers, the neutralizing agent is a base, such as ammonium hydroxide, sodium hydroxide, lithium hydroxide or potassium hydroxide, for example. In another alternative, the neutralizing agent may, for example, be an amine, such as monoethanolamine, triethanolamine, dimethylethanolamine, diethylethanolamine, morpholine or 2-amino-2-methyl-1-propanol (AMP). Advantageously, the neutralizing agent is volatile, leaving upon drying of a neutralized dispersion on a substrate coated therewith a polymeric film (e.g., an EAA, EMAA or AAA copolymer film) substantially free of residual neutralizing agent. When wash-resistance is desired, alkaline metal base is preferably avoided as a neutralizing agent, as the acid moiety of the polymeric material may recombine with the metal ion of the base resulting in ionomers being less resistant to water. Alternatively, if transient coloring is preferred, non-volatile base, such as sodium hydroxide, lithium hydroxide or potassium hydroxide can be used.

Generally, excess of neutralizing agent should preferably be avoided, to allow a more rapid evaporation leading to an accelerated film formation and the reduction of stickiness.

Such evaporation can be either passive, which spontaneously occurs under ambient temperature, or an active evaporation, which can be performed, e.g., by blow-drying at an ambient of elevated temperatures. Additionally, an excess of the neutralizing agent (e.g. base) could block the silanol groups of the amino-silicones of the first coat, by hydrogen bonding therewith, limiting the accessibility of such hydroxyl groups to amine moieties of other amino-silicones and consequently delaying condensation-curing of the amino-silicone coat. In other words, excess base in the second coat can inhibit the curing of the first coat. Calculation of the amount of the base required to neutralize the acidic groups can be done by standard methods, and without any undue experimentation. One such method uses the formula: $B=(W \cdot A \cdot N \cdot E)/1000$, wherein B is the weight of the base in grams, W is the weight of the polymeric material in grams, A is the acidity of the polymeric material in mEq/gram of polymeric material; N is the percent of neutralization desired, in decimal terms from 0 to 1, the latter representing 100% neutralization; and E is the Equivalent weight of the neutralizing agent being used. Furthermore, the amount of base in the neutralized dispersion can be monitored, for instance, by conductivity.

As mentioned, at this stage, following the addition of the neutralizing agent, the pH of the dispersions is generally basic (e.g., between pH 9.5 and 10.5). It is believed that at such basic pH, the neutralized polymeric materials acquire some water solubility, the subsequent film formation occurring with mildly hydrophilic polymeric particles.

In some embodiments, a pH of the aqueous dispersion is basic, optionally within a range of 7.0 to 11.5, 7.0 to 11.0, 7.5 to 11.5, 7.5 to 10.5, or 8.0 to 11.5.

As used herein in the specification and in the claims section that follows, the term "hydrophilic polymer", with respect to a polymeric material such as a neutralized polymeric material, refers to a polymer having at least one of the following solubility properties: (i) a solubility in pure deionized water of at least 1% (and more typically, at least 1.5%, at least 2%, at least 3%, at least 5%, at least 10%, at least 15%, at least 20% or at least 30%), by weight, at 25° C.; and (ii) a solubility of at least 1% (and more typically, at least 1.5%, at least 2%, at least 3%, at least 5%, at least 10%, at least 15%, at least 20% or at least 30%), by weight, in pure deionized water adjusted to a pH of 10, and at 25° C.

Typically, the conjugate acid of the hydrophilic, neutralized polymeric material is a hydrophobic polymeric material.

As used herein in the specification and in the claims section that follows, the term "solubility", with respect to a polymeric material, refers to the amount of polymeric material that can be introduced into the deionized water media of (i) or (ii) above, while maintaining the clarity of the deionized water media.

As used herein in the specification and in the claims section that follows, the term "clarity", with respect to a solution, is meant to include a solution having at least one, and typically both of the following properties: (i) the solution appears clear to the naked eye; and (ii) the average diameter or particle size (as determined by DLS) of any micelles disposed therein is at most 100 nm. More typically such micelles will have an average diameter or particle size of at most 80 nm, at most 70 nm, or at most 50 nm.

Removal of the volatile base from the aqueous dispersions, causes the neutralized acidic moieties in the hydrophilic polymeric material to re-acidify into the conjugate acid thereof. Thus, a hydrophobic polymeric material can be obtained following such elimination. The film resulting from the conversion of the neutralized acid moieties back to their initial non-neutralized state in the original acid-polymer on the hair fiber (e.g. following elimination of the neutralizing agent) may be advantageously water-insoluble (e.g., so as to resist sweat, rain, swimming environment, washing, etc.). Additionally, the film preferably fulfills at least one of being non-tacky, providing gloss and having sufficient abrasion resistance for achieving permanence.

Advantageously, the basic pH of the dispersion, once applied on hair fibers pre-coated with an amino-silicone film, can restore the positive charge of the amino-silicone film (e.g., by way of protonation of the amino groups). In parallel, the basic pH enables a high negative charging of the polymeric material (e.g., by way of protonation of the carboxylic groups). Thus, the basic pH of the aqueous dispersions favors a significant gradient of charge at the beginning of the coating process of the amino-silicone film by the polymeric particles, providing for a strong initial electrostatic drive.

Even in absence of surfactants or post-stabilizing agents, neutralized aqueous dispersions of such polymeric materials (e.g., EAA, EMAA or AAA copolymers) are considered very stable, due to the electrostatic repulsion imparted by the neutralized carboxylic groups. The polymeric material having neutralized acid moieties can cross-link with other molecules via suitable groups. In particular, the acid moieties of such polymeric material can interact with the amine moieties of the afore-discussed condensation-curable amino-silicone reactants.

Curing or film forming of such materials, also referred to herein as "acidic polymeric material", can be promoted, if desired, by the addition of appropriate cross-linkers and/or adequate curing facilitators (e.g., curing catalysts or curing accelerators). As mentioned, film formation can spontaneously occur when such polymeric materials are no longer in the aqueous medium of the dispersion in dry form on the coated substrate.

The type of neutralizing agent (whether volatile or not) can affect the water resistance and mechanical properties of the resulting film. For instance, upon drying, both water and volatile neutralizing agents—such as ammonia or amines—evaporate, and the films resulting from acid-polymers so neutralized are less prone to water sensitivity, optic defects and adhesion deficiencies, as compared to fixed alkali neutralized polymer films. On the other hand, dispersions neutralized with fixed alkali (e.g., KOH, NaOH, etc.) result in the formation of films having greater solvent and chemical resistance, and also higher melting points.

In some embodiments, the method further includes applying an aqueous dispersion on the at least partially cured amino-silicone film, to produce an overlying, pigmented polymeric film that coats said at least partially cured amino-silicone film, wherein the aqueous dispersion contains: (i) a polymeric material having neutralized acid moieties; and (ii) a plurality of pigment particles, at least partially enveloped by said polymeric material, and dispersed within the aqueous dispersion.

In some embodiments, the neutralized polymeric material is self-dispersible in water, i.e., in absence of an added dedicated dispersant. It has been discovered that such polymers may advantageously serve as pigment dispersants, thereby obviating or at least mitigating the need for a dedicated dispersant (for example, as necessary when pigments are optionally dispersed in the amino-silicone film). Hence, much more pigment may be loaded within this overlying polymeric film, thereby improving optical density (coloration) for a given film thickness. Such a dedicated dispersant may also detract from the cohesivity of the overlying polymeric film, and/or from the adhesivity of the overlying polymeric film to the underlying amino-silicone coat, and/or from the water resistance. Such a dedicated dispersant may also (typically disadvantageously) reduce the softening point temperature and/or the glass transition temperature of the film. However, in some embodiments, for instance when the polymeric material does not suffice to disperse a pigment contained therein, there is a need to add a dispersant to the aqueous dispersion neutralized polymeric material.

In some embodiments, the aqueous dispersion is produced by:

(a) mixing in an aqueous carrier containing water at least one hydrophobic polymeric material each independently having neutralizable acid moieties, so as to form a neutralizable mixture including pellets of the hydrophobic polymeric material(s);

(b) adding to the neutralizable mixture a neutralizing agent, said addition being performed under agitation at a temperature above at least one of the highest of the softening temperature and/or of the melting temperature of the at least one hydrophobic polymeric material, said neutralizing agent being added in an amount sufficient to neutralize at least 75% of the neutralizable acid moieties of said polymeric material(s), so as to form a neutralized mixture including a portion of hydrophilic polymeric material(s);

(c) adding at least one pigment to the neutralized mixture; and (d) dispersing the pigmented neutralized mixture, so as to form said aqueous dispersion, the aqueous dispersion including particles of at least one hydrophilic polymeric material, a portion of said hydrophilic polymeric material at least partially enveloping said at least one pigment.

The same procedure can be performed in absence of pigment, if the polymeric coating resulting from the application of such a pigmentless aqueous dispersion is intended for colorless hair styling.

According to features in the described preferred embodiments, the polymeric material having the neutralized acid moieties includes, mainly includes, consists essentially of, or consists of a neutralized ethylene-acrylic acid (EAA) copolymer.

According to features in the described preferred embodiments, the polymeric material having the neutralized acid moieties includes, mainly includes, consists essentially of, or consists of a neutralized ethylene-methacrylic acid (EMAA) copolymer.

According to features in the described preferred embodiments, the polymeric material having the neutralized acid moieties includes, mainly includes, consists essentially of, or consists of a neutralized acrylamide/acrylate (AAA) copolymer.

The aqueous dispersions, including the neutralization of the polymeric material having acid moieties, can be prepared in numerous ways which will be exemplified herein-below and in more details in the Example section of this disclosure. In some embodiments, the at least one pigment is embedded in the polymeric material having acid moieties (or compounded therewith, optionally in presence of a pigment dispersant) before neutralization of the material. In some embodiments, the at least one pigment, in particular if metallic pigment, is dispersed in the aqueous dispersion of neutralized acidic polymeric material, the polymeric material optionally partially coating or enveloping the pigment. In some embodiments, the at least one pigment of the aqueous dispersion can be dispersed therein in two forms (a) embedded prior to neutralization; and (b) partially coated or enveloped by the polymeric material after neutralization. For instance, by way of non-limiting example, an aqueous dispersion may include a first pigment of a first color embedded in a first polymeric material prior to its neutralization and a second pigment of a second color dispersed with a second polymeric material after its neutralization, the first and second pigment, color or polymeric material being the same or different. Such aqueous dispersion comprising two or more pigments and/or two or more polymeric materials can be prepared in one step (e.g., compounding the two or more pigments in the polymeric material or blend thereof) or in more steps (e.g., mixing aqueous dispersions each prepared with a different pigment: polymeric material combination).

The polymeric material is preferably thermoplastic allowing for instance the partial envelopment of pigment particles to occur in compounding processes, such as hot melt compounding.

In some embodiments, the aqueous dispersion further contains at least one surfactant being selected or adapted to wet the washed, at least partially cured amino-silicone film. In such case, the at least one surfactant of the aqueous dispersion preferably includes, mainly includes, or consists essentially of a super-wetting agent.

In some embodiments, the surfactant or super-wetting agent in the aqueous dispersion is selected and added in sufficient quantity whereby the aqueous dispersion exhibits a surface tension, at 25° C., of at most 30, at most 28, at most 26, or at most 24, and optionally, at least 12, at least 14, or at least 16 milliNewtons per meter (mN/m). In some embodiments, the surface tension of the aqueous dispersion is within a range of 12 to 30, 15 to 30, 18 to 28, 18 to 26, 18 to 24, 19 to 24, or 20 to 24 mN/m.

In some embodiments, the surfactant or super-wetting agent in the aqueous dispersion consists of, consists essentially of, or includes a non-ionic surfactant. In some embodiments, the surfactant or super-wetting agent in the aqueous dispersion consists of, consists essentially of, or includes a fluorosurfactant. In some embodiments, the surfactant or super-wetting agent in the aqueous dispersion consists of, consists essentially of, or includes a silicone-based surfactant. In some embodiments, the surfactant or super-wetting agent in the aqueous dispersion consists of, consists essentially of, or includes an anionic surfactant. In some embodiments, the surfactant or super-wetting agent in the aqueous dispersion consists of, consists essentially of, largely includes, or includes a zwitterionic surfactant. In some embodiments, the surfactant or super-wetting agent in the aqueous dispersion consists of, consists essentially of, largely includes, or includes a cationic surfactant.

Not to be bound by theory, it is believed that the need for a surfactant or super-wetting agent depends on the surface energy of the amino-silicone coating. An increased amount of amine moieties on the surface of the amino-silicone coated fiber increases the intimate contact with the basic aqueous dispersion containing the pigment-enveloped polymers, since the coated hair surface becomes more hydrophilic. Thus, the surfactant might not be necessary if the intimate contact is sufficient for adequate bonding between the layers. Metallic pigments having particular surface treatment may require the presence of surfactants, even if the amino-silicone coating has sufficient amount of amine moieties.

In some embodiments, the aqueous dispersion further includes at least one thickening agent.

Typically, the water used for the preparation of the aqueous dispersion is distilled water. Tap water, which may contain variable and/or relatively higher amounts of electrolytes that may form ionomers with the acid moieties of the polymeric material during evaporation of the aqueous carrier could affect the wash-resistance of the resulting polymeric coating. Thus, use of tap water is preferably avoided for the preparation of aqueous dispersions, when wash-resistant coats are desired.

In some embodiments, the aqueous dispersion further contains a cross-linking agent adapted or selected to cure the polymeric material having the neutralized acid moieties.

In some embodiments, the cross-linking agent adapted to cure the polymeric material having the neutralized acid moieties is selected from at least one of the group of (i) a cross-linker adapted or selected to bridge between cross-linkable functions of the polymeric material; (ii) a cross-linking accelerator; and (iii) a cross-linking catalyst.

In some embodiments, the cross-linking agent adapted to cure the polymeric material having the neutralized acid moieties is selected from at least one of the group of a melamine formaldehyde resin, a urea formaldehyde resin, a phenol formaldehyde resin, an epoxy resin, polyethyleneimine, an alkali metal hydroxide, Carbodilite™, a zinc complex, and a zirconium complex.

In some or all of the above embodiments, the total concentration of oxidizing agents within the aqueous dispersion is at most 5%, at most 2%, at most 1%, or at most 0.2%, by weight, of the aqueous dispersion, or wherein the aqueous dispersion is devoid of oxidizing agents.

While at least partially condensation-cured amino-silicone reactants or polymeric material having neutralized acid moieties can also be non-tacky to the touch, the lack of tackiness, or dry non-sticky touch is more generally associated with fully cured polymers. Compositions as used in the present methods may advantageously be rapidly non-tacky to the touch following their application to the hair fibers, so as to increase user compliance when coating or coloring is performed on a living subject. The problem of tackiness has been differently addressed in the art, for instance, by using in hair care products cross-linked polymers, also known as resins (e.g., silicone resins or polycondensates). While this approach can reduce or prevent an unpleasant touch once dried on hair, it also proscribes reactivity amongst such polymers. Therefore, a layer formed by the deposition of cross-linked polymers cannot have sufficient cohesivity to permit a long-lasting attachment to the hair surface, nor, consequently, retention of a second coat of polymeric material.

While some amino-silicone cross-linked polymers can also be purchased under the determination of being possibly only partially cured by their manufacturer, the ability of such commercially available polymers to further cure and form a suitable first coat remains highly hypothetical under typical coloring conditions according to the present teachings. Such condensation reaction, if any, would be very slow at ambient temperature (as suggested by the very long shelf life of almost a year of such cross-linked materials). In other words, using cross-linked amino-silicones for the first coat would require elevated temperatures for the condensation curing to proceed at a fast-enough pace (e.g., achieving sufficient curing to maintain coloration in less than a week). However, such elevated temperatures are not practical for living subjects, so that in fact, commercially available cross-linked polymers can be considered fully cross-linked were they to be used in methods of the present disclosure.

In contrast, by using according to the present teachings reactive materials (or constituents having substantially retained their reactivity), the cross-linking density of the amino-silicone film can be managed by choosing the suitable pre-polymers and cross-linkers, and their respective amounts, allowing control of the initial viscosity of the composition, the mechanical properties and the thickness of the cured film, the cohesion of the cured film, and any other property that may facilitate the subsequent attachment of the polymeric layer.

It should be noted that while silicone polymers are widely used in the field of hair products, for instance for the shine, softness, smoothness, anti-dandruff, hair repair or combability they may provide to hair treated with shampoos or hair conditioners comprising them, such polymers are traditionally elected for their weak and highly reversible attachment to the hair. Such silicones (e.g., polydimethylsiloxanes (PDMS)—non-functional dimethicones) intended to wash away at a first shampoo after their application, some not even resisting natural perspiration, are intrinsically different from the amino-silicone pre-polymers considered for the first coat of the present disclosure. Conventionally used silicones are typically non-reactive, or pre-reacted to form a cross-linked polymer ahead of their formulation in a hair care product, hence would lack the ability to form a cohesive film on the hair fiber, achieving at most transient physical deposition.

As used herein the term "coating composition", unless otherwise clear from context, may refer to an amino-silicone formulation (e.g., an oil-in-water emulsion comprising at least one condensation-curable amino-silicone reactant) and to an aqueous dispersion of acidic polymeric material, as herein described, including when any such composition further includes a coloring agent (e.g., dyes, pigments, metallic particles, etc.). A coating composition including any of the color imparting materials further described herein, can also be referred to as a "coloring composition".

In some embodiments, the coating compositions of the present disclosure are non-tacky within a few seconds (e.g., 10 seconds or less, 5 seconds or less, or even 1 second or less) following at least one of their rinsing, their washing, their drying, their combing and any like step of the present coating method to be further detailed herein-below.

While drying of fibers and/or of compositions applied thereupon can spontaneously occur (e.g., in the ambient environment), such drying can also be an active step facilitated by the use of a suitable drying instrument. The drying device can be an air blower, and typically a heated hair blower, the temperature of operation depending on whether the hair is attached or not to a living subject.

When the drying is an active drying, the total time period of applying of the aqueous dispersion and said washing and/or said active drying is within a range of 2 to 90 minutes, 2 to 75 minutes, 2 to 60 minutes, 2 to 45 minutes, 2 to 30 minutes, 2 to 20 minutes, 2 to 10 minutes, or 2 to 5 minutes, and optionally, at most 7 minutes, at most 4 minutes, at most 3 minutes, or at most 1.5 minutes. Additionally, within 24 to 48 hours, 24 to 36 hours, or 24 to 30 hours immediately succeeding this total time period, with the plurality of fibers being maintained within 7° C., 5° C., 3° C., or 1° C. of room or ambient temperature, the overlying, pigmented polymeric coating achieves wash resistance, permanence, or permanent coloration.

The molecular weights or weight average MW of materials are generally provided by the manufacturer, but can be independently determined by known analytical methods, including for instance gel permeation chromatography, high pressure liquid chromatography (HPLC) or matrix-assisted laser desorption/ionization time-of-flight mass spectroscopy MALDI-TOF MS.

According to features in the described preferred embodiments, the fiber or the core fiber is a natural or synthetic keratinous fiber, the keratinous fiber optionally being human hair or animal fur.

The oil-in-water emulsion formulations according to the present disclosure including the condensation-curable amino-silicone pre-polymers can be applied on dry hair or on wet hair, indifferently. In some embodiments, the hair is pre-dyed, or alternatively, at least one of unpre-degreased, unpre-shampooed, and unpre-bleached.

Preferably, the hair fibers are clean. Application can be made with any appropriate brush, comb or applicator known in the art of hair coloring and even with fingers, if so desired. While contact application is generally preferred, the coating compositions may also be applied by spray and like contactless methods.

According to features in the described preferred embodiments, the fiber or core fiber is unbleached mammalian hair.

According to features in the described preferred embodiments, the exterior surface of said coated fiber has a negative or net negative charge.

According to an aspect of the present disclosure there is provided a plurality of individually coated fibers, each of which coated fibers comprising: (a) a core fiber; (b) an at least partially cured amino-silicone film enveloping the core fiber and adhering thereto; and (c) a coating including a polymeric film having neutralizable acid moieties, the coating at least partially enveloping the at least partially cured amino-silicone film and adhering thereto.

According to features in the described preferred embodiments, the aqueous dispersion further contains at least one pigment. Alternatively and additionally, in some embodiments the formulation containing the condensation-curable amino-silicone reactant, which in particular can be an oil-in-water emulsion, further contains at least one formulation pigment.

When the pigment is contained in the overlying polymeric layer formed of the aqueous dispersion, the total concentration of the pigment particles provided in the polymeric material within the aqueous dispersion is at least 0.1%, at least 0.5%, at least 1%, at least 3%, at least 5%, at least 10%, at least 15%, or at least 20%, and optionally, at most 30%, at most 27%, or at most 25%, and further optionally, within a range of 0.1% to 30%, 0.5% to 27%, 0.5% to 25%, 2% to 25%, 3% to 25%, 5% to 25%, 7% to 25%, 10% to 25%, 7% to 22%, or 10% to 22% by weight of polymeric material of the aqueous dispersion.

The amount of polymeric material in the aqueous dispersion typically does not exceed 30% by weight of the total aqueous dispersion, such weight concentration being generally of no more than 20%, no more than 15% or no more than 10%. The amount of polymeric material in the aqueous dispersion is of at least 1%, at least 2% or at least 5% by weight of the total aqueous dispersion.

When the pigment is contained in the amino-silicone layer, the total concentration of the pigment particles provided in the oil phase of the oil-in-water emulsion is at least 0.1%, at least 0.5%, at least 1%, at least 3%, at least 5%, at least 10%, or at least 12%, and optionally, at most 20%, at most 17%, or at most 15%, or at most 12%, and further optionally, within a range of 0.1% to 20%, 0.5% to 15%, 0.5% to 15%, 3% to 15%, 5% to 15%, 3% to 12%, or 3% to 10% by weight of the oil phase.

The amount of oil phase in the oil-in-water emulsion typically does not exceed 20% by weight of the total emulsion, such weight concentration being generally of no more than 15%, no more than 12.5% or no more than 10%. The amount of oil phase in the emulsion is of at least 0.01%, at least 0.1%, at least 0.5% or at least 1% by weight of the total emulsion.

According to features in the described preferred embodiments, the at least one pigment of the aqueous dispersion is embedded in, or at least partially enveloped by, the (hydrophilic) polymeric material having the neutralized acid moieties. In some embodiments, the at least one formulation pigment of the formulation that includes at least one condensation-curable amino-silicone reactant is dispersed in the formulation.

In some embodiments, the condensation-curable amino-silicone reactant and/or the polymeric material have moieties suitable to disperse a pigment, (acidic carbon black being a common example), such dispersion being in absence of an additional dispersant.

In some embodiments, the aqueous dispersion further contains at least one pigment dispersant, each pigment dispersant selected or adapted to disperse at least one of the pigments within the aqueous dispersion. When the pigment is embedded in the polymeric material, the pigment dispersant is selected or adapted to disperse it therein (e.g., during a compounding process). In some embodiments, the amino-silicone formulation further contains at least one pigment dispersant, each pigment dispersant selected or adapted to disperse at least one of the formulation pigments within the formulation.

In some embodiments, the pigment dispersant may be selected and/or adapted to disperse inorganic pigments and/or organic pigments.

According to features in the described preferred embodiments, each of the at least one pigment dispersant has at least one pigment-affinic moiety or functionality with respect to at least one of the pigments or formulation pigments.

According to features in the described preferred embodiments, the at least one pigment-affinic moiety or functionality is selected from the group of carboxylic acids, amines, hydroxyl groups, and sulfonates.

According to features in the described preferred embodiments, the formulation contains at least one formulation pigment dispersed therein, and the aqueous dispersion contains at least one pigment dispersed therein, a portion of the pigment being preferably embedded in the polymeric material having neutralized acid moieties.

According to features in the described preferred embodiments, the at least one pigment of the aqueous dispersion is identical to or different from the formulation pigment of an oil-in-water emulsion.

According to features in the described preferred embodiments, the polymeric film is linked or bonded to the at least partially cured amino-silicone film by employing a linkage between carboxylic/carboxylate (COO) moieties in the polymeric film and nitrogen-containing (e.g., amine) moieties on the at least partially cured amino-silicone film.

According to some embodiments, the rinsing liquid is (i) water, or (ii) a cationic rinsing liquid containing a cationic surfactant, or (iii) a rinsing liquid devoid of non-cationic surfactants, degreasing agents and/or swelling agents, the degreasing and swelling agent respectively able to degrease and swell the at least partially cured amino-silicone film. In some embodiments, the rinsing liquid has a pH of at least 6, at least 7, at least 8, or at least 9.

According to some embodiments, the cationic shampoo or the cationic rinsing liquid includes a cosmetically-acceptable primary, secondary, tertiary, or quaternary ammonium compound or polymer.

According to some embodiments, the cationic shampoo or the cationic rinsing liquid includes a polyquaternium polycationic polymer having a quaternary ammonium function.

According to features in the described preferred embodiments, the method further comprises, subsequent to the application of the aqueous dispersion, washing the plurality of fibers with water or an aqueous rinsing liquid to remove excess material of the aqueous dispersion from a surface of the plurality of fibers, the rinsing liquid optionally being cationic. In some embodiments, subsequent to the washing of the fibers, either after application of the first coat formulation or after application of the aqueous dispersion of the second coat, the fibers are dried, optionally using a hair dryer.

The step of applying the oil-in-water emulsion and the at least partial curing, optionally followed by a washing and/or a drying step, contribute to the formation of an amino-silicone film, or first coat. In some embodiments, the washing of the hairs is performed within 30 minutes, within 20 minutes, within 15 minutes, within 10 minutes, within 5 minutes, within 3 minutes, within 2 minutes, or within 1 minute, after the application of the oil-in-water emulsion has been completed.

The step of applying the aqueous dispersion on the at least partially cured amino-silicone film, optionally followed by a washing and/or a drying step, contributes to the formation of a polymeric film, or second coat. In some embodiments, these groups of steps can be alternatively repeated, to subsequently form a third coat, a fourth coat, and so on. Such alternating repeats of the sub-series of the afore-described steps can result in a first coat of an amino-silicone film; a second coat of a polymeric film; a third coat of an amino-silicone film; optionally further coated with a fourth coat of a polymeric film, and so on. The formulations for the formation of the amino-silicone films of the first coat, third coat, fifth coat etc., as applicable, need not be the same. Likewise, the aqueous dispersions for the formation of the polymeric films of the second coat, fourth coat, sixth coat etc., as applicable, need not be the same. Each such film may or may not further comprise one or more pigments, and each said pigments may result in colors or shades which need not be the same for each and all films.

It will be readily appreciated that as the fibers may be washed with water or an aqueous rinsing liquid in between steps, for instance to remove excess of the formulation of the first coat or of the dispersion of the second coat, their respective reactive condensation-curable film-forming amino-silicone pre-polymer reactants and polymeric materials having the neutralized acid moieties may preferably be non-soluble in water at the time of excess removal.

In some embodiments, the pigments of an earlier applied coat mask the color of the fibers and/or provide a background effect to a later applied coat. For instance, an earlier applied coat comprising a light-colored pigment (e.g., white mica flakes), can serve to mask a natural darker color of the fibers, such coat being thereafter covered by a coat comprising pigments providing the intended end-color. It can be readily appreciated that such a method of masking the original hair color can advantageously replace conventional bleaching processes typically used to achieve such effect.

Alternatively and additionally, the pigments of an earlier coat, e.g., metallic flakes, may provide a silvery appearance. As used herein an earlier applied and a later applied coat need not refer to immediately adjacent films. Thus, while an earlier coat can be an amino-silicone film and a later coat its proximal polymeric film, it is not essential and the later applied coat may refer for example to a subsequent amino-silicone film (or to a subsequent polymeric film, if the earlier applied coat being considered was itself a polymeric film). Pigments having a flake-like shape, in particular metallic-looking pigments, are deemed particularly suitable to achieve such masking or special effects, however this is not essential.

According to some embodiments, the pigment flakes are metallic pigment flakes containing, coated with, consisting essentially of, or made of metals, alloys and oxides thereof, said flakes being selected from the group comprising aluminum flakes, brass flakes, bronze flakes, copper flakes, gold flakes, mica coated flakes, silica coated flakes and silver flakes.

According to some embodiments, the metallic-looking pigment flakes have an average longest dimension in the range of 2 µm to 20 µm and an average thickness in the range of 50 nm to 500 nm. The dimensions of metallic pigments need not fulfill the size ranges of the non-metallic pigments, generally sub-micronic in at least one of their Dv50 or Dv90 values.

Since metallic pigments are typically larger in particle size than non-metallic pigments, they have smaller surface area per identical volume of pigment particles, and thus, a relatively smaller amount of polymeric material is required to coat larger metallic pigments as compared to a same volume of smaller non-metallic pigments. Metallic pigments also generally have a higher density (weight per volume) than non-metallic pigments. Thus, while on a weight basis non-metallic pigments cannot typically exceed a specific concentration (e.g., maximal non-metallic pigment loading), metallic pigments may be present, if desired, at higher concentrations in the coating compositions of the present disclosure.

In the aqueous dispersion, the total concentration of metallic pigment particles can be of at least 0.1%, at least 0.5%, at least 1%, at least 3%, at least 5%, at least 10%, at least 15%, or at least 20% by weight of the dispersion. In some embodiments, the metallic pigment constitutes at most 60%, at most 50%, at most 40%, at most 30%, at most 27%, or at most 25% by weight of the aqueous dispersion. In some embodiments, the metallic pigment particles are present within a range of 0.1% to 60%, 0.5% to 60%, 1% to 60%, 1% to 50%, 2% to 50%, 5% to 50%, 5% to 40%, 10% to 30%, 10% to 25%, or 10% to 22% by weight of the aqueous dispersion.

Alternatively, when the metallic pigment is provided in the oil phase of the oil-in-water emulsion, the total concentration of the pigment particles is at least 0.1%, at least 0.5%, at least 1%, at least 3%, at least 5%, at least 10%, or at least 12%, and optionally, at most 40%, at most 30%, at most 20%, at most 17%, or at most 15%, or at most 12%, and further optionally, within a range of 0.1% to 40%, 0.1% to 30%, 0.1% to 40%, 0.1% to 20%, 0.5% to 15%, 0.5% to 15%, 3% to 15%, 5% to 15%, 3% to 12%, or 3% to 10% by weight of the oil phase.

According to some embodiments, the metallic-looking pigment flakes are further coated with a least one coupling agent capable of covalently binding the reactive amino-silicone of the pre-polymer formulation or the polymeric material of the aqueous dispersion, depending on the film in which the pigment flakes are to be present.

According to some embodiments, the at least one coupling agent is a cosmetically acceptable coupling agent selected from the group of acrylate coupling agents, thiol coupling agents, anhydride coupling agents, epoxy coupling agents, and silanol coupling agents.

In some embodiments, the acrylate coupling agent is selected from the group comprising of penta erythrytol tetra acrylate, pentaerythrityl triacrylate, di-trimethylol-propane tetraacrylate, PEG-trimethylol-propane triacrylate, and mixtures thereof.

In some embodiments, the thiol coupling agents can be pentaerythrityl tetramercaptopropionate; mercaptopropyltrimethoxysilane; trimethylolpropane tris-mercapto-propionate. In some embodiments, the anhydride coupling agent is polymaleic anhydride. In some embodiments, the epoxy coupling agents can be 4-methylen-2,6-epoxydecane; 3-methyl-1-phenyl-3-hexene 1,5-epoxide. In some embodiments, the silanol coupling agent is glycidoxypropyl trimethoxysilane.

According to some embodiments, the method further comprises, subsequent to the formation of an at least partially cured film, optionally pigmented, on the external surface of the individual hairs, or any step thereafter, further curing the at least partially cured amino-silicone film, typically for a period of at least 4 hours, at least 6 hours, or at least 12 hours at a temperature of at least 15° C. and of at most 38° C., at most 36° C., at most 34° C., or at most 32° C., so as to obtain full curing of the film. In various embodiments, the period may be at most 48 hours, at most 36 hours, at most 24 hours, at most 12 hours, or at most 6 hours, or within a range of 6 to 36 hours, 6 to 24 hours, 6 to 18 hours, or 6 to 12 hours.

According to some such embodiments, further curing over the specified period (for the duration of the period) is effected or transpires solely by or substantially solely by humidity or ambient humidity. According to alternative embodiments, further curing is effected or occurs within at least half-a-day, at least one day, at least two days, at least three days, at least five days, or at least a week of washing of the fibers in the absence of any added non-cationic surfactant. In some embodiments, shampooing of the hair during the period of the further curing is effected with a cationic shampoo, and within at least half-a-day, at least one day, at least two days, at least three days, at least five days, or at least a week of the original liquid rinsing.

As used herein in the specification and in the claims section that follows, the terms "permanence" and "wash resistance", with respect to coated, pigmented mammalian hair fibers, are used interchangeably to refer to such coated fibers (e.g., coated hair fibers), coated with a pigment-containing coating in accordance with a coating protocol, and having (i) a measured baseline Optical Density (OD) value ("$OD_{baseline}$") determined after full curing has ensued following the administration of the coating according to the coating protocol; and (ii) a measured OD value ("$OD_{post\text{-}wash\text{-}protocol}$") obtained after administration of the coating according to the coating protocol and subsequently washing the cured coated fibers according to the below wash protocol, according to a wash protocol, and wherein $OD_{post\text{-}wash\text{-}protocol}$ is at least 80% of $OD_{baseline}$. The wash protocol encompasses applying a standard, sulfate-containing shampoo onto the dried colored hair sample, thoroughly massaging between the fingers of the operating person to ensure full coverage and intimate contact, and squeezing out any excess shampoo. This step is repeated four more times, and after a total of five such shampooing cycles, the hair is rinsed with tap water at about 25° C. The previous step is repeated four more times, bringing the total number of shampooing cycles to 25 at the end of the procedure. Following the last shampooing cycle, the hair sample is thoroughly rinsed with tap water at about 25° C., followed by drying and combing, to complete the wash protocol.

According to some embodiments, the at least partially cured film is wash resistant, meaning that the fibers (e.g., hair), after being washed at least 10 times with a cationic shampoo, retain an Optical Density (OD) value of at least 80% of an original OD value as determined following the at least partial curing. The washing protocol and the OD measurements may be as described in the Examples section herein-below, and may be performed at ambient temperature (circa 23° C.). Typically, hair coloration is achieved by the presence of pigments in the second coat (e.g., also containing neutralized EAA, EMAA and/or AAA). In this case, wash resistance can be assessed on hair fibers coated by the first and second coats.

Washing is performed by completely immersing the fibers in the washing liquid, rinsing liquid, or water, as desired. Washing can be optionally performed after the application of an oil-in-water emulsion forming an amino-silicone coat. In such case, washing is performed within 30 minutes, within 20 minutes, within 15 minutes, within 10 minutes, within 5 minutes, within 3 minutes, within 2 minutes, or within 1 minute, of applying of said oil-in-water emulsion. The fibers are generously massaged with the liquid for about one minute and are optionally rinsed with water if the washing or rinsing liquid other than tap water.

Alternatively and additionally, the washing can be performed after the application of the aqueous dispersions forming the polymeric layer. In such case, washing is performed within at most 20 minutes, at most 10 minutes, at most 5 minutes, at most 3 minutes, at most 2 minutes, at most 1 minute, or at most 30 seconds after completing said applying of said aqueous dispersion. Preferably, shortly after, for instance as soon as 1 minute, 5 minutes, or 30 minutes after completing said applying of said aqueous dispersion, sufficient attachment of said overlying polymeric layer to the external surface of the amino-silicone-coated mammalian hair fiber is attained, such that the coated fibers are non-tacky.

As used herein in the specification and in the claims section that follows, the term "reference OD" and the like refers to an optical density obtained under reference or baseline conditions in which the hair is subjected to identical treatment through the application of the aqueous dispersion, and is subsequently subjected to drying and combing, instead of a washing step.

Human subjects may perform such washing of personal hair at a temperature of up to about 45° C., 40° C., 35° C., 30° C., or 25° C., and optionally, at a temperature of at least 5° C., 10° C., 12° C., 15° C., 17° C., or 20° C., and further optionally, within 7° C., 5° C. or 3° C. of room or ambient temperature. Following optional rinsing with water, if the washing or rinsing liquid is other than tap water, the hair fibers are dried (e.g., passively with ambient air or actively with blowing air at ambient temperature). Unless otherwise stated, in vitro testing of wash resistance of partially cured or fully cured colored hair samples was performed in laboratory settings with liquids at ambient temperature (circa 23° C.).

In some embodiments, the fully cured first film of amino-silicone has a film thickness, average thickness, or multiple-fiber average thickness of at least 20 nm, at least 50 nm, or at least 100 nm, and optionally, at most 3000 nm, at most 2000 nm, at most 1200 nm, at most 800 nm, at most 500 nm, at most 400 nm, at most 300 nm, at most 200 nm, at most 150 nm, or at most 120 nm, and further optionally, within a range of 20 nm to 3000 nm, 20 nm to 1000 nm, 20 nm to 500 nm, 20 nm to 300 nm, 20 nm to 200 nm, 20 nm to 150 nm, 50 nm to 150 nm, 50 nm to 500 nm, 50 nm to 350 nm, 50 nm to 250 nm, or 50 nm to 200 nm.

In some embodiments, the fully cured first film of amino-silicone and the second film formed by polymeric material having neutralized acid moieties can each have a film thickness, average thickness, or multiple-fiber average thickness of at least 100 nm, at least 150 nm, at least 200 nm, at least 250 nm, at least 300 nm, at least 500 nm, at least 800 nm, or at least 1000 nm, at least 1200 nm or at least 2000 nm, the thickness not exceeding 5000 nm, being no greater than 4000 nm, no greater than 3500 nm, no greater than 3000 nm, no greater than 2500 nm, no greater than 2000 nm, no greater than 1700 nm, or no greater than 1400 nm. In some embodiments, the fully cured film has a thickness in the range of between 100 nm to 5000 nm, 100 nm to 4000 nm, 200 nm to 3500 nm, 200 nm to 2500 nm, 200 nm to 1000 nm, 200 nm to 700 nm, 200 nm to 500 nm, 200 nm to 450 nm, or 200 nm to 400 nm, 300 nm to 3000 nm, 300 nm to 2000 nm, 500 nm to 2000 nm, or 500 nm to 1000 nm. Assuming, for illustrative purposes, a hair fiber having a diameter of 50 µm, coated with a first coat having a thickness above fiber surface of 150 nm and a second coat having a thickness above first coat surface of 250 nm, amounting to a total coat of 400 nm, then the diameter of the coated hair will be of 50.8 µm. The thickness of such coats can be measured by standard methods such as by SEM-FIB microscopy.

In some embodiments, the fully cured first film of amino-silicone overlayered by the pigmented polymeric coating can have a first total thickness, first total average thickness, or first total multiple-fiber average thickness, or alternatively a second total thickness, second total average thickness, or second total multiple-fiber average thickness of the amino-silicone layer and the overlying, pigmented polymeric coating, of at least 100 nm, at least 150 nm, at least 200 nm, at least 300 nm, at least 500 nm, at least 800 nm, at least 1200 nm, or at least 2000 nm, and optionally, at most 5000 nm, at most 3500 nm, at most 2500 nm, at most 2000 nm, at most 1700 nm, or at most 1400 nm, and further optionally, within a range of 100 nm to 5000 nm, 200 nm to 3500 nm, 200 nm to 2500 nm, 200 nm to 1000 nm, 200 nm to 700 nm, 200 nm to 500 nm, 200 nm to 450 nm, or 200 nm to 400 nm.

In some embodiments, the ratio of at least one of the first or second total thickness, first or second total average thickness, and first or second total multiple-fiber average thickness to the amino-silicone layer thickness, average thickness, or multiple-fiber average thickness, is within a range of 1.2:1 to 100:1, 1:4 to 100:1, 1:7 to 100:1, 2:1 to 100:1, 3:1 to 100:1, 4:1 to 100:1, 5:1 to 100:1, 7:1 to 100:1, 10:1 to 100:1, 2:1 to 30:1, 2:1 to 20:1, 3:1 to 30:1, 3:1 to 20:1, 5:1 to 30:1, 5:1 to 20:1, 7:1 to 30:1, 7:1 to 20:1, 10:1 to 50:1, 10:1 to 30:1, or 10:1 to 20:1.

As used herein in the specification and in the claims section that follows, the term "average thickness", typically with respect to one or more coatings or layers, is meant to refer to an arithmetic average of a measured thickness of the one or more coatings or layers, along the length of the fiber. Each individual thickness measurement is made using a Focused Ion Beam (FIB) technology, as is known in the art. Ten equally spaced points along the entire length of the coated fiber are determined for the individual thickness measurements, and the arithmetic average of the ten measurements defines the average thickness pertaining to this individual fiber.

The coated fibers of, or produced by, the present disclosure, may exhibit fairly consistent coating thicknesses, irrespective, to a large degree, of the particular, local topographical features of the hair fiber substrate. Moreover, individual coated fibers may exhibit similar coating thicknesses. Nonetheless, it will be appreciated that a more statistical approach to coating thicknesses may better serve to distinguish between the present disclosure and various teachings of the art. Thus, in some embodiments of the present disclosure, a "multiple-fiber average thickness" is defined as the "average thickness" as defined above for an individual coated fiber, but applied to a plurality of at least ten of such coated fibers, selected at random from the fibers subjected together to the coating treatment, and arithmetically averaged over the plurality of coated fibers.

Kit Comprising Coating or Coloring Composition

In another aspect, there is provided a kit for producing a reactive cosmetic composition for coating or coloring an external surface of mammalian hair, the kit comprising:

(a) a first oil phase compartment containing a first oil phase including:
  (i) at least one reactive condensation-curable film-forming amino-silicone monomer having a molecular weight of at most 1000 g/mole; and optionally,
  (ii) a non-amino cross-linking agent; and further optionally, (iii) at least one of an amino-silicone oil and a non-amino-silicone oil; and further optionally, (iv) at least one reactive condensation-curable film-forming amino-silicone pre-polymer including at least one of a reactive condensation-curable film-forming amino-silicone polymer and a reactive condensation-curable film-forming amino-silicone oligomer;

(b) an aqueous dispersion compartment containing an aqueous dispersion including:

(i) an aqueous medium; and (ii) sub-micronic particles including, or made of, a hydrophilic polymeric material having neutralized acid moieties, disposed within the aqueous medium, each of at least a portion of the sub-micronic particles optionally containing at least one pigment particle, the at least one pigment particle optionally being at least partially enveloped by the polymeric material;

(c) an optional second oil phase compartment containing a second oil phase including:

(i) at least one of an or the amino-silicone oil and a or the non-amino-silicone oil, and optionally, (ii) a solid, hydrophobic reactive inorganic filler; and further optionally, (iii) the at least one reactive condensation-curable film-forming amino-silicone pre-polymer including at least one of a reactive condensation-curable film-forming amino-silicone polymer and a reactive condensation-curable film-forming amino-silicone oligomer; and further optionally, (iv) pigment particles, disposed within the second oil phase; and (d) an optional metallic pigment compartment containing at least one metallic pigment, and optionally, an aqueous, organic or oil carrier;

wherein the kit further optionally comprises at least one of a thickening agent, an emulsifier, a surfactant and a dispersant.

The amino-silicone oil-in-water emulsion that can be prepared from the reactive condensation-curable film-forming amino-silicone monomer, optionally in combination with at least one of the other components of the first oil phase compartment. Components of the second oil phase compartment can be combined thereto as well. The aqueous dispersion resulting from the combination of the components of the aqueous dispersion compartment of the kit is able to produce an overlying, pigmented polymeric layer adhering to an external surface of an amino-silicone layer produced by the application of an emulsion prepared as described above.

In some embodiments, the polymeric material in the aqueous dispersion of the kit fulfills at least one of the following:

aa) the acid moieties of the neutralized acid moieties are selected from the group of acrylic acid and methacrylic acid;

bb) the acid moieties of the neutralized acid moieties make up 15-30 wt. % of the total weight of the polymeric material;

cc) the polymeric material has an acid number within the range of 100-230 mg KOH/g;

dd) the polymeric material having neutralized acid moieties is an alkene copolymer; and ee) the polymeric material having neutralized acid moieties is an acrylamide/acrylate copolymer.

In some embodiments, a pigmented amino-silicone layer is obtained by combining the reactive condensation-curable film-forming amino-silicone monomer, optionally with at least one of the other components of the first oil phase compartment with the pigment of the second oil phase compartment or the metallic pigment of the metallic pigment compartment. When pigments are combined into the amino-silicone layer, a dispersant is also added.

In some embodiments, the amino-silicone layer is prepared by combining the reactive condensation-curable film-forming amino-silicone monomer, optionally with other components of the first oil phase compartment with a solid, hydrophobic reactive inorganic filler, disposed within at least one of an amino-silicone oil and a or the non-amino-silicone oil of the second oil phase compartment.

According to some embodiments, the kit may further comprise an additional compartment including water.

According to some embodiments, a thickening agent is included in the kit, for providing a desired viscosity to at least one of the coating compositions, and can be contained in at least one of: I) the aqueous dispersion compartment or II) a dedicated thickening agent compartment, which may optionally contain at least one of water, an emulsifier, a surfactant and a dispersant.

According to some embodiments, an emulsifier is included in the kit, for stabilizing the oil-in-water emulsion resulting from the mixing water and the contents of the compartments of the amino-silicone coat of the kit. The emulsifier can be contained in at least one of: I) the first oil phase compartment, II) the second oil phase compartment, III) the metallic pigment compartment or IV) a dedicated emulsifier compartment, which may optionally contain water and/or a thickening agent.

According to some embodiments, surfactant is included in the kit, for improving the wetting of the at least partially cured amino-silicone layer by a subsequently applied aqueous dispersion containing such surfactant. The surfactant can be contained in at least one of: I) the aqueous dispersion compartment, II) the metallic pigment compartment (if being added to the aqueous dispersion), or III) a dedicated surfactant compartment, optionally with a thickening agent.

According to some embodiments, dispersant is included in the kit, for improving the dispersion of pigment particles within at least one of the coating compositions. The dispersant can be contained in at least one of: I) the second oil phase compartment, II) the aqueous dispersion compartment, III) the metallic pigment compartment or IV) a dedicated dispersant compartment, which may optionally contain a thickening agent and/or an emulsifier.

According to some embodiments, the combination of the aforesaid compartments resulting in an oil-in-water emulsion is adapted for the preparation of the oil-in-water emulsion as herein described.

According to some embodiments, the combination of the aforesaid compartments resulting in an aqueous dispersion is adapted for the preparation of the aqueous dispersion as herein described.

According to some embodiments, the keratinous fibers to be colored or cosmetically treated with the kit are, or include, mammalian hair, optionally attached to the mammalian subject.

According to some embodiments, at least a portion of, or all of, the silicone oil is disposed in the first oil phase compartment.

According to some embodiments, at least a portion of, or all of, the silicone oil is disposed in the second oil phase compartment.

According to some embodiments, the at least one neutralized copolymer of the kit's aqueous dispersion compartment is an alkene copolymer selected from the group of ethylene-acrylic acid (EAA) copolymer, ethylene-methacrylic acid (EMAA) copolymer and acrylamide/acrylate (AAA) copolymer.

According to some embodiments, the compartments containing the amino-silicone coat and/or the aqueous dispersion coat-forming components may contain further excipients such as pH buffering agents, anti-microbial agents, anti-fungal agents, preservative agents and any such agents as customarily used in coloring compositions, in particular in human hair coloring ones.

According to some embodiments, the silicone oil, when present in the first or second oil-phase compartments of the kit, is miscible with the condensation-curable amino-silicone monomer, and/or condensation-curable amino-silicone oligomer and/or condensation-curable amino-silicone polymer, as the case may be.

The kit can further comprise a sealable container, wherein the compartments can be mixed. The container can be optionally capped by a removable applicator, such as a brush or a pad connected through a hollow space to the container's seal, allowing the coloring composition to pass through, and transfer to the keratinous fibers for coloration. Alternatively, the applicator can be a spray head of a spray container, allowing the composition to be sprayed directly onto the fibers.

While not essential, metallic pigment particles (e.g., in flake shape) are generally added to the coloring compositions immediately prior to their application, such pigments being considered more susceptible to deleterious reactions (e.g., oxidation) when in a liquid medium. Thus, if metallic pigments are to be used in a kit for the coloration of keratinous fibers either upon mixing with the emulsion of condensation-curable amino-silicone reactants, or upon mixing with the aqueous dispersion of a polymeric material, or with both, such metallic pigments are preferably supplied in a separate compartment, either as powder, in an aqueous, organic or oil carrier. Typically, compositions including metallic pigments further contain anti-oxidative agents.

According to some embodiments, the kit further comprises a rinsing compartment containing a rinsing formulation or a rinsing agent dispersible or soluble in water. According to some embodiments, the kit further comprises a shampoo compartment containing a cationic shampoo.

According to some embodiments, a kit is provided, comprising:
(a) a first oil phase compartment including at least one reactive condensation-curable film-forming amino-silicone monomer having a molecular weight of at most 1000 g/mole, and
(b) an aqueous dispersion compartment including:
(i) aqueous medium; and
(ii) sub-micronic particles including, or made of, a hydrophilic polymeric material having neutralized acid moieties, disposed within the aqueous medium, each of at least a portion of the sub-micronic particles optionally containing at least one pigment particle, at least partially enveloped by the polymeric material.

According to some embodiments, a kit is provided, comprising:
(a) a first oil phase compartment including:
(i) at least one reactive condensation-curable film-forming amino-silicone monomer having a molecular weight of at most 1000 g/mole; and
(ii) at least one of an amino-silicone oil and a non-amino-silicone oil; and
(b) an aqueous dispersion compartment including:
(i) aqueous medium; and
(ii) sub-micronic particles including, or made of, a hydrophilic polymeric material having neutralized acid moieties, disposed within the aqueous medium, each of at least a portion of the sub-micronic particles optionally containing at least one pigment particle, at least partially enveloped by the polymeric material, and optionally containing a surfactant.

According to some embodiments, a kit is provided, comprising:
(a) a first oil phase compartment including:
(i) at least one reactive condensation-curable film-forming amino-silicone monomer having a molecular weight of at most 1000 g/mole; and
(ii) at least one of an amino-silicone oil and a non-amino-silicone oil;
(b) an aqueous dispersion compartment including:
(i) aqueous medium; and
(ii) sub-micronic particles including, or made of, a hydrophilic polymeric material having neutralized acid moieties, disposed within the aqueous medium, each of at least a portion of the sub-micronic particles optionally containing at least one pigment particle, at least partially enveloped by the polymeric material, and optionally containing a surfactant;
(c) a second oil phase compartment including:
(i) at least one of an or the amino-silicone oil and a or the non-amino-silicone oil, and
(ii) a solid, hydrophobic reactive inorganic filler; and
(d) a thickening compartment including a thickening agent, and optionally water and/or an emulsifier.

According to some embodiments, a kit is provided, comprising:
(a) a first oil phase compartment including:
(i) at least one reactive condensation-curable film-forming amino-silicone monomer having a molecular weight of at most 1000 g/mole;
(ii) at least one of an amino-silicone oil and a non-amino-silicone oil;
(iii) at least one metallic pigment; and optionally
(iv) a dispersant;
(b) an aqueous dispersion compartment including:
(i) aqueous medium; and
(ii) sub-micronic particles including, or made of, a hydrophilic polymeric material having neutralized acid moieties, disposed within the aqueous medium, each of at least a portion of the sub-micronic particles optionally containing at least one pigment particle, at least partially enveloped by the polymeric material; and optionally
(c) a thickening agent compartment containing a thickening agent and an emulsifier, According to some embodiments, a kit is provided, comprising:
(a) a first oil phase compartment including:
(i) at least one reactive condensation-curable film-forming amino-silicone monomer having a molecular weight of at most 1000 g/mole; and
(ii) at least one of an amino-silicone oil and a non-amino-silicone oil;
(b) an aqueous dispersion compartment including:
(i) aqueous medium;
(ii) sub-micronic particles including, or made of, a hydrophilic polymeric material having neutralized acid moieties, disposed within the aqueous medium, and optionally (iii) a thickening agent; and
(d) a metallic pigment compartment including:
(i) at least one metallic pigment; and
(ii) a surfactant.

The methods, compositions and kits according to the present teachings advantageously color the fibers, including natural and synthetic keratinous ones such as mammalian hair, by providing a coating of pigment on the outer surface of the fiber, with minimal or no penetration of the pigment into the interior of the fiber, such as the hair shaft, thus reducing adverse effects and health concerns typically associated with penetration of conventional chemical compounds, which may lead to hair breakage or brittleness.

The methods, compositions and kits disclosed herein, in at least some embodiments, may provide coloring which is permanent i.e. wash resistant, using conventional, over-the-counter shampoos, after at least 30 washes, at least 50 washes, or even after at least 100 washes, as determined by optical density measurements using yak hair or human hair (e.g., Chinese or European hair). A coloring is shampoo-resistant if the OD measured after shampooing is not below 80% of the baseline OD as measured following coloring, before any shampooing. A decrease in OD, with respect to a reference OD, is at most 20%, at most 15%, at most 10%, at most 7%, at most 5%, at most 3%, or at most 1%. Typically, wash-resistance is assessed once the applied coating is deemed substantially cured. In some embodiments, at a relative humidity of 30% to 50%, and at a temperature of 23° C., the at least partially cured film achieves permanence within 24 to 96 hours after the applying of the oil-in-water emulsion on the hair, and optionally, within 24 to 72 hours, within 24 to 48 hours, within 24 to 36 hours, or within 24 to 30 hours.

In some embodiments, the resistance to shampooing is achieved with cationic shampoos. In some embodiments, the cationic shampoo has a high charge density. In some embodiments, cationic shampoos comprise cationic guar gum, optionally having charge density of from about 0.8 to about 7 meq/g and a molecular weight (MW) of from about 5000 to about 10 million. When used in connection with polymers (including pre-polymers) which may be supplied as populations of mildly diverging molecules (e.g., having a slightly different number of repeating units, such as siloxane units for some silicone pre-polymers), the term molecular weight relates to the weighted or weight average MW, unless indicated otherwise by the supplier. The weight average MW can be measured by gel permeation chromatography.

Removal of Coating or Coloring Film

In some embodiments, the coloring is reversible (also referred to as decoloring), and the coloring or coating films can be removed by use of a removal solution or removal formulation, comprising a solvent and optionally a decuring agent.

Such decoloring is believed to be triggered by the decuring of the at least partially cured amino-silicone film formed by the amino-silicone coating on the surface of the keratinous fibers. Without wishing to be bound by any particular theory, the decuring is believed to loosen the bonds formed between the amino-silicone units constituting the cured film and/or its attachment to the fibers. In some embodiments, the decoloring of the fibers colored according to the present teachings is achieved by applying a removal formulation optionally including a decuring agent in an amount sufficient to at least partially decure the cured pigmented film so as to detach it from the fibers by subsequent rinsing.

According to an aspect of the present disclosure there is provided a method of removing a film formed of the coating or coloring compositions as herein described from a plurality of individual hair fibers, the method comprising: (a) applying, on an external surface of the individual hair fibers, at a temperature within a range of 15° C. to 45° C., a removal formulation comprising at least one solvent selected from: i) dipolar aprotic solvents; ii) polar aprotic solvents; iii) protic solvents; and ii) non-polar aprotic solvents; (b) applying, and optionally rubbing, the removal formulation against the external surface of the individual hair fibers; and (c) rinsing the individual hair fibers with an aqueous finishing rinse, to remove at least a portion of the removal formulation from the individual hair fibers.

In some embodiments, the removal formulation further contains at least one decuring agent. Such combinations of decuring agents may result in additive or synergistic effects further facilitating or accelerating the removal of the cured films from the keratinous fibers. The decuring agent is selected from the group including 1) fluoride salts (including but not limited to tetra butyl ammonium fluoride (TBAF) and RonaCare® Olaflur); and 2) organic and inorganic bases and salts thereof (including but not limited to tetra butyl ammonium bromide (TBAB), tetra butyl ammonium chloride (TBAC), tetra butyl ammonium hydroxide (TBAH), potassium hydroxide (KOH) and potassium tert-butoxide ($K(CH_3)_3CO$)). In some embodiments, TBAB or TBAC are used in combination with an inorganic base, and in particular embodiments the additional base can be KOH, NaOH, LiOH, $Mg(OH)_2$, or $Ca(OH)_2$. In one embodiment, the decuring agent can be formed by combining an organic salt (e.g., hydroxyethyl cetyldimonium phosphate, such as commercialized by BASF under tradename Luviquat® Mono CP AT1) and an inorganic base (e.g., magnesium hydroxide).

In some embodiments, the removal formulation is prepared by dispersing or dissolving the decuring agent(s) in a solvent which can be an aqueous solvent which may optionally further comprise one or more water-miscible co-solvents and/or one or more dispersants. Alternatively, the solvent can be an organic solvent optionally comprising one or more dispersants.

In some embodiments, the decuring agent is present in the solvent of the removal formulation in an amount of at least 0.1 wt. %, or at least 1 wt. %, or at least 5 wt. %, or at least 10 wt. %, and optionally at most 20 wt. % or at most 15 wt. % of the weight of the removal formulation.

Fluoride salts which can serve as decuring agents include, but are not limited to, tetra butyl ammonium fluoride (TBAF), RonaCare® Olaflur, ammonium fluoride, octadecenyl-ammonium fluoride, 3-(N-hexadecyl-N-2-hydroxyethylammonio) propylbis (2-hydroxyethyl) ammonium difluoride, ammonium monofluoro-phosphate, calcium fluoride, calcium monofluorophosphate, magnesium fluoride, potassium monofluorophosphate, sodium fluoride, sodium monofluorophosphate, N,N',N'-tris(polyoxyethylene)-N-hexadecyl-propylenediamine dihydrofluoride, and nicomethanol hydrofluoride.

In some embodiments, fluoride salts decuring agents of group 1) described above can be dispersed or dissolved in dipolar aprotic solvents, having high polarity and low reactivity. Suitable dipolar aprotic solvents can be selected from the group comprising acetonitrile (ACN), propionitrile, N-octyl pyrrolidone (NOP) and dimethyl sulfoxide (DMSO).

When the silicone decuring agent is a fluoride salt or a mixture of fluoride salts, a suitable amount can be expressed in terms of fluoride content per total weight of the removal formulation. In such embodiments, a fluoride content of the agent is in an amount of at least 0.01 wt. % and of at most 1 wt. %, per weight of the removal formulation.

In some embodiments, organic bases decuring agents of group 2) described above can be dispersed or dissolved in polar aprotic solvents, containing a polar group. Suitable polar aprotic solvents can be selected from the group comprising methyl isobutyl ketone (MIBK), methyl phenyl ester (MPE), tetrahydrofuran (THF), 1,4 dioxane, anisole and ethyl hexyl stearate.

Alternatively, decuring agents selected from organic bases and inorganic bases of group 2) described above, as well as their combinations, can be dispersed or dissolved in protic solvents containing a labile $H^+$ that can be readily donated. Suitable protic solvents can be selected from the group comprising of water, primary, secondary and tertiary $C_1$-$C_6$ alcohols, including glycerol, butanol, isopropanol, cyclohexanol and $C_4$-$C_{16}$ fatty alcohols, including tert-butyl alcohol and myristyl alcohol.

When the decuring agent is an organic or inorganic base, or a salt thereof, or a blend of the foregoing base and salt, the agent or mixture of decuring agents can be suitably present in an amount of at least 0.1 wt. % and of at most 20 wt. % or at most 15 wt. %, per total weight of the removal formulation, or in the range of 0.5-10 wt. % or in the range of 0.5-5 wt. %.

The decoloring or color removal formulation is applied for a time period sufficient to at least partially decure the cured film, the application of the decuring agent for a sufficient time being followed by rinsing away the decured silicone with an aqueous rinse. The amount of time that may suffice to decure enough of the film so as to permit its removal may depend, among other things, on the concentration of the decuring agent, the viscosity of the removal formulation, the temperature of the decoloring process, the type of the keratinous fibers, the thickness of the cured film, the relative humidity, and any such factors readily appreciated by the skilled person.

In some embodiments, the removal formulation is applied at a temperature in the range of at least ambient temperature of at least 18° C. to at most 40° C., at most 38° C., at most 36° C., at most 34° C., or at most 32° C. In the experimental section herein, ambient temperature, unless otherwise indicated, generally refers to about 23° C. Ambient relative humidity (RH), unless controlled, hence otherwise indicated, is between about 30% RH and about 80% RH. Ambient pressure is typically of about 1 atmosphere.

In some embodiments, the removal formulation is applied to the fibers for at least 1 minute, or at least 5 minutes, or at least 10 minutes, or at least 15 minutes; and optionally, at most 30 minutes. In some embodiments, the removal formulation is applied for a time period between 1 minute and 30 minutes, 2 minutes and 20 minutes or 5 minutes and 10 minutes.

In some embodiments, the removal formulation further comprises water in addition to the at least one solvent. In such embodiments, the weight per weight ratio of the water to the organic solvent(s) is typically in the range of 1:9 to 9:1. If water is added so as to constitute 50 wt. % or more of the removal formulation, the latter can be called an aqueous removal formulation, as opposed to an organic removal formulation in a contrary situation (<50 wt. % of water, including devoid of water). It is to be noted that while the addition of water may increase compliance, it may also prolong the duration of the removal process.

In some embodiments, the viscosity of the removal formulation is sufficient for the removal formulation to coat the fibers and remain thereon for a duration of time enabling the partial decuring, hence the subsequent film removal and decoloring of the fibers. In some embodiments, this viscosity is achieved by further adding to the decuring agent in its solvent, a thickening agent in an amount sufficient to provide the viscosity.

Following the application of the removal formulation for a sufficient amount of time, the fibers are thoroughly washed with an aqueous rinsing agent, the last rinsing being optionally followed by shampooing of the fibers with a shampoo.

In some embodiments, the removal formulation further contains a thickening agent, and optionally any other additive conventionally used in the preparation of creamy cosmetic compositions, in particular as applicable to hair.

The removal from the hair fibers of the films formed according to the present disclosure can be performed at any desired time point after coating or coloration (e.g., within days, within weeks or within months from application).

For instance, conventional permanent coloring methods usually require specific coloration to be reapplied within a few weeks from an initial coloration, coloring then only the region of the newly grown hair near the hair roots. As the present method allows, in some embodiments, for a rapid and non-damaging removal of a coloring film according to the present disclosure, the hair could be advantageously decolored (and if desired recolored) in its entirety, providing for an even coloring of the hair fibers from roots to tips.

In some embodiments, no bleaching is needed during the coloring process. In some embodiments, the compositions according to the present teachings are substantially devoid of bleaching agents. Bleaching agents traditionally include at least oxidizing agent chosen from persulfates, perborates, percarbonates, peracids, bromates, their salts and mixtures thereof, which can be optionally applied with hydrogen peroxide, all generally in an amount of at least 10% by weight of a bleaching composition. As used herein, a composition is substantially devoid of bleaching agent(s), if such agent (or mixture thereof) is to be found at 1 wt. % or less of the composition, or at less than 0.5 wt. %, or at less than 0.1 wt. %.

In some embodiments, subsequent coloration requires coloration only of the hair roots.

The compositions disclosed herein, in at least some embodiments, show improved resistance to discoloration by external agents and factors, as compared to known coloring agents. In some embodiments, the cured pigmented films can resist fading when exposed to light (e.g., maintaining original color for longer periods of time when exposed to sun radiation), and the compositions are said in such cases to have or provide good lightfastness. In some embodiments, the cured pigmented films can resist bleaching, and the compositions are said in such cases to have or provide good chemical resistance, bleach being a relatively harsh agent deemed predictive of resistivity to milder chemical exposures, such as encountered for example in polluted environments or at a swimming pool.

The compositions disclosed herein, in at least some embodiments, provide improved aesthetic properties of keratinous fibers, such as improved appearance, increased volume, softness, smoothness and shine.

The term "condensation-curable amino-functional silicone" (also referred to herein as "reactive condensation-curable amino-functional silicone pre-polymer" and other such variants, in accordance with the present disclosure, refers to an organosilicon pre-polymer which contains at least two silanol groups or two hydrolysable reactive groups, like alkoxy groups, which upon hydrolysis form silanol groups, and at least one carbon bonded amine group in its molecule, the alkoxy radicals, when present, each independently having 1-6 or 1-4 carbon atoms.

According to a further aspect, there is disclosed a coloring composition for forming a pigmented coating on an external surface of individual hairs of mammalian hair comprising:
1) an oil-in-water emulsion comprising:
(A) an aqueous phase containing water; and
(B) an oil phase including at least one reactive condensation-curable film-forming amino-silicone reactant;
wherein the oil phase fulfills at least one of the following:
(i) the at least one reactive condensation-curable film-forming amino-silicone reactant includes at least one reactive condensation-curable film-forming amino-silicone monomer having a molecular weight of at most 1000 g/mol;
(ii) the oil phase further contains a non-amino cross-linking agent adapted or selected to cure the reactant, the non-amino cross-linking agent having a molecular weight of at most 1000 g/mol;
(iii) the oil phase further optionally contains a plurality of sub-micronic pigment particles dispersed in the oil phase, in presence of a pigment dispersant; wherein the at least one reactive condensation-curable film-forming amino-silicone reactant has a solubility in water of less than 1% by weight at 23° C.; wherein the plurality of optional sub-micronic pigment particles are metallic or non-metallic;
2) an aqueous dispersion comprising:
(A) a polymeric material having neutralized acid moieties; and
(B) a plurality of pigment particles, at least partially enveloped by the polymeric material, and dispersed within the aqueous dispersion.

According to a further aspect, there is disclosed a coating composition for forming a coating on an external surface of individual hairs of mammalian hair comprising:
1) an oil-in-water emulsion comprising:
(A) an aqueous phase containing water; and
(B) an oil phase including at least one reactive condensation-curable film-forming amino-silicone reactant;
wherein the oil phase fulfills at least one of the following:
(i) the at least one reactive condensation-curable film-forming amino-silicone reactant includes at least one reactive condensation-curable film-forming amino-silicone monomer having a molecular weight of at most 1000 g/mol;
(ii) the oil phase further contains a non-amino cross-linking agent adapted or selected to cure the reactant, the non-amino cross-linking agent having a molecular weight of at most 1000 g/mol;
wherein the at least one reactive condensation-curable film-forming amino-silicone reactant has a solubility in water of less than 1% by weight at 23° C.;
2) an aqueous dispersion comprising a polymeric material having neutralized acid moieties.

Clauses
Set 1
1. A method of treating an outer surface of a mammalian hair fiber, the method comprising:
(a) forming, on the outer surface of the mammalian hair fiber, an amino-silicone layer;
(b) applying, on said amino-silicone layer, an aqueous dispersion containing:
a plurality of polymeric particles, formed of a hydrophilic polymeric material having neutralized acid moieties, wherein, in each of at least a portion of said polymeric particles, said hydrophilic polymeric material envelops at least one pigment core particle,
said plurality of polymeric particles being dispersed within said aqueous dispersion;
so as to produce an overlying, pigmented polymeric layer adhering to an external surface of said amino-silicone layer.

2. A method according to clause 1, wherein said overlying, pigmented polymeric layer is a self-terminating layer.

3. A method according to clause 1 or clause 2, wherein, at a pH of said aqueous dispersion, said external surface of said amino-silicone layer has a first surface zeta potential ($\zeta_1$), and said aqueous dispersion has a second zeta potential ($\zeta_2$), wherein a zeta differential ($\Delta\zeta$) at said pH is defined as $$\Delta\zeta = \zeta_1 - \zeta_2$$

and wherein $\Delta\zeta$, in millivolts (mV), fulfills at least one of the following:
(i) $\Delta\zeta$ is at least 10, at least 15, at least 20, at least 25, at least 30, at least 40, or at least 50;
(ii) $\Delta\zeta$ is within a range of 10 to 80, 10 to 70, 10 to 60, 15 to 80, 15 to 70, 15 to 60, 20 to 80, 20 to 70, 20 to 60, 25 to 80, 25 to 70, 25 to 60, 30 to 80, 30 to 70, 30 to 60, 35 to 80, 35 to 70, or 35 to 60;
(iii) for said pH being within a range of 4 to 11, 4 to 10.5, 4 to 10, 6 to 11, 6 to 10.5, 6 to 10, 7 to 11, 7 to 10.5, or 7 to 10, said first surface zeta potential ($\zeta_1$), is greater than zero ($\zeta_1 > 0$).

4. A method according to any one of clause 1 to clause 3, wherein a conjugate acid of said hydrophilic polymeric material is a hydrophobic polymeric material.

5. A method according to clause 4, wherein acid moieties of said hydrophobic polymeric material make up at least 8%, at least 10%, at least 12%, at least 15%, at least 16%, at least 17%, at least 18%, at least 19%, at least 20%, at least 21%, or at least 22%, by weight, of said hydrophobic polymeric material, or wherein acid moieties of said hydrophilic polymeric material make up at least 8%, at least 10%, at least 12%, at least 15%, at least 16%, at least 17%, at least 18%, at least 19%, at least 20%, at least 21%, or at least 22%, by weight, of said hydrophilic polymeric material.

6. A method according to clause 4, wherein acid moieties of said hydrophobic polymeric material make up 8% to 30%, 10% to 30%, 12% to 30%, 12% to 28%, 12% to 26%, 15% to 30%, 15% to 28%, 15% to 26%, 17% to 22%, 17% to 23%, 18% to 30%, 18% to 28%, 18% to 26%, 20% to 30%, 20% to 28%, or 20% to 26%, by weight, of said hydrophobic polymeric material, or wherein acid moieties of said hydrophilic polymeric material make up 8% to 30%, 10% to 30%, 12% to 30%, 12% to 28%, 12% to 26%, 15% to 30%, 15% to 28%, 15% to 26%, 17% to 22%, 17% to 23%, 18% to 30%, 18% to 28%, 18% to 26%, 20% to 30%, 20% to 28%, or 20% to 26%, by weight, of said hydrophilic polymeric material.

7. A method according to any one of clause 1 to clause 6, wherein said aqueous dispersion contains a volatile base.

8. A method according to clause 7, wherein said volatile base is selected from the group of ammonia ($NH_3$), monoethanolamine, diethanolamine, triethanolamine and morpholine.

9. A method according to clause 7 or clause 8, further comprising volatizing said volatile base associated with said overlying, pigmented polymeric layer, so as to acidify, largely or mainly acidify, or completely acidify said neutralized acid moieties.

10. A method according to any one of clause 1 to clause 8, further comprising converting a portion of, a major portion of, or all of said hydrophilic polymeric material in said overlying, pigmented polymeric layer, into a conjugate acid thereof.

11. A method according to clause 10, wherein said converting includes, mainly includes, or consists of acidifying said neutralized acid moieties to form said conjugate acid.

12. A method according to any one of clause 1 to clause 9, further comprising sufficiently converting said hydrophilic polymeric material into a conjugate acid thereof, so as to obtain a hydrophobic polymeric material.

13. A method of any one of clause 1 to clause 12, wherein said polymeric material having said neutralized acid moieties includes, mainly includes, consists essentially of, or consists of one or more neutralized copolymer selected from the group consisting of neutralized alkene-acrylic acid copolymer, neutralized alkene-methacrylic acid copolymer and neutralized acrylamide/acrylate copolymer.

14. A method of clause 13, wherein said neutralized alkene-acrylic acid copolymer includes, mainly includes, consists essentially of, or consists of neutralized ethylene-acrylic acid (EAA) copolymer.

15. A method of clause 13, wherein said neutralized alkene-methacrylic acid copolymer includes, mainly includes, consists essentially of, or consists of neutralized ethylene-methacrylic acid (EMAA) copolymer.

16. A method of any one of clauses 1 to 13, wherein said polymeric material having said neutralized acid moieties includes, mainly includes, consists essentially of, or consists of neutralized acrylamide/acrylate (AAA) copolymer.

17. A method of any one clauses 1 to 16, wherein the mammalian hair fiber is a plurality of mammalian hair fibers, the method further comprising, subsequent to said applying of said aqueous dispersion, treating said overlying pigmented polymeric layer of each of the plurality of fibers, so as to produce an overlying, pigmented polymeric coating adhering to said external surface of said amino-silicone layer of each of the fibers.

18. A method of clause 17, wherein said overlying, pigmented polymeric coating is a hydrophobic polymeric coating.

19. A method of clause 17 or clause 18, wherein said treating includes washing and/or combing the plurality of fibers to remove excess material therefrom, and optionally, subsequently drying and/or combing the plurality of fibers.

20. A method of clause 17 or clause 18, wherein said treating includes drying and/or combing the plurality of fibers, and optionally, prior to said drying, washing the plurality of fibers to remove excess material therefrom.

21. A method of clause 19 or clause 20, wherein said washing the plurality of fibers and/or said drying and/or said combing the plurality of fibers is performed at a temperature of at most 45° C., 40° C., 35° C., 30° C., or 25° C., and optionally, at a temperature of at least 5° C., 10° C., 12° C., 15° C., 17° C., or 20° C., and further optionally, within 7° C., 5° C. or 3° C. of room or ambient temperature.

22. A method of any one of clause 19 to clause 21, wherein said washing the plurality of fibers is performed within at most 20 minutes, at most 10 minutes, at most 5 minutes, at most 3 minutes, at most 2 minutes, at most 1 minute, or at most 30 seconds after completing said applying of said aqueous dispersion.

23. A method of any one of clause 19 to clause 22, wherein, when said washing is performed 1 minute after completing said applying of said aqueous dispersion, sufficient attachment of said overlying polymeric layer to said external surface of said amino-silicone layer is attained, such that a decrease in optical density (OD), with respect to a reference OD, is at most 15%, at most 10%, at most 7%, at most 5%, at most 3%, or at most 1%.

24. A method of any one of clause 19 to clause 23, wherein said drying is an active drying, and wherein a total time period of said applying of said aqueous dispersion and said washing and/or said active drying is within a range of 2 to 90 minutes, 2 to 75 minutes, 2 to 60 minutes, 2 to 45 minutes, 2 to 30 minutes, 2 to 20 minutes, 2 to 10 minutes, or 2 to 5 minutes, and optionally, at most 7 minutes, at most 4 minutes, at most 3 minutes, or at most 1.5 minutes.

25. A method of clause 24, wherein, within 24 to 96 hours, within 24 to 72 hours, within 24 to 48 hours, within 24 to 36 hours, or within 24 to 30 hours immediately succeeding said total time period, with the plurality of fibers being maintained within 7° C., 5° C., 3° C., or 1° C. of room or ambient temperature, said overlying, pigmented polymeric coating achieves wash resistance, permanence, or permanent coloration.

26. A method of any one of clause 1 to clause 25, wherein, at a pH within a range of 7.5 to 11, said hydrophilic polymeric material is self-dispersible in water, in an absence of dispersants and all other additives in water.

27. A method of any one of clause 1 to clause 26, wherein said hydrophilic polymeric material is thermoplastic.

28. A method of any one of clause 1 to clause 27, wherein said hydrophilic polymeric material has a solubility of at least 2%, at least 5%, at least 10%, or at least 15%, by weight, at a pH of 10.

29. A method of any one of clause 1 to clause 27, wherein said hydrophilic polymeric material has a solubility within a range of 2 to 30%, 5 to 30%, 10 to 30%, or 15 to 30%, by weight, at a pH of 10.

30. A method of any one of clause 1 to clause 29, wherein at least one of said overlying pigmented polymeric layer and said overlying, pigmented polymeric coating is washed with a cationic rinsing liquid.

31. A method of any one of clauses 1 to 30, further comprising applying, on said overlying, pigmented polymeric coating, an oil-in-water amino-silicone emulsion, to produce an at least partially cured second amino-silicone layer, optionally washed, said at least partially cured second amino-silicone layer enveloping said overlying pigmented polymeric coating and attached thereto.

32. A method of clause 31, further comprising applying on said at least partially cured second amino-silicone layer, an aqueous dispersion, optionally pigmentless, according to at least one of clauses 1 to 30.

33. A method of any one of clauses 1 to 32, wherein a pigment in said overlying, pigmented polymeric layer or coating includes metallic pigment flakes containing, coated with, consisting essentially of, or made of metals, alloys and oxides thereof, said pigment flakes being selected from the group comprising aluminum flakes, brass flakes, bronze flakes, copper flakes, gold flakes, mica coated flakes, silica coated flakes and silver flakes.

34. A method of clause 33, wherein at least one of the oil-in-water emulsion and/or the aqueous dispersion including said metallic pigment flakes further comprises an antioxidant.

35. A method of clause 33 or clause 34, wherein said metallic pigment flakes serve to form a hair masking coating, the method further comprising repeating at least step (b) of clause 1, the aqueous dispersion of repeated step (b) comprising pigment particles other than metallic pigment flakes.

36. A method of any one of clauses 1 to 35, wherein said aqueous dispersion is produced by:

mixing, in an aqueous carrier containing water, at least one hydrophobic polymeric material, each independently having neutralizable acid moieties, the hydrophobic polymeric material being optionally compounded with a pigment, so as to form a neutralizable mixture including pellets of the hydrophobic polymeric material;

adding to the neutralizable mixture a neutralizing agent, said addition being performed under agitation at a temperature above at least one of the highest of the softening temperature and of the melting temperature of the at least one hydrophobic polymeric material, said neutralizing agent being added in an amount sufficient to neutralize at least 75% of the neutralizable acid moieties of said polymeric material, so as to form a neutralized mixture including a portion of hydrophilic polymeric material; and dispersing the neutralized mixture, so as to form said aqueous dispersion, the aqueous dispersion including particles of at least one hydrophilic polymeric material.

37. A method of any one of clauses 1 to 36, wherein said forming includes:
(a) applying, on an external surface of individual hairs of the mammalian hair, an oil-in-water emulsion comprising:
  (A) an aqueous phase containing water; and
  (B) an oil phase containing at least one reactive condensation-curable film-forming amino-silicone pre-polymer that, subsequent to condensation curing, forms an elastomer;
  wherein said oil phase fulfills at least one of the following:
  (i) said at least one reactive condensation-curable film-forming amino-silicone pre-polymer includes at least one reactive condensation-curable film-forming amino-silicone monomer having a molecular weight of at most 1000 g/mole;
  (ii) said oil phase further contains a non-amino cross-linking agent adapted or selected to cure said pre-polymer, said non-amino cross-linking agent having a molecular weight in the range of at most 1000 g/mole;
  wherein said at least one reactive condensation-curable film-forming amino-silicone pre-polymer has a solubility in water of less than 1% by weight at 23° C.;
(b) after partial condensation curing of said pre-polymer has occurred so as to form an at least partially cured film on the external surface of the individual hairs, washing the hair with a rinsing liquid to remove any excess of said oil-in-water emulsion.

38. A method according to clause 37, wherein a first amino-silicone pre-polymer of said at least one reactive condensation-curable film-forming amino-silicone pre-polymer has at least 3 silanol and/or hydrolysable groups, so as to form a 3-dimensional network.

39. A method according to clause 38, wherein a first concentration of said first amino-silicone pre-polymer, within said oil phase, is at least 15%, at least 20%, at least 30%, at least 40%, at least 50%, or at least 60%, by weight, of said oil phase.

40. A method according to clause 39, wherein said first concentration is at most 95%, at most 90%, at most 85%, at most 80%, at most 75%, or at most 70%.

41. A method according to clause 39, wherein said first concentration is within a range of 20-95%, 20-85%, 30-95%, 30-85%, 40-95%, 40-85%, 40-75%, 45-95%, 45-85%, 50-95%, 50-85%, 55-95%, 55-85%, 55-75%, 60-95%, 60-90%, 60-85%, or 60-80%.

42. A method according to clause 38, wherein a combined concentration of said first amino-silicone pre-polymer and said non-amino cross-linking agent, within said oil phase, is within a range of 35-95%, 40-95%, 40-85%, 40-75%, 45-95%, 45-85%, 50-95%, 50-85%, 55-95%, 55-85%, 55-75%, 60-95%, 60-90%, 60-85%, or 60-80%, by weight, of said oil phase.

43. A method according to clause 42, wherein a concentration of said non-amino cross-linking agent within said combined concentration is limited by a condition that said oil-in-water emulsion has a surface zeta potential greater than zero (>0), or at least +1 mV, at least +2 mV, at least +3 mV, at least +5 mV, at least +7 mV, or at least +10 mV.

44. A method according to any one of clause 37 to clause 41, wherein within said oil phase, a total concentration of said amino-silicone oil, said non-amino-silicone oil, and said at least one reactive condensation-curable film-forming amino-silicone pre-polymer, excluding said first amino-silicone pre-polymer, is within a range of 3% to 65%, 3% to 60%, 3% to 55%, 3% to 50%, 3% to 45%, 3% to 40%, 7% to 40%, 10% to 40%, 10% to 50%, 15% to 50%, 15% to 45%, 15% to 40%, 20% to 45%, 25% to 45%, 25% to 50%, 30% to 45%, 30% to 60%, 35% to 50%, or 35% to 60%, by weight; and optionally subject to said oil phase having a viscosity of no more than 500 mPa·s, as measured at 25° C.

45. A method according to any one of clause 37 to clause 44, wherein a concentration of a terminating pre-polymer having a single silanol or hydrolysable group, within said oil phase, is at most 7%, at most 5%, at most 2%, by weight of the oil phase, or wherein said oil phase is devoid of said terminating pre-polymer.

46. A method according to any one of clause 37 to clause 45, wherein a total concentration of organic solvent within said oil phase, on a weight basis, is at most 10%, at most 5%, at most 2%, or at most 1%, or wherein said oil phase is devoid of any organic solvent.

47. A method according to any one of clause 37 to clause 46, wherein a total concentration of co-solvent within said aqueous phase, on a weight basis, is at most 10%, at most 5%, at most 2%, or at most 1%, or wherein said aqueous phase is devoid of any said co-solvent.

48. A method according to any one of clause 37 to clause 47, said oil-in-water emulsion further comprising a solid, hydrophobic reactive inorganic filler, said filler disposed or dispersed within said oil phase, said filler selected or adapted to facilitate curing of said condensation-curable film-forming amino-silicone pre-polymer.

49. A method according to clause 48, wherein said reactive filler includes, mainly includes, or consists of, a hydrophobic fumed silica.

50. A method according to clause 48 or clause 49, wherein an average particle size (Dv50) of said solid, hydrophobic reactive inorganic filler is within a range of 5 to 500 nm, 5 to 250 nm, 20 to 200 nm, 40 to 300 nm, 60 to 300 nm, 60 to 250 nm, or 60 to 200 nm.

51. A method according to any one of clause 48 to clause 50, wherein a concentration of said solid, hydrophobic reactive inorganic filler disposed or dispersed within said oil phase is within a range of 0.2% to 12%, 0.2 to 10%, 0.2 to 8%, 0.4 to 10%, 0.4 to 8%, 0.6 to 10%, 0.6 to 8%, 0.8 to 8%, or 0.8 to 6%, by weight.

52. A method according to clause 51, wherein a concentration of said solid, hydrophobic reactive inorganic filler within said oil-in-water emulsion is within a range of 0.005% to 0.5%, 0.005% to 0.3%, by weight.

53. A method according to any one of clause 49 to clause 52, wherein a refractive index of said solid, hydrophobic reactive inorganic filler, optionally fumed silica, is within a range of 10%, 7%, 5%, or 3%, of a refractive index of said oil phase, exclusive of any pigment particles disposed therein.

54. A method according to any one of clause 37 to clause 53, wherein said at least partially cured film is self-terminated on the external surface of the individual hairs.

55. A method according to any one of clause 37 to clause 54, wherein said at least one reactive condensation-curable film-forming amino-silicone pre-polymer includes a reactive condensation-curable amino-silicone monomer having a solubility in water of less than 1% by weight at 25° C.

56. A method according to any one of clause 37 to clause 55, wherein said partial condensation curing is effected at a temperature of at most 38° C., at most 36° C., at most 34° C., or at most 32° C., and optionally, at least 15° C.

57. A method according to any one of clause 37 to clause 56, wherein said washing is performed within 30 minutes, within 20 minutes, within 15 minutes, within 10 minutes, within 5 minutes, within 3 minutes, within 2 minutes, or within 1 minute, after said applying of said oil-in-water emulsion has been completed.

58. A method according to any one of clause 37 to clause 57, wherein following said washing, further curing transpires solely by or substantially solely by humidity or ambient humidity.

59. A method according to any one of clause 37 to clause 58, wherein within at least two days, at least three days, at least five days, or at least a week of said washing, all further curing proceeds in the absence of any non-cationic surfactant added to the hair.

60. A method according to any one of clause 37 to clause 59, further comprising, within at least two days, at least three days, at least five days, or at least a week of said washing, treating the hair with a hair formulation containing a cationic surfactant.

61. A method according to any one of clause 37 to clause 60, wherein said oil-in-water emulsion has a surface zeta potential greater than zero, or of at least +1 mV, at least +2 mV, at least +3 mV, at least +5 mV, at least +7 mV, at least +10 mV, at least +15 mV, at least +20 mV, at least +30 mV, at least +40 mV, or at least +60 mV; optionally, of at most +100 mV, or at most +80 mV.

62. A method according to any one of clause 37 to clause 60, wherein said oil-in-water emulsion has a surface zeta potential greater than zero and below 90 mV, or within a range of 1-50 mV, 1-30 mV, 1-20 mV, 1-15 mV, 2-100 mV, 2-30 mV, 3-100 mV, 3-50 mV, 3-30 mV, 3-20 mV, 5-100 mV, 5-50 mV, 5-30 mV, 5-20 mV, 7-100 mV, 10-80 mV, 15-80 mV, 20-80 mV, or 20-60 mV.

63. A method according to clause 61 or clause 62, wherein said surface zeta potential is measured at a pH of 9.

64. A method according to clause 61 or clause 62, wherein said surface zeta potential is measured at a native pH of said oil-in-water emulsion.

65. A method according to any one of clause 37 to clause 64, wherein said rinsing liquid is (i) water, or (ii) a cationic rinsing liquid containing a cationic surfactant, or (iii) a rinsing liquid devoid of non-cationic surfactants, degreasing agents and/or swelling agents, the degreasing and swelling agent respectively able to degrease and swell the at least partially cured film.

66. A method according to clause 60 or clause 65, wherein said cationic surfactant is a cosmetically-acceptable primary, secondary, tertiary, or quaternary ammonium compound or polymer.

67. A method according to any one of clause 37 to clause 66, wherein a total concentration of reactive condensation-curable amino-silicone components within said oil phase is at least 45%, at least 55%, at least 60%, or at least 65%, by weight, on a pigmentless basis, and optionally, within a range of 50-100%, 50-95%, 50-90%, 50-85%, 50-80%, 55-95%, 55-85%, 60-95%, 60-85%, 65-95%, 65-90%, or 70-95%.

68. A method according to any one of clause 37 to clause 67, wherein said pre-polymer includes reactive groups selected from the group of alkoxy-silane reactive groups, silanol reactive groups and combinations thereof.

69. A method according to any one of clause 37 to clause 68, wherein said oil phase, exclusive of all inorganic content, has no glass transition temperature.

70. A method according to any one of clause 37 to clause 69, wherein said at least one reactive condensation-curable film-forming amino-silicone pre-polymer is a liquid at 25° C.

71. A method according to any one of clause 37 to clause 70, wherein a viscosity of said at least one reactive condensation-curable film-forming amino-silicone pre-polymer, measured in a suitable rheometer at 25° C., is in a range of 1-2000 milliPascal-second (mPa·s), 2-1000 mPa·s, 2-500 mPa·s, 2-300 mPa·s, 2-200 mPa·s, 5-1000 mPa·s, 5-500 mPa·s, 5-300 mPa·s, 7-500 mPa·s, 7-300 mPa·s, or 7-200 mPa·s.

72. A method according to any one of clause 37 to clause 71, wherein at least one of, and optionally all of said at least one reactive condensation-curable film-forming amino-silicone pre-polymer, and further optionally, said oil phase, has an Amine Number or weight average Amine Number in a range of 3-1000, 3-500 or 3-200.

73. A method according to any one of clause 37 to clause 72, wherein said solubility in water of said at least one reactive condensation-curable film-forming amino-silicone pre-polymer, by weight, is less than 0.5% or less than 0.25%.

74. A method according to any one of clause 37 to clause 73, wherein a total concentration of amino-silicone oil within said oil phase, by weight, is at most 40%, at most 35%, at most 30%, at most 20%, at most 15%, at most 10%, or at most 5%.

75. A method according to any one of clause 37 to clause 73, wherein a total concentration of amino-silicone oil within said oil phase, by weight, is within a range of 1% to 40%, 5% to 40%, 10% to 40%, 20% to 40%, 1% to 30%, 5% to 30%, 10% to 30%, 15% to 30%, 20% to 35%, or 20% to 30%.

76. A method according to any one of clause 37 to clause 75, wherein a total concentration of non-amino-silicone oil within said oil phase, by weight, is at most 15%, at most 12%, at most 10%, at most 7%, or at most 5%, subject to a surface zeta potential of said oil-in-water emulsion being greater than zero, or at least +1 mV, at least +2 mV, at least +3 mV, at least +5 mV, at least +7 mV, or at least +10 mV.

77. A method according to any one of clause 37 to clause 75, wherein a total concentration of non-amino-silicone oil within said oil phase, by weight, is within a range of 1% to 15%, 3% to 15%, 5% to 15%, 8% to 15%, 1% to 12%, 3% to 12%, 5% to 12%, 3% to 10%, 3% to 8%, or 2% to 5%.

78. A method according to any one of clause 37 to clause 77, wherein said non-amino cross-linking agent includes, mainly includes, or consists of a reactive condensation-curable film-forming non-amino-silicone monomer.

79. A method according to any one of clause 37 to clause 78, wherein said non-amino cross-linking agent includes, mainly includes, or consists of an ethyl silicate, a poly (dimethoxysiloxane), and a poly(diethoxysiloxane).

80. A method according to any one of clause 37 to clause 79, wherein a total concentration of said non-amino cross-linking agent within said oil phase is at most 35%, at most 30%, at most 20%, at most 15%, at most 10%, or at most 5%, subject to a surface zeta potential of said oil-in-water emulsion being greater than zero, or at least +1 mV, at least +2 mV, at least +3 mV, at least +5 mV, at least +7 mV, or at least +10 mV.

81. A method according to any one of clause 37 to clause 80, wherein a total concentration of said pre-polymer, said non-amino cross-linking agent, said solid, hydrophobic reactive inorganic filler, said amino-silicone oil and said non-amino-silicone oil, including any pigment particles and dispersant for said pigment particles, within said oil phase, is at least 90%, at least 93%, at least 95%, at least 97%, at least 98%, or at least 95%, by weight.

82. A method according to any one of clause 37 to clause 81, said aqueous phase further containing an oil-in-water emulsifier that is optionally non-ionic, said oil-in-water emulsifier having an HLB number within a range of 12 to 18, 12 to 17, 12 to 16, 12 to 15, or 13 to 16.

83. A method according to any one of clause 37 to clause 82, wherein a total concentration of said water and any emulsifier, within said aqueous phase, is at least 90%, at least 95%, at least 97% at least 99%, on a weight basis.

84. A method according to any one of clause 37 to clause 83, wherein the mammalian hair to which said oil-in-water emulsion is applied is dry or non-wetted mammalian hair, or to pre-dyed hair.

85. A method according to any one of clause 37 to clause 84, wherein the mammalian hair to which said oil-in-water emulsion is applied is at least one of unpre-degreased, unpre-shampooed, and unpre-bleached.

86. A method according to any one of clause 37 to clause 85, said oil phase further containing a pigment, optionally as a plurality of sub-micronic pigment particles.

87. A method according to clause 86, said oil-in-water emulsion further containing a dispersant, said sub-micronic pigment particles being dispersed within said dispersant.

88. A method according to clause 86, said pigment including a plurality of metallic pigment particles.

89. A method according to clause 88, wherein said plurality of metallic pigment particles include metal flakes.

90. A method according to any one of clause 37 to clause 89, wherein said aqueous phase contains, by weight, at most 20%, at most 10%, at most 5%, or at most 2%, of the amount of said pigment within said oil phase, or wherein said aqueous phase is devoid of said pigment.

91. A method according to any one of clause 37 to clause 90, wherein, at a relative humidity of 30% to 50%, and at a temperature of 25° C., said at least partially cured film achieves permanence within 24 to 96 hours after said applying of said oil-in-water emulsion on the hair, and optionally, within 24 to 72 hours, within 24 to 48 hours, within 24 to 36 hours, or within 24 to 30 hours.

92. A method according to any one of clause 1 to clause 91, wherein a total concentration of pigment particles in said aqueous dispersion is at least 0.1%, at least 0.5%, at least 1%, at least 3%, at least 5%, at least 10%, at least 15%, or at least 20%, and optionally, at most 30%, at most 27%, or at most 25%, and further optionally, within a range of 0.1% to 30%, 0.5% to 27%, 0.5% to 25%, 2% to 25%, 3% to 25%, 5% to 25%, 7% to 25%, 10% to 25%, 7% to 22%, or 10% to 22% by weight of the polymeric material in said aqueous dispersion.

93. A method according to any one of clause 1 to clause 92, wherein a total concentration of pigment particles in said oil phase is at least 0.1%, at least 0.5%, at least 1%, at least 3%, at least 5%, at least 10%, or at least 12%, and optionally, at most 20%, at most 17%, or at most 15%, or at most 12%, and further optionally, within a range of 0.1% to 20%, 0.5% to 15%, 0.5% to 15%, 3% to 15%, 5% to 15%, 3% to 12%, or 3% to 10% by weight of said oil phase.

94. A method according to any one of clause 1 to clause 93, wherein a thickness, average thickness, or multiple-fiber average thickness of said amino-silicone layer, after curing, is at least 20 nm, at least 50 nm, or at least 100 nm, and optionally, at most 3000 nm, at most 2000 nm, at most 1200 nm, at most 800 nm, at most 500 nm, at most 400 nm, at most 300 nm, at most 200 nm, at most 150 nm, or at most 120 nm, and further optionally, within a range of 20 nm to 3000 nm, 20 nm to 1000 nm, 20 nm to 500 nm, 20 nm to 300 nm, 20 nm to 200 nm, 20 nm to 150 nm, 50 nm to 150 nm, 50 nm to 500 nm, 50 nm to 350 nm, 50 nm to 250 nm, or 50 nm to 200 nm.

95. A method according to clause 94, wherein a first total thickness, first total average thickness, or first total multiple-fiber average thickness of said amino-silicone layer and said overlying pigmented polymeric layer, or a second total thickness, second total average thickness, or second total multiple-fiber average thickness of said amino-silicone layer and said overlying, pigmented polymeric coating, is at least 100 nm, at least 150 nm, at least 200 nm, at least 300 nm, at least 500 nm, at least 800 nm, at least 1200 nm, or at least 2000 nm, and optionally, at most 5000 nm, at most 3500 nm, at most 2500 nm, at most 2000 nm, at most 1700 nm, or at most 1400 nm, and further optionally, within a range of 100 nm to 5000 nm, 200 nm to 3500 nm, 200 nm to 2500 nm, 200 nm to 1000 nm, 200 nm to 700 nm, 200 nm to 500 nm, 200 nm to 450 nm, or 200 nm to 400 nm.

96. A method according to clause 95, wherein a ratio of at least one of said first total thickness, said first total average thickness, and said first total multiple-fiber average thickness to said thickness, average thickness, or multiple-fiber average thickness of said amino-silicone layer, is within a range of 1.2:1 to 100:1, 1:4 to 100:1, 1:7 to 100:1, 2:1 to 100:1, 3:1 to 100:1, 4:1 to 100:1, 5:1 to 100:1, 7:1 to 100:1, 10:1 to 100:1, 2:1 to 30:1, 2:1 to 20:1, 3:1 to 30:1, 3:1 to 20:1, 5:1 to 30:1, 5:1 to 20:1, 7:1 to 30:1, 7:1 to 20:1, 10:1 to 50:1, 10:1 to 30:1, or 10:1 to 20:1.

97. A method according to clause 95, wherein a ratio of at least one of said second total thickness, said second total average thickness, and said second total multiple-fiber average thickness to said thickness, average thickness, or multiple-fiber average thickness of said amino-silicone layer, is within a range of 1.2:1 to 100:1, 1:4 to 100:1, 1:7 to 100:1, 2:1 to 100:1, 3:1 to 100:1, 4:1 to 100:1, 5:1 to 100:1, 7:1 to 100:1, 10:1 to 100:1, 2:1 to 30:1, 2:1 to 20:1, 3:1 to 30:1, 3:1 to 20:1, 5:1 to 30:1, 5:1 to 20:1, 7:1 to 30:1, 7:1 to 20:1, 10:1 to 50:1, 10:1 to 30:1, or 10:1 to 20:1.

Set 2

1. A method of treating an external coated surface of a pre-coated mammalian hair fiber having an amino-silicone coating, the method comprising:
(a) providing an aqueous dispersion containing:
    a plurality of polymeric particles, formed of a hydrophilic polymeric material having neutralized acid moieties, wherein, in each of at least a portion of said polymeric particles, said hydrophilic polymeric material envelops at least one pigment core particle,
    said plurality of polymeric particles being dispersed within said aqueous dispersion; and
(b) applying said aqueous dispersion to the external coated surface of the pre-coated mammalian hair fiber, to produce an overlying, pigmented polymeric layer adhering to the external coated surface of the pre-coated mammalian hair fiber.

2. A method according to clause 1, wherein said overlying, pigmented polymeric layer is a self-terminating layer.

3. A method according to clause 1 or clause 2, wherein, at a pH of said aqueous dispersion, the pre-coated mammalian hair fiber has a first surface zeta potential ($\zeta_1$), and said aqueous dispersion has a second zeta potential ($\zeta_2$), wherein a zeta differential ($\Delta\zeta$) at said pH is defined as $$\Delta\zeta = \zeta_1 - \zeta_2$$

and wherein $\Delta\zeta$, in millivolts (mV), fulfills at least one of the following:
(i) $\Delta\zeta$ is at least 10, at least 15, at least 20, at least 25, at least 30, at least 40, or at least 50;
(ii) $\Delta\zeta$ is within a range of 10 to 80, 10 to 70, 10 to 60, 15 to 80, 15 to 70, 15 to 60, 20 to 80, 20 to 70, 20 to 60, 25 to 80, 25 to 70, 25 to 60, 30 to 80, 30 to 70, 30 to 60, 35 to 80, 35 to 70, or 35 to 60;
(iii) for said pH being within a range of 4 to 11, 4 to 10.5, 4 to 10, 6 to 11, 6 to 10.5, 6 to 10, 7 to 11, 7 to 10.5, or 7 to 10, said first surface zeta potential ($\zeta_1$), is greater than zero ($\zeta_1 > 0$).

4. A method according to any one of clause 1 to clause 3, wherein a conjugate acid of said hydrophilic polymeric material is a hydrophobic polymeric material.

5. A method according to clause 4, wherein acid moieties of said hydrophobic polymeric material make up at least 8%, at least 10%, at least 12%, at least 15%, at least 16%, at least 17%, at least 18%, at least 19%, at least 20%, at least 21%, or at least 22%, by weight, of said hydrophobic polymeric material, or wherein acid moieties of said hydrophilic polymeric material make up at least 8%, at least 10%, at least 12%, at least 15%, at least 16%, at least 17%, at least 18%, at least 19%, at least 20%, at least 21%, or at least 22%, by weight, of said hydrophilic polymeric material.

6. A method according to clause 4, wherein acid moieties of said hydrophobic polymeric material make up 8 to 30%, 10 to 30%, 12 to 30%, 12 to 28%, 12 to 26%, 15 to 30%, 15 to 28%, 15 to 26%, 17 to 22%, 17 to 23%, 18 to 30%, 18 to 28%, 18 to 26%, 20 to 30%, 20 to 28%, or 20 to 26%, by weight, of said hydrophobic polymeric material, or wherein acid moieties of said hydrophilic polymeric material make up 8 to 30%, 10 to 30%, 12 to 30%, 12 to 28%, 12 to 26%, 15 to 30%, 15 to 28%, 15 to 26%, 17 to 22%, 17 to 23%, 18 to 30%, 18 to 28%, 18 to 26%, 20 to 30%, 20 to 28%, or 20 to 26%, by weight, of said hydrophilic polymeric material.

7. A method according to any one of clause 1 to clause 6, wherein said aqueous dispersion contains a volatile base.

8. A method according to clause 7, wherein said volatile base is selected from the group of ammonia ($NH_3$), monoethanolamine, diethanolamine, triethanolamine and morpholine.

9. A method according to clause 7 or clause 8, further comprising volatizing said volatile base associated with said overlying, pigmented polymeric layer, so as to acidify, largely or mainly acidify, or completely acidify said neutralized acid moieties.

10. A method according to any one of clause 1 to clause 8, further comprising converting a portion of, a major portion of, or all of said hydrophilic polymeric material in said overlying, pigmented polymeric layer, into a conjugate acid thereof, said converting optionally including actively evaporating (e.g., with a air blower, the air being further optionally heated) a liquid carrier of the aqueous dispersion.

11. A method according to clause 10, wherein said converting includes, mainly includes, or consists of acidifying said neutralized acid moieties to form said conjugate acid.

12. A method according to any one of clause 1 to clause 9, further comprising sufficiently converting said hydrophilic polymeric material into a conjugate acid thereof, so as to obtain a hydrophobic polymeric material.

13. A method of any one of clause 1 to clause 12, wherein said polymeric material having said neutralized acid moieties includes, mainly includes, consists essentially of, or consists of one or more neutralized copolymer selected from the group of neutralized alkene-acrylic acid copolymer, neutralized alkene-methacrylic acid copolymer and neutralized acrylamide/acrylate copolymer.

14. A method of clause 13, wherein said neutralized alkene-acrylic acid copolymer includes, mainly includes, consists essentially of, or consists of neutralized ethylene-acrylic acid (EAA) copolymer.

15. A method of clause 13, wherein said neutralized alkene-methacrylic acid copolymer includes, mainly includes, consists essentially of, or consists of neutralized ethylene-methacrylic acid (EMAA) copolymer.

16. A method of any one of clauses 1 to 13, wherein said polymeric material having said neutralized acid moieties includes, mainly includes, consists essentially of, or consists of neutralized acrylamide/acrylate (AAA) copolymer.

17. A method of any one clauses 1 to 16, wherein the pre-coated mammalian hair fiber is a plurality of pre-coated mammalian hair fibers, the method further comprising, subsequent to said applying of said aqueous dispersion, treating said overlying polymeric layer of each of the plurality of fibers, so as to produce an overlying, pigmented polymeric coating adhering to the external surface of each of the respective pre-coated mammalian hair fibers.

18. A method of clause 17, wherein said overlying, pigmented polymeric coating is a hydrophobic polymeric coating.

19. A method of clause 17 or clause 18, wherein said treating includes washing and/or combing the plurality of fibers to remove excess material therefrom, and optionally, subsequently drying and/or combing the plurality of fibers.

20. A method of clause 17 or clause 18, wherein said treating includes drying and/or combing the plurality of fibers, and optionally, prior to said drying, washing the plurality of fibers to remove excess material therefrom.

21. A method of clause 19 or clause 20, wherein said washing the plurality of fibers and/or said drying and/or said combing the plurality of fibers is performed at a temperature of at most 45° C., 40° C., 35° C., 30° C., or 25° C., and optionally, at a temperature of at least 5° C., 10° C., 12° C., 15° C., 17° C., or 20° C., and further optionally, within 7° C., 5° C. or 3° C. of room or ambient temperature.

22. A method of any one of clause 19 to clause 21, wherein said washing the plurality of fibers is performed within at most 20 minutes, at most 10 minutes, at most 5 minutes, at most 3 minutes, at most 2 minutes, at most 1 minute, or at most 30 seconds after completing said applying of said aqueous dispersion.

23. A method of any one of clause 19 to clause 22, wherein when said washing is performed 1 minute after completing said applying of said aqueous dispersion, sufficient attachment of said overlying polymeric layer to the external surface of the pre-coated mammalian hair fiber is attained, such that a decrease in optical density (OD), with respect to a reference OD, is at most 15%, at most 10%, at most 7%, at most 5%, at most 3%, or at most 1%.

24. A method of any one of clause 19 to clause 23, wherein said drying is an active drying, and wherein a total time period of said applying of said aqueous dispersion and said washing and/or said active drying is within a range of 2 to 90 minutes, 2 to 75 minutes, 2 to 60 minutes, 2 to 45 minutes, 2 to 30 minutes, 2 to 20 minutes, 2 to 10 minutes, or 2 to 5 minutes, and optionally, at most 7 minutes, at most 4 minutes, at most 3 minutes, or at most 1.5 minutes.

25. A method of clause 24, wherein, within 24 to 96 hours, within 24 to 72 hours, within 24 to 48 hours, within 24 to 36 hours, or within 24 to 30 hours immediately succeeding said total time period, with the plurality of fibers being maintained within 7° C., 5° C., 3° C., or 1° C. of room or ambient temperature, said overlying, pigmented polymeric coating achieves wash resistance, permanence, or permanent coloration.

26. A method of any one of clause 1 to clause 25, wherein, at a pH within a range of 7.5 to 11, said hydrophilic polymeric material is self-dispersible in water, in an absence of dispersants and all other additives in water.

27. A method of any one of clause 1 to clause 26, wherein said hydrophilic polymeric material is thermoplastic.

28. A method of any one of clause 1 to clause 27, wherein said hydrophilic polymeric material has a solubility of at least 2%, at least 5%, at least 10%, or at least 15%, by weight, at a pH of 10.

29. A method of any one of clause 1 to clause 27, wherein said hydrophilic polymeric material has a solubility within a range of 2 to 30%, 5 to 30%, 10 to 30%, or 15 to 30%, by weight, at a pH of 10.

30. A method of any one of clause 1 to clause 29, wherein at least one of said overlying polymeric layer and said overlying, pigmented polymeric coating is washed with a cationic rinsing liquid.

31. A method of any one of clauses 1 to 30, further comprising applying, on said overlying, pigmented polymeric coating, an oil-in-water amino-silicone emulsion, to produce an at least partially cured second amino-silicone layer, optionally washed, said at least partially cured second amino-silicone layer enveloping said overlying pigmented polymeric coating and attached thereto.

32. A method of clause 31, further comprising applying on said at least partially cured second amino-silicone layer, an aqueous dispersion according to at least one of clauses 1 to 30.

33. A method of any one of clauses 1 to 32, wherein the pigment includes metallic pigment flakes containing, coated with, consisting essentially of, or made of metals, alloys and oxides thereof, said pigment flakes being selected from the group comprising aluminum flakes, brass flakes, bronze flakes, copper flakes, gold flakes, mica coated flakes, silica coated flakes and silver flakes.

34. A method of clause 33, wherein at least one of the oil-in-water emulsion and/or the aqueous dispersion including said metallic pigment flakes further comprises an antioxidant.

35. A method of clause 33 or clause 34, wherein said metallic pigment flakes serve to form a hair masking coating, the method further comprising repeating at least step (b) of clause 1, the aqueous dispersion of repeated step (b) comprising pigment particles other than metallic pigment flakes.

36. A method of any one of clauses 1 to 35, wherein said aqueous dispersion is produced by:
mixing, in an aqueous carrier containing water, at least one hydrophobic polymeric material, each independently having neutralizable acid moieties, the hydrophobic polymeric material being optionally compounded with a pigment, so as to form a neutralizable mixture including pellets of the hydrophobic polymeric material;

adding to the neutralizable mixture a neutralizing agent, said addition being performed under agitation at a temperature above at least one of the highest of the softening temperature and of the melting temperature of the at least one hydrophobic polymeric material, said neutralizing agent being added in an amount sufficient to neutralize at least 75% of the neutralizable acid moieties of said polymeric material, so as to form a neutralized mixture including a portion of hydrophilic polymeric material; and dispersing the neutralized mixture, so as to form said aqueous dispersion, the aqueous dispersion including particles of at least one hydrophilic polymeric material.

37. A method of any one of clauses 1 to 36, wherein a first oil-in-water amino-silicone emulsion able to form a first amino-silicone coating of said pre-coated mammalian hair fiber and/or a second oil-in-water amino-silicone emulsion able to produce said at least partially cured second amino-silicone layer further includes any of the limitations of clauses 37 to 97 of SET 1, and any combination thereof.

Set 3

1. A method of treating an external surface of a mammalian hair fiber, the method comprising:
(a) forming, on the external surface of the mammalian hair fiber, an amino-silicone layer;
(b) applying, on said amino-silicone layer, an aqueous dispersion containing:
a plurality of polymeric particles, formed of a hydrophilic polymeric material having neutralized acid moieties;
said plurality of polymeric particles being dispersed within said aqueous dispersion;
so as to produce an overlying, polymeric layer adhering to the external surface of said amino-silicone layer.

2. A method according to clause 1, wherein a total concentration of pigments in said overlying polymeric layer is at most 0.3%, at most 0.2%, at most 0.1%, at most 0.05%, or at most 0.02%, or wherein said overlying polymeric layer is devoid of said pigments.

3. A method according to clause 1, wherein in each of at least a portion of said plurality of polymeric particles, said hydrophilic polymeric material envelops one, or at least one, pigment core particle.

4. A method according to any one of clause 1 to clause 3, wherein a total concentration of amino-silicone layer pigments in said amino-silicone layer is at most 0.3%, at most 0.2%, at most 0.1%, at most 0.05%, or at most 0.02%, or wherein said amino-silicone layer is devoid of said amino-silicone layer pigments.

5. A method according to any one of clause 1 to clause 4, further including any of the limitations of clauses 2 to 97 of SET 1 and any combination thereof.

Set 4

1. A method of treating an external surface of a mammalian hair fiber, the method comprising:
(a) forming, on the external surface of the mammalian hair fiber, an amino-silicone layer containing pigment particles;
(b) applying, on said amino-silicone layer, an aqueous dispersion containing:
a plurality of polymeric particles, formed of a hydrophilic polymeric material having neutralized acid moieties;
said plurality of polymeric particles being dispersed within said aqueous dispersion;
so as to produce an overlying, polymeric layer adhering to the external surface of said amino-silicone layer.

2. A method according to clause 1, wherein said overlying polymeric layer is devoid of pigments.

3. A method according to clause 1, wherein a total concentration of pigments in said overlying polymeric layer is at most 0.3%, at most 0.2%, at most 0.1%, at most 0.05%, or at most 0.02%.

4. A method according to clause 1 or clause 3, wherein in each of at least a portion of said plurality of polymeric particles, said hydrophilic polymeric material envelops one, or at least one, pigment core particle.

5. A method according to any one of clause 1 to clause 3, wherein a total concentration of underlayer pigments in said amino-silicone layer is at least 0.1%, at least 0.5%, at least 1%, at least 3%, at least 5%, at least 10%, or at least 12%, and optionally, at most 20%, at most 17%, or at most 15%, or at most 12%, and further optionally, within a range of 0.1% to 20%, 0.5% to 15%, 0.5% to 15%, 3% to 15%, 5% to 15%, 3% to 12%, or 3% to 10%.

6. A method according to any one of clause 1 to clause 5, further including any of the limitations of clauses 2 to 97 of SET 1 and any combination thereof.

Set 5

1. A kit for producing an at least two-layer coating on an external surface of mammalian hair, the kit comprising:
   (a) a first compartment containing a first oil phase including:
      (i) at least one reactive condensation-curable film-forming amino-silicone monomer having a molecular weight of at most 1000 g/mole; and optionally,
      (ii) a non-amino cross-linking agent; and further optionally,
      (iii) at least one of an amino-silicone oil and a non-amino-silicone oil; and further optionally,
      (iv) at least one reactive condensation-curable film-forming amino-silicone pre-polymer including at least one of a reactive condensation-curable film-forming amino-silicone polymer and a reactive condensation-curable film-forming amino-silicone oligomer;
   (b) a second compartment containing a formulation including:
      (i) an aqueous medium; and
      (ii) sub-micronic particles including, or made of, a hydrophilic polymeric material having neutralized acid moieties, disposed within said aqueous medium, each of at least a portion of said sub-micronic particles optionally containing at least one pigment particle, at least partially enveloped by said polymeric material;
   (c) an optional third compartment containing a second oil phase including:
      (i) at least one of an or said amino-silicone oil and a or said non-amino-silicone oil, and optionally,
      (ii) a solid, hydrophobic reactive inorganic filler; and further optionally,
      (iii) said at least one reactive condensation-curable film-forming amino-silicone pre-polymer including at least one of a reactive condensation-curable film-forming amino-silicone polymer and a reactive condensation-curable film-forming amino-silicone oligomer; and further optionally,
      (iv) pigment particles, disposed within said second oil phase;
   (d) an optional fourth compartment containing at least one of:
      (i) an emulsifier for said first and second oil phases;
      (ii) water; and
      (iii) a thickening agent
   (e) an optional fifth compartment containing at least one metallic pigment, and optionally, an aqueous or organic carrier.

2. The kit according to clause 1, wherein said filler is selected or adapted to facilitate curing of said condensation-curable film-forming amino-silicone pre-polymer.

3. The kit according to any one of clause 1 to clause 2, wherein said non-amino cross-linking agent is adapted or selected to cure said pre-polymer.

4. The kit according to any one of clause 1 to clause 3, wherein the acid moieties of said neutralized acid moieties are selected from the group of acrylic acid and methacrylic acid.

5. The kit according to any one of clause 1 to clause 4, wherein said hydrophilic polymeric material having neutralized acid moieties is selected from an alkene-acrylic acid copolymer, alkene-methacrylic acid copolymer and an acrylate/acrylamide copolymer.

6. The kit according to any one of clause 1 to clause 5, wherein said hydrophilic polymeric material is an ethylene-acrylic acid copolymer, an ethylene-methacrylic acid copolymer or an acrylate/acrylamide copolymer.

BRIEF DESCRIPTION OF THE DRAWINGS

Some embodiments of the present disclosure are described herein with reference to the accompanying figures. The description, together with the figures, makes apparent to a person having ordinary skill in the art how some embodiments of the present disclosure may be practiced.

The figures are for the purpose of illustrative discussion and no attempt is made to show structural details of an embodiment in more detail than is necessary for a fundamental understanding of the present disclosure. For the sake of clarity, some objects depicted in the figures are not to scale.

In the Figures:

FIG. 1A is a schematic illustration of a single (typically keratinous) fiber in the presence of some of the dispersed components constituting a coating formulation;

FIG. 1B is a schematic illustration representing how some of the components of FIG. 1A have migrated towards the fiber and are arranged thereupon;

Figure 1A:
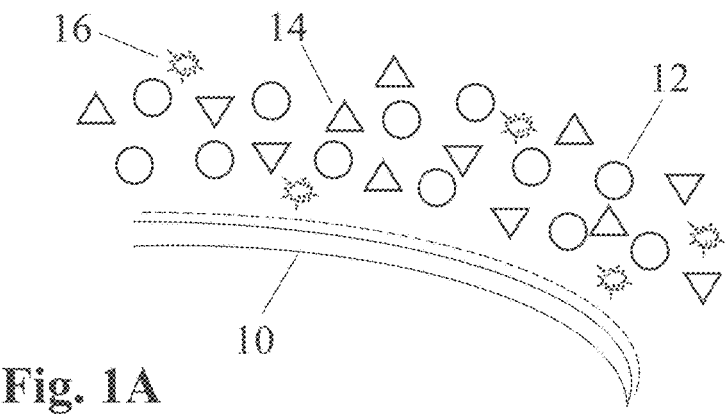
Figure 1B:
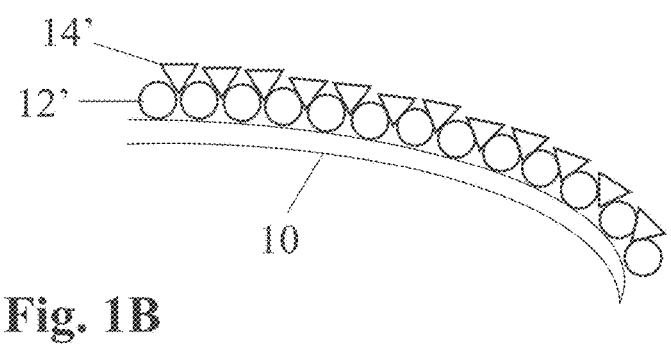
Figure 1C:
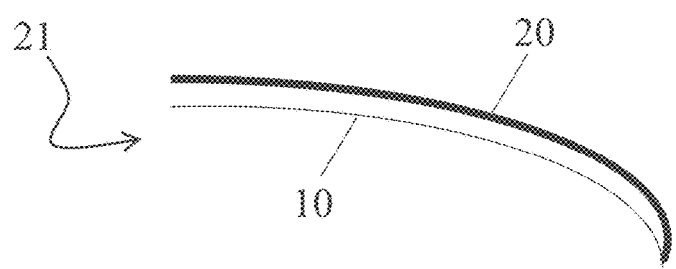
Figure 1D:
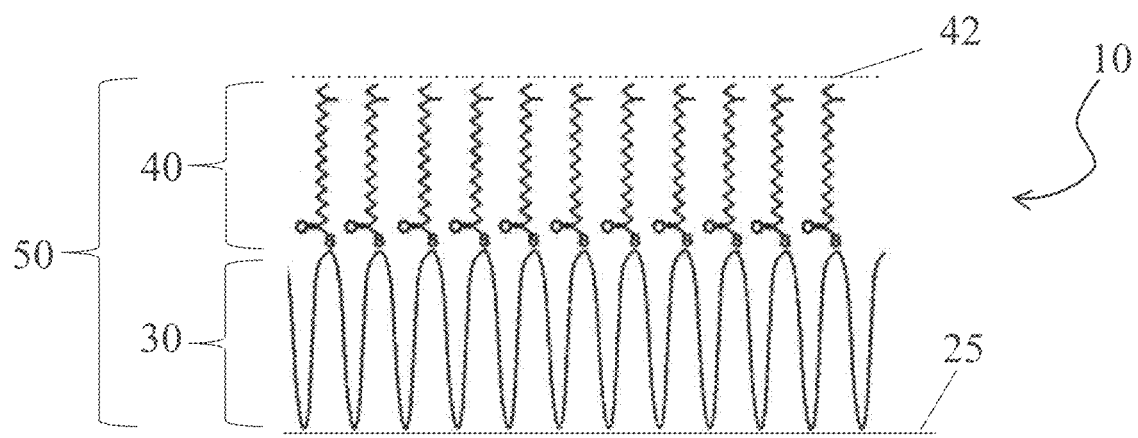
Figure 1E:
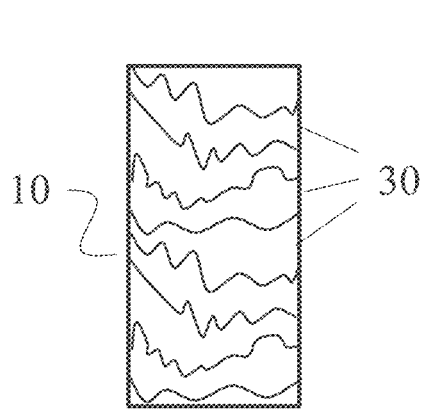
Figure 1F:
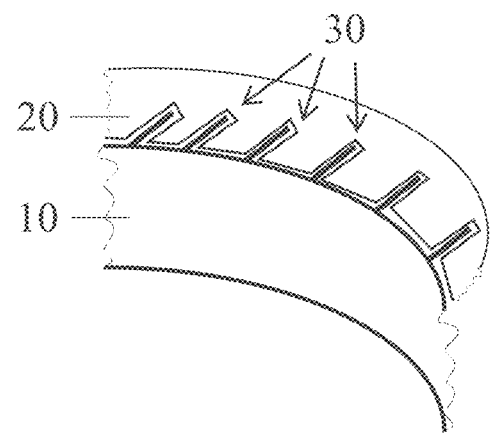
Figure 2A:
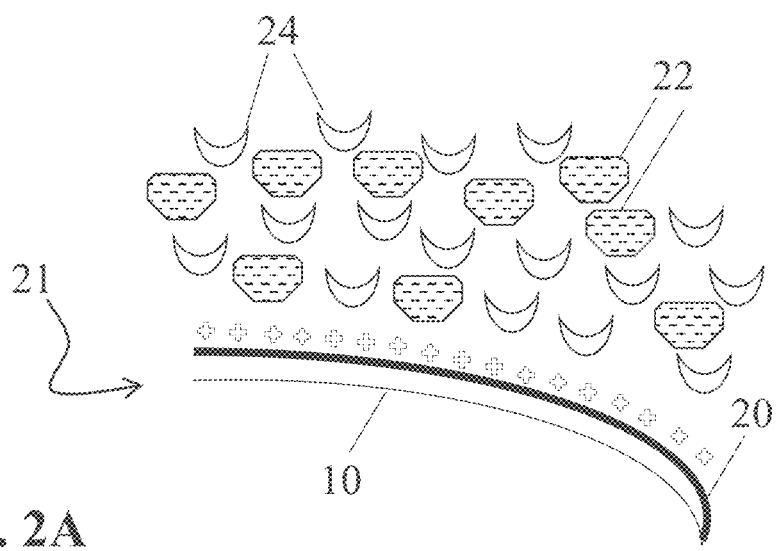
Figure 2B:
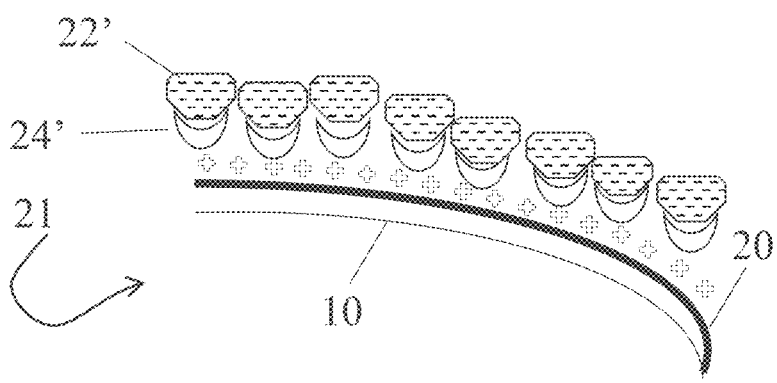
Figure 2C:
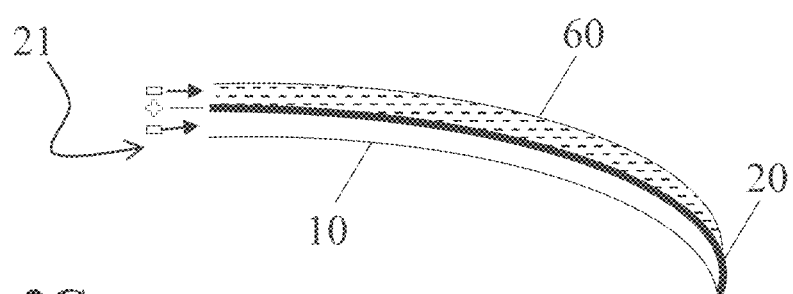
Figure 3:
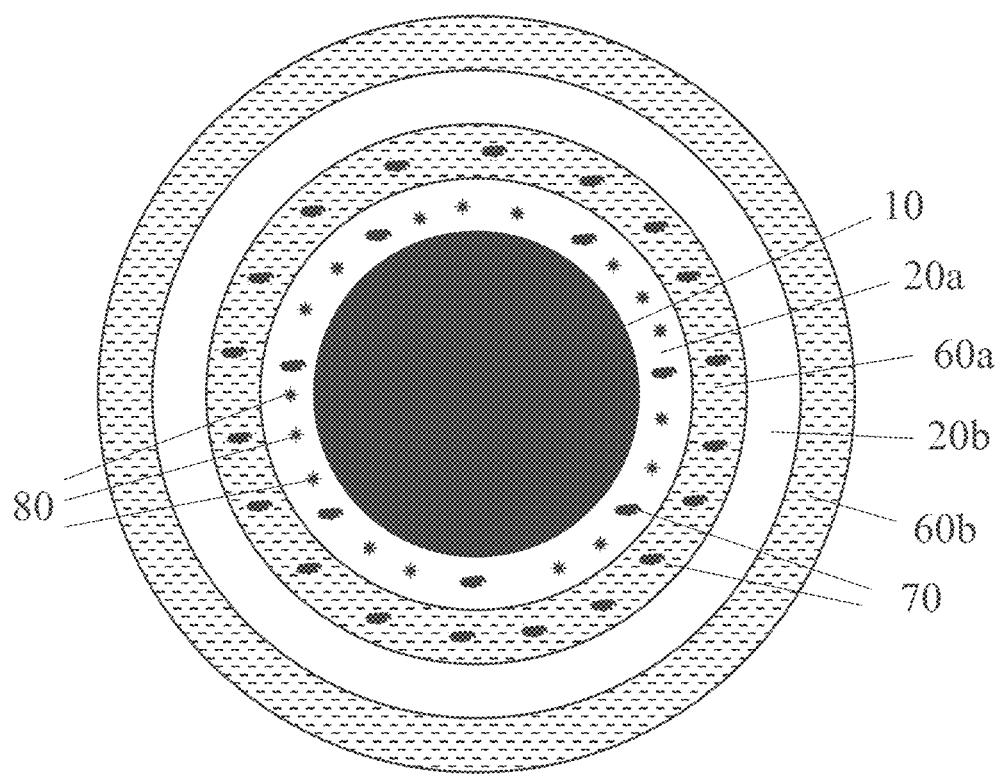
Figure 4:
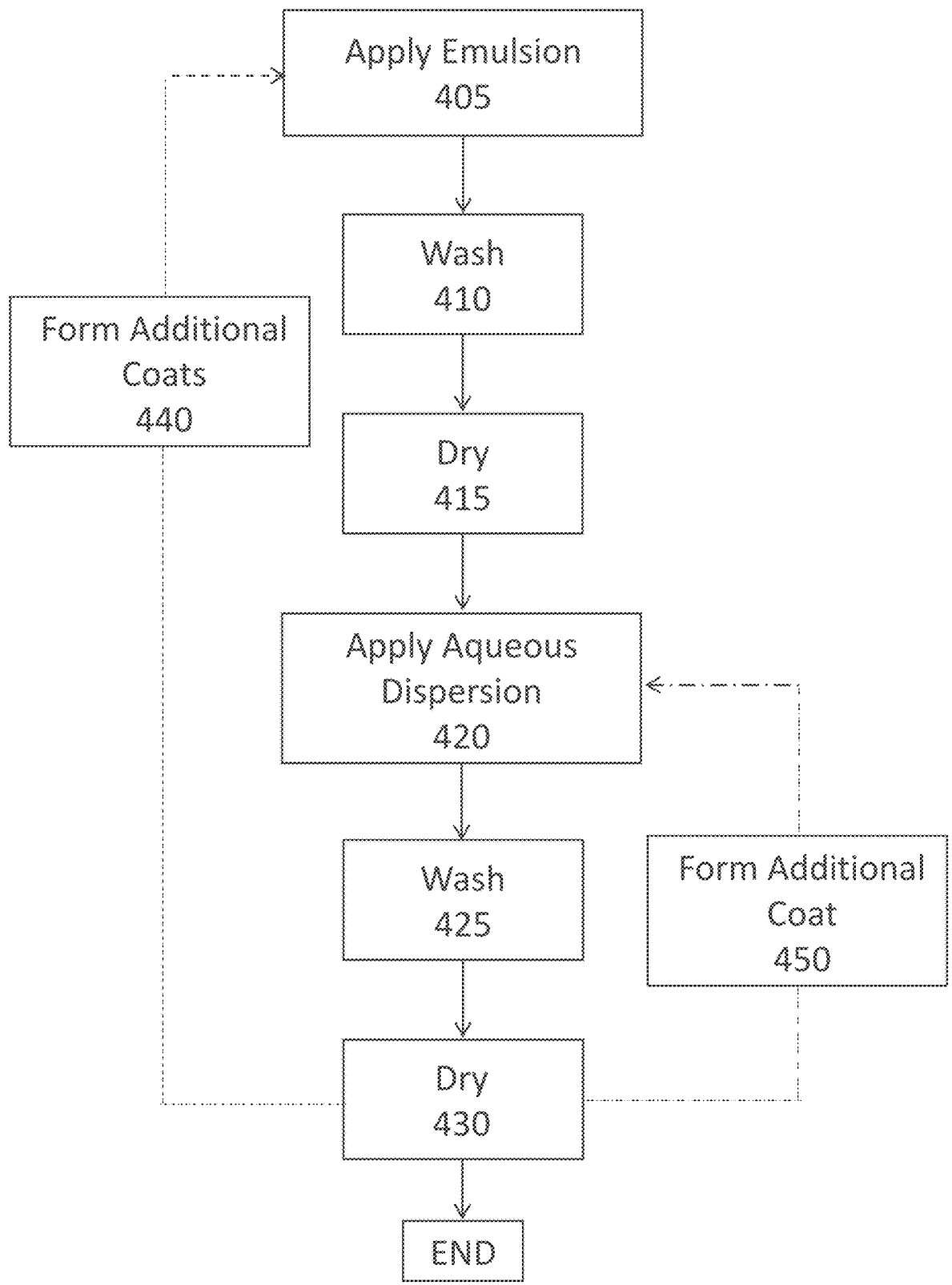

FIG. 1C schematically shows a coated fiber in which the components of FIGS. 1A-1B have coalesced to form a continuous film on the external surface of the fiber;

FIG. 1D schematically illustrates the structure of mammalian hair at enlarged scale;

FIG. 1E schematically illustrates a top view of a hair fiber with cuticle scales;

FIG. 1F schematically illustrates a side view of a hair fiber with its cuticle scales opened up at basic pH;

FIG. 2A is a schematic illustration of the coated fiber of FIG. 1C, in the presence of various dispersed components from an aqueous dispersion, the dispersed components including a neutralized, acid functionalized polymeric material having neutralized acid moieties and optionally a surfactant or super-wetting agent, or a thickening agent;

FIG. 2B is a schematic illustration representing how some of the components of FIG. 2A have migrated towards the coated fiber of FIG. 2A, and are arranged thereupon;

FIG. 2C schematically shows the coated fiber of FIG. 2A, in which the components of FIG. 2A have coalesced to form a continuous layer adhering to the external surface of the coated fiber;

FIG. 3 schematically shows a cross section of a fiber having coatings according to various embodiments of the present teachings;

FIG. 4 depicts a simplified schematic diagram of a coating process according to various embodiments of the present teachings;

FIG. 5A schematically depicts the preparation of an aqueous dispersion that includes a neutralized, acid functionalized polymeric material having acid moieties, according to one embodiment of the disclosure;

FIG. 5B schematically illustrates pigments embedded in neutralized acid functionalized polymeric material, as can be obtained in some embodiments of the simplified process depicted in FIG. 5A; and FIG. 5C is a schematic illustration of a flake-shaped pigment at least partially enveloped by a polymer, which, in some embodiments, may be a neutralized, acid functionalized polymeric material.

DETAILED DESCRIPTION

Aspects of the present disclosure relate to methods of coloring or cosmetically treating fibers such as keratinous fibers, including mammalian hair such as human or animal hair and synthetic versions thereof. Aspects of the present disclosure encompass the coloring of mammalian fibers when attached to a living subject (e.g., as achieved for instance with hair colors or eyelash make-up products) and when isolated therefrom, for instance for the cosmetic treatment of wigs, or any other keratinous fibers detached from their subject of origin, such as a detached fur. Further aspects include compositions enabling the afore-said processes, as well as methods of preparing such compositions. Kits enabling the practice of the method and permitting the adequate packaging of the compositions until use for coloring or cosmetically treating keratinous fibers represent further aspects of the present teachings.

In some embodiments, the pigments for the compositions, kits and methods according to the present teachings, whether sub-micronic organic pigments, sub-micronic inorganic pigments, metallic-looking pigments and the like, as detailed herein, are not only insoluble in water or organic solvents, but additionally insoluble in the reactive condensation-curable amino-silicone reactant, in the polymeric material including acidic moieties, whether neutralized or not, and/or the resulting coating(s). Without wishing to be bound by any particular theory, it is believed that FIGS. 1A-1C schematically illustrate the principles underlying a portion of one aspect of the method contemplated herein. FIG. 1A shows a schematic illustration of a single keratinous fiber 10 in the presence of some of the dispersed components constituting a coloring or coating formulation (e.g., oil-in-water emulsion) as herein disclosed. The reactive condensation-curable amino-functional silicone reactant (or micelles or emulsion droplets containing the same) 12 is represented by circles. The formulation pool of first reactants may also contain non-amino functional cross-linking agents 14 capable of cross-linking the curable amino-silicone coating 12. Such optional materials (or micelles or emulsion droplets containing the cross-linking agent) 14 are represented by triangles. The further optional 3D network formers (e.g., fumed silica), also referred to as curing facilitators (or micelles or emulsion droplets containing such curing facilitators) 16 are represented by stars. For clarity, the dispersant and pigment particles, which in some embodiments can optionally be added to a formulation (e.g., oil-in-water emulsion) containing the at least one amino-silicone reactant, are not shown. For simplicity, all illustrated materials are displayed on a single side of the fiber. FIG. 1A is deemed to represent the situation upon initial exposure of the fibers to the condensation-curable amino-silicone formulation. In some embodiments, the keratinous fiber 10 is mammalian hair and its outer surface is negatively charged as shown in the figure. The hair surface shall be negatively charged when using a composition having a pH above the isoelectric point of the fibers (e.g., >4, preferably >7). In some embodiments, the condensation-curable amino-functional silicone reactant 12 is positively charged when dispersed in a carrier. For instance, amino-silicone pre-polymers can be positively charged as of a pH of 4.0 and until they reach their isoelectric point (typically in the range of pH 10-12). Interestingly, the protonation of the amine groups above the acidic pH (assuming a sufficient concentration) can maintain the composition within the basic pH range even in absence of a dedicated pH buffering agent. It is to be noted that at a relatively high pH (>9), hair scales are sufficiently charged to repulse one another, resulting in the opening of the channels leading to the hair shafts. The lifting of the scales increases the surface area of the hair fibers, enhancing contact surface with the emulsion of reactive amino-silicone pre-polymers. As carrier evaporates, the pH of the coat gradually decreases and the hair scales return to their original positions, possibly entrapping in the process a portion of the amino-silicone film, furthering its adherence to the hair by mechanical interlocking. In some embodiments, the cross-linking agent 14 (e.g., some non-amino materials) and/or the cross-linking facilitator 16 are each negatively charged when dispersed in a carrier. For instance, 12 can represent a condensation-curable amino-silicone monomer, oligomer or polymer, or mixtures thereof, for which non-amino condensation-curable monomers or oligomers can serve as cross-linking agents 14. In such a case, a hydrophobic filler may serve as cross-linking facilitator 16.

FIG. 1B is a schematic macroscopic illustration representing how, with time, some of the components of FIG. 1A can migrate towards the fiber and arrange themselves thereupon. Such migration is believed to be electrostatically driven by the gradient of charge between the pre-polymers of the composition (e.g., positively charged at basic pH) and the surface of the hair fibers (e.g., negatively charged at a similar pH). Based at first on electrostatic interactions, the amino-silicones micelles or emulsion droplets thereof (being in one embodiment positively charged) form a layer 12' on the surface of fiber 10 (being in the same embodiment conversely negatively charged). Similarly, the non-amino functional condensation-curable cross-linking agents (e.g., ethyl silicate), micelles or emulsion droplets thereof (being in the same embodiment negatively charged) will form a layer 14' on the surface of layer 12' (being in the same embodiment conversely positively charged). For clarity, the optional curing facilitators (e.g., fumed silica) shown as 16 in FIG. 1A, which would "intercalate" in layer 14', are omitted from FIG. 1B. Understandingly, according to these principles, nonionic polymers would not be subjected to such an electrostatic drive towards hair fibers, their prospective attachment therewith, if any, being accordingly reduced (e.g., allowing at most physical deposition or hydrophobic: hydrophobic interactions).

FIG. 1C schematically shows how, given further time, the components previously partially represented by 12, 14 and 16, coalesce, merge and/or react to form a continuous film 20 on the external surface of the fiber, so as to form an amino-silicone coated fiber 21. The coalescence of the oil droplets on the hair fibers is believed to force away the aqueous carrier towards the outer surface of the coated fiber, therefore facilitating its evaporation. Such a preliminary wetting of the fibers by the coloring compositions, according to the present teachings, is believed to be a pre-requisite for the entire coloring method. This step, at its beginning, may be herein referred to as "preliminary curing". With time, the amino-silicones of the film will cross-link with one another, the process proceeding towards full curing through a progressive phase of partial-curing. Without wishing to be bound by theory, it is believed that pre-polymers having a relatively low MW (a relatively low viscosity) have a better prospect to sufficiently wet the hair fiber than a pre-polymer having a relatively higher MW (a relatively higher viscosity). Hence, once the composition constituents are driven to be in sufficient proximity to the fiber thanks to electrostatic bonding, additional mechanisms, such as acid:base hydrogen bonding or even covalent bonding, may become available for the attachment of the amino-silicone molecules to the hair surface. Such processes, in combination with the ongoing condensation curing of the pre-polymer molecules are believed to provide (a) attachment ("adhesivity") to the underlying fiber and (b) "cohesivity" of the amino-silicone film.

While not shown in the figure, pigment particles applied in combination with amino-silicone compositions according to the present disclosure are advantageously entrapped within the growing network of the pre-polymers, the curing of which is completed in situ on the hair fiber. Such entrapment is believed to improve the attachment of pigment particles to the hair fibers and to ensure their retention thereon for a longer time period than affordable by mere physical deposition in presence of non-reactive polymers.

While not shown in the figure, it is believed that the film 20 formed according to the above described exemplary embodiment would be positively charged (e.g., under basic pH permitting the protonation of the amine moieties). A polymer is believed to be fully cured when, for instance, its glass transition temperature no longer changes over time, in other words, has reached a substantially stable value, suggesting that no further cross-linking is taking place. Alternatively and additionally, an amino-silicone polymer would be fully cured, when the number of siloxane bonds it can form in the curable fluid and under the curing conditions applicable, does not substantially change over time. The number of siloxane bonds in a cured amino-silicone polymer can be assessed by routine analytical methods, such as by Fourier transform infrared (FTIR) spectroscopy.

It has been surprisingly discovered that applying an AS formulation (e.g., an oil-in-water emulsion) having a basic pH (at least 9.0, at least 9.5 or at least 9.75, and typically 9.0-11.5, 9.0-11.0, 9.5-11.5, 9.5-11.0, or 9.5-10.7) may appreciably enhance the adhesion of the AS film to the hair surface. Without wishing to be limited by theory, it is believed that at such a basic pH, the cuticle scales 30 of the hair fiber 10 (as schematically illustrated in a top view, in FIG. 1E, not drawn to scale) open up. This allows some of the amino-silicone to contact the area "beneath" the opened cuticle scales 30 (FIG. 1F, not drawn to scale). Subsequently, after the pH is reduced (e.g., by evaporation of the volatile base), the cuticle scales of the hair return to their normally closed, overlapping configuration, thereby mechanically trapping or holding portions of the amino-silicone film 20, and strengthening the amino-silicone film adhesion. Such mechanically trapping of the amino-silicone film may be termed "mechanical macro-adhesion" or simply "macro-adhesion".

It is further believed that such basic pH of an oil-in-water emulsion further increases the difference of charge between the hair fibers being coated and the droplets of reactive amino-silicone pre-polymers. At basic pH, the pre-polymers of the composition (cationic as per their amine functions) are positively charged, while the surface of the hair fibers is negatively charged at a similar pH. Understandingly, according to these principles, anionic and nonionic polymers would not be subjected to such an electrostatic drive towards hair fibers, their prospective attachment therewith, if any, being accordingly reduced (e.g., allowing at most physical deposition or hydrophobic:hydrophobic interactions).

As explained, the relative polarity of the fiber substrate to be coated or colored (e.g., a keratinous fiber, whether native, pre-treated, for instance by bleaching, or coated according to present teachings) and of the overall charge of the coating or coloring formulations due to treat the substrate (including the active constituents of these compositions) is believed to facilitate the initial wetting of the substrate by the formulations. Hence, in some embodiments, when a subsequent coating is desired, the subsequent composition (e.g., an aqueous dispersion of acidic polymeric material) can have a polarity opposite to the polarity of the coated substrate. Thus, in the present illustration, if a negatively charged hair fiber is first coated with a film forming amino-silicone formulation resulting in a positively charged amino-silicone film, the now positively charged substrate can be subsequently coated with an overall negatively charged subsequent composition. However, as opposite polarities are not essential, in alternative embodiments, subsequent coatings, if desired, can have similar polarity (positive or negative), the overall charge being similar or different.

It can be readily understood that the relative charge of the surface being coated and of the droplets or particles coating it form a gradient which decreases as the migration of the charged polymer-forming materials to the fiber proceeds. For illustrative example, assuming a negatively charged human hair and positively charged droplets of amino-silicone pre-polymers, at first there is a large gradient driving the positive droplets to the negative hair. As the hair gets coated with the positive droplets, its charge increases and therefore the gradient driving the surrounding droplets towards the fiber decreases until it is too small to drive any additional positively charged droplet to the hair. Without wishing to be bound by the above theory, it is believed that the process of the present method is self-terminating. The film is self-terminated as soon as the migration of the charged species reach a point where repulsion between the stationary layer on the hair fiber and the droplets of the bulk overcomes previous attraction.

This self-termination of the process, once there is no driving gradient any longer, advantageously prevents an endless build-up of material that conventionally lead to uncontrolled thickness of coatings. In extreme cases, the endless deposition of materials builds-up inseparable hair lumps of no practical use. In more tolerable situations, while the build-up of materials cannot be prevented, the coating can be interrupted and the hair fibers which have been liquid bridged in this undesired process can be individualized through often intense combing, such untangling process typically resulting in a poor appearance and/or weakened mechanical resistance/attachment of a color coating, if any. Advantageously, the self-terminating process according to the present teachings results in a coating of reasonable thickness, which allows the coated hair to remain separate in individual fibers and not stuck together. The thickness of the coat can be controlled via the size of the droplets of the emulsion (e.g., droplets having a Dv50 of 1-2 µm, as readily formed by manual shaking, will yield a coat of 0.5-1 µm thickness).

The same principles are deemed to conversely apply when the hair fiber now positively charged by the first coat of amino-silicone polymer becomes the target of negatively charged polymer-embedded pigment particles.

The formation of this polymeric layer, on top of and enveloping the AS film, requires a driving force. Without wishing to be limited by theory, it is believed that in various methods of the present disclosure, the initial driving force for delivering, to the external amino-silicone surface, the polymeric material having neutralized acid moieties, includes or primarily includes an electrostatic attraction between positively-charged functional amine groups disposed on and within the amino-silicone film and negatively-charged functional groups (e.g., carboxylic moieties) in the dispersed polymeric particles within the aqueous dispersion. This electrostatic attraction is enhanced at basic pH.

It is believed that the dispersed polymeric particles, driven by this electrostatic attraction, reach the amino-silicone film surface, where the negatively-charged functional groups near the outer surface of the particles, and facing the film, link up with the positively-charged functional amine groups disposed on the external surface of the amino-silicone film, so as to envelop the film and thereby the underlying fiber. This outer (with respect to the underlying amino-silicone film) polymeric film may advantageously be self-terminating. Again, without wishing to be limited by theory, it is believed that the dispersed, negatively-charged polymeric particles continue to be attracted by the overall positive charge of the amino-silicone film, such that multiple layers of the polymeric particles may become associated therewith. However, since polymeric particles in the "bulk" of the dispersion are repelled by the negative charge of these polymeric particles, the electrostatically driven build-up gradually comes to a halt (substantially as explained hereinabove with respect to the amino-silicone film), such that the build-up of this polymeric layer is also self-terminating.

As the polymeric particles coalesce, a continuous polymeric film forms on the underlying amino-silicone film. With the evaporation of the liquid carrier (e.g., water) and of the volatile alkaline agents having neutralized the polymeric material before its application, film formation proceeds. With the progressive evaporation of the volatile base (e.g., ammonia), the pH of the outer coat diminishes with time, the acid moieties of the polymeric material are converted back to their conjugate form having the hydrogen, resulting in the film becoming increasingly water resistant. The mechanical properties of the polymeric film are also improved.

Over the long term (e.g., 12 to 36 hours), additional bonding between the hair fiber and the amino-silicone film may advantageously ensue and/or further attachment of the polymeric film to the underlying amino-silicone film can arise.

FIG. 1D is a schematic, magnified illustration representing a surface of a mammalian hair fiber 10 as provided in FIG. 1A. The exterior of the hair filament or fiber is made up of cuticle cells. These cells have multiple layers, the outward-most of which is the cell membrane complex 50. The cell membrane complex includes a dense protein matrix 30 attached to the outer surface 25 of the A-layer of the cuticle, and a lipid layer 40 having fatty acid chains attached at a first end (typically, but not exclusively, the fatty acid end) to protein matrix 30, and, at the opposite, free end, extending away from protein matrix 30. These fatty acid chains contribute to the hydrophobicity (and to the lubricity) of the hair.

The height of cell membrane complex 50 may be less than 10 nm, typically about 5-7 nm. It has been observed that penetration through cell membrane complex 50, towards or to outer surface 25 of the A-layer of the cuticle, may be highly impeded for viscous materials, sterically-hindered materials or negatively-charged droplets, particularly in view of the narrow openings (circa 2 nm) between adjacent free ends of the fatty acid chains of cell membrane complex 50. It is believed that the various advantages of utilizing viscous polymeric materials notwithstanding, such materials may be significantly less suitable for achieving permanent hair coloring, with respect to their less viscous, monomeric and/or oligomeric counterparts.

Again, without wishing to be limited by theory, it is believed that for the amino-silicone formulation (e.g., liquid emulsion) according to the present teachings to appreciably contact the hydrophobic upper surface 42 of the fatty acid chains 40, the amino-silicone droplets (or formulation particles) need to be sufficiently hydrophobic. Moreover, this hydrophobicity aids in displacing the air disposed on the surface of the fatty acid chains 40, which is also required to enable penetration there-between.

The wetting process may be driven by charge interactions between the positively-charged amine moieties of the amino-silicone and various negatively-charged counterparts on the hair surface. Such drive can also be assessed by the gap in surface energy of the wetting liquid and the wetted surface. Amino-silicones having a surface energy of no more than the surface energy of the keratinous substrate, are deemed advantageous. For instance, untreated, undamaged human hair typically has a surface energy of 24-28 mN/m, while treated hairs may be in the range of 38-47 mN/m.

Consequently, the Amine Number, or more generally, the charge density of the amino-silicone reactant, appears to be of particular importance. The Amine Number of an amino-silicone reactant is generally supplied by the manufacturer, but can be independently determined by standard methods, as described for example in ASTM D 2074-07. It can be provided in terms of the amount of milliliters of 0.1N HCl needed to neutralize 10 g of the material under study.

This charge relationship, coupled with the requisite viscosity, surface tension and lack of steric hindrance of the amino-silicone reactant, enables "pinning" of the reactant within, or deeply within, the cell membrane complex 50. Such pinning may be grossly insufficient in terms of permanence, but allows at least partial curing of the reactant (e.g., formation of a 3D network of siloxane crosslinking bonds in and around the protruding elements of the cell membrane complex 50).

According to some embodiments, the condensation-curable film-forming amino-functional silicone reactant has an average molecular weight in the range of from about 100 to about 100,000. Typically, a monomer has a MW in the range of from about 100 to about 600, an oligomer has an average MW in the range of from about 200 to about 2,000, and a polymer has an average MW of at least about 2,000, and in some embodiments, of at most 50,000.

According to some embodiments, the condensation-curable amino-functional silicone reactant forms, when in emulsion in the formulation, emulsion droplets having an average size (Dv50) in the range of from 200 nm to 100 μm, or from 200 nm to 50 μm, or from 200 nm to 25 μm, or from 1 μm to 20 μm, or from 200 nm to 1 μm, or from 0.5 μm to 5 μm, or from 0.7 μm to 3 μm, or from 1 μm to 2.5 μm, or from 1 μm to 10 μm.

The size of the droplets and/or the size homogeneity of the population of the droplets can be modified by selecting any desired emulsification method, modulating for instance the energy invested in the process and its duration. Low energy processes (e.g., shaking the mixture manually) may suffice to provide droplets in the 1-5 µm range, which may be heterogeneous in size. Medium energy processes (e.g., using a planetary centrifugal mill) may provide a more homogeneous population, the size of which can be modulated by duration and speed (e.g., providing droplets in the 10-20 µm range, if brief). High energy processes (e.g., using a sonicator) may rapidly provide droplets in the sub-micron range.

Advantageously, as the hair fibers wetted by the positively-charged coat of amino-silicone are repulsing one another, there can be no liquid bridges between adjacent fibers, hence cluster of hairs are prevented, and the fibers remain individual.

Without wishing to be bound by theory, it is believed that pre-polymers having a relatively low MW (a relatively low viscosity) have a better prospect to sufficiently wet the hair fiber than a pre-polymer having a relatively higher MW (a relatively higher viscosity). Hence, once the composition constituents are driven to be in sufficient proximity to the fiber thanks to electrostatic bonding, additional mechanisms, such as acid:base hydrogen bonding or even covalent bonding, may become available for the attachment of the amino-silicone molecules to the hair surface. Such processes, in combination with the ongoing condensation curing of the pre-polymer molecules are believed to provide (a) attachment ("adhesivity") to the underlying fiber and (b) "cohesivity" of the amino-silicone film.

Pigment particles applied in combination with amino-silicone compositions according to the present disclosure are advantageously entrapped within the growing network of the pre-polymers, the curing of which is completed in situ on the hair fiber. Such entrapment is believed to improve the attachment of pigment particles to the hair fibers and to ensure their retention thereon for a longer time period than affordable by mere physical deposition in presence of non-reactive polymers. When a pigment dispersant is used, the pigment particles are believed to be first partially enveloped by the pigment dispersant, which in turn forms the interface with the surrounding amino-silicone matrix.

According to some embodiments, the reactive condensation-curable amino-functional silicone reactant is present at a concentration in the range of from about 0.001 to 20% by weight of the total weight of the formulation (e.g., oil-in-water emulsion), such as from about 0.005 to 10%, from about 0.005 to 5%, from about 0.005 to 2.5% or from 0.01 to 1% by weight of the total weight of the formulation.

According to some embodiments, the concentration of reactive condensation-curable amino-functional silicone compounds is at least 45 wt. % at least 55%, at least 60%, or at least 65%, and optionally within a range of 50-100 wt. %, 50-95 wt. %, 50-90 wt. %, 50-85 wt. %, 50-80 wt. %, 55-95 wt. %, 55-85 wt. %, 60-95 wt. %, 60-85 wt. %, 65-95 wt. %, 65-90 wt. %, or 70-95 wt. % by weight of the oil phase.

According to some embodiments, the total concentration of amino-silicone oil is at most 30 wt. %, at most 20 wt. %, at most 15 wt. %, at most 10 wt. %, or at most 5 wt. % by weight of the oil phase.

According to some embodiments, the total concentration of non-amino-silicone oil is at most 15 wt. %, at most 12 wt. %, at most 10 wt. %, at most 7 wt. %, or at most 5 wt. % by weight of the oil phase.

According to some embodiments, at least one coating composition further contains sub-micronic pigment particles. In such case, the sub-micronic pigment particles can comprise an organic pigment, for example an organic pigment selected from the group of perylene pigments; phthalocyanine pigments; quinacridone pigments; and imidazolone pigments.

According to some embodiments, the sub-micronic pigment particles comprises an inorganic pigment, for example an inorganic pigment selected from the group of titanium dioxide, cadmium sulfoselenide, iron oxide, bismuth vanadate, cobalt titanate, sodium aluminosulfosilicate, mixed Fe—Mg—Ti oxides, manganese ferrite, and metallic or alloy pigments.

In some embodiments, the sub-micronic organic or inorganic pigments (or combinations thereof) serve as color imparting agents. The sub-micronic pigments may also be referred to as light absorbing pigments or simply as absorbing pigments.

According to some embodiments, the sub-micronic pigment of any coloring composition is an organic or inorganic pigment selected from the group of the following EU-approved colors for cosmetic use: CI 10006, CI 10020, CI 10316, CI 11680, CI 11710, CI 11725, CI 11920, CI 12010, CI 12085, CI 12120, CI 12370, CI 12420, CI 12480, CI 12490, CI 12700, CI 13015, CI 14270, CI 14700, CI 14720, CI 14815, CI 15510, CI 15525, CI 15580, CI 15620, CI 15630, CI 15800, CI 15850, CI 15865, CI 15880, CI 15980, CI 15985, CI 16035, CI 16185, CI 16230, CI 16255, CI 16290, CI 17200, CI 18050, CI 18130, CI 18690, CI 18736, CI 18820, CI 18965, CI 19140, CI 20040, CI 20470, CI 21100, CI 21108, CI 21230, CI 24790, CI 26100, CI 27755, CI 28440, CI 40215, CI 40800, CI 40820, CI 40825, CI 40850, CI 42045, CI 42051, CI 42053, CI 42080, CI 42090, CI 42100, CI 42170, CI 42510, CI 42520, CI 42735, CI 44045, CI 44090, CI 45100, CI 45190, CI 45220, CI 45350, CI 45370, CI 45380, CI 45396, CI 45405, CI 45410, CI 45430, CI 47000, CI 47005, CI 50325, CI 50420, CI 51319, CI 58000, CI 59040, CI 60724, CI 60725, CI 60730, CI 61565, CI 61570, CI 61585, CI 62045, CI 69800, CI 69825, CI 71105, CI 73000, CI 73015, CI 73360, CI 73385, CI 73900, CI 73915, CI 74100, CI 74160, CI 74180, CI 74260, CI 75100, CI 75120, CI 75125, CI 75130, CI 75135, CI 75170, CI 75300, CI 75470, CI 75810, CI 77000, CI 77007, CI 77266, CI 77267, CI 77268:1, CI 77891, CI 77947, lactoflavin, caramel, capsanthin, capsorubin, beetroot red, anthocyanins, bromothymol blue, bromocresol green, and acid red 195.

According to some embodiments, the sub-micronic pigment of any coloring composition is selected from the group of the following US-certified organic colors for cosmetic use:

D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10 and D&C Yellow No. 11.

In some embodiments, the sub-micronic organic or inorganic pigments provide a special visual effect, instead of or in addition to a coloring effect. Special effects include, by way of non-limiting example, a fluorescent effect, a glittering effect, a pearlescent effect, a nacreous effect and a phosphorescent effect. These effects may be visible under regular illumination or may require (or be further increased)

by special conditions of observation, such as a function of lighting conditions, angle of observation etc. For instance, fluorescent pigments may become visible or may provide a fluorescent effect when subjected to ultraviolet (UV) light. At the other end of the spectrum, up-converting pigments are luminescent materials which are able to convert near infrared (NIR) light to visible (VIS) light. Additional colorants providing for less typical coloring further include, by way of non-limiting example, thermo-chromic pigments or dyes, allowing the compositions comprising them to change color as a result of a change in temperature, and pH dependent pigments, whose color is modified by pH.

When present in the amino-silicone emulsions, any of the afore-said pigments can further be surface treated, for instance with an organic agent, so as to further improve any desired property of the pigment (e.g., visual effect, chemical stability, dispersibility, charge, ability to adhere to a fiber, ability to interact with the amino-silicone matrix, etc.). Surface treatment techniques need not be detailed herein, and surface-treated pigments may be commercially available in the required form (e.g. non-ionic, cationic, anionic, or positively charged, negatively charged, or substantially non-charged). In one embodiment, the pigment particles can be surface treated (e.g., by acid groups), so as to ameliorate interaction between the pigment and the amino-silicone pre-polymers entrapping them during the formation of a 3D network of amino-silicone on the hair fiber.

Color imparting agents as used in the present disclosure are pigments, which may optionally be combined or replaced by dyes in particular cases (e.g., for tinting). However, even when dyes are used as color imparting agent to a composition or to a pigment coat, they are not oxidative dyes. In some embodiments, compositions according to the present teachings are substantially devoid of oxidative dyes and of any chemical agent conventionally used in combination with oxidative dyes, including by way of non-limiting example, dyes' couplers and oxidizing agents (e.g., a hydrogen peroxide developer).

In some embodiments, to be detailed in the following sections, inorganic pigments can be used in coating compositions, kits or methods according to the present teachings in a size range greater than sub-micronic range. Such inorganic pigments are either made of metals, alloys or oxides thereof, or formed as multilayer pigments based on substrates (such as mica, silica, borosilicate, plastic or even metals) coated with the same afore-mentioned metallic materials. Multilayer pigments having for instance a mica core or a silica core are also referred to as mica coated flakes or silica coated flakes, the coat (e.g., sometimes applied by chemical vapor deposition (CVD) or physical vapor deposition (PVD)) providing the look. These pigments typically provide a metallic appearance, or any such special effect, and are thus collectively termed metallic pigments or metallic-looking pigments irrespective of chemical type.

While some of the above-mentioned metallic pigments may provide for a broad range of light reflection, others may be more specific, reflecting a narrow range of wavelengths or even a single wavelength (e.g., interference pigments). Such narrowly reflective pigments include by way of example mica pigments coated with a thin layer of metals, alloys or oxides thereof. As used herein, the term "reflective pigment" encompasses any metallic pigment able to reflect at least one wavelength. In some embodiments, the reflective pigment is further tinted to provide a coloring effect in addition to a light reflective effect.

In some embodiments, the reflective pigment is tinted with a dye selected from the group of an azo dye (such as Color Index (C.I.) Reactive Yellow 4); an anthraquinone dye (such as C.I. Reactive Blue 19); and a phthalocyanine dye (such as C.I. Direct Blue 86).

In some embodiments, the metallic pigment is selected from the group of aluminum, copper, zinc, iron, titanium, gold, or silver and alloys of these metals, such as brass, bronze or steel alloys. In some embodiments, the metallic pigment is selected from the group of bismuth oxychloride, mica and silica coated with titanium dioxide, silicon dioxide, iron oxide, chromium oxide, zinc oxide, aluminum oxide, and tin dioxide. In some embodiments, the metallic pigment is further coated with dyes or sub-micronic pigments to additionally provide or enhance a coloring effect, such as, for example, aluminum pigment coated with phthalocyanine blue or Cinquasia® red. In some embodiments, there are provided multi-layer pigments based on synthetic substrates such as alumina, silica, calcium sodium borosilicate or calcium aluminium borosilicate, and aluminium.

In addition to having, in some embodiments, at least one dimension above one micrometer, the metallic pigments have advantageously a flake-like or platelet shape.

Depending on their morphology, particles (e.g., submicronic (absorbing) pigments, metallic (reflective) pigments, reinforcement fillers and the like) may be characterized by their length, width, thickness, diameter, or any such representative measurement of their X-, Y- and Z-dimensions. Typically, such sizes are provided as average of the population of particles and are provide by the manufacturer of such materials. These sizes can be determined by any technique known in the art, such as microscopy and Dynamic Light Scattering (DLS). In DLS techniques, the particles are approximated to spheres of equivalent behavior and the size can be provided in terms of hydrodynamic diameter. DLS also allows assessing the size distribution of a population. The same applies to liquid droplets and may assist for instance in the characterization of emulsion droplets or micelles, all typically having a globular shape. As used herein, particles having a size of, for instance, 1 μm or less, have at least one dimension equal to or smaller than 1 μm, and possibly two or even three, depending on shape. When concerned with emulsion droplets having, by way of example, a size of 5 μm or less, the droplets are understood to have an average diameter (Dv50) equal to or smaller than 5 μm.

Though not essential, the particles or emulsion droplets of any particular kind may preferably be uniformly shaped and/or within a symmetrical distribution relative to a median value of the population and/or within a relatively narrow size distribution for this particular kind. In the following, and unless otherwise clear from context, the term "particle" refers both to solid particles (e.g., pigments and the like) and to liquid droplets (e.g., emulsion droplets, micelles and the like).

A particle size distribution (PSD) is said to be relatively narrow if at least one of the two following conditions applies:

A) the difference between the hydrodynamic diameter of 90% of the particles and the hydrodynamic diameter of 10% of the particles is equal to or less than 150 nm, or equal to or less than 100 nm, or equal to or less than 50 nm, which can be mathematically expressed by: (D90–D10)≤150 nm and so on; and/or B) the ratio between a) the difference between the hydrodynamic diameter of 90% of the particles and the hydrodynamic diameter of 10% of the particles; and b) the hydrodynamic diameter of 50% of the particles, is no more than 2.0, or no more than 1.5, or no more than 1.0, which can be mathematically expressed by: (D90−D10)/D50≤2.0 and so on.

D10, D50 and D90 can be assessed by number of particles in the population, in which case they may be provided as $D_N10$, $D_N50$ and $D_N90$, or by volume of particles, in which case they may be provided as Dv10, Dv50 and Dv90. The foregoing measurements can be obtained by DLS techniques when the samples to be studied are suitably fluid or by microscopy when the particles under study are in dry form. As used herein, D50, which can also be termed the "average measured particle size" or simply the "average particle size" may refer, depending on the measuring method most suited to the particles being considered and their media, either to Dv50 (by DLS and the like) or to the volume average size of particles found in a field of view of a microscope adapted to analyze in the scale of the particles. D90 accordingly relate to measurements applying to 90% of the population under study, thus also termed the "predominant measured particle size" or simply the "predominant particle size" which can for instance be assessed by DLS techniques as Dv90.

As mentioned above, such relatively uniform distribution may not be necessary for certain applications. For instance, having a relatively heterogeneously sized population of sub-micronic pigments or of metallic pigments particles may allow, in a coating formed thereby, relatively smaller particles to reside in interstices formed by relatively larger particles providing in combination a relatively uniform coating.

The particles may be characterized by an aspect ratio, i.e., a dimensionless ratio between the smallest dimension of the particle and the longest dimension or equivalent diameter in the largest plane orthogonal to the smallest dimension, as relevant to their shape. The equivalent diameter (Deq) is defined by the arithmetical average between the longest and shortest dimensions of that largest orthogonal plane. Particles having an almost spherical shape, and emulsion droplets amongst them, are characterized by an aspect ratio of approximately 1:1, whereas rod-like particles can have higher aspect ratios and flake-like particles can even have an aspect ratio of up to 1:100, or even more.

Such characteristic dimensions are generally provided by the suppliers of such particles and can be assessed on a number of representative particles by methods known in the art, such as microscopy, including, in particular, by light microscope for particles of several microns or down to estimated dimensions of about 200 nm, by scanning electron microscope SEM for smaller particles having dimensions of less than 200 nm (SEM being in particular suitable for the planar dimensions) and/or by focused ion beam FIB (preferably for the thickness and length (long) dimensions of sub-micronic particles, also referred to herein as nanoparticles or nanosized particles). While selecting a representative particle, or a group of representative particles, that may accurately characterize the population (e.g., by diameter, longest dimension, thickness, aspect ratio and like characterizing measures of the particles), it will be appreciated that a more statistical approach may be desired. When using microscopy for particle size characterization, a field of view of the image-capturing instrument (e.g., light microscope, SEM, FIB-SEM etc.) is analyzed in its entirety. Typically, the magnification is adjusted such that at least 5 particles, at least 10 particles, at least 20 particles, or at least 50 particles are disposed within a single field of view. Naturally, the field of view should be a representative field of view as assessed by one skilled in the art of microscopic analysis. The average value characterizing such a group of particles in such a field of view is obtained by volume averaging. In such case, $Dv50=\Sigma[(Deq(m))^3/m]^{1/3}$, wherein m represents the number of particles in the field of view and the summation is performed over all m particles. As mentioned, when such methods are the technique of choice for the scale of the particles to be studied or in view of their media, such measurements can be referred to as D50.

According to some embodiments, the sub-micronic pigment comprises on average particles having a Dv50 of at most 1,000 nm, at most 750 nm, at most 500 nm, at most 250 nm, at most 150 nm, or at most 100 nm, and optionally, a Dv10 of at least 10 nm, at least 25 nm, or at least 50 nm. In some embodiments, the sub-micronic pigment particles are in a range comprised between a Dv10 of at least 10 nm and a Dv90 of at most 2,500 nm, or in a range between a Dv10 of at least 25 nm and a Dv90 of at most 1,500 nm, or in a range between a Dv10 of at least 50 nm and a Dv90 of at most 1,000 nm.

According to some embodiments, the sub-micronic pigment predominantly comprises particles having a Dv90 of at most 1,000 nm, at most 750 nm, at most 500 nm, at most 250 nm, at most 150 nm, or at most 100 nm, and optionally, a Dv50 of at most 300 nm, at most 250 nm, at most 200 nm, at most 150 nm, at most 100 nm, or at most 75 nm. In some embodiments, the sub-micronic pigment particles have a Dv10 of at least 10 nm, at least 25 nm, or at least 50 nm. In some embodiments, the sub-micronic pigment particles are in a range comprised between a Dv10 of at least 10 nm and a Dv90 of at most 1,000 nm, or in a range between a Dv10 of at least 25 nm and a Dv90 of at most 750 nm, or in a range between a Dv10 of at least 25 nm and a Dv90 of at most 500 nm.

According to some embodiments, the amino-silicone formulation or kit disclosed herein further comprises a cross-linker, for example, an organosilicon compound able to react through all non-amino reactive groups of the reactive silicone, and a cross-linking agent comprising a mercapto group, an epoxy group or an acrylate group, all able to react through amino reactive groups of the reactive silicone.

Generally, cross-linking agents comprise at least three reactive groups for the formation of the network of oligomers and polymers resulting in the amino-silicone network.

The organosilicon cross-linking agent must have hydrolysable groups (Y).

After hydrolysis, the silanol groups obtained can undergo condensation reaction with the reactive amino-silicone polymer to give siloxane bonds.

The condensation-curable amine-silicone monomers, oligomers or polymers can contain:
tetrafunctional hydrolysable groups and include for example silane having Q units ($SiO_{4/2}$), such as $SiY_4$
or trifunctional hydrolysable groups and include silane or siloxane oligomers having T units of the formula $R^aSiO_{3/2}$, like $R^aSiY_3$
or difunctional hydrolysable groups and include silane or siloxane oligomers having D units of the formula $R^b{}_2SiO_{2/2}$, like $R^b{}_2SiY_2$, as long as the cross-linker has a total of at least three hydrolysable groups,
or monofunctional hydrolysable groups having M units, as long as the cross-linker has a total of at least three hydrolysable groups, where the hydrolysable group (Y) can be selected from
Alkoxy (e.g., methoxy, ethoxy, propoxy, isopropoxy, methoxyethoxy and the like)
Oxime (e.g., methylethylketoxime)

Acyloxy (e.g., acetoxy) where the $R^a$ and $R^b$ substituents are selected from $C_1$-$C_6$ or $C_1$-$C_4$ alkyl groups, Alkenyl groups (vinyl, allyl, etc.), Aminoalkyl groups (monoamino, such as aminopropyl $NH_2(CH_2)_3$: diamino, such as aminoethylaminopropyl $NH_2(CH_2)_2NH(CH_2)_3$; or triamino)

Epoxy group (e.g., glycidoxypropyl)

Acrylate group (e.g., methacryloxypropyl)

Mercapto group (e.g., mercaptopropyl)

According to some embodiments, condensation-curable amino-silicone monomer, oligomer or polymer can be a branched or a linear polyorganosiloxane comprising at least one of Q units, T units, D units and M units, with the proviso that the total amount of hydrolysable groups and/or of silanols in the cross-linking agent is of at least three, allowing the formation of a 3D network. When a mixture of cross-linking agents is used, at least one cross-linking agent of the mixture must contain a total of at least three hydrolysable groups and/or of silanols.

According to some embodiments, the first reactant can include (e.g., serving as cross-linker) a condensation-curable monomer or oligomer, not being of the amino-silicone type. For example, the condensation-curable monomer or oligomer can be an ethyl silicate, such as tetraethyl silicate (CAS No 78-10-4), a 3$^+$Sil monomer having a MW of about 208 and a refractive index (RI) of about 1.382, poly(diethoxysiloxane) oligomers, such as Evonik Dynasylan® 40 (a 3$^+$Sil molecule having a MW of ~750; RI of ~1.397) with a silicon dioxide content of approximately 40-42% upon complete hydrolysis, Colcoat® Ethylsilicate 48, a 3$^+$Sil ethyl silicate oligomer with a silicon dioxide content of approximately 48% upon complete hydrolysis (CAS No. 11099-06-2), a propyl silicate, such as tetrapropyl orthosilicate (CAS No. 682-01-9), a 3$^+$Sil monomer having a MW of ~264 and a RI of ~1.401, poly(dimethoxysiloxane) (CAS No. 25498-02-6), a 3$^+$Sil oligomer having a MW of ~106 and a RI of ~1.400, 3-Glycidyloxypropyl trimethoxysilane by Evonik, Carbodilite Emulsion E-05, having 40% multifunctional polycarbodiimide in anionic emulsion, and Carbodilite V02-B, having 100% multifunctional polycarbodiimide. While the aforesaid non-amino monomeric or oligomeric alkyl silicate cross-linkers are per se generally hydrophilic, their presence in the polymer matrix is in such a relatively low amount that the overall nature of the curable oil-in-water emulsion or of the cured amino-silicone film remains hydrophobic, as dictated by the polymer-forming amino-silicone monomers, oligomers and/or polymers.

According to some embodiments, the polymer-forming amino-silicone reactant can be aminopropyltriethoxysilane (CAS No. 919-30-2) a condensation-curable 3Sil amino-silicone monomer having a MW of ~221, an Amine Number of ~450 and a RI of ~1.422 (such as commercially available, for instance, as Dynasylan® AMEO), bis(3-triethoxy-silylpropyl)amine (CAS No. 13497-18-2) a 3$^+$Sil condensation-curable amino-silicone monomer having a MW of ~426, an Amine Number of ~235 and a RI of ~1.426 (such as commercially available as SIB1824.5), (1-(3-triethoxysilyl) propyl)-2,2-diethoxy-1-aza-2-silacyclopentane (CAS No. 1184179-50-7) a 3$^+$Sil condensation-curable amino-silicone monomer having a MW of ~380, an Amine Number of ~263 and a RI of ~1.432 (such as commercially available as SIT8187.2), or mixtures thereof (such as Dynasylan® SIVO 210). Other suitable polymer-forming amino-silicone reactants can be selected from the group comprising: KF-857, GP-145, GP-34, GP-397, GP-657, GP-846, KF-862, SF 1706, TSF 4703, TSF 4707, TSF 4708, OFX 8630, OFX 8822, Dynasylan® 1146, S106629.1, DMS-512, ATM 1322, Bis[methyldiethoxysilyl-propyl] amine, Diethoxydimethylsilane, and any commercially available equivalent of the foregoing. Such amino-silicone monomers or oligomers may be considered as building blocks of the amino-silicone film (i.e., condensation-curable pre-polymers) or as cross-linking agents for such building blocks.

According to some embodiments, suitable pigment dispersants include for example silicone amines such as BYK LPX 21879, by BYK, GP-4, GP-6, GP-344, GP-851, GP-965, GP-967, and GP-988-1, by Genesee Polymers, silicone acrylates such as Tego® RC 902, Tego® RC 922, Tego® RC 1041, and Tego® RC 1043, by Evonik, PDMS silicones with a carboxylic function such as X-22162 and X-22370 by Shin-Etsu, silicone epoxy such as GP-29, GP-32, GP-502, GP-504, GP-514, GP-607, GP-682, and GP-695, by Genesee Polymers, or Tego® RC 1401, Tego® RC 1403, Tego® RC 1412, by Evonik.

According to some embodiments, suitable non-reactive silicone materials are: GP-965, GP-967, Rhodorsil (Bluesil) 21642, SID 2650-D5, Wacker Finish WR 1100 or Siltech® E-2154.

According to some embodiments, the cross-linker is a non-amino silicone having a molecular weight of less than 1000 g/mol, thus includes, mainly includes, or consists of a reactive condensation-curable film-forming non-amino-silicone monomer. In some embodiments, the total concentration of the non-amino cross-linking agent is at most 35 wt. %, at most 30 wt. %, at most 20 wt. %, at most 15 wt. %, at most 10 wt. %, or at most 5 wt. % by weight of the oil phase.

According to some embodiments, the total concentration of: reactive condensation-curable film-forming amino-silicone pre-polymers; amino- and non-amino-silicone oils; non-amino cross-linking agent; and reactive filler, including any pigment particles and dispersant for said pigment particles, within said oil phase, is at least 90 wt. %, at least 93 wt. %, at least 95 wt. %, at least 97 wt. %, at least 98 wt. %, or at least 95 wt. %, by weight of the total composition.

According to some embodiments, the pigment particles are further coated with a chemical coat which does not interfere with the visual effect of the underlying pigment. Such a chemical coat can provide protection to the pigment, such as providing anti-oxidant properties, or any other desired property, by way of example, dispersibility, stability, ability to adhere to the fibers, charge and like characteristics that improves pigment activity and intended effect. For instance, the chemical coat can be a fatty acid, such as oleic acid, stearic acid, an adhesion promoting polymer coat, such as an acrylic polymer, a silane polymer or an amino-silane polymer, and such chemical coats known in the art of pigments.

In other embodiments, the chemical coat provides a visual effect, for instance when the pigment a flake-like shaped metallic pigment (e.g. mica or glass flakes, having an average greatest dimension in the range of 2 to 20 μm), the coating may be a metal oxide, such as, for example, titanium dioxide or ferric oxide.

According to some embodiments, the oil-in-water emulsion is prepared in the presence of a non-ionic emulsifier, preferably having a hydrophile-lipophile balance (HLB) value between 12 to 18, 12 to 17, 12 to 16, 12 to 15, or 13 to 16 on a Griffin scale. Emulsions can be prepared by a number of emulsification techniques known to the skilled person. While manual shaking may suffice, various equipment, such as a vortex, an overhead stirrer, a magnetic stirrer, an ultrasonic disperser, a high shear homogenizer, a sonicator and a planetary centrifugal mill, to name a few, can be used, typically providing more homogenous populations of oil droplets in the aqueous phase. The emulsion can be readily applied following its preparation or within a time period during which it remains suitably stable. For instance, the emulsion can be applied as long as the oil droplets are within their desired size range and providing that the emulsified amino-silicone pre-polymers remain reactive. As the thickness of the coat is believed to be proportional to the average diameter of the droplets, too large droplets are to be avoided if a thin coat is desired, while on the other hand too small droplets would not be able to embed pigment particles having sufficient size to provide for the desired visual effect. The time may vary with the constituents of the emulsion and their respective amounts, the presence of an emulsifier typically extending it. In some embodiments, the emulsion is applied to the hair fibers within at most 30 minutes from its emulsification, or within at most 20 minutes, at most 10 minutes, or at most 5 minutes.

According to some embodiments, the aqueous carrier of the coating composition (e.g., of the amino-silicone formulation or of the aqueous dispersion including the acidic polymeric material) comprises at least 60% water by weight of the liquid carrier, or at least 65 wt. %, or at least 70 wt. %, or at least 75 wt. %, or at least 80 wt. %, or at least 85 wt. %, or at least 90 wt. %, or at least 95 wt. % water. In some embodiments, the total concentration of the water and any emulsifier is at least 90 wt. %, at least 95 wt. %, at least 97 wt. % at least 99 wt. %, by weight of the aqueous phase.

In cases in which the amount of pigments in any of these coating compositions and/or their density is high, while the liquid carrier will predominantly comprise water, the water may constitute only 30% by weight of the total composition.

According to some embodiments, a pH of the amino-silicone formulation is in the range of from about 4 to about 11.5, from about 6 to about 11.5, from about 7.5 to about 10.5, from about 8 to about 11, or from about 9 to about 11.

According to some embodiments, a viscosity of the amino-silicone coating composition is in the range of from about 1 to about 2,000 mPa·s at 25° C., such as from about 10 to about 500 mPa·s at 25° C.

According to some embodiments, the coating compositions according to the present teachings (or the kit s enabling their preparation and use) further comprise at least one additive selected from the group of dispersant, pH modifying agents, preservatives, bactericide, fungicide, viscosity modifiers, thickeners, chelating agents, vitamins and perfumes. Depending on the mode of application, additional agents can be required, for instance, a propellant can be added if the composition is to be applied as a propelled spray.

According to some embodiments, the coating composition is in the form selected from the group of a paste, a gel, a lotion, and a cream.

The coating characteristics, e.g. the presence of cured polymers on the hair surface (as can be determined by the existence of a glass transition temperature, as detectable by DSC), or the presence of particular chemical moieties (as can be determined by suitable analytical methods, including for example, by FTIR spectroscopy) can be detected by direct analysis of the coat while attached to the hair fibers, or by preliminarily separating of the coat to perform the analysis ex situ. Alternatively, the measurement can be done in vivo, on the compositions themselves, not coating any fibers.

According to some embodiments, the fibers are keratinous fibers, and in particular are mammalian hair. In some embodiments, the hair is human hair or animal hair, the hair being selected from body hair, facial hair (including for example moustaches, beards, eyelashes and eyebrows) or head hair. In further embodiments, the hair is attached to a body or scalp of a human or an animal subject. Human hair can be of any human race (e.g., European, Asian, African, etc.) and any type, such as straight, wavy, curly, or kinky, whether naturally or artificially so. Human hair not attached to a subject can be found in wigs, hair extensions, eyelash extensions, and like products. In some embodiments, the mammalian hair fibers are dry, non-wetted, or to pre-dyed. In some embodiments, the mammalian hair fibers are unpre-degreased, unpre-shampooed, and unpre-bleached.

FIG. 2A is a schematic illustration of the amino-silicone coated fiber 21 of FIG. 1C, in the presence of various dispersed components from an aqueous dispersion, the dispersed components including a neutralized, acid functionalized polymeric material having neutralized acid moieties 22 and a surfactant or super-wetting agent 24.

FIG. 2B is a schematic illustration representing how some of the components of FIG. 2A have migrated towards coated fiber 21 of FIG. 2A, and are arranged thereupon as a layer 24' of super-wetting surfactant and a layer 22' of acidic polymeric material. While 22' and 24' are shown for simplicity of illustration as individual layers, the actual contact of their constituents with the coated fiber can assume any other arrangement. The negative charges on the acid-neutralized moieties may be attracted to the positive charges on the surface of coated fiber 21, and a layer may accordingly form, substantially as (schematically) shown.

FIG. 2C schematically shows the coated fiber of FIG. 2A, in which the components of FIG. 2B have coalesced to form a continuous layer 60 adhering to the external surface of coated fiber 21.

FIG. 3 schematically shows a cross section of a fiber coated according to various embodiments of the present method. The hair fiber 10 is coated with a first coat 20a formed by an amino-silicone film. A second coat 60a is adhered to the first coat 20a, the second coat being formed of polymeric materials having neutralizable acid moieties. Layer 20b illustrates an optional third coat, which can be similar in composition to first coat 20a. In some embodiments, the optional third layer over the surface of the core fiber 10 can be as illustrated by 60b, which can be similar in composition to second coat 60a. In other embodiments, the optional third coat can be as illustrated by 20b, this third coat being further optionally coated by a fourth coat, as illustrated by 60b. For simplicity and clarity of illustration, pigments 70, which are optional in the amino-silicone films, are omitted from the optional third and fourth coats. Optional solid three-dimensional (3D) network former 80 may be found in the first amino-silicone coat 20a or in any optional subsequent coat of similar composition, such as illustrated by 20b.

FIG. 4 briefly summarizes as a simplified diagram the various steps that may be employed in various embodiments of a coating process according to the present teachings. In a first step 405, an oil-in-water emulsion including at least one condensation-curable amino-silicone reactant is applied to the external surface of individual fibers. The duration of application step 405 typically allows at least partial condensation curing of the amino-silicone reactant to form an at least partially cured amino-silicone film. In some embodiments, the at least partial curing can be facilitated by the application of heat at a temperature above ambient temperature and generally below 45° C., and more typically, at a drying temperature of at most 40° C., at most 35° C., at most 30° C., or at most 25° C. Following the application of the emulsion, the fibers can optionally be washed 410, for instance, so as to remove excess emulsion. Alternatively, the emulsion coated fibers can be directly dried 415, without a prior washing step 410. In a further alternative, following the application of the emulsion 405, the fibers can be both washed 410 and then dried 415. Independently of the number and identity of the optional steps performed following the application of the emulsion, the fibers following such step(s) will be considered "first coated" by an at least partially cured amino-silicone film. An aqueous dispersion is then applied 420 to the first coated fibers, the aqueous dispersion containing a polymeric material having neutralized acid moieties. Following the application of the aqueous dispersion 420, the fibers can optionally be washed 425, be directly dried 430, or be both washed 425 and then dried 430. Independently of the number and identity of the optional steps performed following the application of the aqueous dispersion, the fibers following such step(s) will be considered "second coated" by a polymeric film. In one embodiment, the coating process may end at this stage, generally following at least a washing step 425. However, further coats may be similarly added to the fibers, wherein the polymeric film second coat forms the under-layer for such subsequent coats.

In a first option, the new underlayer can be subjected to a process as described, wherein additional coats are formed 440 by subsequent application of an emulsion 405 and application of an aqueous dispersion 420, such steps being respectively followed by optional washing 410 and/or 425 and/or drying 415 and/or 430, as herein explained.

In a second option, the new under-layer can be directly further coated with a same or different polymeric film. For this purpose, an aqueous dispersion can be applied 420 to the surface of the under-layer on the fibers, such application being followed by an optional washing 425 and/or drying 430, as herein explained.

While in the simplified diagram of FIG. 4, the options of further applying at least two coats 440 or further applying one coat 450 are depicted as being performed on dried fibers resulting from optional drying step 430, this needs not be construed as limiting. For instance, the further coats can be formed 440 on washed fibers resulting from optional washing step 425.

EXAMPLES

Example 1: Preparation of Amino-Silicone Emulsions

In a vial, were mixed for about 5 seconds using a Vortex Genie 2 mixer (from Scientific Industries Inc., USA) the following:
6 g of reactive condensation-curable amino-silicone polymer, GP-397 (a 2Sil polymer having an Amine Number of 116 and a MW of ~3,754 g/mol), supplied by Genesee Polymers Corp., USA.
4 g of silicone solvent, decamethylcyclopentasiloxane (D5; CAS No. 541-02-6) having a MW of ~371 and a RI of ~1.398, supplied by Gelest Inc., USA.
4 g of amino-functional silane cross-linker, Dynasylan® SIVO 210, supplied by Evonik Industries AG, Germany (which contains primary and secondary aminoalkylethoxysilanes, the blend of condensation-curable monomers having an estimated Amine Number of about 370).

The resulting cross-linkable amino-silicone blend was further sonicated for 15 seconds at 30% of maximal amplitude of a Q700 sonicator (QSonica LLC, USA) until it formed a clear solution, herein termed the Amino-silicone Blend (ASB).

In a separate vessel, a 0.1 wt. % emulsifier dispersion was prepared by adding 0.06 g of polyoxyethylene (20) sorbitan monooleate surfactant (Tween® 80, CAS No. 9005-65-6, supplied by Sigma-Aldrich Co., USA, having an HLB value of 15.0 on the Griffin scale) to 59.94 g of deionized water. They were manually shaken until a clear and homogeneous surfactant solution was obtained.

Unless otherwise stated, the Amino-Silicone Emulsion (ASE) was prepared by adding 0.12 g of ASB clear blend into 60 g of the 0.1 wt. % surfactant solution and by sonicating the mixture for 15 seconds at 50% of maximal amplitude of a Q700 sonicator, until a homogeneous emulsion was obtained. The average size (Dv50) of the resulting emulsion droplets was measured using a laser diffraction particle size analyzer (Mastersizer AWA 2003 from Malvern Instruments Ltd., United Kingdom) and was found to be sub-micronic. While ASE contains constituents, which may ultimately combine and react with one another to yield a film of amino-silicone on the fibers being coated therewith, such reaction did not occur to a significant level in the liquid composition It is believed that in the emulsion the various constituents tend to repulse one another, preventing or reducing polymerization in the liquid medium, at least for one hour following the preparation of the ASE.

Unless otherwise stated, when in the following examples the first coat is said to be as described in Example 1, it refers to the previous representative ASE including as silicon-based materials in the ASB: GP-397, D5 and Dynasylan® SIVO 210.

Additional suitable ASEs can be similarly prepared by replacing the condensation-curable amino-silicone polymer GP-397 by (a) amine/alkoxy functional silicone polymers GP-657 (a 3$^+$Sil molecule having an Amine Number of 54 and a MW of ~3,700 g/mol), or by (b) GP-145 (a 2Sil polymer having an Amine Number of 11 and a MW of ~18,000 g/mol), both supplied by Genesee Polymers Corp., USA., or by (c) KF-857 (a 2Sil polymer having an Amine Number of 127, a RI of ~1.412), purchased from Shin-Etsu.

Additional suitable ASEs can be similarly prepared in absence of added emulsifier, the constituents of the ASB being capable of self-emulsification. An example of such an ASB was prepared by mixing 50 wt. % of Dynasylan® SIVO 210, with 27.7 wt. % of GP-967, 5.55 wt. % of GP-965 and 16.66 wt. % of hexamethyldisiloxane (M2; CAS No. 107-46-0). GP-967 and GP-965 were supplied by Genesee Polymers Corp., USA, the former being an amino-silicone oligomer having as chemical name 1,3-bis(3-aminopropyl)tetramethyl disiloxane and a MW of 248.5, and the latter being an amino-silicone oligomer having a MW of about 1000 and an Amine Number of 200. As GP-967 and GP-965 lack condensation-curable moieties, they can be referred to as amino-silicone oils. An amino-silicone emulsion was prepared by mixing 0.2 g of the afore-described blend of amino-silicone monomers in a mixture of amino-silicone oils and carrier in 60 ml of distilled water.

An additional ASB was prepared by mixing the condensation-curable amino-silicone monomers of Dynasylan® Sivo 210 (73 wt. %) with amino-silicone oils (GP-967 and GP-965, respectively at 20 wt. % and 7 wt. % of the total blend). 0.2 g of this oily phase ASB were added to 60 ml of aqueous forms. In a first reference sample, the ASB was added to plain distilled water. In additional samples, the water carrier was first supplemented with thickening agents, the ASB being subsequently added to an aqueous carrier having a gel form. A first thickened aqueous carrier was prepared by adding 0.5 wt. % Polyquaternium 7 (PQ-7) and 0.1 wt. % Polyquaternium 10 (PQ-10), per weight of distilled water. The Polyquaternium nomenclature is as assigned by the Cosmetic, Toiletry and Fragrance Association (CTFA) to most cationic conditioning polymers. PQ-7 is a poly(acrylamide-co-diallyldimethylammonium chloride) copolymer and PQ-10 is a quaternized hydroxyethyl cellulose, both supplied by Dow. A second thickened aqueous carrier was prepared by further adding 0.1 wt. % Benecel™ K200M (an hydroxypropyl methylcellulose supplied by Ashland) to previous 0.5 wt. % PQ-7 and 0.1 wt. %

PQ-10. A third thickened aqueous carrier was prepared by adding higher amounts of thickening agents, namely 0.5 wt. % Benecel™ K200, 0.5 wt. % PQ-10 and 2.5 wt. % PQ-7, per weight of distilled water. The various thickeners of the different mixtures were generally added one at time under stirring conditions, as soon as the previous one(s) was/were evenly dissolved.

All three thickened samples and aqueous control were manually shaken with the oil phase mixture to obtain three four types of ASE forms, derived from the same ASB. The viscosity of the reference sample (ASB in water) and of the thickened samples was measured at 25° C. using a HAAKE™ MARS™ III Rheometer with Spindle-C60 at a shear rate of 30 sec$^{-1}$. While the reference sample had a viscosity of about 0.89 mPa·sec, the thickened counterparts respectively displayed a viscosity of about 20.1 mPa·sec (PQ-7+PQ-10), and of a viscosity of about 56.7 mPa·sec (PQ-7+PQ-10+0.1 wt. % Benecel™ K200M) and a viscosity of about 2000 mPa·sec (PQ-7+PQ-10+0.5 wt. % Benecel™ K200M). All four samples were used in hair coloring experiments as herein disclosed and provided similarly satisfactory coloring.

Example 2: Preparation of Polymer-Embedded Pigment

Step 1: Compounding of Alkene Copolymers Having Neutralizable Acid Moieties with a Pigment:

Pigments were embedded into ethylene acrylic acid (EAA) or ethylene methacrylic acid (EMAA) copolymers, in weight per weight ratio from 1:2 to 1:4, as follows. The pigments listed in Table 1 were each separately loaded in the amounts indicated therein together with Primacor™ 5980I (an EAA copolymer having an acrylic acid content of 20 wt. % as determined by the supplier, Dow Chemical Company, USA) to a tree roll mixing mill (Mixing mill Model 00, Sailing International Industry Group, China) having its kneading rolls heated to about 150° C. by internal oil circulation. The EAA-pigment paste was reloaded through the kneading rolls, sheared and mixed for about 10 minutes (10 cycles of milling in total). At the end of the melt-kneading compounding process, the relatively dry EAA-pigment stripe-like composite was cut with scissors into small flat squares having edges of about 0.5 cm. The composite flat squares were further ground under cryogenic conditions using liquid nitrogen in a coffee-bean grinder (KG40 from De'Longhi Appliances Srl, Italy), until the EAA-embedded pigments formed a powder of granules having an approximate diameter of a few millimeters. Unless clear from the pigment denomination, the color it may provide is indicated in parentheses in the following tables.

TABLE 1

| Item | Pigment (Color) | Supplier | Pigment (g) | Primacor™ 5980I (g) |
|---|---|---|---|---|
| 1 | Diacetanil Yellow HTT 8318C | Cappelle | 8 g | 32 g |
| 2 | Emperor ® 1200 (Black) | Cabot | 6 g | 24 g |
| 3 | Hansa Red B-IN | Clariant | 3 g | 12 g |
| 4 | Hostaperm Green GNX-C | Clariant | 9 g | 36 g |
| 5 | Lithol ® Rubine (Red) | BASF | 17 g | 30 g |
| 6 | PV Fast Orange H2GL | Clariant | 6 g | 24 g |
| 7 | TiO$_2$ Ti-Pure ® R105 (White) | DuPont | 8 g | 16 g |
| 8 | Vynamon ® Blue 3RFW-H | Heubach | 6 g | 24 g |

The pigments listed in Table 2 were each separately loaded in the amounts indicated therein together with Primacor™ 5990I (an EAA copolymer having an acrylic acid content of 20.5 wt. % as determined by the supplier, Dow Chemical Company, USA), compounded and processed to form a powder of EAA-embedded pigments as previously detailed, except for the temperature of the kneading rolls which was set at about 100° C. In the column indicating the suppliers of the pigments, Kronos stands for Kronos International and Orion stands for Orion Engineered Carbons.

TABLE 2

| Item | Pigment (Color) | Supplier | Pigment (g) | Primacor™ 5990I (g) |
|---|---|---|---|---|
| 1 | Cromophtal ® Orange D 2961 | BASF | 2.5 g | 7.5 g |
| 2 | Cromophtal ® Violet D5800 | BASF | 2.5 g | 7.5 g |
| 3 | Diacetanil Yellow HTT 8318C | Cappelle | 2.5 g | 7.5 g |
| 4 | Heliogen ® Blue D 7079 | BASF | 2.5 g | 7.5 g |
| 5 | Heliogen ® Blue D 7490 | BASF | 2.0 g | 8.0 g |
| 6 | Heliogen ® Green K 8730 | BASF | 2.5 g | 7.5 g |
| 7 | Heuco ® Red 312201 | Heubach | 2.5 g | 7.5 g |
| 8 | Heuco ® Red 312203 | Heubach | 2.5 g | 7.5 g |
| 9 | Kemira 405 (White) | Kemira | 2.5 g | 7.5 g |
| 10 | Kronos ® 2310 (White) | Kronos | 2.5 g | 7.5 g |
| 11 | Microlen ® Violet 5800 MC | BASF | 2.5 g | 7.5 g |
| 12 | Mogul ® L (Black) | Cabot | 2.5 g | 7.5 g |
| 13 | Nipex ® 150 (Black) | Orion | 2.5 g | 7.5 g |

TABLE 2-continued

| Item | Pigment (Color) | Supplier | Pigment (g) | Primacor™ 5990I (g) |
|---|---|---|---|---|
| 14 | Orion FW 182 (Black) | Orion | 2.5 g | 7.5 g |
| 15 | Orion FW 182 (Black) | Orion | 1.5 g | 8.5 g |
| 16 | Orion FW 182 (Black) | Orion | 1.0 g | 9.0 g |
| 17 | Orion FW 182 (Black) | Orion | 0.5 g | 9.5 g |
| 18 | Paliogen ® Red L 4120 | BASF | 2.5 g | 7.5 g |
| 19 | PV Fast Orange H2GL | Clariant | 2.5 g | 7.5 g |
| 20 | PV Fast Orange H2GL | Clariant | 2.0 g | 8.0 g |
| 21 | PV Fast Pink E | Clariant | 2.5 g | 7.5 g |
| 22 | $TiO_2$ Ti-Pure ® R105 (White) | DuPont | 2.5 g | 7.5 g |

Items 3, 6 and 19 of Table 2 were also compounded in same amounts with a further alternative EAA copolymer. Namely, Primacor™ 5990I was replaced by Nucrel® 2806, an EAA copolymer having an acrylic acid content of 18.0 wt. %, as determined by the supplier, DuPont Company, USA. The kneading temperature for the preparation of pigments embedded in Nucrel® 2806 was of about 150° C.

A fourth EAA copolymer, Luwax® EAS-5 manufactured by BASF and having an acrylic acid content of about 21.5 wt. % as calculated based on the acid number of 160-180 mg KOH/g provided by the supplier, was used for the compounding of the pigments listed in Table 3, in respective amounts listed therein. The kneading temperature for the preparation of pigments embedded in Luwax® EAS-5 was of 180° C.

TABLE 3

| Item | Pigment (Color) | Supplier | Pigment (g) | Luwax ® EAS-5 (g) |
|---|---|---|---|---|
| 1 | Cromophtal ® Violet D5800 | BASF | 2.0 g | 8.0 g |
| 2 | Diacetanil Yellow HTT 8318C | Cappelle | 2.0 g | 8.0 g |
| 3 | Heliogen ® Blue D 7079 | BASF | 2.0 g | 8.0 g |
| 4 | Heliogen ® Green K 8730 | BASF | 2.0 g | 8.0 g |
| 5 | Heuco ® Red 312201 | Heubach | 2.0 g | 8.0 g |
| 6 | Orion FW 182 (Black) | Orion | 2.0 g | 8.0 g |
| 7 | PV Fast Orange H2GL | Clariant | 2.0 g | 8.0 g |

A fifth EAA copolymer, A-C® 5180 manufactured by Honeywell International Inc., having an acrylic acid content of about 20 wt. % was compounded in a weight ratio of 4:1 with Cromophtal® Violet K5800 at a kneading temperature of about 130° C.

A sixth copolymer was tested in which the neutralizable acid moieties were methacrylic acid units. Namely Nucrel® 960, an EMAA copolymer manufactured by DuPont and having a methacrylic acid content of about 15 wt. %, was compounded in a weight ratio of 19:1 with Heliogen® Blue D 7086 at a kneading temperature of about 140° C.

A seventh copolymer was tested in which the neutralizable acid moieties included both acrylic acid and methacrylic acid units in an acrylamide copolymer. Namely Dermacryl® 79, an octylacrylamide/acrylate copolymer (AAA) manufactured by AkzoNobel and having an acid value of 133 mg KOH/g polymer, was compounded in a weight ratio of 4:1 with pigment Unipure Red LC3079 (Sensient® Cosmetic Technologies) or with Cromophtal® Violet D5800 at a kneading temperature of about 200° C.

Additionally, two copolymers were co-kneaded in equal amounts. The mixture of neutralizable acid polymers included Nucrel® 2806 (EAA copolymer with 18 wt. % acrylic acid) and Nucrel® 960 (EMAA copolymer with 15 wt. % methacrylic acid). The blend of copolymers was compounded in a weight ratio of 19:1 with pigment Heliogen® Blue D 7086 at a kneading temperature of about 130° C.

Step 2: Neutralization of Polymer-Embedded Pigments with Ammonium Hydroxide:

For each polymer-embedded color sample (items 1-8 of Table 1 compounded with Primacor™ 5980I, items 1-22 of Table 2 compounded with Primacor™ 5990I, items 3, 6 and 19 of Table 2 compounded with Nucrel® 2806 and items 1-7 of Table 3 compounded with Luwax® EAS-5), 20 g powder of EAA-embedded pigments (prepared as described in step 1) were loaded into a 500 mL glass beaker followed by the addition of 180 mL of deionized water. The dispersions were mixed at 3,000 rpm for ten minutes using a high shear mixer (L5M-A, from Silverson Machines Inc., USA), while being heated using a heating plate (Fried Electric Ltd., Israel) to 50° C. The temperature was measured using a standard scientific mercury thermometer (Si-Mada, Israel). To the heated dispersions, 5 mL of ammonium hydroxide (25 wt. %) ($NH_4OH$, CAS No. 1336-21-6, Sigma-Aldrich Co., USA) was added in order to neutralize the EAA polymer in which the pigment was embedded. The mixture was further heated to 80° C. (or any other suitable temperature above the softening temperature of the polymeric material) under continuing mixing at same conditions for about twenty minutes. Then 5 mL of ammonium hydroxide (25 wt. %) were further added to the at least partially neutralized dispersions of EAA-embedded pigments in order to complete the neutralization reaction. The AAA-embedded pigments were similarly dispersed and neutralized, namely by mixing 5 g of Unipure Red LC3079 or Cromophtal® Violet D5800 embedded in Dermacryl® 79 with 5 mL of ammonium hydroxide (25 wt. %) and proceeding as described.

The pigments compounded with EMAA copolymers, or with a blend of EMAA and EAA, were similarly neutralized with the following modifications. 10 g of EMAA-embedded pigments, whether EMAA was the sole copolymer or part of a blend with EAA, were neutralized using 2 g of ammonium hydroxide (25 wt. %) and 2 g of monoethanolamine (Fisher Laboratory Grade).

During the neutralization process of the afore-said examples of polymers having neutralizable acid moieties, namely EAA, EMAA, AAA and blends thereof, samples of 0.1 mL of dispersion were taken and placed between two glass slides in order to visually assess the presence or absence of aggregates. In case of presence of aggregates, additional base (e.g., ammonium hydroxide (25 wt. %) or potassium carbonate) was introduced to the dispersion which was thereafter mixed for longer periods of time.

It is believed that that the alkaline solution of ammonium hydroxide facilitates the water-dispersibility of the EAA, EMAA or AAA copolymers or blends thereof, as the case may be, in the non-limiting examples presented herein. For simplicity, the EAA/EMAA/AAA copolymers, which as mentioned can be used separately or jointly, can also be referred to, following the neutralization process, as neutralized or neutralized acidic polymeric material (including polymers and copolymers variants of such terms).

At the end of the neutralization process, polymer-embedded pigment dispersions were obtained. These dispersions were stable (e.g., displayed a similar PSD over time, retained a relatively constant charge, etc.) under basic pH conditions, such stability being observed even in absence of additional dispersant(s). Generally, the dispersed particles of the various polymers embedding the exemplary pigments as herein described displayed a size distribution having a median value in the sub-micron range (e.g., Dv50<1 µm), typically at the lower end of the range, having Dv50 values, as assessed by DLS, of less than 500 nm, less than 250 nm, or even less than 100 nm. For illustration, the dispersed particles of neutralized Nucrel® 960 embedding Cromophtal® Violet K 5800 displayed a Dv50 of about 200 nm and the dispersed particles of neutralized Dermacryl® 79 embedding Unipure Red LC3079 displayed a Dv50 of about 50 nm.

According to some embodiments, the dispersion of polymeric materials having neutralized acid moieties and embedding the pigments is charged and has a negative surface zeta potential whose negativity is at least −10 mV, at least −20 mV, at least −40 mV, or at least −60 mV; and whose negativity is at most −100 mV, or at most −80 mV.

Zeta potential of aqueous dispersions prepared by neutralizing (with ammonium hydroxide) and dispersing colored polymeric mass including a pigment at a 1:4 w/w ratio into a blend of copolymers comprising 50 wt. % of Primacor™ 5990I and 50 wt. % of Luwax® EAS-5 was assessed. Zeta potential values of diluted samples comprising 0.05 wt. % of solid materials were measured using a Zetasizer Nano Z (by Malvern Instruments) with a folded capillary cell DTS1070. As the tested dispersions varied only by the pigment incorporated in the otherwise similar dispersed particles of neutralized acidic polymer, the results are presented in the following by the name of the dispersed pigment. A dispersion including Chromophtal® Violet K5800 as pigment yielded a zeta potential of −55 mV; a dispersion including Diacetanil Yellow HTT 8318C had a zeta potential of −50 mV; a dispersion including Heliogen® Green K 8730 had a zeta potential of −54 mV; a dispersion including Heliogen® Blue D 7079 had a zeta potential of −35 mV; a dispersion including Heuco Red 312201 had a zeta potential of −50 mV; a dispersion including Orion Black FW 182 had a zeta potential of −27 mV; and a dispersion including Hostaperm® Orange GR had a zeta potential of −45 mV.

The presence of the pigment particles within the dispersed beads of neutralized polymers was confirmed by optical microscopy at a magnification of ×100. The solid content of EAA/EMAA/AAA-embedded pigments in the various dispersions was typically in the range of 9.0 wt. % to 11.0 wt. %. When desired, deionized water was added to compensate for evaporation or reach a particular solid content (e.g., 10.0 wt. %). The pH of the dispersions was generally in the range of about 7.5 to 11.0, 9.0 to 11.0 or of about 9.5 to 10.5.

It is believed that polymeric materials having a lower acid number should be loaded with a lower amount of pigment, as compared to neutralizable polymers having a higher acid number. In any event, it is believed that the extent of the pigment loading should not reach or approach the maximal ability of the polymer having acid groups to be compounded therewith, as a portion of such groups should remain available to ensure the aqueous dispersibility of the polymer-embedded pigment following neutralization. It is assumed that part of the acid moieties serve as pigment affinic groups and are engaged with the pigments being embedded in the polymeric material.

Similarly prepared (and tested for coloring) was a dispersion with a polymeric material lacking acid moieties, this control polymer being a known water-dispersible pigment-affinic polymer. While the control polymer (a modified polyester commercialized as Eastman Δζ ™ polymers by Eastman Chemical Company) was successfully compounded with pigments and water dispersed therewith in particulate form, the resulting aqueous dispersion failed to form an outer coat able to attach to an underlying condensation-cured amino-silicone film. These findings support the hypothesis that the acid moieties of the polymeric material serve not only to ensure water-dispersibility and/or pigment affinity, but also enable attachment to an adjacent amino-silicone, likely by binding with accessible amino side chains of the silicone polymer.

FIG. 5A represents such processes in a schematic manner. In the figure, the polymeric material having acid moieties 500 is loaded in a mixing mill that may be formed of kneading rolls 502, 504 and 506, which mixing mill can be heated to a desired temperature suitable for the process so as to start liquefying the polymer (e.g., around the melting temperature of the polymer). Pigment particles, which in some embodiments can be incorporated in the mass of polymeric material 500 at the beginning of the process, are represented by a pattern of dot-like shapes. The polymeric mass and the pigments, when present, are kneaded in a cyclic manner, as shown by arrows 508a, 508b and 510. Following the last mixing or compounding cycle, illustrated by arrow 512, a bulk or mass of polymeric material with pigments dispersed therein, 520, is obtained. This pigmented polymeric bulk 520 can be cut down (as illustrated by arrow 514) into smaller pieces of polymeric material 530, by any suitable device. For example, pieces of the pigmented polymeric mass can be ground by cryo-milling. The pieces 530 of pigmented polymeric material are then transferred 516 to a liquid in any suitable vessel, represented in the figure by a beaker 542. The vessel, and the pieces of pigmented polymeric material in the liquid 540, can then be heated by any appropriate heating device, illustrated in the figure by a heating plate 544. The heating facilitate the preparation of the dispersion. In the event of high temperature heating, the liquid may include a high boiling point organic solvent and/or be performed under elevated pressure. A neutralizing agent is then added to the heated liquid containing the pieces of polymeric material, typically under stirring conditions. The addition of a neutralizing agent (e.g., ammonia) is schematically represented by arrow 550. When neutralization is completed, as illustrated by arrow 518, a stock aqueous dispersion of neutralized polymeric material 560 is obtained. This stock dispersion can serve for the preparation of aqueous dispersions as used herein as second coat, and can, by way of non-limiting example, be diluted, and/or supplemented with a surfactant (e.g., a super-wetting agent) or with a rheology modifying agent (e.g., a thickener), all such agents not being shown in the figure.

When pigments are compounded with the polymeric material having acid moieties, as illustrated in the present example, at the end of a process such as described in FIG. 5A, the pigment particles 572 are embedded in the neutralized polymeric material, as schematically represented by individual bead 570 of FIG. 5B. Generally, such a bead 570 of neutralized polymeric material, which typically has submicronic dimensions at the end of the process, may contain one or more pigment particles 572. Aqueous dispersions, including as illustrated by stock dispersion 560, contain a multitude of such beads 570.

Example 3: Preparation of Coloring Polymer-Embedded Pigment Dispersion

In a cup, the following were weighted and mixed using a vortex for about 5 seconds.
5 g of neutralized dispersions of EAA, EMAA, and/or AAA-embedded pigments (prepared as described in step 2 of previous example)
5 g of deionized water
0.5 g of fluorosurfactant (Capstone® FS-35, of DuPont Chemicals or Dynax DX 4010N of Dynax Corporation)

The fluorosurfactant is believed to act as a super-wetting agent, facilitating the contacting of the neutralized acidic polymer-embedded pigment dispersions with hydrophobic films, such as generated by curing of an amino-silicone film-forming reactant, such as ASE described in Example 1. Super-wetting agents should bring the surface tension of the aqueous neutralized acidic polymer/pigment dispersion as close as possible to the surface energy of the silicone film (typically in the 18 to 24 millinewtons per meter (mN/m) range). Advantageously, particularly suitable such surfactants can reduce the surface tension of the dispersion serving as second coat below the level of the first coat value.

Suitability of super-wetting surfactants for this purpose was assessed in vitro as follows. The amino-silicone emulsion intended to first coat the purported fibers (e.g., the ASE of Example 1) was applied on a clean microscope glass slide and allowed to at least partially cure for 30 minutes at about 23° C. The surfactants being tested were added at a 5 wt. % concentration to the neutralized dispersion of acidic polymer-embedded pigments of interest diluted 1:1 with deionized water (the final dispersion having an acidic polymer-embedded pigment concentration of about 5 wt. %). The resulting samples were applied with a pipette over the cured surface of the glass-bound amino-silicone film and the behavior of the applied liquids visually monitored. Samples comprising suitable surfactants (in sufficient amount) satisfactorily spread on the cured silicone to form a continuous layer thereon, while samples comprising inappropriate ones (or improper amounts) tended to bead. Anionic and non-ionic super-wetting surfactants were found to better perform than cationic ones. Non-ionic fluorosurfactants as aforementioned (Capstone® FS-35 and Dynax DX 4010N) were found particularly suitable, but amine silicone based fluoro surfactants are expected to also be appropriate for this purpose.

The surface tension of the EAA-embedded pigment dispersions was measured for comparison before and after the addition of a super-wetting surfactant using a tensiometer (Easy Dyne, from Kruss GmbH, Germany). Measurements were performed at ambient temperature. For instance, the surface tension of a 1:1 water diluted dispersion of diacetanil yellow HTT 8318C embedded in Primacor™ 5990I prepared substantially as described for item 3 of Table 2, was found to be 48.4 mN/m in absence of surfactant. The addition of 5 wt. % of Dynax DX 4010N to the same diluted dispersion drastically decreased the surface tension of the mixture down to 14.7 mN/m. Similar effects were obtained when adding super-wetting surfactants to neutralized dispersions of any other pigment embedded in any of the EAA-copolymers illustrating in a non-limiting manner suitable coloring compositions, Primacor™ 5980I, Primacor™ 5990I, Nucrel® 2806, or Luwax® EAS-5 or EMAA-copolymers, exemplified by Nucrel® 960 or AAA-copolymers, exemplified by Dermacryl® 79. All polymers aqueous dispersions were prepared as above-described.

Example 4: Hair Coloring Using ASE and Polymer Embedded Pigment Dispersions

The coloring process may take into account the baseline color of the uncoated hair fibers and their length, darker shades and/or longer hairs typically requiring a prolonged coating duration, the status of the hair (whether or not damaged), the intensity/depth of the desired color, and additional factors readily appreciated by persons skilled in the art of hair coloring. Thus, while the coloring compositions according to the present disclosure (including pigmentless ASE or pigmentless neutralized acidic (e.g., EAA, EMAA and/or AAA) copolymer dispersions, in addition to any other formulation including a color imparting pigment) can be applied and readily coat hair in a few seconds (e.g., 2-4 seconds for the ASE and 4-8 seconds for the neutralized acidic copolymer-embedded pigment super-wetting dispersions), unless otherwise stated, the coating steps in the following experiments were for a duration of five minutes.
Procedure:
1—Hair tufts (human hair (naturally colored or bleached) or white yak body hair, approximately 7 cm long free hair from Kerling International Haarfabrik GmbH, Germany) were dipped in the Amino-Silicone Emulsion (e.g., as prepared in Example 1) for up to five minutes while stirring slightly.
2—The first coated hair tufts were thoroughly rinsed with tap water at about 25° C.
3—The amino-silicone coated hair tufts were dipped in the neutralized polymeric material-embedded pigment super-wetting dispersions (e.g., as prepared in Example 3) for up to five minutes while stirring slightly until the hair was fully colored.
4—The colored hair tufts were rinsed with tap water at about 25° C. for a few seconds to remove excess of coloring dispersion.
5—The rinsed colored hair tufts were washed with a cationic shampoo (Perfectly (un)Done, TRESemme, Unilever, USA) and rinsed with water at about 25° C.
6—The washed colored hair tufts were combed and dried with a Philips compact hair dryer.

Unless otherwise stated, three hair tufts of bleached human hair and of white yak hair samples were colored as above-described with each of the pigmented dispersions. A control experiment was performed with a neutralized EAA-copolymer dispersion lacking an embedded pigment, for reference, to establish which modifications to the hair coloring were due to the coating media rather than to the embedded pigments.
Results:

In this example, the amino-silicone emulsion providing a first coat to the keratinous fibers included a blend of condensation-curable amino silane monomers as cross-linking agents for the amino-silicone condensation-curable polymer and was devoid of a curing facilitator (i.e., a catalyst). All dispersions of super-wetting neutralized acidic polymer-embedded pigments tested in the present example provided a visually satisfactory hair/color coverage. Interestingly, the reference compositions wherein the super-wetting neutralized EAA copolymers dispersions were devoid of pigments each provided by itself a colorless volume improvement, as detailed in Example 18.

Advantageously, the present method and compositions used therein, including by way of non-limiting examples, Primacor™ 5980, Primacor™ 5990, Nucrel® 2806, or Luwax® EAS-5 as EAA copolymers, Nucrel® 960 as EMAA-copolymers and Dermacryl® 79 as AAA-copolymer, for the second coat, readily provided a pleasant non-tacky touch. It may be noted that bleached hair samples not only provide for a light color background, but also exemplify damaged hairs. Therefore, the ability of the present compositions to coat bleached hair supports the suitability of the coloring or coating method for damaged hair.

Example 5: Hair Coloring Using ASE, Pigmentless Polymer Coat and Non-Embedded Metallic Pigments The amino-silicone emulsion serving for the first fiber coating was prepared as described in Example 1 with the following modification. The ASE was prepared by sonicating 0.2 g of ASB, instead of 0.12 g of ASB, with the 60 g of 0.1 wt. % Tween® 80 emulsion solution. The EAA dispersions and neutralizations serving for the intermediate preparation of the second fiber coat were carried out as described in Example 2, with the following modifications. As no pigments were compounded with the EAA-copolymers, prior to neutralization, the EAA dispersions loaded into a 500 mL glass beaker included either 15 g of Primacor™ 5980I with 180 mL of deionized water, or 40 g of Primacor™ 5990I with 160 mL of deionized water, or 40 g of Luwax® EAS-5 with 160 mL of deionized water. The pigmentless EAA dispersions were neutralized with ammonium hydroxide as described until transparent milky dispersions were obtained.

The super-wetting pigmentless EAA polymeric dispersions were prepared by mixing using a vortex, (a) 15 g of neutralized Primacor™ 5980I, 50 g of deionized water and 1.7 g of fluorosurfactant (Capstone® FS-35 or Dynax DX 4010N), (b) 15 g of neutralized Primacor™ 5990i, 60 g of deionized water and 1.7 g of Dynax DX 4010N, or (c) 15 g of neutralized Luwax® EAS-5, 60 g of deionized water and 1.7 g of Dynax DX 4010N.

A first coloring composition was prepared by mixing, using a spatula, 4.66 g of the previously obtained super-wetting pigmentless EAA polymeric dispersion of neutralized Primacor™ 5980I with 2 g of aluminum flakes (VMP (Vacuum metalized pigment) Aluminum Flakes L-12554 (10 wt. % solid content in methoxy propanol, Silberline Manufacturing Co., USA).

A second coloring composition was similarly prepared based on neutralized Primacor™ 5980I, by replacing the aluminum flakes by bronze flakes (Bronze Rich Gold Flakes 12,000, Manfong, China).

A third coloring composition was prepared by mixing, using a spatula, 1.165 g of the previously obtained super-wetting pigmentless EAA polymeric dispersion of neutralized Primacor™ 5990i, 1.165 g of super-wetting pigmentless EAA polymeric dispersion of neutralized Luwax® EAS-5, and 1 g of aluminum flakes (L-12554).

Hair tufts of human bleached hair and yak white hair were colored as described in Example 4 and the dried hair samples respectively displayed a silver-like and a blond appearance pleasant to the touch for aluminum and bronze flakes coatings. Different shades of blond can be obtained by using bronze flakes including different levels of zinc. It is to be noted that the coloring compositions herein disclosed can be supplemented with a variety of suitable additives known to persons skilled in the art of formulation and cosmetic compositions. The various purposes served by such conventional additives (e.g., preservatives, pH buffering agents, fragrances etc.) are readily understood and need not be detailed herein. Still, it can be noted that in the case of pigments being metallic flakes, corrosion inhibitors are to be considered.

This study supports that pigments can be included in a second EAA-based coat either when embedded in the EAA copolymers, as shown in Example 4, or when simply mixed therewith, as herein shown. It is believed that the neutralized acidic polymer particles of the super-wetting dispersions at least partially coat the metallic flakes, so as to facilitate their adhesion to the amino-silicone first coat. Such partial envelopment is schematically illustrated in FIG. 5C, where 582 depicts a flake-shaped pigment and 580 represents an envelope that envelops such a pigment. It is believed that a single pigment flake can be so enveloped, but it cannot be ruled out that a few pigment flakes may be at least partially enveloped jointly.

Example 6: Preparation of Pigmentless Neutralized Acid-Functional Polymers

While in Example 2, the pigments intended for the coloring of keratinous fibers were embedded in EAA, EMAA or AAA copolymers in a process including their compounding with the polymer and their subsequent neutralization with alkali, in the present example, as similarly shown in Example 5, the pigments were later added to independently neutralized polymers.

The EAA copolymers tested are reported in Table 4, including some characteristics reported by respective suppliers.

TABLE 4

| EAA copolymer | Supplier | Acrylic acid content (wt. %) | Vicat Softening point |
|---|---|---|---|
| Primacor ™ 5980I | Dow Chemical Company | 20.5 wt. % | 42° C. |
| Primacor ™ 5990I | Dow Chemical company | 20.0 wt. % | 40° C. |
| Nucrel ® 2806 | DuPont | 18.0 wt. % | 48° C. |
| Luwax ® EAS-5 | BASF | 21.5 wt. % | NA | a. Preparation of Aqueous Dispersions of Neutralized Primacor™ 5980I, Primacor™ 5990I and Luwax® EAS-5 (as Ammonium Salts)

12 g of Primacor™ 5980I, Primacor™ 5990I or Luwax® EAS-5 and 120 g of deionized water were placed in a beaker equipped with a magnetic stirrer and heated under stirring at approximately 400 rpm to about boiling temperature (circa 90-95° C.). 6 mL of aqueous ammonia (25 wt. % NH$_3$ in water) was added during a period of 30 minutes in portions of about 2 ml every 10 minutes to obtain a clear to slightly milky dispersion of neutralized EAA copolymers. The dispersions were allowed to cool under magnetic stirring down to ambient temperature (circa 23° C.). They were then stored without any further stirring at same room temperature and kept for at least one week without any noticeable visual change. Such preliminary observations suggest that the neutralized EAA copolymers form low sub-micronic particles and that no precipitates or other significant agglomeration of such particles occurred during this time period.

b. Preparation of Aqueous Dispersion of Neutralized Nucrel® 2806 (as Ammonium Salt)

12 g of Nucrel® 2806 and 240 g of deionized water were placed in a beaker equipped with a magnetic stirrer and heated under stirring to about boiling temperature (circa 90-95° C.). Six milliliters (6 mL) of aqueous ammonia (25 wt. % $NH_3$ in water) was added during a period of one hour in portions of about 2 ml every 20 minutes to obtain a milky dispersion of neutralized EAA copolymer. The dispersion was allowed to cool under magnetic stirring down to room temperature. Undissolved chunks of Nucrel® 2806 were allowed to separate by decantation and were removed, so as to yield a relatively homogenous milky dispersion of neutralized Nucrel® 2806. Such preliminary observations suggest that the neutralized EAA copolymer form sub-micronic particles.

Example 7: Coloring with Pigmentless EAA and Non-Embedded Pigments

Materials
Bronze Rich Gold Flakes 12,000, Manfong, China. These metallic flakes are reported to have an average longest dimension in the range of 2-20 micrometer (μm) and an average thickness in the range of 50-100 nanometer (nm).
VMP (Vacuum metalized pigment) Aluminum Flakes L-12554 (10 wt. % solid content in methoxy propanol), Silberline, Germany. These metallic flakes are reported to have an average longest dimension in the range of 2-20 μm and an average thickness smaller than 50 nm.
Effect pigment: Pyrisma® T30-20 Color Space Yellow, Merck Ltd, Germany. These mica-based effect pigments are reported to have a flake-shape with an average longest dimension in the range of 2-20 μm and an average thickness in the range of 300-700 nm.
Effect pigment: Iridesium Solar Gold Satin 3325 Pritty, Pearlescent pigments, China Hair: European black human hair 3/0 supplied by Kerling International Haarfabrik GmbH, Germany, as tufts of about 2.5 g of hair having a length of about 7 cm.
Procedure
a. Coating of hair tuft with bronze flakes
 1. Preparation of amino-silicone coat: 5 g of amino-silicone condensation-curable polymer GP-397 was dissolved in the same weight of tert-butyl alcohol (CAS No. 75-65-0, Sigma-Aldrich Co., USA)
Preparation of suspension of bronze flakes in neutralized EAA dispersions: 0.5 g
 2. Bronze Rich Gold Flakes 12,000 were added to 5 g of EAA dispersions prepared as described in Example 6, and the suspensions were mixed at room temperature under vortex for 30 seconds.
 3. A tuft of European black human hair 3/0 was dipped in the GP-397/tert-butyl alcohol (1:1) solution for 30 seconds and rinsed thoroughly in tap water at about 40° C.
 4. The amino-silicone coated hair tuft was then dipped for two minutes in the suspensions of Bronze Rich Gold pigment prepared in each of the neutralized EAA dispersions (i.e., based on Primacor™ 5980I, Primacor™ 5990, Luwax® EAS-5 or Nucrel® 2806).
 5. The EAA/pigment coated hair tufts were then rinsed thoroughly in tap water at about 40° C., combed and dried for about 30 seconds with a Philips compact hair dryer to obtain fully bronze covered hair tuft.

b. Coating of hair tuft with aluminum flakes
 1. Preparation of suspension of aluminum flakes in neutralized EAA dispersions: 0.28 g VMP Aluminum Flakes were added to 5 g of EAA dispersions prepared as described in Example 6, and the suspensions were mixed at room temperature under vortex for 30 seconds.
 2. A tuft of European black human hair 3/0 was treated as above described (dipped 30 seconds in the GP-397/tert-butyl alcohol (1:1) solution, thoroughly rinsed in tap water at about 40° C., dipped two minutes in the VMP Aluminum Flakes suspensions, thoroughly rinsed in tap water, combed and dried). The dried coat provided a silver appearance to the hair.
c. Coating of hair tuft with effect pigment Iridesium 3325
 1. Preparation of suspension of Iridesium 3325 in neutralized EAA dispersions: 2 g Iridesium 3325 were added to 3 g of EAA dispersions prepared as described in Example 6, and the suspensions were mixed at room temperature under vortex for 30 seconds.
 2. A tuft of European black human hair 3/0 was treated as above described (dipped 30 seconds in the GP-397/tert-butyl alcohol (1:1) solution, thoroughly rinsed in tap water at about 40° C., dipped two minutes in the Iridesium 3325 suspensions, thoroughly rinsed in tap water, combed and dried). The dried coat provided a blond appearance to the hair.
d. Coating of hair tuft with effect pigment Pyrisma® T30-20 Color Space Yellow
 1. Preparation of amino-silicone pigmented coat: 2.2 g of Pyrisma® T30-20 were added to 3.0 g of condensation-curable amino-silicone polymer GP-397 in tert-butyl alcohol at a weight ratio of 1:1. The mixture was vortexed for 30 seconds.
 2. Preparation of suspension of Pyrisma® T30-20 in neutralized EAA dispersions: 2 g Pyrisma® T30-20 were added to 3 g of EAA dispersions prepared as described in Example 6, and the suspensions were mixed at room temperature under vortex for 30 seconds.
 3. A tuft of European black human hair 3/0 was treated as above described, the first step being performed with the pigmented amino-silicone coat (dipped 30 seconds in the Pyrisma® T30-20 in GP-397/tert-butyl alcohol (1:1) dispersion, thoroughly rinsed in tap water at about 40° C., dipped two minutes in the Pyrisma T30-20 suspensions, thoroughly rinsed in tap water, combed and dried). The dried coat provided a blond appearance to the hair.
Results
In this example, the amino-silicone solutions providing a first coat to facilitate the later contacting of the neutralized acidic polymer dispersions including the non-embedded pigments were devoid of cross-linking agents or other curing facilitators (e.g., catalysts), comprising only a condensation-curable amino-silicone polymer. Nevertheless, while their full curing is expected to be prolonged by such absence, the amino-silicone compositions sufficiently coated the hair fibers to permit later neutralized acidic polymer/pigment coverage.

Most dispersions of neutralized EAA copolymers/non-embedded pigments tested provided a visually satisfactory hair/color coverage, even when the first coat was transparent and uncolored (hence, unable to mask the original black hair color). One exception was observed with effect pigment Pyrisma® T30-20 Color Space Yellow which was also included in the amino-silicone first coat to achieve a similar effect of suitable color coverage.

Advantageously, the present method and compositions used therein readily provided a pleasant non-tacky touch.

Example 8: Pigment Preparation

As illustrated in Example 7 with Pyrisma® T30-20 Color Space Yellow, it may be beneficial in order, if desired, to further increase the optical density provided by a pigment embedded in a neutralized acidic copolymer serving for the second coat, to include a pigment in the amino-silicone first coat. While the pigments of the first and second coat can be the same, it is not essential and some coloring effect and/or some baseline hair color may benefit from first and second coatings including different pigments.

Pigments can generally be used as supplied by their respective manufacturers, the compounding or dispersing steps herein disclosed being sufficient to reduce the amount of aggregates that may form during storage. However, when the compositions including such pigments are prepared under relatively gentle conditions and/or when the pigments are sought in a size range lower than provided, it may be desirable to size reduce the desired pigments. Numerous methods are known. For instance, if the amino-silicone coat is to include sub-micronic pigments, such can be prepared as follows.

45 g of pigment were mixed with 45 g of dispersant (e.g., BYK LPX 21879, an amino-silicone dispersant) and 210 g of hexamethyldisiloxane. The mixture was bead-milled using 3,700 g of 5 mm stainless steel beads (Glen Mills, USA) in a 01 Lab Attritor (Union Process, USA) at 700 rpm at a controlled temperature of about 25° C. Milling proceeded until the pigments reached an average particle size of in the range of 120-150 nm, as determined by Dv50 using Dynamic Light Scattering Particle Size Analyzer (Zen 3600 Zetasizer by Malvern Instruments, United Kingdom). The size reduced dispersed pigments were oven dried overnight at 80° C. (Mechanical Convection Oven DFO-240N by MRC Ltd., Israel).

Example 9: Removal of Coatings from Keratinous Fibers

Materials

Unless otherwise stated, solvents or materials regulatory approved for cosmetic use were purchased at cosmetic grade.

Anisole; dimethyl sulfoxide (DMSO); 1,4 dioxane; glycerol; isopropanol; methyl isobutyl ketone (MIBK); methyl phenyl ester (MPE); myristyl alcohol; N-octyl pyrrolidone (NOP); potassium tert-butoxide; propionitrile; tert-butyl alcohol; tetra butyl ammonium chloride (TBAC); tetra butyl ammonium fluoride (TBAF); tetra butyl ammonium hydroxide (TBAH) 40% in water; tetrahydrofuran (THF); triethylamine; toluene; and xylene; were all purchased from Sigma-Aldrich Co., USA, at purity level of at least 98%.

Cetiol® A; Cetiol® B; Cetiol® PGL; Cetiol® V; Cetiol® 868; decyl oleate; di-n-butyl adipate; ethyl hexyl stearate; hexadecyl laurate hexyl laurate; were all cosmetic grade materials purchased from BASF, Germany.

Diisostearyl adipate; diisocetyl dodecanedioate; Liquiwax™ DISA-LQ-(MH); Liquiwax™ DICDD-L-Q-(MH), were all cosmetic grade materials purchased from Croda International Plc., United Kingdom.

Hair: White yak body hair, European black human hair 3/0 and Strong bleached human hair (all supplied by Kerling International Haarfabrik GmbH, Germany, as tufts of about 2.5 g of hair having a length of approximately 7 cm).

Procedure

Hair tufts samples which were coated or colored as described in Examples 4-6, as further detailed below, were immersed and gently shaken in excess volume of about 10 mL coloring removal solutions, in 20 mL glass vials. The composition of the coating removal solutions herein tested is presented in Tables 5-8. The slow cyclic immersion was performed at ambient temperature using a fixed angle rotator at 10 rpm (TMO-1550—MRC Ltd., Israel). Samples were taken out of the coloring removal solutions after the periods of time specified in the tables. Typically, the duration of immersion did not exceed 30 minutes in the present experiments.

Following their immersion in the coloring removal solutions being tested, the hair tufts were rinsed thoroughly with tap water at about 35-40° C. Some hair samples were subjected to a single standard shampooing treatment with Shea natural keratin shampoo (Gilam Cosmetics Ltd., Israel), others were directly processed as follows. Samples were dried with a Philips compact hair dryer for approximately 30 seconds. The evaluation of the efficacy of colorant removal was based on visual inspection of the dried hair tufts.

Results

Results are presented in Tables 5 to 8 below, wherein information on the type of the second coats is further detailed. In these tables, ++ indicates complete removal of the coloring composition, + indicate partial removal of the coating and 0 indicates no visible change. NA means Not Applicable.

Table 5 relates to the removal of coating from white yak hair, where the second coat was based on EAA-embedded pigment (namely Diacetanil Yellow HTT 8318C in Primacor™ 5980I, in a neutralized dispersion including Capstone® FS-35, see item 3 in Table 2 in Examples 2-3).

TABLE 5

| Decuring Agent (concentration) | Solvent/medium | Immersion Time | No of shampoos | Result |
|---|---|---|---|---|
| NA | Anisole | 5 minutes | 1 | 0 |
| NA | Cetiol A | 30 minutes | 1 | 0 |
| NA | Cetiol B | 15 minutes | 1 | 0 |
| NA | Cetiol V | 15 minutes | 1 | 0 |
| NA | Cetiol 868 | 30 minutes | 1 | 0 |
| NA | Cetiol PGL | 30 minutes | 1 | 0 |
| NA | Diisostearyl adipate | 15 minutes | 1 | 0 |
| NA | Diisocetyl dodecanedioate | 15 minutes | 1 | 0 |
| NA | 1,4 Dioxane | 5 minutes | 1 | 0 |
| NA | DMSO | 5 minutes | 1 | 0 |
| NA | MIBK | 5 minutes | 1 | + |
| NA | MPE | 5 minutes | 1 | + |

TABLE 5-continued

| Decuring Agent (concentration) | Solvent/medium | Immersion Time | No of shampoos | Result |
|---|---|---|---|---|
| NA | NOP | 5 minutes | 1 | 0 |
| NA | Propionitrile | 5 minutes | 1 | + |
| NA | THF | 5 minutes | 1 | ++ |
| NA | Toluene | 5 minutes | 1 | + |
| NA | Xylene | 5 minutes | 1 | + |
| NaOH (1M) | Water | 5 minutes | 1 | 0 |
| NA | Tert-butyl alcohol | 5 minutes | 1 | 0 |
| Triethylamine (10 wt. %) | Tert-butyl alcohol | 5 minutes | 1 | 0 |
| Potassium tert-butoxide (2.5 wt. %) | Tert-butyl alcohol | 5 minutes | 0 | ++ |
| TBAH (1 wt. %) | Tert-butyl alcohol | 5 minutes | 0 | ++ |
| TBAH (10 wt. %) | Tert-butyl alcohol | 5 minutes | 0 | ++ |
| TBAH (10 wt. %) | Glycerol | 5 minutes | 1 | 0 |
| TBAH (2.5 wt. %) | N-butanol | 5 minutes | 1 | 0 |
| TBAH (10 wt. %) | Tert-butyl alcohol/ Myristyl alcohol (½) | 5 minutes | 1 | ++ |
| TBAH (10 wt. %) | Myristyl alcohol | 5 minutes | 1 | 0 |
| TBAH (10 wt. %) | Water | 5 minutes | 1 | 0 |

Table 6 relates to the removal of coating from strongly bleached human hair, where the second coat was based on EAA-embedded pigment (namely Hansa Red B in Primacor™ 5980I in a neutralized dispersion including Capstone® FS-35, see item 3 in Examples 2-3).

TABLE 6

| Decuring Agent (concentration) | Solvent/medium | Immersion Time | No of shampoos | Result |
|---|---|---|---|---|
| TBAH (1 wt. %) | Tert-butyl alcohol | 5 minutes | 1 | + |
| TBAH (5 wt. %) | Tert- butyl alcohol | 5 minutes | 1 | ++ |

Table 7 relates to the removal of coating from European black human hair, where the second coat was based on non-embedded metallic pigment (namely VMP aluminum flakes added to a separately neutralized dispersion of Primacor™ 58901 including Capstone FS-35, see Example 5).

TABLE 7

| Active ingredient (concentration) | Solvent/medium | Immersion time | No of shampoos | Results |
|---|---|---|---|---|
| TBAH (6 wt. %) | Tert-butyl alcohol | 5 minutes | 1 | + |
| TBAH (12 wt. %) | Tert-butyl alcohol | 5 minutes | 1 | + |
| TBAH (12 wt. %) | Tert-butyl alcohol | 10 minutes | 1 | ++ |

Table 8 relates to the removal of EAA-embedded pigment under neutral pH in presence of fluoride ion. Yak tresses of white body hair were coated with a first coat of condensation-curable amino-silicone reactants followed by aqueous dispersions of EAA-embedded Hostaperm Green GNX-C, Vynamon® Blue 3RFW-H or Cromophtal® Violet D5800, as described in the coloring procedure of Example 4. The pigments were all compounded with Primacor™ 58901 and the dispersions of the EAA-embedded pigments were neutralized using Capstone FS-35, as described in Examples 2-3. The colored yak hair tufts were immersed and gently shaken in the coloring removal solutions presented in the table for five minutes.

TABLE 8

| | Hair coatings including Primacor ™ 5890i embedded: | | |
|---|---|---|---|
| Decuring Agent & medium/solvent | Hostaperm Green GNX-C | Vynamon ® Blue 3RFW-H | Cromophtal ® Violet D5800 |
| N-Octyl pyrrolidone | 0 | 0 | 0 |
| 2 wt. % TBAC in NOP | 0 | 0 | 0 |
| 2 wt. % TBAF in NOP | ++ | ++ | ++ |

As shown in Table 5, complete removal of coloring composition from yak hair was achieved with an immersion time of 5 minutes in coloring removal solutions comprising at least 1 wt. % of TBAH or potassium tert-butoxide (2.5 wt. %) in tert-butyl alcohol. No visible changes were detected with solutions of neat tert-butyl alcohol lacking a base active ingredient. THF was also found to be an effective solvent for color removal, but is less favorable for cosmetic use then tert-butyl alcohol. No base active ingredient was required for THF efficacy. Xylene and toluene which displayed removal activity even in absence of decuring agent would be suitable for non-cosmetic use, such as color removal from animal furs. Strong basic aqueous solution (1M NaOH in water) was found ineffective as a color removal solution under the presently tested conditions.

The efficacy of coloring removal compositions including TBAH in tert-butyl alcohol was confirmed with different pigments and different hair types. For instance, similar removal results were obtained for coloring compositions having as polymer-embedded pigments Hansa red B (see Table 6) and Vynamon® Blue 3RFW-H (data not shown). Table 6 also confirms the suitability of these removal compositions for human hair, in addition to previously shown yak hair.

As shown in Table 7, removal compositions including TBAH in tert-butyl alcohol were also suitable to remove non-embedded VMP Aluminum flakes. However, such coloring removal required a relatively longer period of immersion (e.g., 10 minutes instead of 5 minutes for the earlier exemplified pigments) and/or a higher concentration of TBAH in the solvent (e.g., 12 wt. % instead of 5 wt. % for the earlier exemplified pigments). Table 7 also confirms the suitability of these removal compositions for human native black hair, in addition to previously shown human bleached (damaged) hair.

As shown in Table 8, complete removal of coloring composition from yak hair was achieved with an immersion time of 5 minutes in coloring removal solutions comprising 2 wt. % of TBAF in N-Octyl pyrrolidone (NOP). As no visible changes were detected with solutions of neat NOP or in NOP solutions wherein the fluoride of TBAF was replaced by a chloride as in TBAC, it is believed that the ion facilitating the color removal is the fluoride. Advantageously, TBAF in NOP has a near neutral pH, which is generally preferred over more basic environments.

In laboratory tests, such color removal solutions achieved full decoloration of the various hair samples back to their respective original shades. This full "at will" decoloration provides a clear advantage over existing hair coloring and decoloring techniques, in which decoloration may be based on waiting for hair growth to replace the colored hair or waiting for the fading of conventionally obtained coloration, both of which generally requiring weeks or months. Alternatively, decoloration may be based on bleaching followed by recoloration to a new desired shade. This approach generally further damages the hair.

Following color removal as above described, decolored hair samples were recolored according to the present teachings using an aqueous dispersion of an EAA-embedded orange pigment as recoloring composition. The previously decolored hair samples were successfully recolored, and no traces of their respective earlier colors were detected under the newly applied color. These results support the suitability of the present decoloring compositions allowing the decolored hair to be later recoated or recolored, if desired.

Example 10: Coloring with Combinations of Dispersions to Obtain New Shades

In previous examples, super-wetting coloring dispersions of neutralized EAA, EMAA or AAA copolymers, wherein the pigments were either pre-embedded in the acid polymers or subsequently added to the dispersions in non-embedded form, were individually applied to hair samples pre-coated with an amino-silicone emulsion comprising a condensation-curable amino-silicone polymer optionally supplemented with condensation-curable monomers serving as cross-linking agents.

In the present study, the previously described dispersions were considered and used as the "primary colors" (e.g., yellow, red, blue, black) of a color palette. In other words, two or more pigmented aqueous dispersions of polymeric material having neutralized acid moieties, each providing for a different primary color were combined so as to provide a wider range of coloring options.

In a 50 mL plastic cup, 2 g of a first neutralized dispersion comprising Diacetanil Yellow HTT 8318C embedded in Primacor™ 5990I (see item 3 of Table 2) was mixed with 3 g of a second neutralized dispersion comprising Heliogen® Blue D 7079 embedded in Luwax® EAS-5 copolymer (see item 3 of Table 3). The mixed dispersions were diluted with 20 mL of deionized water and 0.125 g of Dynax DX 4010N was added to the mixture.

White yak hair samples were dipped for 10 seconds in the Amino-Silicone Emulsion prepared as described in Example 1, rinsed with tap water at about 40° C., then dipped for one minute in the mixture of super-wetting neutralized dispersions above-prepared. The hair tufts were then rinsed in water, washed with a cationic shampoo, combed and dried, as described in more details in the coloring procedure of Example 4. The dried hair displayed a green color, as expected from the mixture of yellow and blue "primary dispersions".

Example 11: Embedding Pigments in Combinations of Acid-Polymers

In previous examples, the pigments, when pre-embedded in the acid-polymers prior to their neutralization, were compounded with a single type of EAA/EMEA/AAA-copolymers at a time, even if such materials can by themselves be supplied as a blend of slightly differing oligomers and polymers.

In the present study, the pigments (or combinations thereof, as illustrated with the black coloring mixture listed in Table 9) were compounded as previously described in Example 2 with a combination of acid-polymers as shown in Table 10. All listed blends were found compatible with respect to satisfactory mixing and compounding of the various pigments in the different polymers' compositions.

TABLE 9

| Pigment | Amount (g) |
| --- | --- |
| Orion FW 182 (Black) | 73.0 g |
| Heliogen ® Blue D7079 | 17.8 g |
| Cromophtal ® Violet D5800 | 9.3 g |

The first item listed in Table 10, prepared by mixing and melt-kneading 8 g of Diacetanil Yellow HTT 8318C with 7.2 g of Primacor™ 5990I and 16.8 g of Nucrel® 2806 at a temperature of about 150° C. served to illustrate the suitability of the pigments embedded in blends of polymers having acidic moieties for the preparation of coloring compositions. Dispersions were prepared and neutralized as detailed, and used for coloring, following the addition of super-wetting agents (as in Example 3), in the manner described in the procedure of Example 4. Strongly bleached human hair tufts coated with compositions including in the second formulation pigments embedded in such combinations of EAA copolymers were satisfactorily colored.

TABLE 10

| Pigment (color) | 1st EAA in blend | 2nd EAA in blend |
|---|---|---|
| 8.0 g of Diacetanil Yellow HTT 8318C | 7.2 g of Primacor ™ 5990I | 16.8 g of Nucrel ® 2806 |
| 6.4 g of Diacetanil Yellow HTT 8318C | 12.8 g of Primacor ™ 5980I | 12.8 g of Primacor ™ 5990I |
| 6.4 g of Diacetanil Yellow HTT 8318C | 17.92 g of Primacor ™ 5980I | 7.68 g of Primacor ™ 5990I |
| 6.4 g of Diacetanil Yellow HTT 8318C | 12.8 g of Primacor ™ 5990I | 12.8 g of Nucrel ® 2806 |
| 6.4 g of Diacetanil Yellow HTT 8318C | 17.92 g of Nucrel ® 2806 | 7.68 g of Primacor ™ 5990I |
| 4 g of Black Emperor ® 1200 | 8.0 g of Primacor ™ 5990I | 8.0 g of Nucrel ® 2806 |
| 4 g of Black Emperor ® 1200 | 11.2 g of Nucrel ® 2806 | 4.8 g of Primacor ™ 5990I |
| 4 g of Cromophtal ® Violet K5400 | 8.0 g of Primacor ™ 5990I | 8.0 g of Nucrel ® 2806 |
| 4 g of Cromophtal ® Violet K5400 | 11.2 g of Nucrel ® 2806 | 4.8 g of Primacor ™ 5990I |
| 4 g of Heliogen ® Blue D 7079 | 8.0 g of Primacor ™ 5990I | 8.0 g of Nucrel ® 2806 |
| 4 g of Heliogen ® Blue D 7079 | 11.2 g of Nucrel ® 2806 | 4.8 g of Primacor ™ 5990I |
| 4 g of Heliogen ® Green K 8730 | 8 g of Primacor ™ 5990I | 8 g of Nucrel ® 2806 |
| 4 g of Heliogen ® Green K 8730 | 11.2 g of Nucrel ® 2806 | 4.8 g of Primacor ™ 5990I |
| 4 g of Heuco ® Red 312201 | 11.2 g of Nucrel ® 2806 | 4.8 g of Primacor ™ 5990I |
| 6 g of Heuco ® Red 312201 | 7.0 g of Primacor ™ 5990I | 7.0 g of Nucrel ® 2806 |
| 4.0 g of Orion Black FW 182 | 8.0 g of Primacor ™ 5990I | 8.0 g of Nucrel ® 2806 |
| 3.0 g of Orion Black FW 182 | 11.9 g of Primacor ™ 5990I | 5.1 g of Nucrel ® 2806 |
| 2.6 g of Orion Black FW 182 | 8.5 g of Primacor ™ 5990I | 8.5 g of Nucrel ® 2806 |
| 2.0 g of Orion Black FW 182 | 12.6 g of Primacor ™ 5990I | 5.4 g of Nucrel ® 2806 |
| 1.0 g of Orion Black FW 182 | 13.3 g of Primacor ™ 5990I | 5.7 g of Nucrel ® 2806 |
| 4 g of PV Fast Orange H2GL | 8.0 g of Primacor ™ 5990I | 8.0 g of Nucrel ® 2806 |
| 4 g of PV Fast Orange GRL | 11.2 g of Nucrel ® 2806 | 4.8 g of Primacor ™ 5990I |
| 2.55 g of Table 9 mix (black) | 11.9 g of Nucrel ® 2806 | 5.1 g of Primacor ™ 5990I |
| 4.0 g of Table 9 mix (black) | 8.0 g of Primacor ™ 5990I | 8.0 g of Nucrel ® 2806 |
| 4.0 g of Table 9 mix (black) | 11.2 g of Nucrel ® 2806 | 4.8 g of Primacor ™ 5990I |
| 4.5 g of Table 9 mix (black) | 15.0 g of Primacor ™ 5990I | 15.0 g of Nucrel ® 2806 |

Example 12: Coloring with Combinations of Dispersions Including Blend of Polymers and/or Pigments While Example 10 addresses the combination of dispersions of different colors each including a single pigment embedded in a unique polymer material, the present study demonstrates the feasibility of mixing dispersions containing a same pigment embedded in different polymers or combinations thereof. The resulting coloring dispersions, which all satisfactorily colored human and yak hair with respect to end color and touch, are presented in Table 11.

In the first column the weight per weight ratio of pigment to the combination of all polymers is provided in parenthesis. The weight percentage of each polymer is provided with respect to the combination of the polymers. The 2nd EAA, if any, was compounded with the 1st EAA and provided as part of a first dispersion comprising the EAA-embedded pigment. The 3rd EAA was provided as part of a second dispersion comprising the same pigment.

Each of the dispersions mixed to provide the blends listed in the above table were neutralized and supplemented with 5 wt. % of Dynax DX 4010N as super-wetting surfactant as previously detailed.

Two sets of Caucasian human mixed hair samples were colored according to the present teachings. Each hair tuft predominantly included hair fibers having a light shade (e.g., blond, white, etc.), with a few hair fibers having a darker shade (e.g., grey, black, etc.). In the first series, the coloring included a first condensation-curable amino-silicone coating, and for the second coat, the super-wetting neutralized dispersions prepared from the EAA-blend-embedded polymers listed in Table 11. In the second series, the coloring included a first amino-silicone coating, a second coat including aluminum flakes (see the third coloring composition described in Example 5), a subsequent amino-silicone coating (same as for the first coat), and for fourth coat the super-wetting neutralized dispersions of the EAA-blend-embedded polymers listed in Table 11. The hair samples were rinsed in-between subsequent coating steps and washed with a cationic shampoo after the rinsing of the

TABLE 11

| Pigment (Pigment:Total Polymers) | 1st EAA (wt. % Total Polymers) | 2nd EAA (wt. % Total Polymers) | 3rd EAA (wt. % Total Polymers) |
|---|---|---|---|
| Diacetanil Yellow HTT 8318C (1:4) | Nucrel ® 2806 (53 wt. %) | Primacor ™ 5990I (23 wt. %) | Luwax ® EAS-5 (24 wt. %) |
| PV Fast Orange H2GL (1:4) | Primacor ™ 5990I (33 wt. %) | Nucrel ® 2806 (33 wt. %) | Luwax ® EAS-5 (33 wt. %) |
| Heuco ® Red 312201 (1:3.4) | Primacor ™ 5990I (48 wt. %) | NA | Luwax ® EAS-5 (52 wt. %) |
| Heliogen ® Blue D 7079 (1:3.4) | Primacor ™ 5990I (48 wt. %) | NA | Luwax ® EAS-5 (52 wt. %) |
| Cromophtal ® Violet D5800 (1:3.4) | Primacor ™ 5990I (48 wt. %) | NA | Luwax ® EAS-5 (52 wt. %) |
| Heliogen ® Green K 8730 (1:3.4) | Primacor ™ 5990I (48 wt. %) | NA | Luwax ® EAS-5 (52 wt. %) |
| Orion Black FW 182 (1:3) | Primacor ™ 5990I (33 wt. %) | Nucrel ® 2806 (33 wt. %) | Luwax ® EAS-5 (33 wt. %) | colored dispersions (whether serving as second or fourth coat). The washed hair samples were then combed and dried, as described in more details in the procedure of Example 4.

All colored samples provided a satisfactory visual effect and a pleasant touch. The samples of the second series further provided a "silvery" look to the shades afforded by the different pigments. Moreover, this series supports the feasibility of serially applying multiple coats by the same method (e.g., $ASE_i/EAA_i/ASE_{i+1}$; or $(ASE/EAA)_n$ etc. wherein ASE represents a positively charged amino-silicone coat and EAA represents a negatively charged acid polymer coat, each of ASE and EAA being independently further pigmented, if desired).

Example 13: Resistance to Light Fastness

The two sets of human hair samples colored as described in Example 12, were subjected for 24 hours to continuous illumination in an accelerated test chamber (Suntest MPA+, Atlas Material Testing Technology LLC, USA) at uniform irradiance of 765 Watt per square meter ($W/m^2$) with a daylight filter (295-800 nm). The study was performed at about 65° C. Such artificial exposure is believed to approximate about 12 days of natural outdoor exposure in central Europe, where the average annual radiant exposure for this range of wavelengths is estimated to be of about 2050 megaJoule per square meter ($MJ/m^2$). The optical density (OD) and change in color of the hair samples before and after such exposure, Delta E ($\Delta E$), was monitored using a spectrophotometer (X-Rite 939, of X-Rite Inc., USA) able to translate a color into three variables plotted along the three axis of a standardized color space known as CIE L*a*b*. The illumination used was D65 and the standard observer was set at 10°. Generally, for most colors in the spectrum, two units of Delta E is the minimum amount of change that may be detected by the naked eye and changes in $\Delta E$ of three units or less are considered tolerable. The numbering of the samples, when the pigmented EAA dispersions were applied as $2^{nd}$ or $4^{th}$ final coats, and a succinct description of the coloring dispersions are presented in Table 12A. A comparative hair sample, numbered 15, was prepared with a dye of a semi-permanent coloring preparation, instead of a pigment as used on the compositions according to the present disclosure. This "dye reference" sample was colored with a commercially available kit (Pillarbox Red by La-Riche, England) according to the manufacturer's instructions and the dye colored sample was subjected to the same irradiation conditions together with the fourteen samples according to some embodiments of the present disclosure.

Three hair samples were tested for each color/coating stage at the dominant filter corresponding to the color of the measured hair sample. The averaged results are presented in Table 12B. For reference, the OD of an uncoated/uncolored virgin hair was of 0.47 at filter V, 0.43 at filter C, 0.52 at filter M and 0.69 at filter Y.

TABLE 12A

| Pigment (Pigment:Total Polymers) | EAA Polymers (~wt. % per Total Polymers) | $2^{nd}$ Coat Sample No. | $4^{th}$ Coat Sample No. |
|---|---|---|---|
| Diacetanil Yellow HTT 8318C (1:4) | Nucrel ® 2806:Primacor ™ 5990I:Luwax ® EAS-5 (53, 23 and 24 wt. %) | 1 | 8 |
| PV Fast Orange H2GL (1:4) | Nucrel ® 2806:Primacor ™ 5990I:Luwax ® EAS-5 (33, 33 and 33 wt. %) | 2 | 9 |
| Heuco ® Red 312201 (1:3.4) | Primacor ™ 5990I:Luwax ® EAS-5 (48 and 52 wt. %) | 3 | 10 |
| Heliogen ® Blue D 7079 (1:3.4) | Primacor ™ 5990I:Luwax ® EAS-5 (48 and 52 wt. %) | 4 | 11 |
| Cromophtal ® Violet D5800 (1:3.4) | Primacor ™ 5990I:Luwax ® EAS-5 (48 and 52 wt. %) | 5 | 12 |
| Heliogen ® Green K 8730 (1:3.4) | Primacor ™ 5990I:Luwax ® EAS-5 (48 and 52 wt. %) | 6 | 13 |
| Orion Black FW 182 (1:3) | Nucrel ® 2806:Primacor ™ 5990I:Luwax ® EAS-5 (33, 33 and 33 wt. %) | 7 | 14 |

TABLE 12B

| Sample No. (color) | OD Before | OD After | % OD Decrease | $\Delta E$ |
|---|---|---|---|---|
| 1 (Yellow) | 1.603 | 1.587 | 1.0% | 1.6 |
| 2 (Orange) | 1.508 | 1.494 | 0.9% | 6.2 |
| 3 (Red) | 1.336 | 1.325 | 0.8% | 2.7 |
| 4 (Blue) | 1.553 | 1.542 | 0.7% | 2.8 |
| 5 (Violet) | 1.580 | 1.570 | 0.6% | 2.8 |
| 6 (Green) | 1.514 | 1.502 | 0.8% | 3.4 |
| 7 (Black) | 1.605 | 1.602 | 0.2% | 0.6 |
| 8 (Yellow) | 1.075 | 1.063 | 1.2% | 1.8 |
| 9 (Orange) | 0.898 | 0.884 | 1.6% | 1.6 |
| 10 (Red) | 0.769 | 0.752 | 2.3% | 1.0 |
| 11 (Blue) | 0.921 | 0.904 | 1.8% | 0.7 |
| 12 (Violet) | 0.960 | 0.946 | 1.5% | 0.8 |
| 13 (Green) | 0.793 | 0.774 | 2.4% | 2.4 |
| 14 (Black) | 0.960 | 0.944 | 1.6% | 0.8 |
| 15 (Dye Ref.) | 1.235 | 0.891 | 27.9% | 22.3 |

As can be seen in the table of results, the OD of hair samples wherein the coloring dispersions were used as the second coat were, as expected, generally higher than the OD of hair samples wherein the same coloring dispersions were used as fourth coat over an intermediate layer of aluminum flakes providing a silvery background.

Independently of the baseline OD values of the fourteen hair samples colored by the method and with the compositions of the present disclosure, the decrease in OD after 24 hrs of accelerated light exposure was minor, the percent OD decrease being of no more than 2.4% (see sample 13 in Table 12B). For comparison, hair colored with a dye displayed a significant loss of 27.9% in OD under the same exposure conditions, about an order of magnitude more than the pigment coated samples.

Regarding the $\Delta E$ values, most of the fourteen samples displayed a tolerable change of no more than 3 $\Delta E$ units, eight samples even being below level of naked eye detection of any color change (i.e. less than 2 ΔE units). However, even the most light-sensitive of the fourteen samples, which was obtained with a second coat of orange pigment (see sample 2 in Table 12B, was significantly more stable than the dye colored hair. While the pigment colored hair displayed a ΔE of 6.2, the dye colored hair revealed an almost four-fold higher ΔE of 22.3. Moreover, if comparing the fade resistance for the same color, namely sample 3 to sample 15, the superiority of the present method is even more striking. While the red dye semi-permanent colored sample displayed a % OD decrease of 27.9%, the red pigment colored sample displayed a thirty-fold smaller loss of only 0.9%. Regarding the change in color as assessed by the ΔE measurements, the dye colored sample displayed a change of 22.3 ΔE units, whereas the pigment colored sample displayed a change of only 2.7 ΔE units.

These results demonstrate the relative stability (with respect to light exposure) of hair that is colored using pigment, according to embodiments of the present disclosure, as compared to conventional technologies in which the hair is colored using dyes.

Example 14: Hair Styling—Ironing of Hair and Permanent Hair Curling

The purpose of this study is to show the suitability for hair colored according to the present teachings to undergo further hair styling. Hair ironing subject the hair to a physical stress (i.e. heat and strokes), while permanent hair curling exemplifies a chemical stress.

Hair Ironing

Tufts of strongly bleached human hair were colored with a neutralized super-wetting dispersion of diacetanil Yellow HTT 8318C embedded in a pigment to polymer weight ratio of 1:3 into the 30:70 w/w blend of Primacor™ 5990i and Nucrel® 2806, as described in Example 11. As in previous examples, following the coloration, the hair was washed with a cationic shampoo, rinsed, combed and dried as detailed in the coloring procedure of Example 4.

The dried colored hair tufts were then ironed at 140° C. for 5 strokes, using a BaByliss Pro™ ironing machine by BaByliss® Sarl, France. The resulting hair was smooth and silky, supporting the suitability for hair colored according to the present teachings to undergo further hair styling.

However, when the same experiment was repeated at 200° C., some color transfer was observed and the colored films remaining on the hair fibers provided for an unpleasant sticky feel. To increase heat resistance of the colored hair, and permit hair styling at elevated temperatures of about 200° C. the hair tufts were treated as follows. Following their coloration, washing and drying as above-described, the dried colored hair tufts were subjected to a second shampooing cycle. The second shampoo contained 90 wt. % of the same TRESemme Perfectly (un)Done cationic shampoo used for the first shampooing and 10 wt. % of plant oil (sunflower oil or olive oil). Hair was rinsed and dried, then subjected to 5 strokes of hair ironing at 200° C. The addition of oil to the shampoo provided protection to the hair coloring and the hair was smooth and silky as previously observed when ironing the hair at 140° C.

Hair Curling

Two sets of Caucasian human mixed hair samples were colored as described in Example 12. In the first series, the hair tufts, predominantly including hair fibers having a light shade with a few hair fibers having a darker shade, were colored (as $2^{nd}$ coat), with neutralized super-wetting dispersions of orange or violet pigments (respectively, PV Fast Orange H2GL or Cromophtal® Violet D5800) embedded in a pigment to polymer weight ratio of 1:4 into a 50:50 w/w blend of Primacor™ 5990i and Luwax® EAS-5. In the second series, similar hair tufts were colored with the same coloring dispersions as $4^{th}$ coat, the second layer being formed by aluminum flakes applied as previously described. As in previous examples, following the coloration of both series, the hair samples were washed with a cationic shampoo, rinsed, combed and dried as detailed in the coloring procedure of Example 4. The dried color hair displayed, according to the coloring dispersion applied, an orange or violet color, with a silvery look if applied as $4^{th}$ coat, all samples being pleasant to the touch. Uncoated hair swatches served as control in the following chemical hair styling procedure.

The hair samples were rolled over a 20 mL glass vial to imitate professional hair perming rolls. The tip of the hair fibers was locked by the cap of the vial to maintain the curled position of the fibers during the perming procedure which was carried out with a commercially available set (Dulcia Advanced formula enriched with Ionene G, by L'Oreal SA, France). 10 drops of first step Dulcia G 0 perming composition were applied on the rolled hair, so as to fully cover all hair fibers. After 8 minutes of perming, the hair samples (still rolled on the vials) were abundantly rinsed with tap water. Then, 10 ml of second step neutralizing solution, Dulcia Neutraliser, were poured on the still rolled hair samples. Neutralization was allowed to proceed for 10 minutes. The hair samples were then removed from the supporting vials and massaged by hand for about 1 minute. Hair samples were then rinsed with water, shampooed once with Shea natural keratin shampoo and dried.

All permed hair samples displayed a stable curling/waving, the samples colored according to the present teachings having an even better appearance than the uncoated control. These results further show that hair colored according to the present teachings can undergo further hair styling as conventionally performed.

Example 15: Coloring Form of the Second Coat

While in previous examples, the coloring formulations were typically dispersions or solutions having a relatively low viscosity comparable to water, the present study demonstrates the suitability of similar compositions prepared at an elevated viscosity to form paste-like formulations.

The amino-silicone emulsion required for the first coating of the fibers with condensation-curable amino-silicone polymer was prepared as described in Example 1.

A neutralized dispersion of EAA-embedded pigment was prepared as described in Example 2. The pigment, Diacetanil Yellow HTT 8318C, was compounded at a 1:4 w/w ratio with two distinct EAA copolymers (Primacor™ 5980I or Luwax® EAS-5), and the two compounded samples were processed to form neutralized dispersions having a solid content of 10 wt. %. The two dispersions were supplemented with a super-wetting fluorosurfactant, as follows. 1 g of neutralized dispersion of Primacor™ 5980I-embedded yellow pigment and 1 g of neutralized dispersion of Luwax® EAS-5-embedded yellow pigment were added to 8 mL of deionized water, followed by addition of 0.05 g of Dynax DX 4010N. The diluted super-wetting dispersion including the Primacor™ 5980I—and the Luwax® EAS-5-embedded yellow pigment was slightly mixed by hand before adding 0.3 g of a rheology modifier, Aculyn™ 22 an anionic thickener hydrophobically modified alkali-soluble acrylic polymer emulsion (HASE) of Dow Chemicals. The resulting mixture was mixed by hand and immediately thickened to form a viscous cream. It is believed that the excess ammonia which may remain in the dispersions following their neutralization readily provide the pH environment adapted to trigger the Aculyn™ 22 mediated thickening. The pH of the cream was in the range of about 9.0 to 10.0. The viscosity was assessed at room temperature using a rheometer (Haake MARS III, by Thermo Scientific) under a shear rate of 3000 $sec^{-1}$. The cream had a viscosity of about 3000-5000 mPa·s.

Hair coloring was performed as detailed in Example 4 with the following modifications. The hair samples were immersed in the first coat of the amino-silicone emulsion for 30 seconds, before rinsing. The cream of the second coat as above prepared, was applied with a coloring brush and was allowed to contact the hair for 1 minute. The hair was then rinsed with tap water, shampooed once with a cationic shampoo, combed and dried with a hair dryer, as previously described. A dry colored hair was obtained with excellent silky feel.

Example 16: Hair Analysis—FTIR and SEM-EDS

Hair colored using compositions and methods according to the present teachings were analyzed by Fourier Transform Infrared (FTIR) Spectroscopy, an analytical technique used to identify organic, polymeric, and in some cases, inorganic materials and assess the chemical properties of the tested samples. In the present study, the FTIR analysis was performed in the mid-infrared range (approx. 500-4000 $cm^{-1}$) using a Nicolet™ 6700 FTIR (Thermo Electron Corporation) at a grazing angle of 60 (VariGATR™ Grazing Angle Accessory, Harrick Scientific Products Inc., USA) under nitrogen atmosphere.

The samples tested included (a) uncoated virgin human hair; (b) human hair coated with the amino-silicone emulsion of Example 1 and a coloring dispersion of Diacetanil Yellow HTT 8318C embedded in Primacor™ 5980I (see item 1 of Table 1 and further details in Examples 2 and 3); (c) the major constituents of the aforesaid coloring compositions, namely GP-397, Diacetanil Yellow HTT 8318C and Primacor™ 58901.

Regarding the individual constituents, the spectra of the condensation-curable amino-silicone polymer yielded a peak around 2960 $cm^{-1}$ (related to the secondary amine) and peaks in the 1370-1490 $cm^{-1}$ range related to the silicone backbone. Analysis of the pigment resulted in peaks in the ranges of 910-1050, 790-860, 1080-1300 and 1450-1500 $cm^{-1}$.

The peaks pertaining to the EAA copolymer measured in the spectra were carboxylic group related peaks at 1700, 1390-1480, 1200-1300, and 900-1000 $cm^{-1}$. All measured spectra were in good correlation with peaks' positions expected from the scientific literature.

Regarding the hair samples, subtraction of the uncoated hair from the coated hair spectra resulted in peaks at 1260 $cm^{-1}$ and 800 $cm^{-1}$ and most likely attributed to the aromatic amino groups of the pigment and peaks in the 950-1120 $cm^{-1}$ range most likely contributed by the EAA copolymer and the pigment. The peaks found at 1700 $cm^{-1}$ and in the 1390-1480 $cm^{-1}$ range were attributed to the sole co-polymer. These results show that carboxylic moieties, attributed to the acrylic copolymer of the coloring dispersion, are detectable in the coated film on the surface of the colored hair. Peaks in the 1700 $cm^{-1}$ and in the 1390-1480 $cm^{-1}$ range in spectra of hair samples colored with unknown coloring compositions may suggest the use of polymers or any other type of material having carboxylic moieties able to absorb at the same wave number.

As can be appreciated by persons skilled in the art of chemical analysis, FTIR techniques can similarly be used to identify and characterize other copolymers, such as the EMAA and AAA copolymers additionally used in the neutralized coloring dispersion of the present disclosure.
Identification of Over-Coat by FTIR-ATR Analysis An additional FTIR technique that allows identification of the neutralizeable acidic copolymers of the coating film is based on dissolving the coating in an appropriate medium and obtaining a FTIR-ATR spectrum. The Attenuated Total Reflectance (ATR) spectrum gives information about the presence or absence of specific functional groups and constitutes a "fingerprint" that is unique to the copolymer being used.

A distinctive FTIR-ATR spectrum was obtained by gentle extraction of the external coat of a Yak tress colored with a pigment embedded in Primacor™ 5990I (5 min shaking in 30% aqueous ammonia). Few drops of the extract were brought into contact with the ATR crystal and the spectrum which was obtained was compared against:

a) A reference of Primacor™ 5990I neutralized in ammonia (pigmentless control).

b) A polymer library supplied with the system (Nicolet 6700 FT-IR Thermo Scientific).

Strong bands were observed at 1630-1700 $cm^{-1}$ (CO of free carboxylic acid) both in the test sample and the positive reference containing the EAA copolymer. The foregoing bands were deemed specific, as they did not appear in different families of film forming polymers, such as acrylate ester (e.g., Eudragit E100, which displayed an ester band at 1730 $cm^{-1}$), ethyl cellulose (Sigma Cat No. 46080), and Pluronic® PE 3100 (BASF). Conversely, bands characteristics of these exemplary reference polymers were absent, or below detectable level, from the sample extracted from coatings of the present disclosure. For instance, the test sample (including an EAA copolymer) lacked bands at 1100 $cm^{-1}$ attributed to etheric bonds of Pluronic® polymers.

Additional information was retrieved from this method, by using different modes of sample preparation. For example, by shifting from an aqueous medium to a non protic medium, such as tetrahydrofuran. Such a change of medium revealed in the extract of the present example additional bands in the range of 2700-3300 $cm^{-1}$ that were previously masked by the hydroxylic groups of the protic solvent. These additional bands, revealed by the change of solvent, were attributed to free hydroxyl groups, in the present case of the acrylic acid moiety of the EAA copolymer.
Confirmation of Silicone Under-Coating by SEM-EDS Analysis Analysis of a coated tress by scanning electron microscope (SEM) Energy-dispersive X-ray spectroscopy (EDS) revealed in addition to carbon, oxygen and nitrogen, an appreciable percentage of silicone atom (typically >10% by weight of all elements) attributed to the first coat covering the hair fibers, comprising the amino-silicones. Analysis was performed on a Crossbeam 340 ZEISS/Gemini SEM microscope under the following experimental conditions: energy 5 KV; Apertures 120; working distance 5 mm. The results reported below are average of at least 4 repeats.

A first control of native/uncoated European hair displayed, as expected, an absence of silicone signal with baseline value of 0.2%. A sample of the same hair colored according to the present teachings with a first amino-silicone coat and a second pigmented coat, the color being embedded in neutralized EAA, indicated the presence of about 12.3% of silicone. A mild removal treatment was then applied to the colored hair, so as to gently remove only the colored coat. The removal was achieved by covering the colored hair sample with 30% aqueous ammonia, with mild shaking for 5 minutes. The decolored sample retaining its amino-silicone undercoat also displayed the presence of silicone at about 16.6%. Finally, the sample was further incubated for 5 more minutes in the removal solution, but this time vigorously brushed with a dye brush to eliminate the first coat residuals. The fully decoated sample displayed trace amounts of silicone of approximately 3.4%.

These results demonstrate that the presence of a silicone film on hair coated according to the present teachings can be detected by SEM-EDS. The detection can be done while the silicone film is overcoated with the pigmented polymeric film and when such film is selectively gently removed, exposing the silicone film.

Once exposed, hair fibers coated with the remaining the silicone film were directly apposed on the ATR crystal of the previously described FTIR-ATR system and a spectrum was analyzed and compare to native uncoated hair. The ATR spectrum revealed the presence of low bands at 1450-1470 cm$^{-1}$ and 1580-1620 cm$^{-1}$ indicative of primary and secondary amino groups, as expected from an amino-polymer which in combination with the presence of silicon atoms support the identification of the amino-silicon film.

The detectability of silicon atoms in combination with the presence of amino groups, as derived from an amino-silicone first coat, when relevant, is believed to be suggestive of a first coat, which together with the identification of bands corresponding to neutralizable polymers of the second coat by FTIR-ATR (or any other analytical method) strengthen the possibility that the sampled hair was colored according to the present teachings.

The person skilled in the art of chemical analysis can readily appreciate that additional techniques may allow similar detection of features characterizing the polymers of either the first or the second coat. Mass spectrometry techniques, in particular soft ionization technique such as matrix-assisted laser desorption time-of flight mass spectrometry (MALDI-ToF-MS) may additionally provide unique information related to polymer end-groups and branching structure, as well as establishing the molecular mass distribution of the studied materials.

Example 17: Wash Resistance

While Example 13 addresses resistance of hair samples to a non-contacting agent, namely irradiation, the present study assesses the effect of direct mechanical and chemical factors, namely wash resistance.

All coloring compositions and methods described so far provided, in addition to the desired coloring resulting from the elected pigments, a pleasant touch/feel both on wet and dry hair. Generally, they also enabled comb-ability of the colored hair tufts, in wet and dry form, but to an extent typically inferior to reference uncoated hairs. This preliminary observation was not quantified by any standard method.

Yak hair samples were colored with an Amino-Silicone Emulsion as described in Example 1 followed, for second coat, by super-wetting neutralized dispersions containing either (a) Diacetanil Yellow HTT 8318C embedded in Primacor™ 5990I; (b) PV Fast Orange H2GL embedded in Nucrel® 2806; and (c) Heuco® Red 312201 embedded in Primacor™ 5990I. All pigments were embedded at a 1:3 weight ratio in their respective EAA copolymers. Coloring was performed as described in the procedure of Example 4. The colored hair samples were then incubated for a week at 80° C. and 100% RH in a Mechanical Convection Oven DFO-240N to ensure full curing of the coats.

The cured samples were then subjected to a series of wash, in which for each cycle the hair fibers were generously massaged with Shea Natural Keratin Shampoo (Saryna Key, Israel) for about one minute, rinsed with tap water at about 40° C. and then dried with a Philips Compact Hair Dryer. The optical density of the samples was measured using an X-Rite 939 spectrophotometer and the change in OD was monitored at most every 10 cycles until the OD value of the washed samples dropped below 800 of the original OD value determined following full curing. The yellow and orange colored samples were measured using a Y filter, while the red colored samples were measured using an M filter.

Coloring films (once the curable polymers are fully cured) are considered wash resistant when the hair can be washed at least 20 times with water (or at least 10 times with a cationic shampoo) and retain an OD value of at least 80% of the original OD value before washing cycles.

For each colored sample and assessed cycle, the OD measurements were performed in at least five repeats. The averaged results and the percent from baseline for each color are presented in Table 13A.

TABLE 13A

| Wash Cycle | Diacetanil Yellow HTT 8318C Colored | | PV Fast Orange H2GL Colored | | Heuco ® Red 312201 Colored | |
|---|---|---|---|---|---|---|
| | OD | % baseline | OD | % baseline | OD | % baseline |
| 0 | 1.643 | 100.0 | 1.444 | 100.0 | 1.466 | 100.0 |
| 2 | 1.665 | 101.4 | 1.471 | 101.9 | 1.456 | 99.3 |
| 4 | 1.648 | 100.3 | 1.470 | 101.7 | 1.401 | 95.6 |
| 10 | 1.654 | 100.7 | 1.471 | 101.9 | 1.432 | 97.7 |
| 20 | 1.583 | 96.4 | 1.341 | 92.8 | 1.332 | 90.9 |
| 30 | 1.639 | 99.8 | 1.251 | 86.6 | 1.299 | 88.6 |
| 40 | 1.620 | 98.6 | 1.175 | 81.3 | 1.230 | 83.9 |
| 45 | NA | NA | 1.102 | 76.3 | NA | NA |
| 50 | 1.548 | 94.2 | NA | NA | 1.217 | 83.0 |
| 55 | NA | NA | NA | NA | 1.161 | 79.2 |
| 60 | 1.614 | 98.2 | NA | NA | NA | NA |
| 70 | 1.539 | 93.7 | NA | NA | NA | NA |
| 80 | 1.477 | 89.9 | NA | NA | NA | NA |
| 90 | 1.468 | 89.4 | NA | NA | NA | NA |
| 100 | 1.361 | 82.9 | NA | NA | NA | NA |
| 105 | 1.377 | 83.8 | NA | NA | NA | NA |
| 110 | 1.310 | 79.7 | NA | NA | NA | NA |

As can be seen from the table, all hair samples colored with the exemplary compositions prepared according to the present disclosure qualify as "wash resistant", sustaining at least 40 shampooing cycles (Orange colored), at least 50 (Red colored) or about 110 (Yellow colored), with an OD decrease of less than 20% from baseline. Such results support the classification of the present coloring methods and compositions as suitable for permanent coloring.

Similar experiments were done with alternative shampoos and with the addition of a conditioning step, as below reported for the set of shampoo and conditioner of Elseve Color-Vive by L'Oreal SA, France. Comparable results were obtained.

Human hair samples having light shades (bleached and formed of a mixed swatch) were colored with super-wetting neutralized dispersions resulting in a yellow or pink coloring (respectively provided by Diacetanil Yellow HTT 8318C or PV Fast Pink E embedded in Primacor™ 5990, see item 3 and 21 of Table 2. Coloring was performed as described in the procedure of Example 4. The colored hair samples were then incubated for three days in a humidity chamber at 70° C. and 70% RH using a KBF-240 Incubator (Binder GmbH, Germany) to ensure curing of the coats.

The cured hair samples having 15-20 cm long fibers and weighing about 1.2 g were then subjected to the following cycle of (a) shampooing with of 0.4 g of Elseve Color-Vive shampoo; (b) rinsing with tap water at 40° C.; (c) conditioning with 1.0 g of Elseve Color-Vive conditioner; (d) rinsing with tap water at 40° C.; and (e) hair drying. The washing cycles were repeated three times and the OD of the hair samples was measured using an X-Rite 939 spectrophotometer after each cycle. The yellow colored samples were monitored using a Y filter, while the pink colored samples were measured using a M filter.

For each colored sample and assessed cycle, the OD measurements were performed in at least four repeats. The averaged results and the percent from baseline for each color are presented in Table 13B.

TABLE 13B

| Wash Cycle | Diacetanil Yellow HTT 8318C Colored | | PV Fast Pink E Colored | |
|---|---|---|---|---|
| | OD | % baseline | OD | % baseline |
| 0 | 1.659 | 100.0 | 1.368 | 100.0 |
| 1 | 1.584 | 95.5 | 1.314 | 96.1 |
| 2 | 1.608 | 96.9 | 1.361 | 99.5 |
| 3 | 1.530 | 92.2 | 1.295 | 94.7 |

By linear extrapolation of the preliminary results of the above table, it was calculated that the yellow colored hair samples should withstand about 10 cycles of shampooing and conditioning before their OD would drop by more than 20% from baseline value, while the pink colored hair samples are expected to withstand about 16 such cycles.

A similar study was performed on hair samples colored with a first coat resulting from the application of ASE(PF)1 and a second coat based on neutralized Dermacryl® 79-embedded Unipure Red LC3079 pigment, the aqueous dispersion being prepared as previously described. The colored samples were allowed to cure 48 hrs at ambient temperature, at which time they were subjected to series of washes with either water at 37° C. or Pure Shea shampoo at 23° C. The OD was monitored as above-detailed for up to 25 wash cycles. The hair samples washed with plain water displayed a decrease in OD of only about 4% (from 1.420 at baseline to 1.366 after 25 washes), whereas the samples washed with shampoo displayed a decrease of about 11% (from 1.572 at baseline to 1.395 after 25 washes). These results further support the wash resistance of hair colored by the present method using the compositions herein disclosed.

Such experiments assessing the wash resistance (hence the degree of permanence of the coloring achieved by the present methods) were repeated with a variety of first coat and second coat compositions. Based on the results (not shown) of such tests, it is believed that the resistance is predominantly governed by the first coat, in other words by the initial attachment of the condensation-curable aminosilicone film to the hair fiber. Nevertheless, variations in wash resistance can be observed depending on the polymeric material of the second coat. Without wishing to be bound by any particular theory, it is believed that the second coat may to some extent, if at all, affect the exposure of the first coat to ambient humidity. As condensation curing can be modulated by the level of humidity, it is assumed that a second coat reducing the diffusion of external humidity towards the hair fiber would accordingly delay the curing of the first coat.

Example 18: Volume Improvement and Shine

As mentioned in Example 4, it was found that the present coating compositions, even when devoid of coloring pigments, advantageously improved the volume of the hair fibers coated therewith. In this study, the shine was monitored using a Samba hair system, Bossa Nova Technologies, USA, the measurements being collected using a polarized incident light for the identification between specular and diffused light on a cylinder mount in which the fibers of the hair tuft were combed and aligned. The shine parameter is the first reflection that carries the same polarization of the incident light. The volume was visually assessed and qualitatively compared to an uncoated control. Observations were made by independent observers and provided in ranking of the five samples, 1 indicating the highest observed volume and 5 the lowest one. Averaged results are presented in the first line of Table 14.

European black human hair tufts were first coated with a pigmentless ASE emulsion prepared as described in Example 1, rinsed and then coated with super-wetting neutralized dispersions of pigmentless EAA copolymers listed in Table 14, which were prepared at a solid content concentration of 10 wt. % as previously described in Example 5 and in Example 7. The coated samples were then washed and dried. For each dried hair samples, gloss measurements were taken in at least three different areas of the tuft. Averaged results, including of an uncoated control of the same hairs, are presented in the second line of Table 14, where AU stands for Arbitrary Units of shine. For reference, changes in 1 AU or less are generally not detectable to the naked eye, while changes in 2 AU or less are considered tolerable for most colors.

TABLE 14

| Uncoated Control | Primacor™ 5980I | Primacor™ 5990I | Nucrel® 2806 | Lumax® EAS-5 |
|---|---|---|---|---|
| 5 | 2 | 3 | 1 | 4 |
| 7.3 + 1 AU | 6.2 + 0.7 AU | 5.5 + 0.5 AU | 4.8 + 0.2 AU | 5.9 + 0.8 AU |

As can be seen from the table, all hair samples simply coated, for second layer upon an amino-silicone undercoat, with the non-limiting exemplary compositions of pigmentless EAA copolymers of the present disclosure, generally provided a superior volume as compared to the uncoated control and an equivalent shine. Advantageously such shine will be stable as long as the coating is not removed from the fibers. These results suggest that the present coloring method does not harm the hair fibers, and may even improve their volume.

Example 19: Bleach Resistance

In Example 17, it was demonstrated that hair samples colored according to the present disclosure were resistant to a high amount of shampooing cycle to an extent allowing classifying coloring methods according to some embodiments of the present disclosure as permanent coloring. While shampooing can be considered as a chemical treatment of the hair fibers, it is typically intended to be a gentle one, not significantly damaging the hair. In the present study colored hair samples were subjected to a harsher chemical treatment, commonly used in the field and feared for the severe damages it causes, namely hair bleaching.

Dark hair samples were colored in two series, as described in Example 13. Briefly, in the first series the coloring dispersions were applied as second coating (over an ASE applied first coat), while in the second series the coloring dispersions were applied as fourth coating (over an ASE first coat, a second layer of aluminum flakes and a third layer of amino-silicone). The super-wetting neutralized coloring dispersions contained either Cromophtal® Violet D5800 or Heliogen® Green K 8730 as pigment, each separately embedded at a 1:4 weight ratio in a blend of Primacor™ 5990I and Luwax® EAS-5, the copolymers being at 1:1 weight ratio. The hair samples were colored as described in Example 13.

A bleaching composition was prepared by mixing in a coloring bowl the components of a bleaching kit (Blond Studio Majimeches, by L'Oreal S A, France) according to the manufacturer instructions. Briefly, 10 ml of hydrogen peroxide (Blond Studio 30 vol. (9%)) were added to a mixture of 10 g of Blond Studio Majimeches 1 with 10 g of Blond Studio Majimeches 2. Mixing was conducted with a coloring brush until a homogenous viscous cream was obtained. The bleaching cream was then applied on the four above-described hair samples (colored in violet and green, either as $2^{nd}$ or $4^{th}$ coat) and on an uncoated control. Bleaching was allowed to proceed for 35 minutes at room temperature. The bleaching cream was then washed off from the hair samples, which were abundantly rinsed with tap water. The hair samples were then shampooed once with Shea natural keratin shampoo (Gilam Cosmetics Ltd., Israel), rinsed and dried with a hair dryer.

While the dark hair uncoated control displayed a drastic drop in color (i.e. a successful bleaching), no visible changes in color were detected in the samples prepared by the present methods. These results suggest that the coatings formed with the present compositions protect the hair from harsh chemical penetration. It is therefore expected that these films would afford protection of the hair fibers against milder chemical exposure (e.g., disinfecting agents found in swimming pools etc.).

Example 20: Preparation of Amino-Silicone Emulsions Including a Reactive Filler While in Example 1 the amino-silicone emulsion of the first coat relied on condensation-curable amino-silane monomers (one type of amino-silicone reactants) as cross-linkers for the formation of the amino-silicone film network in presence of an amino-silicone polymer, in the present example alternative formulations were prepared in which the three-dimensional (3D) network former included an amorphous hydrophobic fumed silica, typically surface after treated. The surface treatment of the fumed silica, when known, included one or more of silicone oils, poly siloxanes, hexamethyl disilazane (HMDS, as available for example under CAS No. 68909-20-6) and amino silanes. The particles of reactive fumed silica were provided either in dry form or in dispersions, the below amounts referring to the solid contents of the materials. The particles tested differed in their surface treatment and/or in their size (as estimated by their specific surface area). The particles tested had a specific surface area (as assessed by BET and reported by their respective manufacturers) between about 25 $m^2/g$ and about 245 $m^2/g$. All fillers were selected to have a refractive index identical or similar (±10%) to the refractive index of the amino-silicone matrix. Even in powder form the fumed silica may be provided with a residual water content of up to 2.5 wt. %.

The overall specific external and internal surface area of porous solids, such as fumed silica, can be determined by measuring the amount of physically adsorbed gas according to the Brunauer, Emmett and Teller (BET) method. In one embodiment, the surface area is determined according to ISO 9277.

In a vial, were mixed for about 5 seconds using a Vortex Genie 2 mixer (from Scientific Industries Inc., USA) the following series of formulations containing reactive hydrophobic fumed silica in the reactive oil phase:

First Series 0.012 g of condensation-curable amino-silicone polymer, GP-397 (having an Amine Number of 116 and a MW~3,754 g/mol) supplied by Genesee Polymers Corp., USA.

0.048 g of amino-functional silane cross-linker, Dynasylan® SIVO 210 including according to its manufacturer a combination of three condensation-curable monomers each having MW between about 221 g/mol and about 425 g/mol, supplied by Evonik Industries AG, Germany.

0.02 g of an amorphous hydrophobic fumed silica (30 wt. % of the combined weight of the afore-listed amino-silicone pre-polymers) selected from Aerosil® R 8200, Aerosil® NA 50 H, Aerosil® R 812 S, and Aerosil® NA 50 Y, supplied by Evonik Resource Efficiency GmbH, NanoBYK 3650 and NanoBYK 3652, supplied by BYK USA Inc.

Second Series 0.04 g of condensation-curable amino-silicone polymer, KF-857 (a 2Sil molecule having an Amine Number of 127), supplied by Shin Etsu.

0.16 g of amino-functional silane cross-linker, Dynasylan® SIVO 210 (Evonik) or of (1-(3-triethoxysilyl)propyl)-2,2-diethoxy-1-aza-2-silacyclopentane (such as commercialized by Gelest as SIT8187.2).

0.006 g of silicone oil being a slow cure amine/alkoxy end-blocked silicone, GP-145 (having an Amine Number of 11 and a MW of 18,000) by Genesee.

0.004 g, 0.006 g, 0.008 g or 0.012 g of Aerosil® R 8200 (corresponding to 10 wt. %, 15 wt. %, 20 wt. % or 30 wt. % of the combined weight of KF-857).

The resulting cross-linkable amino-silicone blends were optionally further sonicated for 15 seconds at 30% of maximal amplitude of a Q700 sonicator (QSonica LLC, USA) until it formed a clear solution, herein termed the Amino-silicone Blend (ASB).

In a separate vessel, a 0.1 wt. % emulsifier dispersion was prepared by adding 0.06 g of polyoxyethylene (20) sorbitan monooleate surfactant (Tween® 80, CAS No. 9005-65-6, supplied by Sigma-Aldrich Co., USA) to 59.94 g of deionized water. They were manually shaken until a clear and homogeneous surfactant solution was obtained.

Unless otherwise stated, each Amino-silicone Emulsion (ASE) was prepared by adding the total weight of each ASB clear blend into 60 g of the 0.1 wt. % surfactant solution and by sonicating the mixture for 15 seconds at 50% of maximal amplitude of a Q700 sonicator, until a homogeneous emulsion was obtained. The average size (Dv50) of the resulting emulsion droplets was measured using a laser diffraction particle size analyzer (Mastersizer AWA 2003 from Malvern Instruments Ltd., United Kingdom) and was found to be sub-micronic for all tested emulsions.

Hair samples were dipped in the various ASEs prepared with each of the afore-described hydrophobic fumed silica and rinsed as previously detailed. All samples provided for the formation of amino-silicone films which coated the hair fibers at least as well as the formulation of Example 1 devoid of fumed silica. Among the hydrophobic fumed silica samples tested, Aerosil® R 8200, surface treated with HMDS, was found particularly suitable.

Comparative examples prepared using hydrophilic fumed silica or hydrophilic fumed alumina (respectively, Aerosil® OX 50 or Aerodisp® W630 by Evonik Resource Efficiency GmbH), each in an amount of 0.004 g in otherwise similarly compounded ASB blends, were found less favorable.

Unless otherwise stated, coloring examples wherein the first coat shall comprise, among others, an amino-silicone polymer and a reactive filler, shall be performed with an ASE prepared from an ASB including the 0.04 g of KF-857, 0.16 g of Dynasylan® SIVO 210, 0.006 g of GP-145 and 0.031 g of Aerosil® R 8200 (corresponding to 15 wt. % of the total weight of the amino-silicone reactants). This composition may be referred to as ASE(PF)1.

The zeta potential of the ASE(PF)1 emulsion, slightly acidified (e.g., with glacial acetic acid) to pH 9, was measured using a Zetasizer Nano Z (by Malvern Instruments) with a folded capillary cell DTS1070, and was found to be of +24 mV.

Example 21: Preparation of Amino-Silicone Emulsions Lacking Reactive Amino-Silicone Polymers While in Examples 1 and 20, for instance, the amino-silicone emulsions of the first coat included an amino-silicone condensation-curable polymer for film formation assisted or triggered by 3D network formers including at least one of amino-silane cross-linkers (generally monomers) or amorphous hydrophobic fumed silicas, in the present example the first coat is achieved in absence of amino-silicone reactive polymer.

Exemplary formulations are provided in Table 15 where the amounts of the compounds are provided in grams. In the table, M2 stands for hexamethyldisiloxane, a silicone oil having a MW of 162.38 and a RI of 1.377 provided under CAS No. 107-46-0 by Gelest, and DMDES stands for diethoxydimethyl silane (a slow curing 2Sil condensation-curable monomer having a MW of 148.28 and an RI of ~1.381) provided under CAS No. 78-62-6 by Sigma-Aldrich.

TABLE 15

| Compound | ASE (NP) 1 | ASE (NP) 2 | ASE (NP) 3 | ASE (NP) 4 | ASE (NP) 5 | ASE (NP) 6 |
| --- | --- | --- | --- | --- | --- | --- |
| Dynasylan® SIVO 210 | 2.0 | 1.8 | 1.6 | 1.6 | | |
| Dynasylan® 1146 | | | | | 2.0 | |
| Dynasylan® AMEO | | | | | | 1.0 |
| Gelest SIO6629.1 | | 0.2 | | | | |
| Gelest DMS-S12 | | | | 0.4 | | |
| DMDES | | | 0.4 | | | |
| M2 | 8.0 | 8.0 | 8.0 | 8.0 | 8.0 | |
| Deionized Water | 10.0 | 10.0 | 10.0 | 10.0 | 10.0 | 10.0* |

*The deionized water included 50 wt. % water acidified to pH 4 with acetic acid.

In a vial, were mixed for about 5 seconds using a Vortex Genie 2 mixer (from Scientific Industries Inc., USA) all the materials listed for each ASE in the amounts reported in the table. The cross-linkable amino-silicone mixtures were then emulsified by sonication for 15 seconds at 50% of maximal amplitude of a Q700 sonicator, until a homogeneous emulsion was obtained in absence of added dedicated emulsifier. The average size (Dv50) of the resulting emulsion droplets was measured using a laser diffraction particle size analyzer (Mastersizer AWA 2003 from Malvern Instruments Ltd., United Kingdom) and was found to be sub-micronic.

It is to be noted that Dynasylan® SIVO 210 (having an estimated Amine Number of 370) contains, according to its manufacturer, a blend of three monomers: 3-aminopropyl-triethoxysilane (CAS No. 919-30-2, generally present at 25% or more) having an Amine Number of 450, bis(triethoxy-silylpropyl) amine (CAS No. 13497-18-2, generally present at more than 20%) having an Amine Number of 235 and 1-(3-(triethoxysilyl)propyl)-2,2-diethoxi-1-aza-2-sila-cyclopentane (CAS No. 1184179-50-7, generally present in the range of 1-5%) having an Amine Number of 263. These materials are individually available respectively as Dynasylan® AMEO from Evonik, SIB1824.5 and SIT8187.2 from Gelest. Formulations similar to ASE(NP)1 wherein the 2 g of Dynasylan® SIVO 210 was replaced by 2 g of each of its constituent molecules were also prepared.

Dynasylan® 1146, used for the preparation of ASE(NP)5, is a condensation-curable oligomer having an Amine Number of 455 and more than three silanol-forming groups per molecule (i.e., a 3⁺Sil molecule), purchased from Evonik. S106629.1, used for the preparation of ASE(NP)2, is a non-amino hydrophobic 2Sil condensation-curable monomer having a MW of ~359 and a RI of ~1.443, supplied by Gelest under CAS No. 70851-50-2. DMS-S12, used for the preparation of ASE(NP)4, is a non-amino hydrophobic condensation—curable oligomer having a MW in the range of ~400-700 and a RI of ~1.401, supplied by Gelest under CAS No. 70131-67-8.

Hair samples were dipped in the ASEs prepared with each of the afore-described condensation-curable reactants, excluding amino-silicone reactive polymers, and rinsed as previously detailed. All samples provided for the formation of amino-silicone films which coated the hair fibers at least as well as the formulation of Example 1 additionally comprising an amino-silicone reactive polymer. However, the resulting films generally displayed a more brittle behavior. The ASE(NP)2 formulation displayed the best behavior, providing for an acceptable feel to the touch. From the comparison of the results obtained with ASE(NP)1 formulation including Dynasylan® SIVO 210 and the comparative formulations each including one of the three molecules of the blend, it appeared that all constituents similarly provided a good initial adhesion to the hair fibers, while SIT8187.2 seemed to be the more prominent contributor to the coloration (as respectively confirmed by lack of color transfer and relatively higher OD, detailed in the following example). The formulation including relatively water-soluble Dynasylan® AMEO as the sole reactive amino-silicone pre-polymer, (see ASE(NP)6) was later found to provide only transient coloration Example 22: Coloring Over First Coats Comprising a Filler or Lacking a Reactive Amino-Silicone Polymer The purpose of this example is to demonstrate the suitability of first coats prepared as exemplified in Example 20 and 21 for further coating with coloring compositions according to the present teachings, wherein the polymeric material of the second coat includes neutralizable acid monomers (e.g., EAA, EMAA, AAA, or mixtures thereof).

The first coat exemplifying a composition including a filler, as further described in Example 20, was achieved using ASE(PF)1, the ASE prepared from the ASB including the 0.04 g of KF-857, 0.16 g of Dynasylan® SIVO 210, 0.006 g of GP-145 and 0.031 g of Aerosil® R 8200 (corresponding to 15 wt. % of the total weight of the amino-silicone reactants).

The first coat exemplifying a composition excluding amino-silicone polymers, as further described in Example 21, was achieved using ASE(NP)2, the ASE prepared by emulsifying 1.8 g of Dynasylan® SIVO 210, 0.2 g of SI06629.1, and 8 g of hexamethyldisiloxane (M2) in 10 g deionized water.

The second coat included EAA-embedded pigment violet prepared as described in Examples 2 and 3, the second coat composition including 2 g of Pigment Violet Cromophtal® K5800, 4 g of Primacor™ 5990I, 4 g of Luwax® EAS-5 and 5 g of Dynnax 4010 N for a neutralized aqueous dispersion of 100 g.

Hair tufts (human hair bleached or white yak body hair, approximately 7 cm long) were dipped for about 10 seconds in the afore-described ASEs. After 10 sec, the hair was washed with warm water (at about 40° C.) to remove excess material. The wet hair tufts were then dipped into a cup filled with the coloring aqueous dispersion for the second coat. The hair samples were gently mixed for about a minute, following which they were rinsed with warm water, washed with a cationic shampoo and dried with a hot air blower. Dry colored hair samples were obtained.

Hair samples colored using the afore-mentioned first coat including a filler (using ASE(PF)1) were allowed to further cure for one day at ambient temperature, following which time they were found to resist 30 washing cycles, such resistance being assessed as generally described in Example 17, all washing liquids being at ambient temperature.

Fibers coated with ASE(PF)1 and pigment violet embedded in Primacor™ 5990I:Luwax® EAS-5 were analyzed by microscopy (SEM-FIB) to assess the thickness achieved by the two coats on the surface of the hair. Thickness was assessed at numerous locations along the hair fibers and found to be generally between about 200 nm and 600 nm, the two coats providing on average a thickness of about 400-450 nm.

Hair samples colored using the aforementioned first coat excluding an amino-silicone polymer (using ASE(NP)2) were allowed to further cure for one day at ambient temperature, following which time they were found to resist 20 washing cycles, such resistance being assessed as generally described in Example 17, all washing liquids being at ambient temperature.

Moreover, when the colored hair samples having a first coat devoid of an amino-silicone condensation-curable polymer (i.e., prepared using ASE(NP)2) were tested for color transfer, within an hour of their coloration, no transfer was observed. Such transfer, or lack thereof, was assessed by placing the hair samples between two sheets of a white testing substrate (paper sheets or tissues), then applying pressure (e.g., with a roller) on the samples so wrapped, and visually assessing if any color was transferred from the hair samples to the white paper. When the substrate remains white in absence of any color transfer, the adhesion of the coats to the hair fiber is said to be satisfactory.

Similar coloring was achieved by using second coats wherein the following pigments were used instead of pigment violet in otherwise identical aqueous dispersions: Black FW182, Black Monarch 580, Diacetanil Yellow HTT 8318C, Heliogen® Blue D 7079, Heliogen® Blue D 7086, Heliogen® Green K 8730, Heuco® Red 312201, and PV Fast Orange H2GL.

Special effect pigments, namely Radglo® JST-17 Pink and colorless Radglo® P-09 UV Blue, both fluorescent pigments by Radiant Color N.V., were also successfully tested. While the pink fluorescent pigment provided a pinky shade to white yak hairs under normal illumination (visible light), the colorless fluorescent pigment did not modify the shade of the white hair fibers. However, both hair samples became fluorescent when exposed to UV light (having a spectral peak at 368 nm, Blacklight Blue F8T5BLB from Ushio) in a Datacolor® Tru-Vue 4D Light Booth.

Special effect pigments, Thermochromic MC Pigment 31° C. D-Blue and Photochromic MC Pigment, both supplied by NCC Taiwan, were also successfully tested, albeit in a mildly modified experimental setup. The pigments were each separately compounded in a w/w ratio of 1:4 with EAA-copolymer (Primacor® 5990I) and the resulting colored polymers having acid moieties were dispersed and neutralized with ammonium hydroxide according to the teachings of Example 2. The dispersions were further prepared according to Example 3 and applied on hair samples previously first coated with ASE(PF)1, the coloring method being substantially as described in Example 4.

White yak hair samples colored with Thermochromic MC Pigment 31° C. D-Blue were observed following exposure to various temperatures. At low temperatures below 31° C., including specifically at ambient temperature, the hair samples displayed a blue coloring. At elevated temperatures, above 31° C. (e.g., as obtained by hot air flow), the hair samples lost the blue coloration and the coatings became "transparent" with respect to baseline hair color. If applied on a living subject having a body temperature of about 37° C., it is expected that the portions of the hair fibers closer to the scalp (acting as heat source) remain "uncolored", whereas more distal portions (subject under most climates to temperatures lower than 31° C.) would turn blue, forming a gradient of colors between hair roots and hair tips.

White yak hair samples colored with Photochromic MC Pigment were observed before and after exposure to UV light, as above-described. While the coating comprising the photochromic pigment was colorless under normal illumination (visible light), it turned violet when exposed to UV light.

As shown in Example 10, wherein the first coat of amino-silicone included a polymer and excluded an inorganic filler, the dispersions of a second coat can be combined to form new shades, such combinations being able to bind alternative first coats as herein described. In the present series of experiments, the tested alternative first coat included an amino-silicone condensation-curable polymer and 15 wt. % of Aerosil® R 8200 hydrophobic fumed silica.

The combinations of coloring aqueous dispersions (all pigments being embedded in Primacor™ 5990I:Luwax® EAS-5 1:1) that satisfactorily colored hair samples included the following compositions (the wt. % of a pigment relating to its presence in its respective dispersion and not to its final concentration in the total composition):

a) 77.7 ml of 1 wt. % Black FW 182 dispersion, 12.6 ml of 1 wt. % PV Fast Orange H2GL dispersion and 9.7 ml of 0.5 wt. % Heuco® Red 312201 dispersion, the mixture providing for a brown shade on light natural human hair.

b) 91.4 ml of 0.015 wt. % Heuco® Red 312201 dispersion and 8.6 ml of 0.1 wt. % PV Fast Orange H2GL dispersion, the mixture providing for a rose gold shade on untreated natural human white hair.

c) 72.9 ml of 1.5 wt. % Black FW 182 dispersion, 11.6 ml of 1.5 wt. % PV Fast Orange H2GL dispersion and 15.5 ml of 1 wt. % Diacetanil Yellow HTT 8318C dispersion, the mixture providing for a blond shade on untreated natural human white hair.

As illustrated in Example 7 with Pyrisma® T30-20 Color Space Yellow, it may be beneficial in order, if desired, to further increase the optical density provided by a pigment embedded in a neutralized acid-copolymer serving for the second coat, to include a pigment in the amino-silicone first coat. In the present experiment, ASE(PF)1 was supplemented with EAA-embedded black pigment (prepared according to Example 2) to form a dark emulsion including 5 wt. % black pigment. Untreated natural human white hair was first coated with this dark emulsion, then second coated with an aqueous super-wetting dispersion of neutralize EAA-embedded Black FW182 or of Black Monarch 580. The hair samples so colored displayed a black shade, which was darker than control samples in which the first coat was the reference uncolored ASE(PF)1.

Example 23: Coloring with More than a First Coat and a Second Coat

The purpose of this example is to demonstrate the suitability of the present method and compositions for multiple coloring coats. A first coloring was achieved by a first coat including the reactive reinforcement filler (as detailed in Example 20) and a second coat including a yellow pigment (Diacetanil Yellow HTT 8318C) embedded in EAA (1:1 Primacor™ 59901:Luwax® EAS, as described in Example 22). Once the hairs were suitably colored in yellow and dried, they were further colored by dipping in a third coat (identical to the first coat), rinsing with water and dipping into a fourth coat including an orange pigment (PV Fast Orange H2GL) embedded in the same EAA blend. Following rinsing with water and washing with a cationic shampoo, the multi-steps colored hairs were dried and displayed a light orange coloration, supporting the combination of the color of the pigment of the second coat by the color of the pigment of the fourth coat. Interestingly, in a control experiment wherein the "fourth" coat was directly applied to the second coat, (without an intermediate "third" coat, a mild coloration was also obtained. Therefore, this example supports alternating coatings of the fibers by more than a single pair of first and second coats.

Example 24: Coloration Removal for Different First Coats

While in Example 9, the removal of the coloring compositions was effected on hair samples wherein the first coat included an amino-silicone polymer and lacked a reactive filler, in the present example removal was tested in alternatively colored samples wherein the first coat either (a) included a reactive filler or (b) lacked an amino-silicone polymer.

The first coat exemplifying a composition including a filler, as further described in Example 20, was achieved using ASE(PF)1 prepared from the ASB including the 0.04 g of KF-857, 0.16 g of Dynasylan® SIVO 210, 0.006 g of GP-145 and 0.031 g of Aerosil® R 8200 (corresponding to 15 wt. % of the total weight of the amino-silicone reactants).

The first coat exemplifying a composition excluding amino-silicone polymers, as further described in Example 21, was achieved using ASE(NP)2 prepared by emulsifying 1.8 g Dynasylan® SIVO 210, 0.2 g 5106629.1, and 8 g hexamethyldisiloxane (M2) in 10 g of deionized water (the non-polymeric amino-silicone reactants providing self-emulsification of the mixture).

The second coat included EAA-embedded pigment violet prepared as described in Examples 2 and 3, the second coat composition including 2 g of Pigment Violet Cromophtal® D5800, 4 g of Primacor™ 5990I, 4 g of Luwax® EAS-5 and 5 g of Dynnax 4010 N for a neutralized aqueous dispersion of 100 g.

Hair tufts (human hair bleached or white yak body hair, approximately 7 cm long) were dipped for about 10 seconds in the afore-described ASEs. After 10 sec, the hair was washed with warm water (at about 40° C.) to remove excess material. The wet hair tufts were then dipped into a cup filled with the second coat. The hair samples were gently mixed for about a minute in the coloring aqueous dispersion, following which they were rinsed with warm water, washed with a cationic shampoo and dried with a hot air blower. Dry hair samples colored in violet were obtained.

The colored hair tufts, the first coatings of which being presently studied, were placed in a mixing bowl and covered with about 10 ml of coloring removal solutions, the contents of which are presented in Tables 16-19. The tufts were thoroughly brushed with the aid of a dye brush with the removal solution to ensure their complete coverage thereby. Samples were taken out of the coloring removal solutions after the periods of time specified in the tables. Typically, the duration of immersion did not exceed 10 minutes in the present experiments.

Following their immersion in the coloring removal solutions, the hair tufts were rinsed thoroughly with tap water at about 35-40° C. The samples were subjected to a single standard shampooing treatment with Shea natural keratin shampoo (Gilam Cosmetics Ltd., Israel) and dried for approximately 30 seconds (with a Philip compact hair dryer). The evaluation of the efficacy of colorant removal was based on visual inspection of the dried hair tufts. In the tables, the results are provided as ++, which indicates complete removal of the coloring composition, +, which indicates partial removal of the coating or 0, which indicates no visible change in the colored sample.

The coloring removal solutions included materials not previously tested in Example 9. These materials were purchased as follows: cyclohexanol, N,N-dimethylaminoethanol, glyceryl tristearate, magnesium hydroxide ($Mg(OH)_2$), potassium hydroxide (KOH), tetrabutylammonium bromide (TBAB) and tetraglycol and were purchased from Sigma-Aldrich Co., USA, at purity level of at least 98%. Benecel™ K200M, an hydroxypropyl methylcellulose, was supplied by Ashland, Luviquat® Mono CP AT1, a 30% aqueous solution of hydroxyethyl cetyldimonium phosphate, was supplied by BASF, Germany, polypropylene powder Micropro® 600VF and Micropoly® 220L were supplied by Micro-Powders Inc., USA, RonaCare® Olaflur, including a fluoride salt, was purchased from Merck, Germany, and Zonyl® 1300 PTFE powder was acquired from DuPont Fluor Additives, USA.

Table 16 provides the results of color removal experiments performed on white yak body hair first coated with a first coat including a reactive hydrophobic filler, namely a surface-treated fumed silica, the second coat included EAA-embedded pigment violet.

TABLE 16

| Decuring Agent (concentration) | Solvent/medium | Immersion Time | Result |
|---|---|---|---|
| KOH (2.3 wt. %) | N-Octyl pyrrolidone | 10 minutes | 0 |
| KOH (3.6 wt. %) | Tert-butyl alcohol | 10 minutes | + |
| KOH (3.6 wt. %) | Ethanol | 10 minutes | 0 |
| KOH (3.3 wt. %) + TBAC (10 wt. %) | Tert-butyl alcohol | 5 minutes | ++ |
| KOH (2.8 wt. %) + TBAC (5.6 wt. %) | N-Octyl pyrrolidone | 5 minutes | + |

It should be noted that both potassium hydroxide (KOH) and tetrabutylammonium chloride (TBAC) did not fully dissolve within their respective solvents. The results of the above-table indicate that potassium hydroxide in combination with tetrabutylammonium chloride in tert-butanol is effective in removing the coloring based on a first coat including a filler. Potassium hydroxide alone in protic solvents, such as ethanol and tert-butanol, or in dipolar aprotic solvents, such as N-octyl pyrrolidone (NOP), did not provide effective color removal under the conditions of the present experiment. However, combination of potassium hydroxide and tetrabutylammonium chloride in N-octyl pyrrolidone provide partial efficiency in such color removal.

Table 17 provides the results of color removal experiments performed on white yak body hair first coated with a first coat including a reactive hydrophobic filler, namely a surface-treated fumed silica, the second coat included EAA-embedded pigment violet. The experiments differed from those reported in the previous table by the viscosity of the color removal formulation, which in the following were prepared in cream form as a result of the inclusion of thickening agents.

TABLE 17

| Decuring Agent (concentration) | Solvent/medium | Thickening Agent | Immersion Time | Result |
|---|---|---|---|---|
| TBAH (2.45 wt. %) | N-Octyl pyrrolidone | 35 wt. % Zonyl ® MP1300 | 5 minutes | ++ |
| TBAH (1 wt. %) | N-Octyl pyrrolidone | 40 wt. % Micropro ® 600VF | 5 minutes | ++ |
| TBAH (2.45 wt. %) | N-Octyl pyrrolidone | 40 wt. % Micropoly ® 220L | 5 minutes | ++ |
| KOH* (0.6 wt. %) + TBAB* (11 wt. %) | Tert-butyl alcohol | 40 wt. % Micropoly ® 220L | 10 minutes | ++ |
| KOH* (0.6 wt. %) + TBAB*(11 wt. %) | Cyclohexanol | 40 wt. % Micropoly ® 220L | 10 minutes | + |
| KOH* (0.6 wt. %) + TBAB*(11 wt. %) | Tetraglycol | 40 wt. % Micropoly ® 220L | 10 minutes | + |

*partially soluble in the medium

The thickening agents (all based on polymers which are cosmetically approved) in the amounts listed in the above-table provided color removal formulations having a creamy texture and an efficiency comparable to the previous non-thickened compositions. The combination of potassium hydroxide with tetrabutylammonium bromide in tert-butanol was the most effective given 10 minutes of immersion.

Table 18 provides the results of color removal experiments performed with creamy formulations on strongly bleached human hair first coated with a first coat excluding a reactive amino-silicone polymer, the second coat included EAA-embedded pigment violet.

TABLE 18

| Decuring Agent (concentration) | Solvent/medium | Thickening agent | Immersion Time | Result |
|---|---|---|---|---|
| TBAH (2.45 wt. %) | N-Octyl pyrrolidone | 40 wt. % Micropoly ® 220L | 5 minutes | ++ |
| KOH* (0.6 wt. %) + TBAB* (11 wt. %) | Tert-butyl alcohol | 40 wt. % Micropoly ® 220L | 10 minutes | + |
| KOH* (0.6 wt. %) + TBAB* (11 wt. %) | Cyclohexanol | 40 wt. % Micropoly ® 220L | 10 minutes | + |

*partially soluble in the medium

The creamy color removal composition including TBHA in N-Octyl pyrrolidone was the most efficient in the present experimental setup. Combination of KOH/TBAB in tert-butanol or in cyclohexanol resulted in partial color removal after a 10 minute period.

Table 19 provides the results of color removal experiments performed with neutral pH color removal formulations in presence of fluoride ion. Items 1-3 relate to white yak hair first coated with a first coat including a reactive filler, while items 4-7 relate to strongly bleached human hair first coated with a first coat excluding a reactive amino-silicone polymer. In all cases, the second coat included EAA-embedded pigment violet. All color removal formulations were prepared in N-Octyl pyrrolidone (NOP) and included 40 wt. % Micropoly 220L for the creamy form.

TABLE 19

| Item | Decuring Agent (concentration) | Immersion Time | Result |
| --- | --- | --- | --- |
| 1 | TBAF (2 wt. %) in NOP | 5 minutes | ++ |
| 2 | TBAB* (20 wt. %) in NOP | 5 minutes | 0 |
| 3 | None - Only NOP | 5 minutes | 0 |
| 4 | TBAF (2 wt. %) in NOP | 10 minutes | + |
| 5 | TBAF (2 wt. %) in NOP | 20 minutes | ++ |
| 6 | TBAB* (20 wt. %) in NOP | 20 minutes | 0 |
| 7 | None - Only NOP | 20 minutes | 0 |

*partially soluble in the medium

As shown in the above-table, neutral coloring removal compositions comprising 2 wt. % of tetrabutylammonium fluoride in N-octyl pyrrolidone achieved complete removal of a coloration based on a first coat including a reactive filler in 5 minutes, while it took about 20 minutes to achieve the same effect when the first coat excluded an amino-silicone polymer. As no visible changes were detected with solutions of neat NOP or with solutions wherein the fluoride of TBAF was replaced by a bromide in TBAB, it is believed that the ion facilitating the color removal is the fluoride.

Taken together, the results illustrated in Tables 16-19 support the ability to rapidly decolor hair previously colored according to the methods or with the compositions herein taught. While the decoloring capacities presented herein were demonstrated on coloring films wherein the pigments were enveloped or embedded in neutralized EAA copolymers, similar results were obtained with hair previously coated with dispersions prepared with EMAA and AAA copolymers.

Non-aqueous removal cream: Dodecane (64.5 wt. %), NOP (16.1 wt. %) and glyceryl stearate (7.5 wt. %) were mixed and sonicated using Qsonica Sonicator Q700 at 500 W 70% for 2 minutes until a clear solution was obtained. RonaCare® Olaflur (10.8 wt. %) and N,N-dimethylaminoethanol (1.1 wt. %) were added to the solution and the resulting mixture was vortexed for 30 seconds to obtain a white viscous cream wherein RonaCare® Olaflur is believed to serve as decuring agent.

Aqueous removal cream: Luviquat® Mono CP AT1 (48.7 wt. %) and distilled water (48.7 wt. %) were mixed in equal amounts and stirred for about 30 seconds until a clear solution was obtained. Benecel™ K200M (0.5 wt. %) and magnesium hydroxide (2.1 wt. %) were added to the solution and the resulting mixture was stirred at 600 rpm for 20 hours at RT to obtain a white cream wherein the decuring agent is believed to be an organic base resulting from the reaction of Luviquat® Mono CP AT1 organic phosphate salt with inorganic base, magnesium hydroxide.

Hair tufts were coated with ASE(PF)1 then colored as previously detailed with second coat compositions prepared as described in Examples 2-3, wherein the pigmented copolymer included either (a) 20 wt. % of Pigment Yellow 83 CI 21108, 40 wt. % of Primacor™ 5990I and 40 wt. % of Luwax® EAS-5; (b) 20 wt. % of Acid Green 25 CI 61570, 40 wt. % of Primacor™ 5990I and 40 wt. % of Luwax® EAS-5; or (c) 20 wt. % Pigment Red 57:1 CI 15850:1 and 80 wt. % Dermacryl® 79.

The colored hair samples were placed in a mixing bowl, covered with about 10 ml of either aqueous or non-aqueous cream prepared as afore-said and thoroughly brushed to ensure complete coverage thereby. After five minutes the hair samples were rinsed and subjected to a single shampooing with Shea Natural Keratin shampoo, then dried. The removal creams, whether aqueous or non-aqueous, succeeded in removing all colored coats from the hair samples.

Example 25: Desolubilization Pre-Treatment of Coating Materials

While in previous examples, the amino-silicone pre-polymers used for the preparation of the first coat ASE were preferably inherently water-insoluble (enabling the formation of an emulsion), the present study demonstrated that water-soluble pre-polymers (their solubility optionally resulting from hydrolysis), can also be used. However, the resulting relatively weak coloration prompted preference for first rendering such relatively soluble materials less soluble or insoluble ahead of emulsification and application.

The "desolubilization" or "insolubilization" step was performed by mixing 20 wt. % of a water soluble aminopropyltriethoxysilane (APTES; CAS No. 919-30-2) (Dynasylan® AMEO from Evonik), with 70 wt. % of a water insoluble non-amine functionalized silane, methyltrimethoxysilane (MTMS; CAS No. 1185-55-3, purchased from Sigma Aldrich) and 10 wt. % distilled water, the constituents being added to a vial in the listed order. After a brief stirring by Vortex, the mixture was left to react in the open vial for two hours at ambient temperature. During such time, MTMS is expected to react with APTES forming condensation bonds therewith, so as to render APTES less water soluble. Following the reaction, the blend including the at least "desolubilized" material is mixed with hexamethyldisoxane (M2) in a w/w ratio of 2:1, and the two are stirred for about 5 sec at ambient temperature. 0.2 g of the resulting product (forming an ASB) was added to 60 g of distilled water and manually shaken for about 10 seconds. The resulting ASE was used to coat hair fibers as previously described. Briefly, hair tufts were dipped in this ASE, washed with tap water to remove excess, then dipped into a coloring aqueous dispersion of neutralized acidic-polymers. Following washing of the colored hair (with running water and once with a cationic shampoo), the colored samples were dried using a hair dryer. The method provided coloration of the fibers.

In addition, polymer analysis was performed by matrix-assisted laser desorption/ionization time-of-flight mass spectroscopy MALDI-TOF MS, and the molecular weight was found to be of at least 362 g/mole, indicating the presence of at least 4 silicone atoms. These results also indicate various levels of hydrolysis.

Example 26: Selective Coloring

Traditional hair coloration is generally considered messy, the colorants often staining in a non-selective manner the areas surrounding their preparation or application. They may, for instance, undesirably stain skin (including facial and scalp skin), vessels and any other such surfaces, sometimes in a non-reversible manner. The purpose of the present study was to show that coloration using the methods and compositions disclosed herein can be selective to hair fibers.

Coloring compositions according to the present teachings were applied to ventral and dorsal segments of pig skin and to surfaces made of metal (aluminum plates), laminated composite (Formica®) or polyethylene terephthalate (PET). Two series of experiments were performed on each tested target surface. In a first series, the surfaces were sequentially coated with a condensation-curable amino-silicone emulsion (namely ASE(PF)1) and with a colored dispersion of neutralized acid-polymers, the coating process being essentially as described for hair fibers. In a second series of experiments, the colored dispersions were directly applied on the target surfaces. Following the last application, excess compositions were removed and the surfaces were rinsed with water and dried. All surfaces were stained by the present compositions, however, and in contrast with traditional coloring methods, this was easily reversed by simple wash with soap and water. The coloring compositions tested included relatively dark pigments, black, violet and blue, and even the black shades were removed following no more than 3 soap wash/rinse cycles, undesired coloring being often readily with a single cycle. These results support the selectivity of the present coloring compositions towards hair fibers and the relative ease to remove them from undesired areas.

Example 27: Differential Scanning Calorimetry (DSC) Study

Hair samples colored by a first-coat of amino-silicone followed by a second pigmented coat as extensively exemplified in previous examples were analyzed by Differential Scanning Calorimetry. The colored hair was cut into small pieces (about 2 mm long) using regular scissors. For each measurement, about 10 mg of hair pieces were placed in a 100 µl aluminum DSC crucible. Distilled water was added to fill the crucible using a pipette. The crucible was sealed and allowed to stand for 12 hours at room temperature.

The ON moisture equilibrated samples were placed in a Differential Scanning Calorimeter DSC Q200 (TA Instruments, USA) and DSC measurements were carried out. Specifically, the samples were first heated to and maintained at 80° C. for 5 minutes to allow thermal equilibration. Then, while data acquisition and storage were activated, the samples were heated to 300° C. at a rate of 20° C./min.

The stored data was then used to obtain a DSC curve for the sample. The DSC curve of each colored sample was compared to a reference DSC curve obtained in the same way for uncolored/uncoated native hair from the same hair batch. All samples displayed similar patterns in the DSC curve. Therefore, it may be concluded that the coloring process as described herein, maintains integrity of the hair. For comparison, hair colored by a conventional oxidative chemistry resulted in a significant shift in the DSC pattern, as compared to the uncolored reference.

Furthermore, the hair colored by the present methods and a corresponding uncoated control were subjected to measurements of force at breakpoint in a tensiometer (load of 20 N at a load speed of 1 mm/min). The results, all normalized to the diameter of each fiber, were found comparable, further supporting that the present method and associated compositions do not impair hair mechanical resilience.

Example 28: Additional Amino-Silicone Emulsions

In the present example, five amino-silicone blends were prepared by replacing a single reactant in an otherwise identical reactive oil phase formulation (OP1). In each ASB, 73 wt. % of the tested reactant were mixed with amino-silicone oils GP-967 and GP-965, respectively at 20 wt. % and 7 wt. % per weight of the total blend. The tested reactants included condensation-curable amino-silicone monomers (Dynasylan® Sivo 210, SIB1824.5 and SIT8187.2) and oligomers (Silquest® VX-225, having an Amine Number of about 277, and a molecular weight of between 670 and 4500 g/mole, or Silquest® Y-15744, having an Amine Number of about 280, and a molecular weight of between 630 and 12,000 g/mole, Momentive Performance Materials). 0.2 g of each of the five OP1 reactive oil phase blends were added to 60 ml of distilled water and emulsified to form accordingly five OP1-amino-silicone emulsions.

Five additional amino-silicone blends were prepared from another reactive oil phase formulation (OP2), and replacing a single reactant each time as done before. In each ASB, 78 wt. % of the tested reactant were mixed with 2% hydrophobic fumed silica (Aerosil® R 8200), and the reactive amino-silicones GP-145 and KF-857, respectively at 3 wt. % and 17 wt. % per weight of the total blend. Each one of these blends included the one of the same condensation-curable amino-silicone monomers and oligomers used in the first 5 formulations. 0.2 g of each of the five OP2 reactive oil phase blends were added to 60 ml of distilled water solution containing 0.1% Tween® 80 as emulsifier, and emulsified to form accordingly five OP2-amino-silicone emulsions.

Hair samples (white yak hair) were coated with these ASEs as first coats. Each sample was then dipped in a coloring dispersion containing particles of neutralized EAA copolymers embedding a violet pigment (20% Cromopthal® Violet K5800 in a 1:1 w/w mixture of Primacor™ 5990I:Luwax® EAS-5), prepared as described in previous examples.

Coloration was performed as previously detailed, the colored hair sampled being rinsed and washed with a cationic shampoo to remove any excess. The washed colored hair samples were then dried for approximately 30 seconds with a Philips compact hair dryer operated to blow hot air at a distance of about 20 cm from the hair fibers, enabling a temperature of about 50° C. on hair surface. The hair samples were generally combed during the drying process to facilitate exposure of all fibers to the air flow, so as to shorten the drying step. However, combing is not essential to the present disclosure, as the coatings of hair fibers according to the present teachings are self-terminating. Baseline post-coloration OD was measured.

After 24 hrs at ambient temperature, the colored hair samples were subjected to a shampoo-resistance test, as follows. A standard (non-cationic) shampoo (Shea natural keratin shampoo by Saryna Key, Israel), was applied on the dried colored hair samples and thoroughly massaged between the fingers of the operating person to ensure full coverage and intimate contact. Excess shampoo was squeezed away, and this step was repeated four more times. After a total of five such shampooing cycles, the hair was rinsed with tap water at about 25° C. Previous step was repeated four more times, the total number of shampooing cycles amounting to 25 at the end of the procedure. Following the last shampooing cycle, the hair samples were thoroughly rinsed with tap water at about 25° C., followed by drying and combing as above-described. OD was measured at the end of the resistance test.

Results are reported in Table 20 where the different samples are identified by the name of the condensation-curable amino-silicone reactant used for the preparation of the emulsions of the first coat. For reference, virgin hair displayed an OD of about 0.30.

TABLE 20

| Amino-silicone reactant | Coloration OD (OP1) | Post-Wash OD (OP1) | Coloration OD (OP2) | Post-Wash OD (OP2) |
|---|---|---|---|---|
| Dynasylan ® Sivo 210 | 1.40 | 1.31 | 1.38 | 1.31 |
| SIB1824.5 | 1.26 | None | 1.58 | None |
| SIT8187.2 | 1.25 | 1.13 | 1.25 | 1.13 |
| Silquest ® VX-225 | 1.57 | None | 1.51 | None |
| Silquest ® Y-15744 | 1.41 | None | 1.31 | None |

The above-results show that all tested reactants (monomers and oligomers) provided a satisfactory hair coloration at least 4-times greater than control uncoated hairs. Both monomers Dynasylan® Sivo 210 and SIT8187.2 (a water insoluble constituent of the former) displayed resistance to the shampoo-fastness test of the example, showing permanency of coloration (the OD decreasing by less than 20% from baseline). Among the tested oligomers, Silquest VX-225 (having an Amine Number of about 277, and a molecular weight of between 670 and 4500 g/mole) displayed the better results with a strong coloration. While not permanent by the present standard of withstanding 25 shampooing cycles, the post-wash OD achieved with emulsions comprising this oligomer nevertheless suggests good resilience of coloration to shampooing. The use of this condensation-curable amino-silicone oligomer in the blend presently exemplified may support semi-permanent or demi-permanent coloration.

The zeta potential of the OP1 and OP2 emulsions, having Dynasylan® Sivo 210 as the condensation-curable amino-silicone monomers in both, was measured using a Zetasizer Nano Z (by Malvern Instruments) with a folded capillary cell DTS1070. These OP1 and OP2 emulsions displayed at native pH (~10) a zeta potential of +6 mV and +4 mV, respectively.

Similarly, the zeta potential of the aqueous dispersion prepared for the $2^{nd}$ coating was measured, and found to be −55 Mv, thus yielding a zeta differential ($\Delta\zeta$) of 59 mV for the OP1 emulsion, and of 61 mV for the OP2 emulsion.

In some or all of the above embodiments, the polymeric material having the neutralized acid moieties includes, mainly includes, consists essentially of, or consists of at least one neutralized copolymer selected from the group consisting of ethylene-acrylic acid (EAA) copolymer, ethylene-methacrylic acid (EMAA) copolymer and acrylamide/acrylate (AAA) copolymer.

In some or all of the above embodiments, the at least one surfactant is selected or adapted to wet the washed, at least partially cured amino-silicone film, the at least one surfactant optionally including a super-wetting agent.

In some or all of the above embodiments, the formulation includes, or consists of, an emulsion.

In some or all of the above embodiments, the polymeric material, prior to neutralization of the neutralized acid moieties, has at least one of the following properties (a) an acid number of at least 100 mg KOH/g, at least 115 mg KOH/g, at least 130 mg KOH/g, or at least 145 mg KOH/g; and (b) a percent weight content of monomer having acid moieties per total weight of the polymeric material of at least 15%, at least 16%, at least 17%, or at least 18%, the monomer being optionally an acrylic acid monomer.

In some or all of the above embodiments, the acid number of the polymeric material is at most 230 mg KOH/g, at most 215 mg KOH/g, at most 200 mg KOH/g, or at most 185 mg KOH/g, and/or the percent weight content of monomer is at most 30%, at most 28%, at most 26%, at most 24%, or at most 22%.

In some or all of the above embodiments, the polymeric material, prior to neutralization of the neutralized acid moieties, has an acid number within a range of 100 to 230 mg KOH/g, 115 to 215 mg KOH/g, 130 to 200 mg KOH/g, 130 to 185 mg KOH/g, 145 to 185 mg KOH/g, or 145 to 170 mg KOH/g, and/or a percent weight content of monomer having acid moieties per total weight of the polymeric material within a range of 15% to 30%, 16% to 28%, 17% to 26%, 17% to 24%, 18% to 24%, or 18% to 22%, the monomer being optionally an acrylic acid monomer.

In some or all of the above embodiments, the at least one pigment is disposed or embedded in the polymeric material having the neutralized acid moieties.

In some or all of the above embodiments, at least one of the pigments is intrinsically dispersed within the aqueous dispersion.

In some or all of the above embodiments, the aqueous dispersion further contains at least one pigment dispersant, each selected or adapted to disperse at least one of the at least one pigment within the aqueous dispersion or within the polymeric material when pigment embedded therein, wherein the weight to weight ratio of the pigment dispersant to the pigment is optionally in the range of 4:1 to 1:4, 2:1 to 1:2 or 1.5:1 to 1:1.5.

In some or all of the above embodiments, the formulation further contains at least one formulation pigment, and optionally further contains at least one formulation pigment dispersant, each selected or adapted to disperse at least one of the at least one formulation pigment within the formulation, wherein the weight to weight ratio of the formulation pigment dispersant to the formulation pigment is optionally in the range of 4:1 to 1:4, 2:1 to 1:2 or 1.5:1 to 1:1.5.

In some or all of the above embodiments, the pigment dispersant or formulation pigment dispersant has at least one pigment-affinic moiety or functionality with respect to the at least one of the at least one pigment or the at least one formulation pigment, respectively.

In some or all of the above embodiments, the formulation contains at least one formulation pigment dispersed therein, and the aqueous dispersion contains at least one pigment dispersed therein.

In some or all of the above embodiments, the pigment of the aqueous dispersion is identical to or different from the formulation pigment.

In some or all of the above embodiments, the surfactant in the aqueous dispersion is selected and added in sufficient quantity whereby the aqueous dispersion exhibits a surface tension, at 25° C., of at most 30, at most 28, at most 26, or at most 24, and optionally, at least 12, at least 14, or at least 16, or wherein the surface tension is within a range of 12 to 30, 15 to 30, 18 to 28, 18 to 26, 18 to 24, 19 to 24, or 20 to 24 milliNewtons per meter (mN/m).

In some or all of the above embodiments, the aqueous dispersion contains particles or pigment particles, optionally excluding metallic pigments, that are at most sub-micronic, or wherein the Dv90 of these particles or pigment particles within the aqueous dispersion is at most 800 nm, at most 600 nm, at most 400 nm, at most 300 nm, at most 200 nm, at most 150 nm, or at most 100 nm, and optionally, at least 20 nm, at least 35 nm, at least 50 nm, at least 70 nm, or at least 90 nm.

In some or all of the above embodiments, the aqueous dispersion contains particles or pigment particles of metallic pigments having a flake shape wherein a maximal thickness of the flake is at most 1000 nm, at most 800 nm, at most 600 nm, at most 400 nm, at most 300 nm, at most 200 nm, at most 150 nm, or at most 100 nm, and optionally, at least 20 nm, at least 35 nm, at least 50 nm, at least 70 nm, or at least 90 nm.

In some or all of the above embodiments, the at least partially cured amino-silicone film or the formulation contains at most 3%, at most 1%, at most 0.5%, at most 0.2%, or at most 0.1% of the formulation pigment, by weight, or is devoid of a formulation pigment.

In some or all of the above embodiments, the method further comprises, subsequent to the applying of the aqueous dispersion to produce the polymeric film, applying, on the polymeric film, additional coloring compositions. In one such embodiment, the additional coloring compositions can be according to the present teachings, a first additional coloring composition being a formulation comprising condensation-curable amino-silicone film forming reactants, exemplary suitable condensation-curable amino-silicone oil-in-water emulsions being as herein taught. Following at least partial curing of such second amino-silicone film, the subsequently applied amino-silicone film is disposed on, and adherent to, an external surface of the previously applied polymeric film.

In some or all of the above embodiments, the method further comprises, subsequent to producing the second, at least partially cured amino-silicone film, applying, on the second, at least partially cured amino-silicone film, a second aqueous dispersion containing a second polymeric material having neutralized acid moieties, exemplary suitable aqueous dispersions being as herein taught, to produce a second polymeric film that coats the second, at least partially cured amino-silicone film.

In some or all of the above embodiments, neutralized acid moieties are linked or bonded to nitrogen moieties on the cured amino-silicone film.

In some or all of the above embodiments, the neutralized acid moieties include carboxylic or carboxylate (COO) moieties.

In some or all of the above embodiments, the nitrogen-containing moieties include, mainly include, or consist of amine groups.

In some or all of the above embodiments, an exterior surface of the coated fiber has a negative or net negative charge.

In some or all of the above embodiments, the core fiber is unbleached.

In some or all of the above embodiments, the core fiber is a keratinous fiber.

In the description and claims of the present disclosure, each of the verbs, "comprise" "include" and "have", and conjugates thereof, are used to indicate that the object or objects of the verb are not necessarily a complete listing of members, components, elements, steps or parts of the subject or subjects of the verb.

As used herein, the singular form "a", "an" and "the" include plural references and mean "at least one" or "one or more" unless the context clearly dictates otherwise.

Unless otherwise stated, the use of the expression "and/or" between the last two members of a list of options for selection indicates that a selection of one or more of the listed options is appropriate and may be made.

As used herein in the specification and in the claims section that follows, the term "largely includes", with respect to a component within a formulation, refers to a weight content of at least 30% of that component.

As used herein in the specification and in the claims section that follows, the term "mostly includes" or "mainly includes", with respect to a component within a formulation, refers to a weight content of at least 50% of that component.

As used herein in the specification and in the claims section that follows, the term "polymeric material" refers to a co-polymer.

As readily known to those of skill in the art, "super-wetting agents" are surface tension modifying agents—a sub-class of wetting agents such as surfactants—known for their ability to reduce surface tension substantially.

A super-wetting agent is a highly efficient, low surface energy surfactant. As used herein in the specification and in the claims section that follows, the term "super-wetting agent" and the like may refer to any wetting agent or surfactant having an equilibrium surface tension of at most 35 mN/m at 0.1 wt. % concentration in water and as measured by the DuNouy method. Preferably, the equilibrium surface tension is at most 32 mN/m, or at most 30 mN/m.

Fundamentally, any such super-wetting agent is typically suitable for use in conjunction with the present disclosure, as long as it exhibits sufficient compatibility with the amino-silicone reactants (and the film formed thereby) and with the acidic polymeric materials of the coating composition. As readily understood, this principle of chemical compatibility of any material used herein with any other material in the same coating composition and/or with the materials which may serve for the preparation of adjacent coats should preferably guide the selection of all materials necessary for the coating compositions disclosed herein. A material is compatible with another if it does not prevent its activity or does not reduce it to an extent that would significantly affect the intended purpose. For instance, a super-wetting agent would not be compatible if, among other things, unable to wet a film of partially cured amino-silicone, or prevents its full curing, or reduces or retards its curing to an extent that the amino-silicone film would not sufficiently and/or rapidly attach to a target fiber, or would not preferably be miscible with the aqueous dispersion, or deleterious to the acidic polymeric material or to the pigments, or preventing or reducing the attachment of the acidic polymeric material to the amino-silicone polymer, and any like undesired effect.

The term "hydrophobic" is used generally as is used in the art. Thus, for a surface, "hydrophobic" indicates at least one of an advancing contact angle of at least 90°, or a surface energy of at most 40 mN/m.

For a liquid, such as a "hydrophobic" liquid monomer, the surface tension should be at most 45 mN/m, and more typically, at most 40 mN/m, or at most 35 mN/m.

As used herein in the specification and in the claims section that follows, the term "self-emulsifying" may be used to characterize a material whose droplets, when disposed in an oil-in-water emulsion, maintain a Dv50 of at most 5 micrometers after the emulsion rests in an unagitated state for 60 minutes.

As used herein in the claims section that follows, the term "average molecular weight" and the like refer to weight average molecular weight.

As used herein in the specification and in the claims section that follows, the term "average thickness", with respect to one or more films having a total thickness of up to 10 μm, and a length of at least 5 μm, refers to the average thickness as determined by a skilled operator of SEM-FIB or similar instrument, over a length of at least 5 μm of the film.

In the discussion, unless otherwise stated, adjectives such as "substantially" and "about" that modify a condition or relationship characteristic of a feature or features of an embodiment of the present technology, are to be understood to mean that the condition or characteristic is defined to within tolerances that are acceptable for operation of the embodiment for an application for which it is intended, or within variations expected from the measurement being performed and/or from the measuring instrument being used.

Furthermore, unless otherwise stated, the terms used in this disclosure should be construed as having tolerances which may depart from the precise meaning of the relevant term but would enable the present disclosure or the relevant portion thereof to operate and function as described, and as understood by a person skilled in the art.

When the term "about" precedes a numerical value, it is intended to indicate +/−10%, or +/−5%, or even only +/−1%, and in all instances is meant to include the precise value.

Although the subject matter as contemplated herein has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification, British Patent Application Nos. GB 1705315.8, filed on Apr. 2, 2017, GB 1714730.7, filed on Sep. 13, 2017, and GB 1720264.9, filed on Dec. 5, 2017, U.S. Provisional Patent Application No. 62/536,378, filed on Jul. 24, 2017, and International Patent Application No. PCT/US18/13411, filed on Jan. 11, 2018, are herein incorporated in their entirety by reference into the specification, to the same extent as if each individual publication, patent or patent application was specifically and individually indicated to be incorporated herein by reference.

Certain marks referenced herein may be common law or registered trademarks of third parties. Use of these marks is by way of example and shall not be construed as descriptive or limit the scope of this disclosure to material associated only with such marks. For instance, aminopropyltriethoxysilane (CAS No. 919-30-2) can be available, by way of non-limiting example, as Dynasylan® AMEO from Evonik, Silquest® A-1100 from Momentive, Geniosil® GF 93 from Wacker Chemie, and KBE-903 from Shin-Etsu, to name a few.

The invention claimed is:

1. A method of treating an outer surface of a mammalian hair fiber, the method comprising:
   (a) forming, on the outer surface of the mammalian hair fiber, an amino-silicone layer; and
   (b) applying, on said amino-silicone layer, an aqueous dispersion comprising:
   a plurality of polymeric particles, formed of a hydrophilic polymeric material having neutralized acid moieties, wherein, in each of at least a portion of said polymeric particles, said hydrophilic polymeric material envelops at least one pigment core particle,
   said plurality of polymeric particles being dispersed within said aqueous dispersion;
   so as to produce an overlying, pigmented polymeric layer adhering to an external surface of said amino-silicone layer.

2. A method according to claim 1, wherein, at a pH of said aqueous dispersion, said external surface of said amino-silicone layer has a first surface zeta potential ($\zeta_1$), and said aqueous dispersion has a second zeta potential ($\zeta_2$), wherein a zeta differential ($\Delta\zeta$) at said pH is defined as $$\Delta\zeta = \zeta_1 - \zeta_2$$

and wherein $\Delta\zeta$, in millivolts (mV), fulfills at least one of the following:
   (i) $\Delta\zeta$ is at least 10;
   (ii) $\Delta\zeta$ is within a range of 10 to 80;
   (iii) for said pH being within a range of 4 to 10.5, said first surface zeta potential ($\zeta_1$), is greater than zero ($\zeta_1 > 0$).

3. A method according to claim 1, wherein said aqueous dispersion comprises a volatile base, optionally selected from the group consisting of ammonia ($NH_3$), monoethanolamine, diethanolamine, triethanolamine and morpholine, the method further comprising volatizing said volatile base associated with said overlying, pigmented polymeric layer, so as to acidify said neutralized acid moieties.

4. A method according to claim 1, further comprising converting at least a portion of said hydrophilic polymeric material in said overlying, pigmented polymeric layer, into a conjugate acid thereof, said converting optionally including active or passive evaporation of a liquid carrier of said aqueous dispersion.

5. A method according to claim 1, further comprising converting said hydrophilic polymeric material into a conjugate acid thereof, so as to obtain a hydrophobic polymeric material, said converting optionally including active or passive evaporation of a liquid carrier of said aqueous dispersion.

6. A method according to claim 1, wherein said polymeric material having said neutralized acid moieties comprises one or more neutralized copolymer selected from the group consisting of neutralized alkene-acrylic acid copolymer, neutralized alkene-methacrylic acid copolymer and neutralized acrylamide/acrylate copolymer.

7. A method according to claim 6, wherein said neutralized alkene-acrylic acid copolymer is neutralized ethylene-acrylic acid (EAA) copolymer.

8. A method according to claim 6, wherein said neutralized alkene-methacrylic acid copolymer is neutralized ethylene-methacrylic acid (EMAA) copolymer.

9. A method according to claim 1, wherein said polymeric material having said neutralized acid moieties is neutralized acrylamide/acrylate (AAA) copolymer.

10. A method according to claim 1, wherein said overlying, pigmented polymeric layer is a hydrophobic polymeric coating.

11. A method according to claim 1, wherein, at a pH within a range of 7.5 to 11, said hydrophilic polymeric material is self-dispersible in water, in an absence of dispersants and all other additives in water.

12. A method according to claim 1, wherein said hydrophilic polymeric material is thermoplastic.

13. A method according to claim 1, wherein said hydrophilic polymeric material has a solubility of at least 2%, by weight, at a pH of 10.

14. A method according to claim 1, wherein said overlying, pigmented polymeric layer washed with a cationic rinsing liquid.

15. A method according to claim 1, wherein said forming includes:

(a) applying, on an external surface of individual hairs of the mammalian hair, an oil-in-water emulsion comprising:
(A) an aqueous phase containing water; and
(B) an oil phase comprising at least one reactive condensation-curable film-forming amino-silicone pre-polymer that, subsequent to condensation curing, forms an elastomer;
wherein said oil phase fulfills at least one of the following:
(i) said at least one reactive condensation-curable film-forming amino-silicone pre-polymer includes at least one reactive condensation-curable film-forming amino-silicone monomer having a molecular weight of at most 1000 g/mole;
(ii) said oil phase further contains a non-amino cross-linking agent adapted or selected to cure said pre-polymer, said non-amino cross-linking agent having a molecular weight in the range of at most 1000 g/mole;
wherein said at least one reactive condensation-curable film-forming amino-silicone pre-polymer has a solubility in water of less than 1% by weight at 23° C.;
(b) after partial condensation curing of said pre-polymer has occurred so as to form an at least partially cured film on the external surface of the individual hairs, washing the hair with a rinsing liquid to remove any excess of said oil-in-water emulsion.

16. A method according to claim 15, said oil-in-water emulsion further comprising a solid, hydrophobic reactive inorganic filler, said filler disposed or dispersed within said oil phase, said filler selected or adapted to facilitate curing of said condensation-curable film-forming amino-silicone pre-polymer.

17. A method according to claim 15, wherein said at least one reactive condensation-curable film-forming amino-silicone pre-polymer comprises a reactive condensation-curable amino-silicone monomer having a solubility in water of less than 1% by weight at 25° C.

18. A method according to claim 15, said oil phase further comprising a pigment, optionally as a plurality of sub-micronic pigment particles, optionally in presence of a dispersant.

19. A kit for producing an at least two-layer coating on an external surface of mammalian hair, the kit comprising:
(a) a first oil phase compartment comprising a first oil phase comprising:
(i) at least one reactive condensation-curable film-forming amino-silicone monomer having a molecular weight of at most 1000 g/mole; and optionally,
(ii) a non-amino cross-linking agent; and further optionally,
(iii) at least one of an amino-silicone oil and/or a non-amino-silicone oil; and further optionally,
(iv) at least one reactive condensation-curable film-forming amino-silicone pre-polymer comprising at least one of a reactive condensation-curable film-forming amino-silicone polymer and/or a reactive condensation-curable film-forming amino-silicone oligomer;
(b) an aqueous dispersion compartment comprising an aqueous dispersion comprising:
(i) an aqueous medium; and
(ii) sub-micronic particles including, or made of, a hydrophilic polymeric material having neutralized acid moieties, disposed within said aqueous medium, each of at least a portion of said sub-micronic particles optionally comprising at least one pigment particle, said at least one pigment particle optionally being at least partially enveloped by said polymeric material;
(c) an optional second oil phase compartment comprising a second oil phase comprising:
(i) at least one of an amino-silicone oil and/or a non-amino-silicone oil, and optionally,
(ii) a solid, hydrophobic reactive inorganic filler; and further optionally,
(iii) said at least one reactive condensation-curable film-forming amino-silicone pre-polymer including at least one of a reactive condensation-curable film-forming amino-silicone polymer and/or a reactive condensation-curable film-forming amino-silicone oligomer; and
further optionally,
(iv) pigment particles, disposed within said second oil phase; and
(d) an optional metallic pigment compartment comprising at least one metallic pigment, and optionally, an aqueous, organic or oil carrier;
wherein the kit further optionally comprises at least one of: a thickening agent, an emulsifier, a surfactant and/or a dispersant.

20. The kit according to claim 19, wherein the thickening agent is contained in at least one of: I) said aqueous dispersion compartment, or II) a dedicated thickening agent compartment, which may optionally comprise at least one of water, an emulsifier, a surfactant and/or a dispersant.

21. The kit according to claim 19, wherein said hydrophilic polymeric material having neutralized acid moieties is selected from an alkene-acrylic acid copolymer, an alkene-methacrylic acid copolymer or an acrylate/acrylamide copolymer.

22. The kit according to claim 19, wherein said first oil phase compartment further comprises at least one of an amino-silicone oil or a non-amino-silicone oil.

23. The kit according to claim 19, wherein said first oil phase compartment further comprises at least one of an amino-silicone oil or a non-amino-silicone oil; and wherein the kit further comprises:
the second oil phase compartment including:
(i) at least one of said amino-silicone oil or said non-amino-silicone oil, and
(ii) a solid, hydrophobic reactive inorganic filler; and
a thickening agent compartment including a thickening agent, and optionally water and/or an emulsifier.

24. The kit according to claim 19, wherein said first oil phase compartment further includes:
(i) at least one of an amino-silicone oil or a non-amino-silicone oil,
(ii) at least one metallic pigment; and optionally
(iii) a dispersant within the first oil phase compartment; and
wherein the kit optionally further comprises a thickening agent compartment including a thickening agent and an emulsifier.

25. The kit according to claim 19, wherein said first oil phase compartment further includes at least one of an amino-silicone oil or a non-amino-silicone oil;
wherein the aqueous dispersion compartment optionally further includes a thickening agent; and
wherein the kit further comprises the metallic pigment compartment including:
(i) at least one metallic pigment; and
a surfactant.

* * * * *